US008465741B2

(12) United States Patent
Frey et al.

(10) Patent No.: US 8,465,741 B2
(45) Date of Patent: *Jun. 18, 2013

(54) ANTIBODIES AND METHODS FOR MAKING AND USING THEM

(75) Inventors: Gerhard Frey, San Diego, CA (US);
Bruce E. Kimmel, San Diego, CA (US);
Abraham Anderson, Sherman Oaks, CA (US)

(73) Assignee: MMRGlobal, Inc., Los Angeles, CA (US)

( * ) Notice: Subject to any disclaimer, the term of this patent is extended or adjusted under 35 U.S.C. 154(b) by 737 days.

This patent is subject to a terminal disclaimer.

(21) Appl. No.: 11/855,943

(22) Filed: Sep. 14, 2007

(65) Prior Publication Data

US 2010/0104553 A1  Apr. 29, 2010

Related U.S. Application Data

(60) Provisional application No. 60/871,069, filed on Dec. 20, 2006.

(51) Int. Cl.
*A61K 39/395* (2006.01)
*C07K 16/28* (2006.01)
*C07K 16/30* (2006.01)
*C07K 16/18* (2006.01)

(52) U.S. Cl.
USPC ............... 424/133.1; 424/135.1; 424/144.1; 424/153.1; 424/155.1; 424/173.1; 424/174.1; 424/809; 424/800; 424/801; 530/387.3; 530/388.22; 530/388.73; 530/388.8; 530/389.6; 530/389.7; 530/866; 530/867

(58) Field of Classification Search
None
See application file for complete search history.

(56) References Cited

U.S. PATENT DOCUMENTS

| 2005/0025764 A1 | 2/2005 | Watkins et al. |
| 2005/0271658 A1 | 12/2005 | Brunetta et al. |
| 2009/0285813 A1 | 11/2009 | Frey et al. |

FOREIGN PATENT DOCUMENTS

| WO | WO 03/068821 A2 | 8/2003 |
| WO | WO 2004/106380 A2 | 12/2004 |
| WO | WO 2005/040220 A1 | 5/2005 |
| WO | WO2005044859 A2 | 5/2005 |
| WO | WO2006020114 A2 | 2/2006 |
| WO | WO2006044908 A2 | 4/2006 |
| WO | WO2006130458 A2 | 12/2006 |
| WO | WO2006130458 A3 | 12/2006 |
| WO | WO2007059188 A1 | 5/2007 |
| WO | WO2007059782 A1 | 5/2007 |

OTHER PUBLICATIONS

Rudikoff et al. "Single amino acid substitution altering antigen binding specificity", Proceedings of the National Academy of Sciences, 1982. vol. 79, pp. 1979-1983.*
MacCallum et al. "Antibody-antigen interactions: contact analysis and binding site topography", Journal of Molecular Biology, 1996. vol. 262, pp. 732-745.*
De Pascalis et al. "Grafting of abbreviated complementarity determining regions containing specificity determining residues essential for ligand contact to engineer a less immunogenic humanzied monoclonal antibody", Journal of Immunology, 2002. vol. 169, pp. 3076-3084.*
PRNewsWire News Releases, "Favrille Acquires Anti-CD20 Monoclonal Antibodies from Diversa", http://markets.financialcontent.com/stocks/news/read?GUID=2308524 &Symbol=DVSA, retrieved Dec. 9, 2010, pp. 1-3.*
Ewert, Stefan et al., Biophysical Properties of Human Antibody Variable Domains, J. Mol. Biol. (2003) 325, 531-553.
Ewert, Stefan et al., "Stability improvement of antibodies for extracellular and intracellular applications: CDR grafting to stable frameworks and structure-based framework engineering", Methods 34 (2004) 184-199.
Knappik, Achim et al., "Fully Synthetic Human Combinatorial Antibody Libraries (HuCAL) Based on Modular Consensus Frameworks and CDRs Randomized with Trinucleotides", J. Mol. Biol. (2000) 296, 57-86.
Luo, Guang X. et al., "Humanization of an anti-ICAM-1 antibody with over 50-fold affinity and functional improvement", Journal of Immunological Methods 275 (2003) 31-40.
Rogers, J. et al., "Rapid discovery and optimization of therapeutic antibodies against emerging infectious diseases", Protein Engineering, Design & Selection, vol. 21, No. 8, pp. 495-505, 2008.
Farvrille, Press Release, dated Aug. 9, 2007 [retrieved from the Internet on Dec. 20, 2007: http://ir.favrille.com/phoenix.zhtml?c=178404&p=irol-newsArticle_Print&ID=1038714&hi] (5 pages).

* cited by examiner

*Primary Examiner* — Ronald Schwadron
(74) *Attorney, Agent, or Firm* — McKee, Voorhees & Sease, P.L.C.

(57) ABSTRACT

The invention provides antibodies, including chimeric human antibodies, recombinant antibodies, synthetic antibodies, and the nucleic acids encoding them, and methods for making and using these immunoglobulins. The invention provides recombinant and synthetic polypeptide and nucleic acid embodiments of these polypeptides and/or antibodies. The invention also provides polypeptides comprising, or consisting of, consensus human framework regions, or "Independently Consensused Frameworks (ICFs)", nucleic acids encoding them, and libraries and kits comprising these ICFs and/or antibodies of the invention, individually and in combinatorial libraries and combinations.

8 Claims, 12 Drawing Sheets

FIG. 2

FIG. 3 heavy chain construct: (SEQ ID NO :356)

ATGGAGTTTGGGCTGAGCTGGCTTTTTCTTGTGGCTATTTTAAAAGGTGTCCAGTGTCAGGTCCAGCTGCAGC
AGTCTGGGGCTGAACTGGCAAGACCTGGGGCCTCAGTGAAGATGTCCTGCAAGGCTTCTGGCTACACCTTTAC
TAGGTACACGATGCACTGGGTAAAACAGAGGCCTGGACAGGGTCTGGAATGGATTGGATACATTAATCCTAGC
CGTGGTTATACTAATTACAATCAGAAGTTCAAGGACAAGGCCACATTGACTACAGACAAATCCTCCAGCACAG
CCTACATGCAACTGAGCAGCCTGACATCTGAGGACTCTGCAGTCTATTACTGTGCAAGATATTATGATGATCA
TTACTGCCTTGACTACTGGGGCCAAGGCACCACTCTCACAGTCTCCTCAGCCTCCACCAAGGGCCCATCGGTC
TTCCCCCTGGCACCCTCCTCCAAGAGCACCTCTGGGGGCACAGCGGCCCTGGGCTGCCTGGTCAAGGACTACT
TCCCCGAACCGGTGACGGTGTCGTGGAACTCAGGCGCCCTGACCAGCGGCGTGCACACCTTCCCGGCTGTCCT
ACAGTCCTCAGGACTCTACTCCCTCAGCAGCGTGGTGACCGTGCCCTCCAGCAGCTTGGGCACCCAGACCTAC
ATCTGCAACGTGAATCACAAGCCCAGCAACACCAAGGTGGACAAGAGAGTTGAGCCCAAATCTTGTGACAAAA
CTCACACATGCCCACCGTGCCCAGCACCTGAACTCCTGGGGGGACCGTCAGTCTTCCTCTTCCCCCCAAAACC
CAAGGACACCCTCATGATCTCCCGGACCCCTGAGGTCACATGCGTGGTGGTGGACGTGAGCCACGAAGACCCT
GAGGTCAAGTTCAACTGGTACGTGGACGGCGTGGAGGTGCATAATGCCAAGACAAAGCCGCGGGAGGAGCAGT
ACAACAGCACGTACCGTGTGGTCAGCGTCCTCACCGTCCTGCACCAGGACTGGCTGAATGGCAAGGAGTACAA
GTGCAAGGTCTCCAACAAAGCCCTCCCAGCCCCCATCGAGAAAACCATCTCCAAAGCCAAAGGGCAGCCCCGA
GAACCACAGGTGTACACCCTGCCCCCATCCCGGGATGAGCTGACCAAGAACCAGGTCAGCCTGACCTGCCTGG
TCAAAGGCTTCTATCCCAGCGACATCGCCGTGGAGTGGGAGAGCAATGGGCAGCCGGAGAACAACTACAAGAC
CACGCCTCCCGTGCTGGACTCCGACGGCTCCTTCTTCCTCTACAGCAAGCTCACCGTGGACAAGAGCAGGTGG
CAGCAGGGGAACGTCTTCTCATGCTCCGTGATGCATGAGGCTCTGCACAACCACTACACGCAGAAGAGCCTCT
CCCTGTCTCCGGGTAAATGA light chain construct: (SEQ ID NO :357)

ATGGACATGAGGGTCCCCGCTCAGCTCCTGGGGCTCCTGCTGCTCTGGCTCCCAGGTGCCAAATGTCAAATTG
TTCTCACCCAGTCTCCAGCAATCATGTCTGCATCTCCAGGGGAGAAGGTCACCATGACCTGCAGTGCCAGCTC
AAGTGTAAGTTACATGAACTGGTACCAGCAGAAGTCAGGCACCTCCCCCAAAAGATGGATTTATGACACATCC
AAACTGGCTTCTGGAGTCCCTGCTCACTTCAGGGGCAGTGGGTCTGGGACCTCTTACTCTCTCACAATCAGCG
GCATGGAGGCTGAAGATGCTGCCACTTATTACTGCCAGCAGTGGAGTAGTAACCCATTCACGTTCGGCTCGGG
GACAAAGTTGGAAATAAACCGGGCTGATCGAACTGTGGCTGCACCATCTGTCTTCATCTTCCCGCCATCTGAT
GAGCAGTTGAAATCTGGAACTGCCTCTGTTGTGTGCCTGCTGAATAACTTCTATCCCAGAGAGGCCAAAGTAC
AGTGGAAGGTGGATAACGCCCTCCAATCGGGTAACTCCCAGGAGAGTGTCACAGAGCAGGACAGCAAGGACAG
CACCTACAGCCTCAGCAGCACCCTGACGCTGAGCAAAGCAGACTACGAGAAACACAAAGTCTACGCCTGCGAA
GTCACCCATCAGGGCCTGAGCTCGCCCGTCACAAAGAGCTTCAACAGGGGAGAGTGTTAA

FIG. 10

HC DVSA-CD3 (Fc Null): (SEQ ID NO :358)

MEFGLSWLFLVAILKGVQCQVQLQQSGAELARPGASVKMSCKASGYTFTRYTMHWVKQRPGQGLEWIGYINPSRG
YTNYNQKFKDKATLTTDKSSSTAYMQLSSLTSEDSAVYYCARYYDDHYCLDYWGQGTTLTVSSASTKGPSVFPLA
PSSKSTSGGTAALGCLVKDYFPEPVTVSWNSGALTSGVHTFPAVLQSSGLYSLSSVVTVPSSSLGTQTYICNVNH
KPSNTKVDKRVEPKSCDKTHTCPPCPAPELLGGPSVFLFPPKPKDTLMISRTPEVTCVVVDVSHEDPEVKFNWYV
DGVEVHNAKTKPREEQYNSVYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSKLTVDKSRWQQGNVFSCSVMH
EALHNHYTQKSLSLSPGK

HC DVSA-CD3: (SEQ ID NO :359)

MEFGLSWLFLVAILKGVQCQVQLQQSGAELARPGASVKMSCKASGYTFTRYTMHWVKQRPGQGLEWIGYINPSRG
YTNYNQKFKDKATLTTDKSSSTAYMQLSSLTSEDSAVYYCARYYDDHYCLDYWGQGTTLTVSSASTKGPSVFPLA
PSSKSTSGGTAALGCLVKDYFPEPVTVSWNSGALTSGVHTFPAVLQSSGLYSLSSVVTVPSSSLGTQTYICNVNH
KPSNTKVDKRVEPKSCDKTHTCPPCPAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSKLTVDKSRWQQGNVFSCSVMH
EALHNHYTQKSLSLSPGK

LC DVSA-CD3: (SEQ ID NO :360)

MDMRVPAQLLGLLLLWLPGAKCQIVLTQSPAIMSASPGEKVTMTCSASSSVSYMNWYQQKSGTSPKRWIYDTSKL
ASGVPAHFRGSGSGTSYSLTISGMEAEDAATYYCQQWSSNPFTFGSGTKLEINRADRTVAAPSVFIFPPSDEQLK
SGTASVVCLLNNFYPREAKVQWKVDNALQSGNSQESVTEQDSKDSTYSLSSTLTLSKADYEKHKVYACEVTHQGL
SSPVTKSFNRGEC

FIG. 11

Top Heavy chains (SEQ ID NOS :361-363)

```
                1                                                50
   BD20610  QVQLVESGAEVKKPGASVKVSCKASGYTFTRYTMHWVRQAPGKGLEWMGY
   BD20611  QVQLVESGAEVKKPGASVKVSCKASGYTFTRYTMHWVRQAPGKGLEWMGY
   BD20613  QVQLQESGPGLVKPSETLSLTCAVSGYTFTRYTMHWVRQAPGKGLEWVGY 51                                               100
   BD20610  INPSRGYTNYNQKFKDRVTISVDTSKNQFSLKLSSVTAADTAVYYCARYY
   BD20611  INPSRGYTNYNQKFKDRLTISKDTSKNQVVLTMTNMDPVDTATYYCARYY
   BD20613  INPSRGYTNYNQKFKDRFTISRDDSKNTAYLQMNSLKTEDTAVYYCTRYY 101                            136
   BD20610  DDHYCLDYWGQGTLVTVSSASTKGPSVFPLAPSSKS
   BD20611  DDHYCLDYWGQGTLVTVSSASTKGPSVFPLAPSSKS
   BD20613  DDHYCLDYWGQGTLVTVSSASTKGPSVFPLAPSSKS
```

Top Light (kappa) chains (SEQ ID NOS :364-372)

```
                1                                                      55
   BD21130  DIQMTQSPSSLSASVGDRVTITCSASSSVSYMNWYQQKPGQPPKLLIYDTSKLAS
   BD21131  DIQMTQSPSTLSASVGDRVTITCSASSSVSYMNWYQQKPGQAPRLLIYDTSKLAS
   BD21132  EIVLTQSPATLSLSPGERATLSCSASSSVSYMNWYQQKPGKAPKLLIYDTSKLAS
   BD21133  DIVMTQSPLSLPVTPGEPASISCSASSSVSYMNWYQQKPGQPPKLLIYDTSKLAS
   BD21134  EIVMTQSPATLSVSPGERATLSCSASSSVSYMNWYQQKPGQPPKLLIYDTSKLAS
   BD21135  EIVMTQSPATLSVSPGERATLSCSASSSVSYMNWYQQKPGQAPRLLIYDTSKLAS
   BD21136  DIQMTQSPSTLSASVGDRVTITCSASSSVSYMNWYQQKPGKAPKLLIYDTSKLAS
   BD21137  DIQMTQSPSTLSASVGDRVTITCSASSSVSYMNWYQQKPGQPPKLLIYDTSKLAS
   BD21138  DIQMTQSPSTLSASVGDRVTITCSASSSVSYMNWYQQKPGKAPKLLIYDTSKLAS 56                                                    106
   BD21130  GVPDRFSGSGSGTDFTLKISRVEAEDVGVYYCQQWSSNPFTFGQGTKVEIK
   BD21131  GVPDRFSGSGSGTDFTLKISRVEAEDVGVYYCQQWSSNPFTFGQGTKVEIK
   BD21132  GVPSRFSGSGSGTEFTLTISSLQPDDFATYYCQQWSSNPFTFGQGTKVEIK
   BD21133  GVPSRFSGSGSGTEFTLTISSLQPDDFATYYCQQWSSNPFTFGQGTKVEIK
   BD21134  GVPSRFSGSGSGTEFTLTISSLQPDDFATYYCQQWSSNPFTFGQGTKVEIK
   BD21135  GVPDRFSGSGSGTDFTLTISSLQAEDVAVYYCQQWSSNPFTFGQGTKVEIK
   BD21136  GIPDRFSGSGSGTDFTLTISRLEPEDFAVYYCQQWSSNPFTFGQGTKVEIK
   BD21137  GVPSRFSGSGSGTDFTFTISSLQPEDIATYYCQQWSSNPFTFGQGTKVEIK
   BD21138  GVPDRFSGSGSGTDFTLKISRVEAEDVGVYYCQQWSSNPFTFGQGTKVEIK
```

FIG. 12

SEQUENCE LISTING

```
<160> NUMBER OF SEQ ID NOS: 372

<210> SEQ ID NO 1
<211> LENGTH: 25
<212> TYPE: PRT
<213> ORGANISM: Artificial Sequence
<220> FEATURE:
<223> OTHER INFORMATION: Chemically synthesized

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 2
<211> LENGTH: 25
<212> TYPE: PRT
<213> ORGANISM: Artificial Sequence
<220> FEATURE:
<223> OTHER INFORMATION: Chemically synthesized

<400> SEQUENCE: 2

Gln Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 3
<211> LENGTH: 25
<212> TYPE: PRT
<213> ORGANISM: Artificial Sequence
```

```
<220> FEATURE:
<223> OTHER INFORMATION: Chemically synthesized

<400> SEQUENCE: 3

Gln Val Gln Leu Gln Glu Ser Gly Pro Gly Leu Val Lys Pro Ser Glu
 1               5                  10                  15

Thr Leu Ser Leu Thr Cys Ala Val Ser
            20                  25

<210> SEQ ID NO 4
<211> LENGTH: 25
<212> TYPE: PRT
<213> ORGANISM: Artificial Sequence
<220> FEATURE:
<223> OTHER INFORMATION: Chemically synthesized

<400> SEQUENCE: 4

Gln Val Thr Leu Lys Glu Ser Gly Pro Ala Leu Val Lys Pro Thr Gln
 1               5                  10                  15

Thr Leu Thr Leu Thr Cys Thr Phe Ser
            20                  25

<210> SEQ ID NO 5
<211> LENGTH: 25
<212> TYPE: PRT
<213> ORGANISM: Artificial Sequence
<220> FEATURE:
<223> OTHER INFORMATION: Chemically synthesized

<400> SEQUENCE: 5

Gln Val Gln Leu Gln Glu Ser Gly Pro Gly Leu Val Lys Pro Ser Gln
 1               5                  10                  15

Thr Leu Ser Leu Thr Cys Thr Val Ser
            20                  25

<210> SEQ ID NO 6
<211> LENGTH: 25
<212> TYPE: PRT
<213> ORGANISM: Artificial Sequence
<220> FEATURE:
<223> OTHER INFORMATION: Chemically synthesized

<400> SEQUENCE: 6

Glu Val Gln Leu Val Gln Ser Gly Ala Glu Val Lys Lys Pro Gly Glu
 1               5                  10                  15

Ser Leu Lys Ile Ser Cys Lys Gly Ser
            20                  25

<210> SEQ ID NO 7
<211> LENGTH: 25
<212> TYPE: PRT
<213> ORGANISM: Artificial Sequence
<220> FEATURE:
<223> OTHER INFORMATION: Chemically synthesized

<400> SEQUENCE: 7

Gln Val Gln Leu Val Gln Ser Gly Ala Glu Val Lys Lys Pro Gly Ala
 1               5                  10                  15

Ser Val Lys Val Ser Cys Lys Ala Ser
            20                  25

<210> SEQ ID NO 8
<211> LENGTH: 14
<212> TYPE: PRT
<213> ORGANISM: Artificial Sequence
```

```
<220> FEATURE:
<223> OTHER INFORMATION: Chemically synthesized

<400> SEQUENCE: 8

Trp Val Arg Gln Ala Pro Gly Lys Gly Leu Glu Trp Val Ser
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Chemically synthesized

<400> SEQUENCE: 9

Trp Val Arg Gln Ala Pro Gly Lys Gly Leu Glu Trp Val Gly
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Chemically synthesized

<400> SEQUENCE: 10

Trp Val Arg Gln Ala Pro Gly Gln Gly Leu Glu Trp Met Gly
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Chemically synthesized

<400> SEQUENCE: 11

Trp Val Arg Gln Ala Pro Gly Lys Gly Leu Glu Trp Met Gly
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Chemically synthesized

<400> SEQUENCE: 12

Trp Ile Arg Gln Pro Pro Gly Lys Gly Leu Glu Trp Ile Gly
1               5                   10

<210> SEQ ID NO 13
<211> LENGTH: 32
<212> TYPE: PRT
<213> ORGANISM: Artificial Sequence
<220> FEATURE:
<223> OTHER INFORMATION: Chemically synthesized

<400> SEQUENCE: 13

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
                20                  25                  30

<210> SEQ ID NO 14
<211> LENGTH: 32
<212> TYPE: PRT
```

<213> ORGANISM: Artificial Sequence
<220> FEATURE:
<223> OTHER INFORMATION: Chemically synthesized

<400> SEQUENCE: 14

Arg Phe Thr Ile Ser Arg Asp Asn Ser Lys Asn Thr Leu His Leu Gln
1               5                   10                  15

Met Asn Ser Leu Arg Ala Glu Asp Thr Ala Val Tyr Tyr Cys Lys Arg
            20                  25                  30

<210> SEQ ID NO 15
<211> LENGTH: 32
<212> TYPE: PRT
<213> ORGANISM: Artificial Sequence
<220> FEATURE:
<223> OTHER INFORMATION: Chemically synthesized

<400> SEQUENCE: 15

Arg Phe Thr Ile Ser Arg Asp Asp Ser Lys Asn Thr Ala Tyr Leu Gln
1               5                   10                  15

Met Asn Ser Leu Lys Thr Glu Asp Thr Ala Val Tyr Tyr Cys Thr Arg
            20                  25                  30

<210> SEQ ID NO 16
<211> LENGTH: 32
<212> TYPE: PRT
<213> ORGANISM: Artificial Sequence
<220> FEATURE:
<223> OTHER INFORMATION: Chemically synthesized

<400> SEQUENCE: 16

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 17
<211> LENGTH: 32
<212> TYPE: PRT
<213> ORGANISM: Artificial Sequence
<220> FEATURE:
<223> OTHER INFORMATION: Chemically synthesized

<400> SEQUENCE: 17

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 18
<211> LENGTH: 32
<212> TYPE: PRT
<213> ORGANISM: Artificial Sequence
<220> FEATURE:
<223> OTHER INFORMATION: Chemically synthesized

<400> SEQUENCE: 18

Arg Phe Val Phe Ser Leu Asp Thr Ser Val Ser Thr Ala Tyr Leu Gln
1               5                   10                  15

Met Ser Ser Leu Lys Ala Glu Asp Thr Ala Val Tyr Tyr Cys Ala Arg
            20                  25                  30

<210> SEQ ID NO 19
<211> LENGTH: 32
<212> TYPE: PRT

```
<213> ORGANISM: Artificial Sequence
<220> FEATURE:
<223> OTHER INFORMATION: Chemically synthesized

<400> SEQUENCE: 19

Arg Val Thr Ile Ser Ala Asp Lys Ser Ile Ser Thr Ala Tyr Leu Gln
 1               5                  10                  15

Trp Ser Ser Leu Lys Ala Ser Asp Thr Ala Met Tyr Tyr Cys Ala Arg
                20                  25                  30

<210> SEQ ID NO 20
<211> LENGTH: 32
<212> TYPE: PRT
<213> ORGANISM: Artificial Sequence
<220> FEATURE:
<223> OTHER INFORMATION: Chemically synthesized

<400> SEQUENCE: 20

Arg Val Thr Ile Thr Ala Asp Lys Ser Thr Ser Thr Ala Tyr Met Glu
 1               5                  10                  15

Leu Ser Ser Leu Arg Ser Glu Asp Thr Ala Val Tyr Tyr Cys Ala Arg
                20                  25                  30

<210> SEQ ID NO 21
<211> LENGTH: 12
<212> TYPE: PRT
<213> ORGANISM: Artificial Sequence
<220> FEATURE:
<223> OTHER INFORMATION: Chemically synthesized

<400> SEQUENCE: 21

Val Thr Val Ser Ser Ala Ser Thr Lys Gly Pro Ser
 1               5                  10

<210> SEQ ID NO 22
<211> LENGTH: 75
<212> TYPE: DNA
<213> ORGANISM: Artificial Sequence
<220> FEATURE:
<223> OTHER INFORMATION: Chemically synthesized

<400> SEQUENCE: 22
gaagtgcagc tggtggagtc tgggggaggc ttggtacagc ctggcgggtc cctgagactc    60
tcctgtgcag cctct                                                    75

<210> SEQ ID NO 23
<211> LENGTH: 75
<212> TYPE: DNA
<213> ORGANISM: Artificial Sequence
<220> FEATURE:
<223> OTHER INFORMATION: Chemically synthesized

<400> SEQUENCE: 23
caggtgcagc tggtggagtc tgggggaggc gtggtccagc ctggggaggtc cctgagactc    60 tcctgtgcag cctct                                                    75

<210> SEQ ID NO 24
<211> LENGTH: 75
<212> TYPE: DNA
<213> ORGANISM: Artificial Sequence
<220> FEATURE:
<223> OTHER INFORMATION: Chemically synthesized

<400> SEQUENCE: 24
caggtgcagc tgcaggagtc gggcccagga ctggtgaagc cttcggagac cctgtccctc    60
```

```
acctgcgctg tctct                                              75

<210> SEQ ID NO 25
<211> LENGTH: 75
<212> TYPE: DNA
<213> ORGANISM: Artificial Sequence
<220> FEATURE:
<223> OTHER INFORMATION: Chemically synthesized

<400> SEQUENCE: 25
caggtcacct tgaaggagtc tggtcctgcg ctggtgaaac ccacacagac cctcacactg     60
acctgcacct tctct                                              75

<210> SEQ ID NO 26
<211> LENGTH: 75
<212> TYPE: DNA
<213> ORGANISM: Artificial Sequence
<220> FEATURE:
<223> OTHER INFORMATION: Chemically synthesized

<400> SEQUENCE: 26
caggtgcagc tgcaggagtc gggcccagga ctggtgaagc cttcacagac cctgtccctc     60
acctgcactg tctct                                              75

<210> SEQ ID NO 27
<211> LENGTH: 75
<212> TYPE: DNA
<213> ORGANISM: Artificial Sequence
<220> FEATURE:
<223> OTHER INFORMATION: Chemically synthesized

<400> SEQUENCE: 27
gaggtgcagc tggtgcagtc tggagcagag gtgaaaaagc ccggggagtc tctgaagatc     60
tcctgtaagg gttct                                              75

<210> SEQ ID NO 28
<211> LENGTH: 75
<212> TYPE: DNA
<213> ORGANISM: Artificial Sequence
<220> FEATURE:
<223> OTHER INFORMATION: Chemically synthesized

<400> SEQUENCE: 28
caggtgcagc tgtgcagtc tggggctgag gtgaagaagc ctggggcttc ggtgaaggtc     60
tcctgcaagg cttct                                              75

<210> SEQ ID NO 29
<211> LENGTH: 42
<212> TYPE: DNA
<213> ORGANISM: Artificial Sequence
<220> FEATURE:
<223> OTHER INFORMATION: Chemically synthesized

<400> SEQUENCE: 29
tgggtccgcc aggctccagg gaaggggctg gagtgggtct ca                 42

<210> SEQ ID NO 30
<211> LENGTH: 42
<212> TYPE: DNA
<213> ORGANISM: Artificial Sequence
<220> FEATURE:
<223> OTHER INFORMATION: Chemically synthesized

<400> SEQUENCE: 30
```
tgggtccgcc aggctccagg caagggcta gagtgggtgg ca                              42

<210> SEQ ID NO 31
<211> LENGTH: 42
<212> TYPE: DNA
<213> ORGANISM: Artificial Sequence
<220> FEATURE:
<223> OTHER INFORMATION: Chemically synthesized

<400> SEQUENCE: 31
tgggtccgcc aggctccagg gaagggctg gagtgggttg gc                              42

<210> SEQ ID NO 32
<211> LENGTH: 42
<212> TYPE: DNA
<213> ORGANISM: Artificial Sequence
<220> FEATURE:
<223> OTHER INFORMATION: Chemically synthesized

<400> SEQUENCE: 32
tgggtgcgac aggcccctgg acaagggctt gagtggatgg ga                             42

<210> SEQ ID NO 33
<211> LENGTH: 42
<212> TYPE: DNA
<213> ORGANISM: Artificial Sequence
<220> FEATURE:
<223> OTHER INFORMATION: Chemically synthesized

<400> SEQUENCE: 33
tgggtgcgac aggctcctgg aaagggctt gagtggatgg ga                              42

<210> SEQ ID NO 34
<211> LENGTH: 96
<212> TYPE: DNA
<213> ORGANISM: Artificial Sequence
<220> FEATURE:
<223> OTHER INFORMATION: Chemically synthesized

<400> SEQUENCE: 34
cgattcacca tctccagaga caacgccaag aactcactgt atctgcaaat gaacagcctg          60
agagccgagg acacggctgt gtattactgt gcgaga                                   96

<210> SEQ ID NO 35
<211> LENGTH: 96
<212> TYPE: DNA
<213> ORGANISM: Artificial Sequence
<220> FEATURE:
<223> OTHER INFORMATION: Chemically synthesized

<400> SEQUENCE: 35
cgattcacca tctccagaga caacagcaaa aactccctgt atctgcaaat gaacagtctg          60
agaactgagg acaccgcctt gtattactgt gcaaga                                   96

<210> SEQ ID NO 36
<211> LENGTH: 96
<212> TYPE: DNA
<213> ORGANISM: Artificial Sequence
<220> FEATURE:
<223> OTHER INFORMATION: Chemically synthesized

<400> SEQUENCE: 36
aggttcacca tctccagaga tgattcaaag aacacggcgt atctgcaaat gaacagcctg          60
aaaaccgagg acacggccgt gtattactgt actaga                                   96

<210> SEQ ID NO 37
<211> LENGTH: 96
<212> TYPE: DNA
<213> ORGANISM: Artificial Sequence
<220> FEATURE:
<223> OTHER INFORMATION: Chemically synthesized

<400> SEQUENCE: 37
cgagttacca tatcagtaga cacgtctaag aaccagttct ccctgaagct gagctctgtg    60
actgccgcgg acacggccgt gtattactgt gcgaga                             96

<210> SEQ ID NO 38
<211> LENGTH: 96
<212> TYPE: DNA
<213> ORGANISM: Artificial Sequence
<220> FEATURE:
<223> OTHER INFORMATION: Chemically synthesized

<400> SEQUENCE: 38
aggctcacca tctccaagga cacctccaaa aaccaggtgg tccttacaat gaccaacatg    60
gaccctgtgg acacagccac gtattactgt gcacgg                             96

<210> SEQ ID NO 39
<211> LENGTH: 96
<212> TYPE: DNA
<213> ORGANISM: Artificial Sequence
<220> FEATURE:
<223> OTHER INFORMATION: Chemically synthesized

<400> SEQUENCE: 39
cgatttgtct tctccctcga cacgtctgtc agcacggcgt atcttcagat gtctagccta    60
aaggctgagg acacggccgt ctattactgt gcgcga                             96

<210> SEQ ID NO 40
<211> LENGTH: 96
<212> TYPE: DNA
<213> ORGANISM: Artificial Sequence
<220> FEATURE:
<223> OTHER INFORMATION: Chemically synthesized

<400> SEQUENCE: 40
cgcgtcacca tctcagctga caagtccatc agcactgcct acctgcagtg gagcagcctg    60
aaggcctcgg acaccgccat gtattactgt gcgaga                             96

<210> SEQ ID NO 41
<211> LENGTH: 96
<212> TYPE: DNA
<213> ORGANISM: Artificial Sequence
<220> FEATURE:
<223> OTHER INFORMATION: Chemically synthesized

<400> SEQUENCE: 41
agagtcacga ttaccgcgga caaatccacg agcacagcct acatggagct gagcagcctg    60
agatctgagg acacggccgt gtattactgt gcgaga                             96

<210> SEQ ID NO 42
<211> LENGTH: 36
<212> TYPE: DNA
<213> ORGANISM: Artificial Sequence
<220> FEATURE:
<223> OTHER INFORMATION: Chemically synthesized

<400> SEQUENCE: 42
gtcaccgtct cctccgcctc caccaagggc ccatcg         36

<210> SEQ ID NO 43
<211> LENGTH: 23
<212> TYPE: PRT
<213> ORGANISM: Artificial Sequence
<220> FEATURE:
<223> OTHER INFORMATION: Chemically synthesized

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 44
<211> LENGTH: 23
<212> TYPE: PRT
<213> ORGANISM: Artificial Sequence
<220> FEATURE:
<223> OTHER INFORMATION: Chemically synthesized

<400> SEQUENCE: 44

Asp Ile Gln Met Thr Gln Ser Pro Ser Thr Leu Ser Ala Ser Val Gly
1               5                   10                  15

Asp Arg Val Thr Ile Thr Cys
            20

<210> SEQ ID NO 45
<211> LENGTH: 23
<212> TYPE: PRT
<213> ORGANISM: Artificial Sequence
<220> FEATURE:
<223> OTHER INFORMATION: Chemically synthesized

<400> SEQUENCE: 45

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 46
<211> LENGTH: 23
<212> TYPE: PRT
<213> ORGANISM: Artificial Sequence
<220> FEATURE:
<223> OTHER INFORMATION: Chemically synthesized

<400> SEQUENCE: 46

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 47
<211> LENGTH: 23
<212> TYPE: PRT
<213> ORGANISM: Artificial Sequence
<220> FEATURE:
<223> OTHER INFORMATION: Chemically synthesized

<400> SEQUENCE: 47

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 48
<211> LENGTH: 23
<212> TYPE: PRT
<213> ORGANISM: Artificial Sequence
<220> FEATURE:
<223> OTHER INFORMATION: Chemically synthesized

<400> SEQUENCE: 48

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 49
<211> LENGTH: 23
<212> TYPE: PRT
<213> ORGANISM: Artificial Sequence
<220> FEATURE:
<223> OTHER INFORMATION: Chemically synthesized

<400> SEQUENCE: 49

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 50
<211> LENGTH: 22
<212> TYPE: PRT
<213> ORGANISM: Artificial Sequence
<220> FEATURE:
<223> OTHER INFORMATION: Chemically synthesized

<400> SEQUENCE: 50

Gln Ser Val Leu Thr Gln Pro Pro Ser Val Ser Ala Ala Pro Gly Gln
1               5                   10                  15

Lys Val Thr Ile Ser Cys
            20

<210> SEQ ID NO 51
<211> LENGTH: 22
<212> TYPE: PRT
<213> ORGANISM: Artificial Sequence
<220> FEATURE:
<223> OTHER INFORMATION: Chemically synthesized

<400> SEQUENCE: 51

Gln Ser Val Leu Thr Gln Pro Pro Ser Ala Ser Gly Thr Pro Gly Gln
1               5                   10                  15

Arg Val Thr Ile Ser Cys
            20

<210> SEQ ID NO 52
<211> LENGTH: 22
<212> TYPE: PRT
<213> ORGANISM: Artificial Sequence
<220> FEATURE:
<223> OTHER INFORMATION: Chemically synthesized

<400> SEQUENCE: 52

Gln Ser Ala Leu Thr Gln Pro Ala Ser Val Ser Gly Ser Pro Gly Gln
1               5                   10                  15

```
Ser Ile Thr Ile Ser Cys
            20

<210> SEQ ID NO 53
<211> LENGTH: 22
<212> TYPE: PRT
<213> ORGANISM: Artificial Sequence
<220> FEATURE:
<223> OTHER INFORMATION: Chemically synthesized

<400> SEQUENCE: 53

Gln Ser Ala Leu Thr Gln Pro Arg Ser Val Ser Gly Ser Pro Gly Gln
1               5                   10                  15

Ser Val Thr Ile Ser Cys
            20

<210> SEQ ID NO 54
<211> LENGTH: 22
<212> TYPE: PRT
<213> ORGANISM: Artificial Sequence
<220> FEATURE:
<223> OTHER INFORMATION: Chemically synthesized

<400> SEQUENCE: 54

Ser Tyr Val Leu Thr Gln Pro Pro Ser Val Ser Val Ala Pro Gly Lys
1               5                   10                  15

Thr Ala Arg Ile Thr Cys
            20

<210> SEQ ID NO 55
<211> LENGTH: 22
<212> TYPE: PRT
<213> ORGANISM: Artificial Sequence
<220> FEATURE:
<223> OTHER INFORMATION: Chemically synthesized

<400> SEQUENCE: 55

Ser Ser Glu Leu Thr Gln Asp Pro Ala Val Ser Val Ala Leu Gly Gln
1               5                   10                  15

Thr Val Arg Ile Thr Cys
            20

<210> SEQ ID NO 56
<211> LENGTH: 22
<212> TYPE: PRT
<213> ORGANISM: Artificial Sequence
<220> FEATURE:
<223> OTHER INFORMATION: Chemically synthesized

<400> SEQUENCE: 56

Ser Tyr Glu Leu Thr Gln Pro Pro Ser Val Ser Val Ser Pro Gly Gln
1               5                   10                  15

Thr Ala Ser Ile Thr Cys
            20

<210> SEQ ID NO 57
<211> LENGTH: 22
<212> TYPE: PRT
<213> ORGANISM: Artificial Sequence
<220> FEATURE:
<223> OTHER INFORMATION: Chemically synthesized

<400> SEQUENCE: 57

Gln Leu Val Leu Thr Gln Ser Pro Ser Ala Ser Ala Ser Leu Gly Ala
1               5                   10                  15
```

```
Ser Val Lys Leu Thr Cys
            20

<210> SEQ ID NO 58
<211> LENGTH: 15
<212> TYPE: PRT
<213> ORGANISM: Artificial Sequence
<220> FEATURE:
<223> OTHER INFORMATION: Chemically synthesized

<400> SEQUENCE: 58

Trp Tyr Gln Gln Lys Pro Gly Lys Ala Pro Lys Leu Leu Ile Tyr
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Chemically synthesized

<400> SEQUENCE: 59

Trp Tyr Gln Gln Lys Pro Gly Gln Ala Pro Arg Leu Leu Ile Tyr
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Chemically synthesized

<400> SEQUENCE: 60

Trp Tyr Gln Gln Lys Pro Gly Gln Pro Pro Lys Leu Leu Ile Tyr
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Chemically synthesized

<400> SEQUENCE: 61

Trp Tyr Leu Gln Lys Pro Gly Gln Ser Pro Gln Leu Leu Ile Tyr
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Chemically synthesized

<400> SEQUENCE: 62

Trp Tyr Gln Gln Leu Pro Gly Thr Ala Pro Lys Leu Leu Ile Tyr
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Chemically synthesized

<400> SEQUENCE: 63

Trp Tyr Gln Gln His Pro Gly Lys Ala Pro Lys Leu Met Ile Tyr
1               5                   10                  15
```

```
<210> SEQ ID NO 64
<211> LENGTH: 15
<212> TYPE: PRT
<213> ORGANISM: Artificial Sequence
<220> FEATURE:
<223> OTHER INFORMATION: Chemically synthesized

<400> SEQUENCE: 64

Trp Tyr Gln Gln Lys Pro Gly Gln Ala Pro Val Leu Val Ile Tyr
 1               5                  10                  15

<210> SEQ ID NO 65
<211> LENGTH: 15
<212> TYPE: PRT
<213> ORGANISM: Artificial Sequence
<220> FEATURE:
<223> OTHER INFORMATION: Chemically synthesized

<400> SEQUENCE: 65

Trp Tyr Gln Gln Lys Pro Gly Gln Ser Pro Val Leu Val Ile Tyr
 1               5                  10                  15

<210> SEQ ID NO 66
<211> LENGTH: 15
<212> TYPE: PRT
<213> ORGANISM: Artificial Sequence
<220> FEATURE:
<223> OTHER INFORMATION: Chemically synthesized

<400> SEQUENCE: 66

Trp His Gln Gln Gln Pro Glu Lys Gly Pro Arg Tyr Leu Met Tyr
 1               5                  10                  15

<210> SEQ ID NO 67
<211> LENGTH: 32
<212> TYPE: PRT
<213> ORGANISM: Artificial Sequence
<220> FEATURE:
<223> OTHER INFORMATION: Chemically synthesized

<400> SEQUENCE: 67

Gly Val Pro Ser Arg Phe Ser Gly Ser Gly Ser Gly Thr Asp Phe Thr
 1               5                  10                  15

Leu Thr Ile Ser Ser Leu Gln Pro Glu Asp Phe Ala Thr Tyr Tyr Cys
            20                  25                  30

<210> SEQ ID NO 68
<211> LENGTH: 32
<212> TYPE: PRT
<213> ORGANISM: Artificial Sequence
<220> FEATURE:
<223> OTHER INFORMATION: Chemically synthesized

<400> SEQUENCE: 68

Gly Val Pro Ser Arg Phe Ser Gly Ser Gly Ser Gly Thr Asp Phe Thr
 1               5                  10                  15

Phe Thr Ile Ser Ser Leu Gln Pro Glu Asp Ile Ala Thr Tyr Tyr Cys
            20                  25                  30

<210> SEQ ID NO 69
<211> LENGTH: 32
<212> TYPE: PRT
<213> ORGANISM: Artificial Sequence
<220> FEATURE:
<223> OTHER INFORMATION: Chemically synthesized
```

-continued

```
<400> SEQUENCE: 69

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 70
<211> LENGTH: 32
<212> TYPE: PRT
<213> ORGANISM: Artificial Sequence
<220> FEATURE:
<223> OTHER INFORMATION: Chemically synthesized

<400> SEQUENCE: 70

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 71
<211> LENGTH: 32
<212> TYPE: PRT
<213> ORGANISM: Artificial Sequence
<220> FEATURE:
<223> OTHER INFORMATION: Chemically synthesized

<400> SEQUENCE: 71

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 72
<211> LENGTH: 32
<212> TYPE: PRT
<213> ORGANISM: Artificial Sequence
<220> FEATURE:
<223> OTHER INFORMATION: Chemically synthesized

<400> SEQUENCE: 72

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 73
<211> LENGTH: 32
<212> TYPE: PRT
<213> ORGANISM: Artificial Sequence
<220> FEATURE:
<223> OTHER INFORMATION: Chemically synthesized

<400> SEQUENCE: 73

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 74
<211> LENGTH: 32
<212> TYPE: PRT
<213> ORGANISM: Artificial Sequence
<220> FEATURE:
<223> OTHER INFORMATION: Chemically synthesized
```

-continued

```
<400> SEQUENCE: 74

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 75
<211> LENGTH: 32
<212> TYPE: PRT
<213> ORGANISM: Artificial Sequence
<220> FEATURE:
<223> OTHER INFORMATION: Chemically synthesized

<400> SEQUENCE: 75

Gly Ile Pro Asp Arg Phe Ser Gly Ser Lys Ser Gly Thr Ser Ala Thr
1               5                   10                  15

Leu Gly Ile Thr Gly Leu Gln Thr Gly Asp Glu Ala Asp Tyr Tyr Cys
            20                  25                  30

<210> SEQ ID NO 76
<211> LENGTH: 32
<212> TYPE: PRT
<213> ORGANISM: Artificial Sequence
<220> FEATURE:
<223> OTHER INFORMATION: Chemically synthesized

<400> SEQUENCE: 76

Gly Val Pro Asp Arg Phe Ser Gly Ser Lys Ser Gly Thr Ser Ala Ser
1               5                   10                  15

Leu Ala Ile Ser Gly Leu Gln Ser Glu Asp Glu Ala Asp Tyr Tyr Cys
            20                  25                  30

<210> SEQ ID NO 77
<211> LENGTH: 32
<212> TYPE: PRT
<213> ORGANISM: Artificial Sequence
<220> FEATURE:
<223> OTHER INFORMATION: Chemically synthesized

<400> SEQUENCE: 77

Gly Val Ser Asn Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 78
<211> LENGTH: 32
<212> TYPE: PRT
<213> ORGANISM: Artificial Sequence
<220> FEATURE:
<223> OTHER INFORMATION: Chemically synthesized

<400> SEQUENCE: 78

Gly Val Pro Asp Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 79
<211> LENGTH: 32
<212> TYPE: PRT
<213> ORGANISM: Artificial Sequence
<220> FEATURE:
<223> OTHER INFORMATION: Chemically synthesized
```

-continued

```
<400> SEQUENCE: 79

Gly Ile Pro Glu Arg Phe Ser Gly Ser Asn Ser Gly Asn Thr Ala Thr
1               5                   10                  15

Leu Thr Ile Ser Arg Val Glu Ala Gly Asp Glu Ala Asp Tyr Tyr Cys
            20                  25                  30

<210> SEQ ID NO 80
<211> LENGTH: 32
<212> TYPE: PRT
<213> ORGANISM: Artificial Sequence
<220> FEATURE:
<223> OTHER INFORMATION: Chemically synthesized

<400> SEQUENCE: 80

Gly Ile Pro Asp Arg Phe Ser Gly Ser Ser Gly Asn Thr Ala Ser
1               5                   10                  15

Leu Thr Ile Thr Gly Ala Gln Ala Glu Asp Glu Ala Asp Tyr Tyr Cys
            20                  25                  30

<210> SEQ ID NO 81
<211> LENGTH: 32
<212> TYPE: PRT
<213> ORGANISM: Artificial Sequence
<220> FEATURE:
<223> OTHER INFORMATION: Chemically synthesized

<400> SEQUENCE: 81

Gly Ile Pro Glu Arg Phe Ser Gly Ser Asn Ser Gly Asn Thr Ala Thr
1               5                   10                  15

Leu Thr Ile Ser Gly Thr Gln Ala Met Asp Glu Ala Asp Tyr Tyr Cys
            20                  25                  30

<210> SEQ ID NO 82
<211> LENGTH: 32
<212> TYPE: PRT
<213> ORGANISM: Artificial Sequence
<220> FEATURE:
<223> OTHER INFORMATION: Chemically synthesized

<400> SEQUENCE: 82

Gly Ile Pro Asp Arg Phe Ser Gly Ser Ser Ser Gly Ala Glu Arg Tyr
1               5                   10                  15

Leu Thr Ile Ser Ser Leu Gln Ser Glu Asp Ala Asp Tyr Tyr Cys
            20                  25                  30

<210> SEQ ID NO 83
<211> LENGTH: 21
<212> TYPE: PRT
<213> ORGANISM: Artificial Sequence
<220> FEATURE:
<223> OTHER INFORMATION: Chemically synthesized

<400> SEQUENCE: 83

Phe Gly Gln Gly Thr Lys Val Glu Ile Lys Phe Gly Gln Gly Thr Lys
1               5                   10                  15

Val Glu Ile Lys Arg
            20

<210> SEQ ID NO 84
<211> LENGTH: 10
<212> TYPE: PRT
<213> ORGANISM: Artificial Sequence
<220> FEATURE:
<223> OTHER INFORMATION: Chemically synthesized
```

<400> SEQUENCE: 84

Phe Gly Gly Gly Thr Lys Leu Thr Val Leu
 1               5                  10

<210> SEQ ID NO 85
<211> LENGTH: 69
<212> TYPE: DNA
<213> ORGANISM: Artificial Sequence
<220> FEATURE:
<223> OTHER INFORMATION: Chemically synthesized

<400> SEQUENCE: 85
gacatccaga tgacccagtc tccatcctcc ctgtctgcat ctgtaggaga cagagtcacc     60
atcacttgc                                                             69

<210> SEQ ID NO 86
<211> LENGTH: 69
<212> TYPE: DNA
<213> ORGANISM: Artificial Sequence
<220> FEATURE:
<223> OTHER INFORMATION: Chemically synthesized

<400> SEQUENCE: 86
gacatccaga tgacccagtc tccttccacc ctgtctgcat ctgtaggaga cagagtcacc     60
atcacttgc                                                             69

<210> SEQ ID NO 87
<211> LENGTH: 69
<212> TYPE: DNA
<213> ORGANISM: Artificial Sequence
<220> FEATURE:
<223> OTHER INFORMATION: Chemically synthesized

<400> SEQUENCE: 87
gaaatagtga tgacgcagtc tccagccacc ctgtctgtgt ctccagggga aagagccacc     60
ctctcctgc                                                             69

<210> SEQ ID NO 88
<211> LENGTH: 69
<212> TYPE: DNA
<213> ORGANISM: Artificial Sequence
<220> FEATURE:
<223> OTHER INFORMATION: Chemically synthesized

<400> SEQUENCE: 88
gaaattgtgt tgacacagtc tccagccacc ctgtctttgt ctccagggga aagagccacc     60
ctctcctgc                                                             69

<210> SEQ ID NO 89
<211> LENGTH: 69
<212> TYPE: DNA
<213> ORGANISM: Artificial Sequence
<220> FEATURE:
<223> OTHER INFORMATION: Chemically synthesized

<400> SEQUENCE: 89
gaaattgtgt tgacgcagtc tccaggcacc ctgtctttgt ctccagggga aagagccacc     60
ctctcctgc                                                             69

<210> SEQ ID NO 90
<211> LENGTH: 69
<212> TYPE: DNA
<213> ORGANISM: Artificial Sequence

```
<220> FEATURE:
<223> OTHER INFORMATION: Chemically synthesized

<400> SEQUENCE: 90
gacatcgtga tgacccagtc tccagactcc ctggctgtgt ctctgggcga gagggccacc    60
atcaactgc                                                           69

<210> SEQ ID NO 91
<211> LENGTH: 69
<212> TYPE: DNA
<213> ORGANISM: Artificial Sequence
<220> FEATURE:
<223> OTHER INFORMATION: Chemically synthesized

<400> SEQUENCE: 91
gatattgtga tgacccagtc tccactctcc ctgcccgtca cccctggaga gccggcctcc    60
atctcctgc                                                           69

<210> SEQ ID NO 92
<211> LENGTH: 66
<212> TYPE: DNA
<213> ORGANISM: Artificial Sequence
<220> FEATURE:
<223> OTHER INFORMATION: Chemically synthesized

<400> SEQUENCE: 92
cagtctgtgt tgacgcagcc gccctcagtg tctgcggccc caggacagaa ggtcaccatc    60
tcctgc                                                              66

<210> SEQ ID NO 93
<211> LENGTH: 66
<212> TYPE: DNA
<213> ORGANISM: Artificial Sequence
<220> FEATURE:
<223> OTHER INFORMATION: Chemically synthesized

<400> SEQUENCE: 93
cagtctgtgc tgactcagcc accctcagcg tctgggaccc ccgggcagag ggtcaccatc    60
tcttgt                                                              66

<210> SEQ ID NO 94
<211> LENGTH: 66
<212> TYPE: DNA
<213> ORGANISM: Artificial Sequence
<220> FEATURE:
<223> OTHER INFORMATION: Chemically synthesized

<400> SEQUENCE: 94
cagtctgccc tgactcagcc tgcctccgtg tctgggtctc ctggacagtc gatcaccatc    60
tcctgc                                                              66

<210> SEQ ID NO 95
<211> LENGTH: 66
<212> TYPE: DNA
<213> ORGANISM: Artificial Sequence
<220> FEATURE:
<223> OTHER INFORMATION: Chemically synthesized

<400> SEQUENCE: 95
cagtctgccc tgactcagcc tcgctcagtg tccgggtctc ctggacagtc agtcaccatc    60
tcctgc                                                              66
```

<210> SEQ ID NO 96
<211> LENGTH: 66
<212> TYPE: DNA
<213> ORGANISM: Artificial Sequence
<220> FEATURE:
<223> OTHER INFORMATION: Chemically synthesized

<400> SEQUENCE: 96

```
tcctatgtgc tgactcagcc accctcagtg tcagtggccc caggaaagac ggccaggatt    60
acctgt                                                                66
```

<210> SEQ ID NO 97
<211> LENGTH: 66
<212> TYPE: DNA
<213> ORGANISM: Artificial Sequence
<220> FEATURE:
<223> OTHER INFORMATION: Chemically synthesized

<400> SEQUENCE: 97

```
tcttctgagc tgactcagga ccctgctgtg tctgtggcct gggacagac agtcaggatc     60 acatgc                                                                66
```

<210> SEQ ID NO 98
<211> LENGTH: 66
<212> TYPE: DNA
<213> ORGANISM: Artificial Sequence
<220> FEATURE:
<223> OTHER INFORMATION: Chemically synthesized

<400> SEQUENCE: 98

```
tcctatgagc tgactcagcc accctcagtg tccgtgtccc caggacagac agccagcatc    60
acctgc                                                                66
```

<210> SEQ ID NO 99
<211> LENGTH: 366
<212> TYPE: DNA
<213> ORGANISM: Artificial Sequence
<220> FEATURE:
<223> OTHER INFORMATION: Chemically synthesized

<400> SEQUENCE: 99

```
caggtgcagc tggtgcagtc tggggctgag gtgaagaagc ctggggcttc ggtgaaggtc    60
tcctgcaagg cttctggcta cacatttacc agttacaata tgcactgggt ccgccaggct   120
ccaggcaagg ggctagagtg ggtgggtgct atttatccag gaaatggtga tacttcctac   180
aatcagaagt tcaaaggcag agtcaccatc tcagctgaca gtccatcag cactgcctac    240 ctgcagtgga gcagcctgaa ggcctcggac accgccatgt attactgtgc gagatcgcac   300
tacggtagta actacgtaga ctactttgac tactggggcc agggcaccct ggtcaccgtc   360
tcctcc                                                              366
```

<210> SEQ ID NO 100
<211> LENGTH: 45
<212> TYPE: DNA
<213> ORGANISM: Artificial Sequence
<220> FEATURE:
<223> OTHER INFORMATION: Chemically synthesized

<400> SEQUENCE: 100

```
tggtatcagc agaaaccagg gaaagcccct aagctcctga tctat                    45
```

<210> SEQ ID NO 101
<211> LENGTH: 45

```
<212> TYPE: DNA
<213> ORGANISM: Artificial Sequence
<220> FEATURE:
<223> OTHER INFORMATION: Chemically synthesized

<400> SEQUENCE: 101
tggtaccagc agaaacctgg ccaggctccc aggctcctca tctat            45

<210> SEQ ID NO 102
<211> LENGTH: 45
<212> TYPE: DNA
<213> ORGANISM: Artificial Sequence
<220> FEATURE:
<223> OTHER INFORMATION: Chemically synthesized

<400> SEQUENCE: 102
tggtaccagc agaaaccagg acagcctcct aagctgctca tttac            45

<210> SEQ ID NO 103
<211> LENGTH: 45
<212> TYPE: DNA
<213> ORGANISM: Artificial Sequence
<220> FEATURE:
<223> OTHER INFORMATION: Chemically synthesized

<400> SEQUENCE: 103
tggtatctgc agaagccagg gcagtctcca cagctcctga tctat            45

<210> SEQ ID NO 104
<211> LENGTH: 45
<212> TYPE: DNA
<213> ORGANISM: Artificial Sequence
<220> FEATURE:
<223> OTHER INFORMATION: Chemically synthesized

<400> SEQUENCE: 104
tggtaccagc agctcccagg aacagccccc aaactcctca tctat            45

<210> SEQ ID NO 105
<211> LENGTH: 45
<212> TYPE: DNA
<213> ORGANISM: Artificial Sequence
<220> FEATURE:
<223> OTHER INFORMATION: Chemically synthesized

<400> SEQUENCE: 105
tggtaccaac agcacccagg caaagccccc aaactcatga tttat            45

<210> SEQ ID NO 106
<211> LENGTH: 45
<212> TYPE: DNA
<213> ORGANISM: Artificial Sequence
<220> FEATURE:
<223> OTHER INFORMATION: Chemically synthesized

<400> SEQUENCE: 106
tggtaccagc agaagccagg ccaggcccct gtgctggtca tctat            45

<210> SEQ ID NO 107
<211> LENGTH: 45
<212> TYPE: DNA
<213> ORGANISM: Artificial Sequence
<220> FEATURE:
<223> OTHER INFORMATION: Chemically synthesized

<400> SEQUENCE: 107
tggtatcagc agaagccagg ccagtcccct gtgctggtca tctat            45
```

<210> SEQ ID NO 108
<211> LENGTH: 366
<212> TYPE: DNA
<213> ORGANISM: Artificial Sequence
<220> FEATURE:
<223> OTHER INFORMATION: Chemically synthesized

<400> SEQUENCE: 108
caggtgcagc tggtgcagtc tggggctgag gtgaagaagc ctggggcttc ggtgaaggtc      60
tcctgcaagg cttctggcta cacatttacc agttacaata tgcactgggt ccgccaggct     120
ccagggaagg gctggagtg gttggtgct atttatccag gaaatggtga tacttcctac       180
aatcagaagt tcaaaggcag agtcacgatt accgcggaca atccacgag cacagcctac      240 atggagctga gcagcctgag atctgaggac acggccgtgt attactgtgc gagatcgcac     300
tacggtagta actacgtaga ctactttgac tactggggcc agggcaccct ggtcaccgtc     360
tcctcc                                                                366

<210> SEQ ID NO 109
<211> LENGTH: 96
<212> TYPE: DNA
<213> ORGANISM: Artificial Sequence
<220> FEATURE:
<223> OTHER INFORMATION: Chemically synthesized

<400> SEQUENCE: 109
ggggtcccat caaggttcag tggcagtgga tctgggacag atttcactct caccatcagc      60
agtctgcaac ctgaagattt tgcaacttac tactgt                                96

<210> SEQ ID NO 110
<211> LENGTH: 96
<212> TYPE: DNA
<213> ORGANISM: Artificial Sequence
<220> FEATURE:
<223> OTHER INFORMATION: Chemically synthesized

<400> SEQUENCE: 110
ggggtcccat caaggttcag tggaagtgga tctgggacag attttacttt caccatcagc      60
agcctgcagc ctgaagatat tgcaacatat tactgt                                96

<210> SEQ ID NO 111
<211> LENGTH: 96
<212> TYPE: DNA
<213> ORGANISM: Artificial Sequence
<220> FEATURE:
<223> OTHER INFORMATION: Chemically synthesized

<400> SEQUENCE: 111
ggggtcccat caaggttcag cggcagtgga tctgggacag aattcactct caccatcagc      60
agcctgcagc ctgatgattt tgcaacttat tactgc                                96

<210> SEQ ID NO 112
<211> LENGTH: 96
<212> TYPE: DNA
<213> ORGANISM: Artificial Sequence
<220> FEATURE:
<223> OTHER INFORMATION: Chemically synthesized

<400> SEQUENCE: 112
ggcatcccag ccaggttcag tggcagtggg tctgggacag agttcactct caccatcagc      60
agcctgcagt ctgaagattt tgcagtttat tactgt                                96

<210> SEQ ID NO 113
<211> LENGTH: 96
<212> TYPE: DNA
<213> ORGANISM: Artificial Sequence
<220> FEATURE:
<223> OTHER INFORMATION: Chemically synthesized

<400> SEQUENCE: 113
ggcatcccag ccaggttcag tggcagtggg tctgggacag acttcactct caccatcagc    60
agcctagagc ctgaagattt tgcagtttat tactgt    96

<210> SEQ ID NO 114
<211> LENGTH: 96
<212> TYPE: DNA
<213> ORGANISM: Artificial Sequence
<220> FEATURE:
<223> OTHER INFORMATION: Chemically synthesized

<400> SEQUENCE: 114
ggcatcccag acaggttcag tggcagtggg tctgggacag acttcactct caccatcagc    60
agactggagc ctgaagattt tgcagtgtat tactgt    96

<210> SEQ ID NO 115
<211> LENGTH: 96
<212> TYPE: DNA
<213> ORGANISM: Artificial Sequence
<220> FEATURE:
<223> OTHER INFORMATION: Chemically synthesized

<400> SEQUENCE: 115
ggggtccctg accgattcag tggcagcggg tctgggacag atttcactct caccatcagc    60
agcctgcagg ctgaagatgt ggcagtttat tactgt    96

<210> SEQ ID NO 116
<211> LENGTH: 96
<212> TYPE: DNA
<213> ORGANISM: Artificial Sequence
<220> FEATURE:
<223> OTHER INFORMATION: Chemically synthesized

<400> SEQUENCE: 116
ggggtccctg acaggttcag tggcagtgga tcaggcacag attttacact gaaaatcagc    60
agagtggagg ctgaggatgt tggggtttat tactgt    96

<210> SEQ ID NO 117
<211> LENGTH: 96
<212> TYPE: DNA
<213> ORGANISM: Artificial Sequence
<220> FEATURE:
<223> OTHER INFORMATION: Chemically synthesized

<400> SEQUENCE: 117
gggattcctg accgattctc tggctccaag tctggcacgt cagccaccct gggcatcacc    60
ggactccaga ctggggacga ggccgattat tactgc    96

<210> SEQ ID NO 118
<211> LENGTH: 96
<212> TYPE: DNA
<213> ORGANISM: Artificial Sequence
<220> FEATURE:
<223> OTHER INFORMATION: Chemically synthesized

<400> SEQUENCE: 118

```
ggggtccctg accgattctc tggctccaag tctggcacct cagcctccct ggccatcagt    60
gggctccagt ctgaggatga ggctgattat tactgt                              96
```

<210> SEQ ID NO 119
<211> LENGTH: 96
<212> TYPE: DNA
<213> ORGANISM: Artificial Sequence
<220> FEATURE:
<223> OTHER INFORMATION: Chemically synthesized

<400> SEQUENCE: 119

```
ggggtttcta atcgcttctc tggctccaag tctggcaaca cggcctccct gaccatctct    60
gggctccagg ctgaggacga ggctgattat tactgc                              96
```

<210> SEQ ID NO 120
<211> LENGTH: 96
<212> TYPE: DNA
<213> ORGANISM: Artificial Sequence
<220> FEATURE:
<223> OTHER INFORMATION: Chemically synthesized

<400> SEQUENCE: 120

```
ggggtccctg atcgcttctc tggctccaag tctggcaaca cggcctccct gaccatctct    60
gggctccagg ctgaggatga ggctgattat tactgc                              96
```

<210> SEQ ID NO 121
<211> LENGTH: 96
<212> TYPE: DNA
<213> ORGANISM: Artificial Sequence
<220> FEATURE:
<223> OTHER INFORMATION: Chemically synthesized

<400> SEQUENCE: 121

```
gggatccctg agcgattctc tggctccaac tctgggaaca cggccaccct gaccatcagc    60
agggtcgaag ccggggatga ggccgactat tactgt                              96
```

<210> SEQ ID NO 122
<211> LENGTH: 96
<212> TYPE: DNA
<213> ORGANISM: Artificial Sequence
<220> FEATURE:
<223> OTHER INFORMATION: Chemically synthesized

<400> SEQUENCE: 122

```
gggatcccag accgattctc tggctccagc tcaggaaaca cagcttcctt gaccatcact    60
ggggctcagg cggaagatga ggctgactat tactgt                              96
```

<210> SEQ ID NO 123
<211> LENGTH: 96
<212> TYPE: DNA
<213> ORGANISM: Artificial Sequence
<220> FEATURE:
<223> OTHER INFORMATION: Chemically synthesized

<400> SEQUENCE: 123

```
gggatccctg agcgattctc tggctccaac tctgggaaca cagccactct gaccatcagc    60
gggacccagg ctatggatga ggctgactat tactgt                              96
```

<210> SEQ ID NO 124
<211> LENGTH: 366
<212> TYPE: DNA
<213> ORGANISM: Artificial Sequence

```
<220> FEATURE:
<223> OTHER INFORMATION: Chemically synthesized

<400> SEQUENCE: 124
caggtgcagc tggtgcagtc tggggctgag gtgaagaagc ctggggcttc ggtgaaggtc      60
tcctgcaagg cttctggcta cacatttacc agttacaata tgcactgggt gcgacaggct     120
cctggaaaag gcttgagtg gatgggtgct atttatccag gaaatggtga tacttcctac     180
aatcagaagt tcaaaggcag attcaccatc tccagagaca acgccaagaa ctcactgtat     240
ctgcaaatga acagcctgag agccgaggac acggctgtgt attactgtgc gagatcgcac     300
tacggtagta actacgtaga ctactttgac tactggggcc agggcaccct ggtcaccgtc     360
tcctcc                                                                366

<210> SEQ ID NO 125
<211> LENGTH: 30
<212> TYPE: DNA
<213> ORGANISM: Artificial Sequence
<220> FEATURE:
<223> OTHER INFORMATION: Chemically synthesized

<400> SEQUENCE: 125
ttcggccaag ggaccaaggt ggaaatcaaa                                       30

<210> SEQ ID NO 126
<211> LENGTH: 30
<212> TYPE: DNA
<213> ORGANISM: Artificial Sequence
<220> FEATURE:
<223> OTHER INFORMATION: Chemically synthesized

<400> SEQUENCE: 126
ttcggcggag ggaccaagct gaccgtccta                                       30

<210> SEQ ID NO 127
<211> LENGTH: 30
<212> TYPE: DNA
<213> ORGANISM: Artificial Sequence
<220> FEATURE:
<223> OTHER INFORMATION: Chemically synthesized

<400> SEQUENCE: 127
ggctacacat ttaccagtta caatatgcac                                       30

<210> SEQ ID NO 128
<211> LENGTH: 51
<212> TYPE: DNA
<213> ORGANISM: Artificial Sequence
<220> FEATURE:
<223> OTHER INFORMATION: Chemically synthesized

<400> SEQUENCE: 128
gctatttatc caggaaatgg tgatacttcc tacaatcaga agttcaaagg c               51

<210> SEQ ID NO 129
<211> LENGTH: 57
<212> TYPE: DNA
<213> ORGANISM: Artificial Sequence
<220> FEATURE:
<223> OTHER INFORMATION: Chemically synthesized

<400> SEQUENCE: 129
tcgcactacg gtagtaacta cgtagactac tttgactact ggggccaggg caccctg         57
```

<210> SEQ ID NO 130
<211> LENGTH: 366
<212> TYPE: DNA
<213> ORGANISM: Artificial Sequence
<220> FEATURE:
<223> OTHER INFORMATION: Chemically synthesized

<400> SEQUENCE: 130

```
caggtgcagc tggtgcagtc tggggctgag gtgaagaagc ctggggcttc ggtgaaggtc      60
tcctgcaagg cttctggcta cacatttacc agttacaata tgcactgggt ccgccaggct     120
ccagggaagg gctggagtg ggttggtgct atttatccag gaaatggtga tacttcctac      180
aatcagaagt tcaaaggcag attcaccatc tccagagaca cgccaagaa ctcactgtat      240
ctgcaaatga acagcctgag agccgaggac acggctgtgt attactgtgc gagatcgcac     300
tacggtagta actacgtaga ctactttgac tactggggcc agggcaccct ggtcaccgtc     360
tcctcc                                                                 366
```

<210> SEQ ID NO 131
<211> LENGTH: 366
<212> TYPE: DNA
<213> ORGANISM: Artificial Sequence
<220> FEATURE:
<223> OTHER INFORMATION: Chemically synthesized

<400> SEQUENCE: 131

```
caggtgcagc tggtgcagtc tggggctgag gtgaagaagc ctggggcttc ggtgaaggtc      60
tcctgcaagg cttctggcta cacatttacc agttacaata tgcactgggt gcgacaggcc     120
cctggacaag gcttgagtg gatgggtgct atttatccag gaaatggtga tacttcctac      180
aatcagaagt tcaaaggcag agtcaccatc tcagctgaca gtccatcag cactgcctac      240
ctgcagtgga gcagcctgaa ggcctcggac accgccatgt attactgtgc gagatcgcac     300
tacggtagta actacgtaga ctactttgac tactggggcc agggcaccct ggtcaccgtc     360
tcctcc                                                                 366
```

<210> SEQ ID NO 132
<211> LENGTH: 366
<212> TYPE: DNA
<213> ORGANISM: Artificial Sequence
<220> FEATURE:
<223> OTHER INFORMATION: Chemically synthesized

<400> SEQUENCE: 132

```
gaggtgcagc tggtgcagtc tggggcagag gtgaaaaagc ccggggagtc tctgaagatc      60
tcctgtaagg gttctggcta cacatttacc agttacaata tgcactgggt gcgacaggct     120
cctggaaaag gcttgagtg gatgggtgct atttatccag gaaatggtga tacttcctac      180
aatcagaagt tcaaaggcag agtcaccatc tcagctgaca gtccatcag cactgcctac      240
ctgcagtgga gcagcctgaa ggcctcggac accgccatgt attactgtgc gagatcgcac     300
tacggtagta actacgtaga ctactttgac tactggggcc agggcaccct ggtcaccgtc     360
tcctcc                                                                 366
```

<210> SEQ ID NO 133
<211> LENGTH: 30
<212> TYPE: DNA
<213> ORGANISM: Artificial Sequence
<220> FEATURE:
<223> OTHER INFORMATION: Chemically synthesized

<400> SEQUENCE: 133

```
ggctacacct ttactaggta cacgatgcac                                       30

<210> SEQ ID NO 134
<211> LENGTH: 51
<212> TYPE: DNA
<213> ORGANISM: Artificial Sequence
<220> FEATURE:
<223> OTHER INFORMATION: Chemically synthesized

<400> SEQUENCE: 134
tacattaatc ctagccgtgg ttatactaat tacaatcaga agttcaagga c               51

<210> SEQ ID NO 135
<211> LENGTH: 30
<212> TYPE: DNA
<213> ORGANISM: Artificial Sequence
<220> FEATURE:
<223> OTHER INFORMATION: Chemically synthesized

<400> SEQUENCE: 135
tattatgatg atcattactg ccttgactac                                       30

<210> SEQ ID NO 136
<211> LENGTH: 366
<212> TYPE: DNA
<213> ORGANISM: Artificial Sequence
<220> FEATURE:
<223> OTHER INFORMATION: Chemically synthesized

<400> SEQUENCE: 136
caggtgcagc tggtgcagtc tggggctgag gtgaagaagc ctggggcttc ggtgaaggtc      60
tcctgcaagg cttctggcta cacatttacc agttacaata tgcactgggt gcgacaggct    120
cctggaaaag ggcttgagtg gatgggtgct atttatccag gaaatggtga tacttcctac    180
aatcagaagt tcaaaggcag agtcacgatt accgcggaca atccacgag cacagcctac     240 atggagctga gcagcctgag atctgaggac acggccgtgt attactgtgc gagatcgcac    300
tacggtagta actacgtaga ctactttgac tactggggcc agggcaccct ggtcaccgtc    360
tcctcc                                                               366

<210> SEQ ID NO 137
<211> LENGTH: 366
<212> TYPE: DNA
<213> ORGANISM: Artificial Sequence
<220> FEATURE:
<223> OTHER INFORMATION: Chemically synthesized

<400> SEQUENCE: 137
caggtgcagc tggtgcagtc tggggctgag gtgaagaagc ctggggcttc ggtgaaggtc      60
tcctgcaagg cttctggcta cacatttacc agttacaata tgcactgggt gcgacaggcc    120
cctggacaag ggcttgagtg gatgggtgct atttatccag gaaatggtga tacttcctac    180
aatcagaagt tcaaaggcag agtcacgatt accgcggaca atccacgag cacagcctac     240 atggagctga gcagcctgag atctgaggac acggccgtgt attactgtgc gagatcgcac    300
tacggtagta actacgtaga ctactttgac tactggggcc agggcaccct ggtcaccgtc    360
tcctcc                                                               366

<210> SEQ ID NO 138
<211> LENGTH: 122
<212> TYPE: PRT
<213> ORGANISM: Artificial Sequence
```

```
<220> FEATURE:
<223> OTHER INFORMATION: Chemically synthesized

<400> SEQUENCE: 138

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Asp Thr Ser Tyr Asn Gln Lys Phe
    50                  55                  60

Lys Gly Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser His Tyr Gly Ser Asn Tyr Val Asp Tyr Phe Asp Tyr Trp
            100                 105                 110

Gly Gln Gly Thr Leu Val Thr Val Ser Ser
        115                 120

<210> SEQ ID NO 139
<211> LENGTH: 30
<212> TYPE: DNA
<213> ORGANISM: Artificial Sequence
<220> FEATURE:
<223> OTHER INFORMATION: Chemically synthesized

<400> SEQUENCE: 139
agggccagct caagtttaag tttcatgcac                                    30

<210> SEQ ID NO 140
<211> LENGTH: 21
<212> TYPE: DNA
<213> ORGANISM: Artificial Sequence
<220> FEATURE:
<223> OTHER INFORMATION: Chemically synthesized

<400> SEQUENCE: 140
gccacatcca acctggcttc t                                             21

<210> SEQ ID NO 141
<211> LENGTH: 27
<212> TYPE: DNA
<213> ORGANISM: Artificial Sequence
<220> FEATURE:
<223> OTHER INFORMATION: Chemically synthesized

<400> SEQUENCE: 141
catcagtgga gtagtaaccc gctcacg                                       27

<210> SEQ ID NO 142
<211> LENGTH: 122
<212> TYPE: PRT
<213> ORGANISM: Artificial Sequence
<220> FEATURE:
<223> OTHER INFORMATION: Chemically synthesized

<400> SEQUENCE: 142

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30
```

Asn Met His Trp Val Arg Gln Ala Pro Gly Lys Gly Leu Glu Trp Val
            35                  40                  45

Gly Ala Ile Tyr Pro Gly Asn Gly Asp Thr Ser Tyr Asn Gln Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser His Tyr Gly Ser Asn Tyr Val Asp Tyr Phe Asp Tyr Trp
                100                 105                 110

Gly Gln Gly Thr Leu Val Thr Val Ser Ser
            115                 120

<210> SEQ ID NO 143
<211> LENGTH: 122
<212> TYPE: PRT
<213> ORGANISM: Artificial Sequence
<220> FEATURE:
<223> OTHER INFORMATION: Chemically synthesized

<400> SEQUENCE: 143

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Asn Met His Trp Val Arg Gln Ala Pro Gly Lys Gly Leu Glu Trp Met
            35                  40                  45

Gly Ala Ile Tyr Pro Gly Asn Gly Asp Thr Ser Tyr Asn Gln Lys Phe
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser His Tyr Gly Ser Asn Tyr Val Asp Tyr Phe Asp Tyr Trp
                100                 105                 110

Gly Gln Gly Thr Leu Val Thr Val Ser Ser
            115                 120

<210> SEQ ID NO 144
<211> LENGTH: 122
<212> TYPE: PRT
<213> ORGANISM: Artificial Sequence
<220> FEATURE:
<223> OTHER INFORMATION: Chemically synthesized

<400> SEQUENCE: 144

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Asn Met His Trp Val Arg Gln Ala Pro Gly Lys Gly Leu Glu Trp Val
            35                  40                  45

Gly Ala Ile Tyr Pro Gly Asn Gly Asp Thr Ser Tyr Asn Gln Lys Phe
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

```
Ala Arg Ser His Tyr Gly Ser Asn Tyr Val Asp Tyr Phe Asp Tyr Trp
            100                 105                 110

Gly Gln Gly Thr Leu Val Thr Val Ser Ser
            115                 120

<210> SEQ ID NO 145
<211> LENGTH: 30
<212> TYPE: DNA
<213> ORGANISM: Artificial Sequence
<220> FEATURE:
<223> OTHER INFORMATION: Chemically synthesized

<400> SEQUENCE: 145
agtgccagct caagtgtaag ttacatgaac                                           30

<210> SEQ ID NO 146
<211> LENGTH: 21
<212> TYPE: DNA
<213> ORGANISM: Artificial Sequence
<220> FEATURE:
<223> OTHER INFORMATION: Chemically synthesized

<400> SEQUENCE: 146
gacacatcca aactggcttc t                                                    21

<210> SEQ ID NO 147
<211> LENGTH: 27
<212> TYPE: DNA
<213> ORGANISM: Artificial Sequence
<220> FEATURE:
<223> OTHER INFORMATION: Chemically synthesized

<400> SEQUENCE: 147
cagcagtgga gtagtaaccc attcacg                                              27

<210> SEQ ID NO 148
<211> LENGTH: 122
<212> TYPE: PRT
<213> ORGANISM: Artificial Sequence
<220> FEATURE:
<223> OTHER INFORMATION: Chemically synthesized

<400> SEQUENCE: 148

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
            35                  40                  45

Gly Ala Ile Tyr Pro Gly Asn Gly Asp Thr Ser Tyr Asn Gln Lys Phe
        50                  55                  60

Lys Gly Arg Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg Ser His Tyr Gly Ser Asn Tyr Val Asp Tyr Phe Asp Tyr Trp
            100                 105                 110

Gly Gln Gly Thr Leu Val Thr Val Ser Ser
            115                 120

<210> SEQ ID NO 149
<211> LENGTH: 122
```

```
<212> TYPE: PRT
<213> ORGANISM: Artificial Sequence
<220> FEATURE:
<223> OTHER INFORMATION: Chemically synthesized

<400> SEQUENCE: 149

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Thr Phe Thr Ser Tyr
                20                  25                  30

Asn Met His Trp Val Arg Gln Ala Pro Gly Lys Gly Leu Glu Trp Met
             35                  40                  45

Gly Ala Ile Tyr Pro Gly Asn Gly Asp Thr Ser Tyr Asn Gln Lys Phe
         50                  55                  60

Lys Gly Arg Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Ser His Tyr Gly Ser Asn Tyr Val Asp Tyr Phe Asp Tyr Trp
            100                 105                 110

Gly Gln Gly Thr Leu Val Thr Val Ser Ser
            115                 120

<210> SEQ ID NO 150
<211> LENGTH: 122
<212> TYPE: PRT
<213> ORGANISM: Artificial Sequence
<220> FEATURE:
<223> OTHER INFORMATION: Chemically synthesized

<400> SEQUENCE: 150

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Asn Met His Trp Val Arg Gln Ala Pro Gly Lys Gly Leu Glu Trp Met
             35                  40                  45

Gly Ala Ile Tyr Pro Gly Asn Gly Asp Thr Ser Tyr Asn Gln Lys Phe
         50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser His Tyr Gly Ser Asn Tyr Val Asp Tyr Phe Asp Tyr Trp
            100                 105                 110

Gly Gln Gly Thr Leu Val Thr Val Ser Ser
            115                 120

<210> SEQ ID NO 151
<211> LENGTH: 10
<212> TYPE: PRT
<213> ORGANISM: Artificial Sequence
<220> FEATURE:
<223> OTHER INFORMATION: Chemically synthesized

<400> SEQUENCE: 151

Gly Tyr Thr Phe Thr Ser Tyr Asn Met His
 1               5                  10

<210> SEQ ID NO 152
```

```
<211> LENGTH: 17
<212> TYPE: PRT
<213> ORGANISM: Artificial Sequence
<220> FEATURE:
<223> OTHER INFORMATION: Chemically synthesized

<400> SEQUENCE: 152

Ala Ile Tyr Pro Gly Asn Gly Asp Thr Ser Tyr Asn Gln Lys Phe Lys
 1               5                  10                  15

Gly

<210> SEQ ID NO 153
<211> LENGTH: 19
<212> TYPE: PRT
<213> ORGANISM: Artificial Sequence
<220> FEATURE:
<223> OTHER INFORMATION: Chemically synthesized

<400> SEQUENCE: 153

Ser His Tyr Gly Ser Asn Tyr Val Asp Tyr Phe Asp Tyr Trp Gly Gln
 1               5                  10                  15

Gly Thr Leu

<210> SEQ ID NO 154
<211> LENGTH: 122
<212> TYPE: PRT
<213> ORGANISM: Artificial Sequence
<220> FEATURE:
<223> OTHER INFORMATION: Chemically synthesized

<400> SEQUENCE: 154

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Asn Met His Trp Val Arg Gln Ala Pro Gly Gln Gly Leu Glu Trp Met
            35                  40                  45

Gly Ala Ile Tyr Pro Gly Asn Gly Asp Thr Ser Tyr Asn Gln Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Tyr Gly Ser Asn Tyr Val Asp Tyr Phe Asp Tyr Trp
            100                 105                 110

Gly Gln Gly Thr Leu Val Thr Val Ser Ser
        115                 120

<210> SEQ ID NO 155
<211> LENGTH: 57
<212> TYPE: DNA
<213> ORGANISM: Artificial Sequence
<220> FEATURE:
<223> OTHER INFORMATION: Chemically synthesized

<400> SEQUENCE: 155
atggagtttg ggctgagctg gcttttctt gtggctattt taaaaggtgt ccagtgt      57

<210> SEQ ID NO 156
<211> LENGTH: 19
<212> TYPE: PRT
<213> ORGANISM: Artificial Sequence
<220> FEATURE:
```

<223> OTHER INFORMATION: Chemically synthesized

<400> SEQUENCE: 156

Met Glu Phe Gly Leu Ser Trp Leu Phe Leu Val Ala Ile Leu Lys Gly
1               5                   10                  15

Val Gln Cys

<210> SEQ ID NO 157
<211> LENGTH: 10
<212> TYPE: PRT
<213> ORGANISM: Artificial Sequence
<220> FEATURE:
<223> OTHER INFORMATION: Chemically synthesized

<400> SEQUENCE: 157

Gly Tyr Thr Phe Thr Arg Tyr Thr Met His
1               5                   10

<210> SEQ ID NO 158
<211> LENGTH: 17
<212> TYPE: PRT
<213> ORGANISM: Artificial Sequence
<220> FEATURE:
<223> OTHER INFORMATION: Chemically synthesized

<400> SEQUENCE: 158

Tyr Ile Asn Pro Ser Arg Gly Tyr Thr Asn Tyr Asn Gln Lys Phe Lys
1               5                   10                  15

Asp

<210> SEQ ID NO 159
<211> LENGTH: 10
<212> TYPE: PRT
<213> ORGANISM: Artificial Sequence
<220> FEATURE:
<223> OTHER INFORMATION: Chemically synthesized

<400> SEQUENCE: 159

Tyr Tyr Asp Asp His Tyr Cys Leu Asp Tyr
1               5                   10

<210> SEQ ID NO 160
<211> LENGTH: 993
<212> TYPE: DNA
<213> ORGANISM: Artificial Sequence
<220> FEATURE:
<223> OTHER INFORMATION: Chemically synthesized

<400> SEQUENCE: 160
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagag agttgagccc   300
aaatcttgtg acaaaactca cacatgccca ccgtgcccag cacctgaact cctgggggga   360
ccgtcagtct tcctcttccc cccaaaaccc aaggacaccc tcatgatctc ccggaccccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacaac   540
agcacgtacc gtgtggtcag cgtcctcacc gtcctgcacc aggactggct gaatggcaag   600

```
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa tga                                 993
```

<210> SEQ ID NO 161
<211> LENGTH: 330
<212> TYPE: PRT
<213> ORGANISM: Artificial Sequence
<220> FEATURE:
<223> OTHER INFORMATION: Chemically synthesized

<400> SEQUENCE: 161

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 162
<211> LENGTH: 318
<212> TYPE: DNA
<213> ORGANISM: Artificial Sequence
<220> FEATURE:
<223> OTHER INFORMATION: Chemically synthesized

<400> SEQUENCE: 162
gatattgtga tgacccagtc tccactctcc ctgcccgtca cccctggaga gccggcctcc      60
atctcctgca gggccagctc aagtttaagt ttcatgcact ggtatcagca gaaaccagga     120
cagcctccta agctgctcat ttatgccaca tccaacctgg cttctgggat cccagccagg     180
ttcagtggca gtgggtctgg gacagacttc actctcacca tcagcagcct agagcctgaa     240
gattttgcag tttattactg tcatcagtgg agtagtaacc cgctcacgtt cggccaaggt     300
accaaggtgg aaatcaaa                                                  318

<210> SEQ ID NO 163
<211> LENGTH: 10
<212> TYPE: PRT
<213> ORGANISM: Artificial Sequence
<220> FEATURE:
<223> OTHER INFORMATION: Chemically synthesized

<400> SEQUENCE: 163

Arg Ala Ser Ser Ser Leu Ser Phe Met His
1               5                   10

<210> SEQ ID NO 164
<211> LENGTH: 7
<212> TYPE: PRT
<213> ORGANISM: Artificial Sequence
<220> FEATURE:
<223> OTHER INFORMATION: Chemically synthesized

<400> SEQUENCE: 164

Ala Thr Ser Asn Leu Ala Ser
1               5

<210> SEQ ID NO 165
<211> LENGTH: 9
<212> TYPE: PRT
<213> ORGANISM: Artificial Sequence
<220> FEATURE:
<223> OTHER INFORMATION: Chemically synthesized

<400> SEQUENCE: 165

His Gln Trp Ser Ser Asn Pro Leu Thr
1               5

<210> SEQ ID NO 166
<211> LENGTH: 318
<212> TYPE: DNA
<213> ORGANISM: Artificial Sequence
<220> FEATURE:
<223> OTHER INFORMATION: Chemically synthesized

<400> SEQUENCE: 166
gatattgtga tgacccagtc tccactctcc ctgcccgtca cccctggaga gccggcctcc      60

```
atctcctgca gggccagctc aagtttaagt tcatgcact ggtatctgca gaagccaggg    120
cagtctccac agctcctgat ctatgccaca tccaacctgg cttctgggat cccagccagg   180
ttcagtggca gtgggtctgg gacagacttc actctcacca tcagcagcct agagcctgaa   240
gattttgcag tttattactg tcatcagtgg agtagtaacc cgctcacgtt cggccaaggt   300
accaaggtgg aaatcaaa                                                 318

<210> SEQ ID NO 167
<211> LENGTH: 318
<212> TYPE: DNA
<213> ORGANISM: Artificial Sequence
<220> FEATURE:
<223> OTHER INFORMATION: Chemically synthesized

<400> SEQUENCE: 167
gatattgtga tgacccagtc tccactctcc ctgcccgtca cccctggaga gccggcctcc    60
atctcctgca gggccagctc aagtttaagt tcatgcact ggtatcagca gaaacctggc   120
caggctccca ggctcctcat ctatgccaca tccaacctgg cttctggggt ccctgaccga   180
ttcagtggca gcgggtctgg gacagatttc actctcacca tcagcagcct gcaggctgaa   240
gatgtggcag tttattactg tcatcagtgg agtagtaacc cgctcacgtt cggccaaggt   300
accaaggtgg aaatcaaa                                                 318

<210> SEQ ID NO 168
<211> LENGTH: 318
<212> TYPE: DNA
<213> ORGANISM: Artificial Sequence
<220> FEATURE:
<223> OTHER INFORMATION: Chemically synthesized

<400> SEQUENCE: 168
gatattgtga tgacccagtc tccactctcc ctgcccgtca cccctggaga gccggcctcc    60
atctcctgca gggccagctc aagtttaagt tcatgcact ggtatcagca gaaaccaggg   120
aaagccccta agctcctgat ctatgccaca tccaacctgg cttctggggt ccctgaccga   180
ttcagtggca gcgggtctgg gacagatttc actctcacca tcagcagcct gcaggctgaa   240
gatgtggcag tttattactg tcatcagtgg agtagtaacc cgctcacgtt cggccaaggt   300
accaaggtgg aaatcaaa                                                 318

<210> SEQ ID NO 169
<211> LENGTH: 10
<212> TYPE: PRT
<213> ORGANISM: Artificial Sequence
<220> FEATURE:
<223> OTHER INFORMATION: Chemically synthesized

<400> SEQUENCE: 169

Ser Ala Ser Ser Ser Val Ser Tyr Met Asn
1               5                   10

<210> SEQ ID NO 170
<211> LENGTH: 7
<212> TYPE: PRT
<213> ORGANISM: Artificial Sequence
<220> FEATURE:
<223> OTHER INFORMATION: Chemically synthesized

<400> SEQUENCE: 170

Asp Thr Ser Lys Leu Ala Ser
1               5
```

<210> SEQ ID NO 171
<211> LENGTH: 9
<212> TYPE: PRT
<213> ORGANISM: Artificial Sequence
<220> FEATURE:
<223> OTHER INFORMATION: Chemically synthesized

<400> SEQUENCE: 171

Gln Gln Trp Ser Ser Asn Pro Phe Thr
 1               5

<210> SEQ ID NO 172
<211> LENGTH: 318
<212> TYPE: DNA
<213> ORGANISM: Artificial Sequence
<220> FEATURE:
<223> OTHER INFORMATION: Chemically synthesized

<400> SEQUENCE: 172
gatattgtga tgacccagtc tccactctcc ctgcccgtca cccctggaga gccggcctcc      60
atctcctgca gggccagctc aagtttaagt ttcatgcact ggtatcagca gaaaccagga     120
cagcctccta agctgctcat ttatgccaca tccaacctgg cttctggggt cccatcaagg     180
ttcagtggaa gtggatctgg gacagatttt actttcacca tcagcagcct gcagcctgaa     240
gatattgcaa catattactg tcatcagtgg agtagtaacc cgctcacgtt cggccaaggt     300
accaaggtgg aaatcaaa                                                    318

<210> SEQ ID NO 173
<211> LENGTH: 318
<212> TYPE: DNA
<213> ORGANISM: Artificial Sequence
<220> FEATURE:
<223> OTHER INFORMATION: Chemically synthesized

<400> SEQUENCE: 173
gatattgtga tgacccagtc tccactctcc ctgcccgtca cccctggaga gccggcctcc      60
atctcctgca gggccagctc aagtttaagt ttcatgcact ggtatcagca gaaacctggc     120
caggctccca ggctcctcat ctatgccaca tccaacctgg cttctggggt cccatcaagg     180
ttcagtggaa gtggatctgg gacagatttt actttcacca tcagcagcct gcagcctgaa     240
gatattgcaa catattactg tcatcagtgg agtagtaacc cgctcacgtt cggccaaggt     300
accaaggtgg aaatcaaa                                                    318

<210> SEQ ID NO 174
<211> LENGTH: 318
<212> TYPE: DNA
<213> ORGANISM: Artificial Sequence
<220> FEATURE:
<223> OTHER INFORMATION: Chemically synthesized

<400> SEQUENCE: 174
gatattgtga tgacccagtc tccactctcc ctgcccgtca cccctggaga gccggcctcc      60
atctcctgca gggccagctc aagtttaagt ttcatgcact ggtatcagca gaaacctggc     120
caggctccca ggctcctcat ctatgccaca tccaacctgg cttctggggt cccatcaagg     180
ttcagcggca gtggatctgg gacagaattc actctcacca tcagcagcct gcagcctgat     240
gattttgcaa cttattactg tcatcagtgg agtagtaacc cgctcacgtt cggccaaggt     300
accaaggtgg aaatcaaa                                                    318

```
<210> SEQ ID NO 175
<211> LENGTH: 323
<212> TYPE: PRT
<213> ORGANISM: Artificial Sequence
<220> FEATURE:
<223> OTHER INFORMATION: Chemically synthesized

<400> SEQUENCE: 175
```

| | | | | | | | | | | | | | | | |
|---|---|---|---|---|---|---|---|---|---|---|---|---|---|---|---|
| Val | Phe | Pro | Leu | Ala | Pro | Ser | Ser | Lys | Ser | Thr | Ser | Gly | Gly | Thr | Ala |
| 1 | | | | 5 | | | | | 10 | | | | | 15 | |
| Ala | Leu | Gly | Cys | Leu | Val | Lys | Asp | Tyr | Phe | Pro | Glu | Pro | Val | Thr | Val |
| | | | 20 | | | | | 25 | | | | | 30 | | |
| Ser | Trp | Asn | Ser | Gly | Ala | Leu | Thr | Ser | Gly | Val | His | Thr | Phe | Pro | Ala |
| | | | 35 | | | | | 40 | | | | | 45 | | |
| Val | Leu | Gln | Ser | Ser | Gly | Leu | Tyr | Ser | Leu | Ser | Ser | Val | Val | Thr | Val |
| | 50 | | | | | 55 | | | | | 60 | | | | |
| Pro | Ser | Ser | Ser | Leu | Gly | Thr | Gln | Thr | Tyr | Ile | Cys | Asn | Val | Asn | His |
| 65 | | | | | 70 | | | | | 75 | | | | | 80 |
| Lys | Pro | Ser | Asn | Thr | Lys | Val | Asp | Lys | Arg | Val | Glu | Pro | Lys | Ser | Cys |
| | | | | 85 | | | | | 90 | | | | | 95 | |
| Asp | Lys | Thr | His | Thr | Cys | Pro | Pro | Cys | Pro | Ala | Pro | Glu | Leu | Leu | Gly |
| | | | 100 | | | | | 105 | | | | | 110 | | |
| Gly | Pro | Ser | Val | Phe | Leu | Phe | Pro | Pro | Lys | Pro | Lys | Asp | Thr | Leu | Met |
| | | | 115 | | | | | 120 | | | | | 125 | | |
| Ile | Ser | Arg | Thr | Pro | Glu | Val | Thr | Cys | Val | Val | Val | Asp | Val | Ser | His |
| | 130 | | | | | 135 | | | | | 140 | | | | |
| Glu | Asp | Pro | Glu | Val | Lys | Phe | Asn | Trp | Tyr | Val | Asp | Gly | Val | Glu | Val |
| 145 | | | | | 150 | | | | | 155 | | | | | 160 |
| His | Asn | Ala | Lys | Thr | Lys | Pro | Arg | Glu | Glu | Gln | Tyr | Asn | Ser | Thr | Tyr |
| | | | | 165 | | | | | 170 | | | | | 175 | |
| Arg | Val | Val | Ser | Val | Leu | Thr | Val | Leu | His | Gln | Asp | Trp | Leu | Asn | Gly |
| | | | 180 | | | | | 185 | | | | | 190 | | |
| Lys | Glu | Tyr | Lys | Cys | Lys | Val | Ser | Asn | Lys | Ala | Leu | Pro | Ala | Pro | Ile |
| | | | 195 | | | | | 200 | | | | | 205 | | |
| Glu | Lys | Thr | Ile | Ser | Lys | Ala | Lys | Gly | Gln | Pro | Arg | Glu | Pro | Gln | Val |
| | 210 | | | | | 215 | | | | | 220 | | | | |
| Tyr | Thr | Leu | Pro | Pro | Ser | Arg | Asp | Glu | Leu | Thr | Lys | Asn | Gln | Val | Ser |
| 225 | | | | | 230 | | | | | 235 | | | | | 240 |
| Leu | Thr | Cys | Leu | Val | Lys | Gly | Phe | Tyr | Pro | Ser | Asp | Ile | Ala | Val | Glu |
| | | | | 245 | | | | | 250 | | | | | 255 | |
| Trp | Glu | Ser | Asn | Gly | Gln | Pro | Glu | Asn | Asn | Tyr | Lys | Thr | Thr | Pro | Pro |
| | | | 260 | | | | | 265 | | | | | 270 | | |
| Val | Leu | Asp | Ser | Asp | Gly | Ser | Phe | Phe | Leu | Tyr | Ser | Lys | Leu | Thr | Val |
| | | | 275 | | | | | 280 | | | | | 285 | | |
| Asp | Lys | Ser | Arg | Trp | Gln | Gln | Gly | Asn | Val | Phe | Ser | Cys | Ser | Val | Met |
| | 290 | | | | | 295 | | | | | 300 | | | | |
| His | Glu | Ala | Leu | His | Asn | His | Tyr | Thr | Gln | Lys | Ser | Leu | Ser | Leu | Ser |
| 305 | | | | | 310 | | | | | 315 | | | | | 320 |
| Pro | Gly | Lys | | | | | | | | | | | | | |

```
<210> SEQ ID NO 176
<211> LENGTH: 66
<212> TYPE: PRT
<213> ORGANISM: Artificial Sequence
<220> FEATURE:
<223> OTHER INFORMATION: Chemically synthesized

<400> SEQUENCE: 176
```

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr
65
```

<210> SEQ ID NO 177
<211> LENGTH: 318
<212> TYPE: DNA
<213> ORGANISM: Artificial Sequence
<220> FEATURE:
<223> OTHER INFORMATION: Chemically synthesized

<400> SEQUENCE: 177

```
gacatcgtga tgacccagtc tccagactcc ctggctgtgt ctctgggcga gagggccacc      60
atcaactgca gggccagctc aagtttaagt ttcatgcact ggtatcagca gaaacctggc     120
caggctccca ggctcctcat ctatgccaca tccaacctgg cttctggggt cccatcaagg     180
ttcagtggca gtggatctgg gacagatttc actctcacca tcagcagtct gcaacctgaa     240
gattttgcaa cttactactg tcatcagtgg agtagtaacc cgctcacgtt cggccaaggt     300
accaaggtgg aaatcaaa                                                   318
```

<210> SEQ ID NO 178
<211> LENGTH: 972
<212> TYPE: DNA
<213> ORGANISM: Artificial Sequence
<220> FEATURE:
<223> OTHER INFORMATION: Chemically synthesized

<400> SEQUENCE: 178

```
gtcttccccc tggcaccctc ctccaagagc acctctgggg gcacagcggc cctgggctgc      60
ctggtcaagg actacttccc cgaaccggtg acggtgtcgt ggaactcagg cgccctgacc     120
agcggcgtgc acaccttccc ggctgtccta cagtcctcag gactctactc cctcagcagc     180
gtggtgaccg tgccctccag cagcttgggc acccagacct acatctgcaa cgtgaatcac     240
aagcccagca acaccaaggt ggacaagaga gttgagccca atcttgtgac aaaaactcac     300
acatgcccac cgtgcccagc acctgaactc ctggggggac cgtcagtctt cctcttcccc     360
ccaaaaccca aggacaccct catgatctcc cggacccctg aggtcacatg cgtggtggtg     420
gacgtgagcc acgaagaccc tgaggtcaag ttcaactggt acgtggacgg cgtggaggtg     480
cataatgcca agacaaagcc gcgggaggag cagtacaaca gcacgtaccg tgtggtcagc     540
gtcctcaccg tcctgcacca ggactggctg aatggcaagg agtacaagtg caaggtctcc     600
aacaaagccc tcccagcccc catcgagaaa accatctcca aagccaaagg gcagccccga     660
gaaccacagg tgtacaccct gcccccatcc cgggatgagc tgaccaagaa ccaggtcagc     720
ctgacctgcc tggtcaaagg cttctatccc agcgacatcg ccgtggagtg ggagagcaat     780
gggcagccgg agaacaacta caagaccacg cctcccgtgc tggactccga cggctccttc     840
ttcctctaca gcaagctcac cgtggacaag agcaggtggc agcaggggaa cgtcttctca     900
tgctccgtga tgcatgaggc tctgcacaac cactacacgc agaagagcct ctccctgtct     960
```
ccgggtaaat ga  972

<210> SEQ ID NO 179
<211> LENGTH: 198
<212> TYPE: DNA
<213> ORGANISM: Artificial Sequence
<220> FEATURE:
<223> OTHER INFORMATION: Chemically synthesized

<400> SEQUENCE: 179
cgaactgtgg ctgcaccatc tgtcttcatc ttcccgccat ctgatgagca gttgaaatct  60
ggaactgcct ctgttgtgtg cctgctgaat aacttctatc ccagagaggc caaagtacag  120
tggaaggtgg ataacgccct ccaatcgggt aactcccagg agagtgtcac agagcaggac  180
agcaaggaca gcacctac  198

<210> SEQ ID NO 180
<211> LENGTH: 33
<212> TYPE: PRT
<213> ORGANISM: Artificial Sequence
<220> FEATURE:
<223> OTHER INFORMATION: Chemically synthesized

<400> SEQUENCE: 180

Arg Phe Thr Ile Ser Arg Asp Asn Ala Lys Asn Ser Leu Tyr Leu Gln
 1               5                  10                  15
Met Asn Ser Leu Arg Ala Glu Asp Thr Ala Leu Tyr Tyr Cys Ala Lys
            20                  25                  30
Asp

<210> SEQ ID NO 181
<211> LENGTH: 25
<212> TYPE: PRT
<213> ORGANISM: Artificial Sequence
<220> FEATURE:
<223> OTHER INFORMATION: Chemically synthesized

<400> SEQUENCE: 181

Gln Val Gln Leu Val Glu Ser Gly Ala Glu Val Lys Lys Pro Gly Ala
 1               5                  10                  15
Ser Val Lys Val Ser Cys Lys Ala Ser
            20                  25

<210> SEQ ID NO 182
<211> LENGTH: 32
<212> TYPE: PRT
<213> ORGANISM: Artificial Sequence
<220> FEATURE:
<223> OTHER INFORMATION: Chemically synthesized

<400> SEQUENCE: 182

Arg Phe Thr Ile Ser Arg Asp Asn Ser Lys Asn Thr Leu His Leu Gln
 1               5                  10                  15
Met Asn Ser Leu Arg Ala Glu Asp Thr Ala Val Tyr Tyr Cys Lys Lys
            20                  25                  30

<210> SEQ ID NO 183
<211> LENGTH: 33
<212> TYPE: PRT
<213> ORGANISM: Artificial Sequence
<220> FEATURE:
<223> OTHER INFORMATION: Chemically synthesized

<400> SEQUENCE: 183

```
Arg Leu Thr Ile Ser Lys Asp Thr Ser Lys Asn Gln Val Val Leu Thr
 1               5                  10                  15

Met Thr Asn Met Asp Pro Val Asp Thr Ala Thr Tyr Tyr Cys Ala Arg
            20                  25                  30

Ile
```

<210> SEQ ID NO 184
<211> LENGTH: 32
<212> TYPE: PRT
<213> ORGANISM: Artificial Sequence
<220> FEATURE:
<223> OTHER INFORMATION: Chemically synthesized

<400> SEQUENCE: 184

```
His Val Thr Ile Ser Ala Asp Lys Ser Ile Ser Thr Ala Tyr Leu Gln
 1               5                  10                  15

Trp Ser Ser Leu Lys Ala Ser Asp Thr Ala Met Tyr Tyr Cys Ala Arg
            20                  25                  30
```

<210> SEQ ID NO 185
<211> LENGTH: 32
<212> TYPE: PRT
<213> ORGANISM: Artificial Sequence
<220> FEATURE:
<223> OTHER INFORMATION: Chemically synthesized

<400> SEQUENCE: 185

```
Arg Val Thr Met Thr Arg Asp Thr Ser Thr Ser Thr Ala Tyr Met Glu
 1               5                  10                  15

Leu Ser Ser Leu Arg Ser Glu Asp Thr Ala Val Tyr Tyr Cys Ala Arg
            20                  25                  30
```

<210> SEQ ID NO 186
<211> LENGTH: 25
<212> TYPE: PRT
<213> ORGANISM: Artificial Sequence
<220> FEATURE:
<223> OTHER INFORMATION: Chemically synthesized

<400> SEQUENCE: 186

```
Gln Val Gln Leu Val Gln Ser Gly Ala Glu Val Lys Lys Pro Gly Ser
 1               5                  10                  15

Ser Val Lys Val Ser Cys Lys Ala Ser
            20                  25
```

<210> SEQ ID NO 187
<211> LENGTH: 25
<212> TYPE: PRT
<213> ORGANISM: Artificial Sequence
<220> FEATURE:
<223> OTHER INFORMATION: Chemically synthesized

<400> SEQUENCE: 187

```
Gln Val Thr Leu Arg Glu Ser Gly Pro Ala Leu Val Lys Pro Thr Gln
 1               5                  10                  15

Thr Leu Thr Leu Thr Cys Thr Phe Ser
            20                  25
```

<210> SEQ ID NO 188
<211> LENGTH: 25
<212> TYPE: PRT
<213> ORGANISM: Artificial Sequence
<220> FEATURE:
<223> OTHER INFORMATION: Chemically synthesized

<400> SEQUENCE: 188

Gln Val Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 189
<211> LENGTH: 25
<212> TYPE: PRT
<213> ORGANISM: Artificial Sequence
<220> FEATURE:
<223> OTHER INFORMATION: Chemically synthesized

<400> SEQUENCE: 189

Gln Val Gln Leu Gln Gln Ser Gly Pro Gly Leu Val Lys Pro Ser Gln
1               5                   10                  15

Thr Leu Ser Leu Thr Cys Ala Ile Ser
            20                  25

<210> SEQ ID NO 190
<211> LENGTH: 14
<212> TYPE: PRT
<213> ORGANISM: Artificial Sequence
<220> FEATURE:
<223> OTHER INFORMATION: Chemically synthesized

<400> SEQUENCE: 190

Trp Ile Arg Gln Pro Pro Gly Lys Ala Leu Glu Trp Leu Gly
1               5                   10

<210> SEQ ID NO 191
<211> LENGTH: 14
<212> TYPE: PRT
<213> ORGANISM: Artificial Sequence
<220> FEATURE:
<223> OTHER INFORMATION: Chemically synthesized

<400> SEQUENCE: 191

Trp Val Arg Gln Met Pro Gly Lys Gly Leu Glu Trp Met Gly
1               5                   10

<210> SEQ ID NO 192
<211> LENGTH: 14
<212> TYPE: PRT
<213> ORGANISM: Artificial Sequence
<220> FEATURE:
<223> OTHER INFORMATION: Chemically synthesized

<400> SEQUENCE: 192

Trp Ile Arg Gln Ser Pro Ser Arg Gly Leu Glu Trp Leu Gly
1               5                   10

<210> SEQ ID NO 193
<211> LENGTH: 32
<212> TYPE: PRT
<213> ORGANISM: Artificial Sequence
<220> FEATURE:
<223> OTHER INFORMATION: Chemically synthesized

<400> SEQUENCE: 193

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

-continued

```
<210> SEQ ID NO 194
<211> LENGTH: 32
<212> TYPE: PRT
<213> ORGANISM: Artificial Sequence
<220> FEATURE:
<223> OTHER INFORMATION: Chemically synthesized

<400> SEQUENCE: 194

Arg Val Thr Met Thr Arg Asn Thr Ser Ile Ser Thr Ala Tyr Met Glu
 1               5                  10                  15

Leu Ser Ser Leu Arg Ser Glu Asp Thr Ala Val Tyr Tyr Cys Ala Arg
                20                  25                  30

<210> SEQ ID NO 195
<211> LENGTH: 33
<212> TYPE: PRT
<213> ORGANISM: Artificial Sequence
<220> FEATURE:
<223> OTHER INFORMATION: Chemically synthesized

<400> SEQUENCE: 195

Arg Phe Thr Ile Ser Arg Asp Asn Ser Lys Asn Ser Leu Tyr Leu Gln
 1               5                  10                  15

Met Asn Ser Leu Arg Thr Glu Asp Thr Ala Leu Tyr Tyr Cys Ala Lys
                20                  25                  30

Asp

<210> SEQ ID NO 196
<211> LENGTH: 32
<212> TYPE: PRT
<213> ORGANISM: Artificial Sequence
<220> FEATURE:
<223> OTHER INFORMATION: Chemically synthesized

<400> SEQUENCE: 196

Arg Phe Thr Ile Ser Arg Asp Asn Ser Lys Asn Thr Leu Tyr Leu Gln
 1               5                  10                  15

Met Asn Ser Leu Arg Ala Glu Asp Thr Ala Val Tyr Tyr Cys Ala Arg
                20                  25                  30

<210> SEQ ID NO 197
<211> LENGTH: 32
<212> TYPE: PRT
<213> ORGANISM: Artificial Sequence
<220> FEATURE:
<223> OTHER INFORMATION: Chemically synthesized

<400> SEQUENCE: 197

Arg Phe Val Phe Ser Leu Asp Thr Ser Val Ser Thr Ala Tyr Leu Gln
 1               5                  10                  15

Ile Cys Ser Leu Lys Ala Glu Asp Thr Ala Val Tyr Tyr Cys Ala Arg
                20                  25                  30

<210> SEQ ID NO 198
<211> LENGTH: 32
<212> TYPE: PRT
<213> ORGANISM: Artificial Sequence
<220> FEATURE:
<223> OTHER INFORMATION: Chemically synthesized

<400> SEQUENCE: 198

Arg Ile Thr Ile Asn Pro Asp Thr Ser Lys Asn Gln Phe Ser Leu Gln
 1               5                  10                  15

Leu Asn Ser Val Thr Pro Glu Asp Thr Ala Val Tyr Tyr Cys Ala Arg
                20                  25                  30
```

```
<210> SEQ ID NO 199
<211> LENGTH: 25
<212> TYPE: PRT
<213> ORGANISM: Artificial Sequence
<220> FEATURE:
<223> OTHER INFORMATION: Chemically synthesized

<400> SEQUENCE: 199

Gln Val Gln Leu Val Gln Ser Gly Gly Gly Val Val Gln Pro Gly Arg
1               5                   10                  15

Ser Leu Arg Leu Ser Cys Ala Ala Ser
            20                  25

<210> SEQ ID NO 200
<211> LENGTH: 23
<212> TYPE: PRT
<213> ORGANISM: Artificial Sequence
<220> FEATURE:
<223> OTHER INFORMATION: Chemically synthesized

<400> SEQUENCE: 200

Asp Ile Val Met Thr Gln Ser Pro Ser Ser Leu Ser Ala Ser Val Gly
1               5                   10                  15

Asp Arg Val Thr Ile Thr Cys
            20

<210> SEQ ID NO 201
<211> LENGTH: 23
<212> TYPE: PRT
<213> ORGANISM: Artificial Sequence
<220> FEATURE:
<223> OTHER INFORMATION: Chemically synthesized

<400> SEQUENCE: 201

Glu Ile Val Met Thr Gln Ser Pro Ala Thr Leu Ser Leu Ser Pro Gly
1               5                   10                  15

Glu Arg Ala Thr Leu Ser Cys
            20

<210> SEQ ID NO 202
<211> LENGTH: 23
<212> TYPE: PRT
<213> ORGANISM: Artificial Sequence
<220> FEATURE:
<223> OTHER INFORMATION: Chemically synthesized

<400> SEQUENCE: 202

Asp Ile Gln Met Thr Gln Ser Pro Asp Phe Leu Ala Val Ser Leu Gly
1               5                   10                  15

Glu Arg Ala Thr Ile Asn Cys
            20

<210> SEQ ID NO 203
<211> LENGTH: 23
<212> TYPE: PRT
<213> ORGANISM: Artificial Sequence
<220> FEATURE:
<223> OTHER INFORMATION: Chemically synthesized

<400> SEQUENCE: 203

Glu Ile Val Leu Thr Gln Ser Pro Ser Ser Leu Ser Ala Ser Val Gly
1               5                   10                  15

Asp Arg Val Thr Ile Thr Cys
            20
```

```
<210> SEQ ID NO 204
<211> LENGTH: 15
<212> TYPE: PRT
<213> ORGANISM: Artificial Sequence
<220> FEATURE:
<223> OTHER INFORMATION: Chemically synthesized

<400> SEQUENCE: 204

Trp Tyr Gln Gln Lys Pro Cys Gln Ala Pro Arg Leu Leu Ile Tyr
 1               5                  10                  15

<210> SEQ ID NO 205
<211> LENGTH: 316
<212> TYPE: DNA
<213> ORGANISM: Artificial Sequence
<220> FEATURE:
<223> OTHER INFORMATION: Chemically synthesized

<400> SEQUENCE: 205
catcgtgatg acccagtctc cagactccct ggctgtgtct ctgggcgaga gggccaccat     60
caactgcagg ccagctcaa gtttaagttt catgcactgg tatcagcaga aaccaggaca    120
gcctcctaag ctgctcattt atgccacatc caacctggct tctgggatcc cagccaggtt    180
cagtggcagt gggtctggga cagacttcac tctcaccatc agcagcctag agcctgaaga    240
ttttgcagtt tattactgtc atcagtggag tagtaacccg ctcacgttcg gccaaggtac    300
caaggtggaa atcaaa                                                   316

<210> SEQ ID NO 206
<211> LENGTH: 11
<212> TYPE: PRT
<213> ORGANISM: Artificial Sequence
<220> FEATURE:
<223> OTHER INFORMATION: Chemically synthesized

<400> SEQUENCE: 206

Val Thr Val Ser Ala Ser Thr Lys Gly Pro Ser
 1               5                  10

<210> SEQ ID NO 207
<211> LENGTH: 16
<212> TYPE: PRT
<213> ORGANISM: Artificial Sequence
<220> FEATURE:
<223> OTHER INFORMATION: Chemically synthesized

<400> SEQUENCE: 207

Trp Gly Gln Gly Thr Val Thr Val Ser Ala Ser Thr Lys Gly Pro Ser
 1               5                  10                  15

<210> SEQ ID NO 208
<211> LENGTH: 233
<212> TYPE: PRT
<213> ORGANISM: Artificial Sequence
<220> FEATURE:
<223> OTHER INFORMATION: Chemically synthesized

<400> SEQUENCE: 208

Val Glu Pro Lys Ser Cys Asp Lys Thr His Thr Cys Pro Pro Cys Pro
 1               5                  10                  15

Ala Pro Glu Leu Leu Gly Gly Pro Ser Val Phe Leu Phe Pro Pro Lys
             20                  25                  30

Pro Lys Asp Thr Leu Met Ile Ser Arg Thr Pro Glu Val Thr Cys Val
         35                  40                  45
```

Val Val Asp Val Ser His Glu Asp Pro Glu Val Lys Phe Asn Trp Tyr
 50                  55                  60

Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
                 85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys
225                 230

<210> SEQ ID NO 209
<211> LENGTH: 106
<212> TYPE: PRT
<213> ORGANISM: Artificial Sequence
<220> FEATURE:
<223> OTHER INFORMATION: Chemically synthesized

<400> SEQUENCE: 209

Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
 50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
            100                 105

<210> SEQ ID NO 210
<211> LENGTH: 318
<212> TYPE: DNA
<213> ORGANISM: Artificial Sequence
<220> FEATURE:
<223> OTHER INFORMATION: Chemically synthesized

<400> SEQUENCE: 210
gatattgtga tgacccagtc tccactctcc ctgcccgtca cccctggaga gccggcctcc      60

```
atctcctgca gggccagctc aagtttaagt tcatgcact ggtatctgca gaagccaggg    120
cagtctccac agctcctgat ctatgccaca tccaacctgg cttctggggt ccctgacagg   180
ttcagtggca gtggatcagg cacagatttt acactgaaaa tcagcagagt ggaggctgag   240
gatgttgggg tttattactg tcatcagtgg agtagtaacc cgctcacgtt cggccaaggt   300
accaaggtgg aaatcaaa                                                 318
```

<210> SEQ ID NO 211
<211> LENGTH: 318
<212> TYPE: DNA
<213> ORGANISM: Artificial Sequence
<220> FEATURE:
<223> OTHER INFORMATION: Chemically synthesized

<400> SEQUENCE: 211

```
gacatccaga tgacccagtc tccatcctcc ctgtctgcat ctgtaggaga cagagtcacc    60
atcacttgca gggccagctc aagtttaagt tcatgcact ggtatctgca gaagccaggg   120
cagtctccac agctcctgat ctatgccaca tccaacctgg cttctggggt ccctgaccga   180
ttcagtggca gcgggtctgg gacagatttc actctcacca tcagcagcct gcaggctgaa   240
gatgtggcag tttattactg tcatcagtgg agtagtaacc cgctcacgtt cggccaaggt   300
accaaggtgg aaatcaaa                                                 318
```

<210> SEQ ID NO 212
<211> LENGTH: 318
<212> TYPE: DNA
<213> ORGANISM: Artificial Sequence
<220> FEATURE:
<223> OTHER INFORMATION: Chemically synthesized

<400> SEQUENCE: 212

```
gacatccaga tgacccagtc tccttccacc ctgtctgcat ctgtaggaga cagagtcacc    60
atcacttgca gggccagctc aagtttaagt tcatgcact ggtatcagca gaaacctggc   120
caggctccca ggctcctcat ctatgccaca tccaacctgg cttctggggt cccatcaagg   180
ttcagtggaa gtggatctgg gacagatttt actttcacca tcagcagcct gcagcctgaa   240
gatattgcaa catattactg tcatcagtgg agtagtaacc cgctcacgtt cggccaaggt   300
accaaggtgg aaatcaaa                                                 318
```

<210> SEQ ID NO 213
<211> LENGTH: 318
<212> TYPE: DNA
<213> ORGANISM: Artificial Sequence
<220> FEATURE:
<223> OTHER INFORMATION: Chemically synthesized

<400> SEQUENCE: 213

```
gaaattgtgt tgacccagtc tccaggcacc ctgtctttgt ctccagggga aagagccacc    60
ctctcctgca gggccagctc aagtttaagt tcatgcact ggtatctgca gaagccaggg   120
cagtctccac agctcctgat ctatgccaca tccaacctgg cttctggggt ccctgaccga   180
ttcagtggca gcgggtctgg gacagatttc actctcacca tcagcagcct gcaggctgaa   240
gatgtggcag tttattactg tcatcagtgg agtagtaacc cgctcacgtt cggccaaggt   300
accaaggtgg aaatcaaa                                                 318
```

<210> SEQ ID NO 214
<211> LENGTH: 318
<212> TYPE: DNA

<213> ORGANISM: Artificial Sequence
<220> FEATURE:
<223> OTHER INFORMATION: Chemically synthesized

<400> SEQUENCE: 214

```
gacatcgtga tgacccagtc tccagactcc ctggctgtgt ctctgggcga gagggccacc      60
atcaactgca gggccagctc aagtttaagt ttcatgcact ggtatcagca gaaaccaggg     120
aaagccccta agctcctgat ctatgccaca tccaacctgg cttctggggt cccatcaagg     180
ttcagcggca gtggatctgg gacagaattc actctcacca tcagcagcct gcagcctgat     240
gattttgcaa cttattactg tcatcagtgg agtagtaacc cgctcacgtt cggccaaggt     300
accaaggtgg aaatcaaa                                                   318
```

<210> SEQ ID NO 215
<211> LENGTH: 318
<212> TYPE: DNA
<213> ORGANISM: Artificial Sequence
<220> FEATURE:
<223> OTHER INFORMATION: Chemically synthesized

<400> SEQUENCE: 215

```
gaaatagtga tgacccagtc tccagccacc ctgtctgtgt ctccagggga aagagccacc      60
ctctcctgca gggccagctc aagtttaagt ttcatgcact ggtatctgca gaagccaggg     120
cagtctccac agctcctgat ctatgccaca tccaacctgg cttctggggt cccatcaagg     180
ttcagtggca gtggatctgg gacagatttc actctcacca tcagcagtct gcaacctgaa     240
gattttgcaa cttactactg tcatcagtgg agtagtaacc cgctcacgtt cggccaaggt     300
accaaggtgg aaatcaaa                                                   318
```

<210> SEQ ID NO 216
<211> LENGTH: 318
<212> TYPE: DNA
<213> ORGANISM: Artificial Sequence
<220> FEATURE:
<223> OTHER INFORMATION: Chemically synthesized

<400> SEQUENCE: 216

```
gaaattgtgt tgacccagtc tccaggcacc ctgtctttgt ctccagggga aagagccacc      60
ctctcctgca gggccagctc aagtttaagt ttcatgcact ggtatcagca gaaaccaggg     120
aaagccccta agctcctgat ctatgccaca tccaacctgg cttctggggt cccatcaagg     180
ttcagcggca gtggatctgg gacagaattc actctcacca tcagcagcct gcagcctgat     240
gattttgcaa cttattactg tcatcagtgg agtagtaacc cgctcacgtt cggccaaggt     300
accaaggtgg aaatcaaa                                                   318
```

<210> SEQ ID NO 217
<211> LENGTH: 318
<212> TYPE: DNA
<213> ORGANISM: Artificial Sequence
<220> FEATURE:
<223> OTHER INFORMATION: Chemically synthesized

<400> SEQUENCE: 217

```
gaaattgtgt tgacccagtc tccagccacc ctgtctttgt ctccagggga aagagccacc      60
ctctcctgca gggccagctc aagtttaagt ttcatgcact ggtatcagca gaaaccaggg     120
aaagccccta agctcctgat ctatgccaca tccaacctgg cttctggggt cccatcaagg     180
ttcagcggca gtggatctgg gacagaattc actctcacca tcagcagcct gcagcctgat     240
```

```
gattttgcaa cttattactg tcatcagtgg agtagtaacc cgctcacgtt cggccaaggt    300
accaaggtgg aaatcaaa                                                  318

<210> SEQ ID NO 218
<211> LENGTH: 318
<212> TYPE: DNA
<213> ORGANISM: Artificial Sequence
<220> FEATURE:
<223> OTHER INFORMATION: Chemically synthesized

<400> SEQUENCE: 218
gaaattgtgt tgacccagtc tccagccacc ctgtctttgt ctccagggga aagagccacc    60
ctctcctgca gggccagctc aagtttaagt ttcatgcact ggtatcagca gaaaccagga    120
cagcctccta agctgctcat ttatgccaca tccaacctgg cttctgggat cccagccagg    180
ttcagtggca gtgggtctgg gacagagttc actctcacca tcagcagcct gcagtctgaa    240
gattttgcag tttattactg tcatcagtgg agtagtaacc cgctcacgtt cggccaaggt    300
accaaggtgg aaatcaaa                                                  318

<210> SEQ ID NO 219
<211> LENGTH: 318
<212> TYPE: DNA
<213> ORGANISM: Artificial Sequence
<220> FEATURE:
<223> OTHER INFORMATION: Chemically synthesized

<400> SEQUENCE: 219
gaaattgtgt tgacccagtc tccagccacc ctgtctttgt ctccagggga aagagccacc    60
ctctcctgca gggccagctc aagtttaagt ttcatgcact ggtatcagca gaaaccagga    120
cagcctccta agctgctcat ttatgccaca tccaacctgg cttctggggt cccatcaagg    180
ttcagtggaa gtggatctgg gacagatttt actttcacca tcagcagcct gcagcctgaa    240
gatattgcaa catattactg tcatcagtgg agtagtaacc cgctcacgtt cggccaaggt    300
accaaggtgg aaatcaaa                                                  318

<210> SEQ ID NO 220
<211> LENGTH: 318
<212> TYPE: DNA
<213> ORGANISM: Artificial Sequence
<220> FEATURE:
<223> OTHER INFORMATION: Chemically synthesized

<400> SEQUENCE: 220
gaaatagtga tgacccagtc tccagccacc ctgtctgtgt ctccagggga aagagccacc    60
ctctcctgca gggccagctc aagtttaagt ttcatgcact ggtatcagca gaaaccagga    120
cagcctccta agctgctcat ttatgccaca tccaacctgg cttctggggt cccatcaagg    180
ttcagtggaa gtggatctgg gacagatttt actttcacca tcagcagcct gcagcctgaa    240
gatattgcaa catattactg tcatcagtgg agtagtaacc cgctcacgtt cggccaaggt    300
accaaggtgg aaatcaaa                                                  318

<210> SEQ ID NO 221
<211> LENGTH: 318
<212> TYPE: DNA
<213> ORGANISM: Artificial Sequence
<220> FEATURE:
<223> OTHER INFORMATION: Chemically synthesized

<400> SEQUENCE: 221
```

```
gaaattgtgt tgacccagtc tccaggcacc ctgtctttgt ctccagggga aagagccacc    60
ctctcctgca gggccagctc aagtttaagt ttcatgcact ggtatcagca gaaacctggc   120
caggctccca ggctcctcat ctatgccaca tccaacctgg cttctggggt cccatcaagg   180
ttcagtggaa gtggatctgg gacagatttt actttcacca tcagcagcct gcagcctgaa   240
gatattgcaa catattactg tcatcagtgg agtagtaacc cgctcacgtt cggccaaggt   300
accaaggtgg aaatcaaa                                                 318

<210> SEQ ID NO 222
<211> LENGTH: 318
<212> TYPE: DNA
<213> ORGANISM: Artificial Sequence
<220> FEATURE:
<223> OTHER INFORMATION: Chemically synthesized

<400> SEQUENCE: 222
gaaattgtgt tgacccagtc tccaggcacc ctgtctttgt ctccagggga aagagccacc    60
ctctcctgca gggccagctc aagtttaagt ttcatgcact ggtatcagca gaaaccagga   120
cagcctccta agctgctcat ttatgccaca tccaacctgg cttctggggt cccatcaagg   180
ttcagtggca gtggatctgg gacagatttc actctcacca tcagcagtct gcaacctgaa   240
gattttgcaa cttactactg tcatcagtgg agtagtaacc cgctcacgtt cggccaaggt   300
accaaggtgg aaatcaaa                                                 318

<210> SEQ ID NO 223
<211> LENGTH: 318
<212> TYPE: DNA
<213> ORGANISM: Artificial Sequence
<220> FEATURE:
<223> OTHER INFORMATION: Chemically synthesized

<400> SEQUENCE: 223
gaaattgtgt tgacccagtc tccagccacc ctgtctttgt ctccagggga aagagccacc    60
ctctcctgca gggccagctc aagtttaagt ttcatgcact ggtatcagca gaaaccagga   120
cagcctccta agctgctcat ttatgccaca tccaacctgg cttctggggt cccatcaagg   180
ttcagtggca gtggatctgg gacagatttc actctcacca tcagcagtct gcaacctgaa   240
gattttgcaa cttactactg tcatcagtgg agtagtaacc cgctcacgtt cggccaaggt   300
accaaggtgg aaatcaaa                                                 318

<210> SEQ ID NO 224
<211> LENGTH: 318
<212> TYPE: DNA
<213> ORGANISM: Artificial Sequence
<220> FEATURE:
<223> OTHER INFORMATION: Chemically synthesized

<400> SEQUENCE: 224
gaaatagtga tgacccagtc tccagccacc ctgtctgtgt ctccagggga aagagccacc    60
ctctcctgca gggccagctc aagtttaagt ttcatgcact ggtatcagca gaaaccagga   120
cagcctccta agctgctcat ttatgccaca tccaacctgg cttctggggt cccatcaagg   180
ttcagtggca gtggatctgg gacagatttc actctcacca tcagcagtct gcaacctgaa   240
gattttgcaa cttactactg tcatcagtgg agtagtaacc cgctcacgtt cggccaaggt   300
accaaggtgg aaatcaaa                                                 318

<210> SEQ ID NO 225
```

```
<211> LENGTH: 106
<212> TYPE: PRT
<213> ORGANISM: Artificial Sequence
<220> FEATURE:
<223> OTHER INFORMATION: Chemically synthesized

<400> SEQUENCE: 225

Asp Ile Val Met Thr Gln Ser Pro Leu Ser Leu Pro Val Thr Pro Gly
1               5                   10                  15

Glu Pro Ala Ser Ile Ser Cys Arg Ala Ser Ser Leu Ser Phe Met
            20                  25                  30

His Trp Tyr Gln Gln Lys Pro Gly Gln Pro Pro Lys Leu Leu Ile Tyr
        35                  40                  45

Ala Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys His Gln Trp Ser Ser Asn Pro Leu Thr
                85                  90                  95

Phe Gly Gln Gly Thr Lys Val Glu Ile Lys
            100                 105

<210> SEQ ID NO 226
<211> LENGTH: 106
<212> TYPE: PRT
<213> ORGANISM: Artificial Sequence
<220> FEATURE:
<223> OTHER INFORMATION: Chemically synthesized

<400> SEQUENCE: 226

Asp Ile Val Met Thr Gln Ser Pro Leu Ser Leu Pro Val Thr Pro Gly
1               5                   10                  15

Glu Pro Ala Ser Ile Ser Cys Arg Ala Ser Ser Leu Ser Phe Met
            20                  25                  30

His Trp Tyr Leu Gln Lys Pro Gly Gln Ser Pro Gln Leu Leu Ile Tyr
        35                  40                  45

Ala Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys His Gln Trp Ser Ser Asn Pro Leu Thr
                85                  90                  95

Phe Gly Gln Gly Thr Lys Val Glu Ile Lys
            100                 105

<210> SEQ ID NO 227
<211> LENGTH: 106
<212> TYPE: PRT
<213> ORGANISM: Artificial Sequence
<220> FEATURE:
<223> OTHER INFORMATION: Chemically synthesized

<400> SEQUENCE: 227

Asp Ile Val Met Thr Gln Ser Pro Leu Ser Leu Pro Val Thr Pro Gly
1               5                   10                  15

Glu Pro Ala Ser Ile Ser Cys Arg Ala Ser Ser Leu Ser Phe Met
            20                  25                  30

His Trp Tyr Gln Gln Lys Pro Gly Gln Ala Pro Arg Leu Leu Ile Tyr
        35                  40                  45
```

```
Ala Thr Ser Asn Leu Ala Ser Gly Val Pro Asp Arg Phe Ser Gly Ser
        50                  55                  60

Gly Ser Gly Thr Asp Phe Thr Leu Thr Ile Ser Ser Leu Gln Ala Glu
 65                  70                  75                  80

Asp Val Ala Val Tyr Tyr Cys His Gln Trp Ser Ser Asn Pro Leu Thr
                 85                  90                  95

Phe Gly Gln Gly Thr Lys Val Glu Ile Lys
                100                 105
```

<210> SEQ ID NO 228
<211> LENGTH: 106
<212> TYPE: PRT
<213> ORGANISM: Artificial Sequence
<220> FEATURE:
<223> OTHER INFORMATION: Chemically synthesized

<400> SEQUENCE: 228

```
Asp Ile Val Met Thr Gln Ser Pro Leu Ser Leu Pro Val Thr Pro Gly
  1               5                  10                  15

Glu Pro Ala Ser Ile Ser Cys Arg Ala Ser Ser Ser Leu Ser Phe Met
                 20                  25                  30

His Trp Tyr Gln Gln Lys Pro Gly Lys Ala Pro Lys Leu Leu Ile Tyr
             35                  40                  45

Ala Thr Ser Asn Leu Ala Ser Gly Val Pro Asp Arg Phe Ser Gly Ser
        50                  55                  60

Gly Ser Gly Thr Asp Phe Thr Leu Thr Ile Ser Ser Leu Gln Ala Glu
 65                  70                  75                  80

Asp Val Ala Val Tyr Tyr Cys His Gln Trp Ser Ser Asn Pro Leu Thr
                 85                  90                  95

Phe Gly Gln Gly Thr Lys Val Glu Ile Lys
                100                 105
```

<210> SEQ ID NO 229
<211> LENGTH: 106
<212> TYPE: PRT
<213> ORGANISM: Artificial Sequence
<220> FEATURE:
<223> OTHER INFORMATION: Chemically synthesized

<400> SEQUENCE: 229

```
Asp Ile Val Met Thr Gln Ser Pro Leu Ser Leu Pro Val Thr Pro Gly
  1               5                  10                  15

Glu Pro Ala Ser Ile Ser Cys Arg Ala Ser Ser Ser Leu Ser Phe Met
                 20                  25                  30

His Trp Tyr Gln Gln Lys Pro Gly Gln Pro Pro Lys Leu Leu Ile Tyr
             35                  40                  45

Ala Thr Ser Asn Leu Ala Ser Gly Val Pro Ser Arg Phe Ser Gly Ser
        50                  55                  60

Gly Ser Gly Thr Asp Phe Thr Phe Thr Ile Ser Ser Leu Gln Pro Glu
 65                  70                  75                  80

Asp Ile Ala Thr Tyr Tyr Cys His Gln Trp Ser Ser Asn Pro Leu Thr
                 85                  90                  95

Phe Gly Gln Gly Thr Lys Val Glu Ile Lys
                100                 105
```

<210> SEQ ID NO 230
<211> LENGTH: 106
<212> TYPE: PRT
<213> ORGANISM: Artificial Sequence
<220> FEATURE:

```
<223> OTHER INFORMATION: Chemically synthesized

<400> SEQUENCE: 230

Asp Ile Val Met Thr Gln Ser Pro Leu Ser Leu Pro Val Thr Pro Gly
 1               5                  10                  15

Glu Pro Ala Ser Ile Ser Cys Arg Ala Ser Ser Ser Leu Ser Phe Met
            20                  25                  30

His Trp Tyr Gln Gln Lys Pro Gly Gln Ala Pro Arg Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys His Gln Trp Ser Ser Asn Pro Leu Thr
                85                  90                  95

Phe Gly Gln Gly Thr Lys Val Glu Ile Lys
            100                 105

<210> SEQ ID NO 231
<211> LENGTH: 106
<212> TYPE: PRT
<213> ORGANISM: Artificial Sequence
<220> FEATURE:
<223> OTHER INFORMATION: Chemically synthesized

<400> SEQUENCE: 231

Asp Ile Val Met Thr Gln Ser Pro Leu Ser Leu Pro Val Thr Pro Gly
 1               5                  10                  15

Glu Pro Ala Ser Ile Ser Cys Arg Ala Ser Ser Ser Leu Ser Phe Met
            20                  25                  30

His Trp Tyr Gln Gln Lys Pro Gly Gln Ala Pro Arg Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys His Gln Trp Ser Ser Asn Pro Leu Thr
                85                  90                  95

Phe Gly Gln Gly Thr Lys Val Glu Ile Lys
            100                 105

<210> SEQ ID NO 232
<211> LENGTH: 106
<212> TYPE: PRT
<213> ORGANISM: Artificial Sequence
<220> FEATURE:
<223> OTHER INFORMATION: Chemically synthesized

<400> SEQUENCE: 232

Asp Ile Val Met Thr Gln Ser Pro Asp Ser Leu Ala Val Ser Leu Gly
 1               5                  10                  15

Glu Arg Ala Thr Ile Asn Cys Arg Ala Ser Ser Ser Leu Ser Phe Met
            20                  25                  30

His Trp Tyr Gln Gln Lys Pro Gly Gln Ala Pro Arg Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80
```

Asp Phe Ala Thr Tyr Tyr Cys His Gln Trp Ser Ser Asn Pro Leu Thr
                85                  90                  95

Phe Gly Gln Gly Thr Lys Val Glu Ile Lys
            100                 105

<210> SEQ ID NO 233
<211> LENGTH: 106
<212> TYPE: PRT
<213> ORGANISM: Artificial Sequence
<220> FEATURE:
<223> OTHER INFORMATION: Chemically synthesized

<400> SEQUENCE: 233

Asp Ile Val Met Thr Gln Ser Pro Asp Ser Leu Ala Val Ser Leu Gly
1               5                   10                  15

Glu Arg Ala Thr Ile Asn Cys Arg Ala Ser Ser Ser Leu Ser Phe Met
            20                  25                  30

His Trp Tyr Gln Gln Lys Pro Gly Gln Pro Lys Leu Leu Ile Tyr
        35                  40                  45

Ala Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys His Gln Trp Ser Ser Asn Pro Leu Thr
                85                  90                  95

Phe Gly Gln Gly Thr Lys Val Glu Ile Lys
            100                 105

<210> SEQ ID NO 234
<211> LENGTH: 106
<212> TYPE: PRT
<213> ORGANISM: Artificial Sequence
<220> FEATURE:
<223> OTHER INFORMATION: Chemically synthesized

<400> SEQUENCE: 234

Asp Ile Val Met Thr Gln Ser Pro Leu Ser Leu Pro Val Thr Pro Gly
1               5                   10                  15

Glu Pro Ala Ser Ile Ser Cys Arg Ala Ser Ser Ser Leu Ser Phe Met
            20                  25                  30

His Trp Tyr Leu Gln Lys Pro Gly Gln Ser Pro Gln Leu Leu Ile Tyr
        35                  40                  45

Ala Thr Ser Asn Leu Ala Ser Gly Val Pro Asp Arg Phe Ser Gly Ser
    50                  55                  60

Gly Ser Gly Thr Asp Phe Thr Leu Lys Ile Ser Arg Val Glu Ala Glu
65                  70                  75                  80

Asp Val Gly Val Tyr Tyr Cys His Gln Trp Ser Ser Asn Pro Leu Thr
                85                  90                  95

Phe Gly Gln Gly Thr Lys Val Glu Ile Lys
            100                 105

<210> SEQ ID NO 235
<211> LENGTH: 106
<212> TYPE: PRT
<213> ORGANISM: Artificial Sequence
<220> FEATURE:
<223> OTHER INFORMATION: Chemically synthesized

<400> SEQUENCE: 235

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Leu Ser Phe Met
            20                  25                  30

His Trp Tyr Leu Gln Lys Pro Gly Gln Ser Pro Gln Leu Leu Ile Tyr
        35                  40                  45

Ala Thr Ser Asn Leu Ala Ser Gly Val Pro Asp Arg Phe Ser Gly Ser
    50                  55                  60

Gly Ser Gly Thr Asp Phe Thr Leu Thr Ile Ser Ser Leu Gln Ala Glu
65                  70                  75                  80

Asp Val Ala Val Tyr Tyr Cys His Gln Trp Ser Ser Asn Pro Leu Thr
                85                  90                  95

Phe Gly Gln Gly Thr Lys Val Glu Ile Lys
            100                 105

<210> SEQ ID NO 236
<211> LENGTH: 106
<212> TYPE: PRT
<213> ORGANISM: Artificial Sequence
<220> FEATURE:
<223> OTHER INFORMATION: Chemically synthesized

<400> SEQUENCE: 236

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Leu Ser Phe Met
            20                  25                  30

His Trp Tyr Gln Gln Lys Pro Gly Gln Ala Pro Arg Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys His Gln Trp Ser Ser Asn Pro Leu Thr
                85                  90                  95

Phe Gly Gln Gly Thr Lys Val Glu Ile Lys
            100                 105

<210> SEQ ID NO 237
<211> LENGTH: 106
<212> TYPE: PRT
<213> ORGANISM: Artificial Sequence
<220> FEATURE:
<223> OTHER INFORMATION: Chemically synthesized

<400> SEQUENCE: 237

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Leu Ser Phe Met
            20                  25                  30

His Trp Tyr Leu Gln Lys Pro Gly Gln Ser Pro Gln Leu Leu Ile Tyr
        35                  40                  45

Ala Thr Ser Asn Leu Ala Ser Gly Val Pro Asp Arg Phe Ser Gly Ser
    50                  55                  60

Gly Ser Gly Thr Asp Phe Thr Leu Thr Ile Ser Ser Leu Gln Ala Glu
65                  70                  75                  80

Asp Val Ala Val Tyr Tyr Cys His Gln Trp Ser Ser Asn Pro Leu Thr
                85                  90                  95

```
Phe Gly Gln Gly Thr Lys Val Glu Ile Lys
            100                 105
```

<210> SEQ ID NO 238
<211> LENGTH: 106
<212> TYPE: PRT
<213> ORGANISM: Artificial Sequence
<220> FEATURE:
<223> OTHER INFORMATION: Chemically synthesized

<400> SEQUENCE: 238

```
Asp Ile Val Met Thr Gln Ser Pro Asp Ser Leu Ala Val Ser Leu Gly
 1               5                  10                  15

Glu Arg Ala Thr Ile Asn Cys Arg Ala Ser Ser Ser Leu Ser Phe Met
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys His Gln Trp Ser Ser Asn Pro Leu Thr
                85                  90                  95

Phe Gly Gln Gly Thr Lys Val Glu Ile Lys
            100                 105
```

<210> SEQ ID NO 239
<211> LENGTH: 106
<212> TYPE: PRT
<213> ORGANISM: Artificial Sequence
<220> FEATURE:
<223> OTHER INFORMATION: Chemically synthesized

<400> SEQUENCE: 239

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Ser Ser Leu Ser Phe Met
            20                  25                  30

His Trp Tyr Leu Gln Lys Pro Gly Gln Ser Pro Gln Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys His Gln Trp Ser Ser Asn Pro Leu Thr
                85                  90                  95

Phe Gly Gln Gly Thr Lys Val Glu Ile Lys
            100                 105
```

<210> SEQ ID NO 240
<211> LENGTH: 106
<212> TYPE: PRT
<213> ORGANISM: Artificial Sequence
<220> FEATURE:
<223> OTHER INFORMATION: Chemically synthesized

<400> SEQUENCE: 240

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Ser Ser Leu Ser Phe Met
            20                  25                  30
```

His Trp Tyr Gln Gln Lys Pro Gly Lys Ala Pro Lys Leu Leu Ile Tyr
            35                  40                  45

Ala Thr Ser Asn Leu Ala Ser Gly Val Pro Ser Arg Phe Ser Gly Ser
 50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys His Gln Trp Ser Ser Asn Pro Leu Thr
                 85                  90                  95

Phe Gly Gln Gly Thr Lys Val Glu Ile Lys
            100                 105

<210> SEQ ID NO 241
<211> LENGTH: 106
<212> TYPE: PRT
<213> ORGANISM: Artificial Sequence
<220> FEATURE:
<223> OTHER INFORMATION: Chemically synthesized

<400> SEQUENCE: 241

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Ser Ser Leu Ser Phe Met
                20                  25                  30

His Trp Tyr Gln Gln Lys Pro Gly Lys Ala Pro Lys Leu Leu Ile Tyr
            35                  40                  45

Ala Thr Ser Asn Leu Ala Ser Gly Val Pro Ser Arg Phe Ser Gly Ser
 50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys His Gln Trp Ser Ser Asn Pro Leu Thr
                 85                  90                  95

Phe Gly Gln Gly Thr Lys Val Glu Ile Lys
            100                 105

<210> SEQ ID NO 242
<211> LENGTH: 106
<212> TYPE: PRT
<213> ORGANISM: Artificial Sequence
<220> FEATURE:
<223> OTHER INFORMATION: Chemically synthesized

<400> SEQUENCE: 242

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Ser Ser Leu Ser Phe Met
                20                  25                  30

His Trp Tyr Gln Gln Lys Pro Gly Gln Pro Pro Lys Leu Leu Ile Tyr
            35                  40                  45

Ala Thr Ser Asn Leu Ala Ser Gly Ile Pro Ala Arg Phe Ser Gly Ser
 50                  55                  60

Gly Ser Gly Thr Glu Phe Thr Leu Thr Ile Ser Ser Leu Gln Ser Glu
 65                  70                  75                  80

Asp Phe Ala Val Tyr Tyr Cys His Gln Trp Ser Ser Asn Pro Leu Thr
                 85                  90                  95

Phe Gly Gln Gly Thr Lys Val Glu Ile Lys
            100                 105

<210> SEQ ID NO 243

```
<211> LENGTH: 106
<212> TYPE: PRT
<213> ORGANISM: Artificial Sequence
<220> FEATURE:
<223> OTHER INFORMATION: Chemically synthesized

<400> SEQUENCE: 243

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Leu Ser Phe Met
            20                  25                  30

His Trp Tyr Gln Gln Lys Pro Gly Gln Pro Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys His Gln Trp Ser Ser Asn Pro Leu Thr
                85                  90                  95

Phe Gly Gln Gly Thr Lys Val Glu Ile Lys
            100                 105

<210> SEQ ID NO 244
<211> LENGTH: 106
<212> TYPE: PRT
<213> ORGANISM: Artificial Sequence
<220> FEATURE:
<223> OTHER INFORMATION: Chemically synthesized

<400> SEQUENCE: 244

Glu Ile Val Met Thr Gln Ser Pro Ala Thr Leu Ser Val Ser Pro Gly
1               5                   10                  15

Glu Arg Ala Thr Leu Ser Cys Arg Ala Ser Ser Ser Leu Ser Phe Met
            20                  25                  30

His Trp Tyr Gln Gln Lys Pro Gly Gln Pro Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys His Gln Trp Ser Ser Asn Pro Leu Thr
                85                  90                  95

Phe Gly Gln Gly Thr Lys Val Glu Ile Lys
            100                 105

<210> SEQ ID NO 245
<211> LENGTH: 106
<212> TYPE: PRT
<213> ORGANISM: Artificial Sequence
<220> FEATURE:
<223> OTHER INFORMATION: Chemically synthesized

<400> SEQUENCE: 245

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Leu Ser Phe Met
            20                  25                  30

His Trp Tyr Gln Gln Lys Pro Gly Gln Ala Pro Arg Leu Leu Ile Tyr
        35                  40                  45
```

```
Ala Thr Ser Asn Leu Ala Ser Gly Val Pro Ser Arg Phe Ser Gly Ser
 50                  55                  60

Gly Ser Gly Thr Asp Phe Thr Phe Thr Ile Ser Ser Leu Gln Pro Glu
 65                  70                  75                  80

Asp Ile Ala Thr Tyr Tyr Cys His Gln Trp Ser Ser Asn Pro Leu Thr
                 85                  90                  95

Phe Gly Gln Gly Thr Lys Val Glu Ile Lys
            100                 105

<210> SEQ ID NO 246
<211> LENGTH: 106
<212> TYPE: PRT
<213> ORGANISM: Artificial Sequence
<220> FEATURE:
<223> OTHER INFORMATION: Chemically synthesized

<400> SEQUENCE: 246

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Ser Ser Leu Ser Phe Met
                 20                  25                  30

His Trp Tyr Gln Gln Lys Pro Gly Gln Pro Pro Lys Leu Leu Ile Tyr
             35                  40                  45

Ala Thr Ser Asn Leu Ala Ser Gly Val Pro Ser Arg Phe Ser Gly Ser
 50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys His Gln Trp Ser Ser Asn Pro Leu Thr
                 85                  90                  95

Phe Gly Gln Gly Thr Lys Val Glu Ile Lys
            100                 105

<210> SEQ ID NO 247
<211> LENGTH: 106
<212> TYPE: PRT
<213> ORGANISM: Artificial Sequence
<220> FEATURE:
<223> OTHER INFORMATION: Chemically synthesized

<400> SEQUENCE: 247

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Ser Ser Leu Ser Phe Met
                 20                  25                  30

His Trp Tyr Gln Gln Lys Pro Gly Gln Pro Pro Lys Leu Leu Ile Tyr
             35                  40                  45

Ala Thr Ser Asn Leu Ala Ser Gly Val Pro Ser Arg Phe Ser Gly Ser
 50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys His Gln Trp Ser Ser Asn Pro Leu Thr
                 85                  90                  95

Phe Gly Gln Gly Thr Lys Val Glu Ile Lys
            100                 105

<210> SEQ ID NO 248
<211> LENGTH: 106
<212> TYPE: PRT
<213> ORGANISM: Artificial Sequence
<220> FEATURE:
```

-continued

<223> OTHER INFORMATION: Chemically synthesized

<400> SEQUENCE: 248

Glu Ile Val Met Thr Gln Ser Pro Ala Thr Leu Ser Val Ser Pro Gly
1               5                   10                  15

Glu Arg Ala Thr Leu Ser Cys Arg Ala Ser Ser Leu Ser Phe Met
            20                  25                  30

His Trp Tyr Gln Gln Lys Pro Gly Gln Pro Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys His Gln Trp Ser Asn Pro Leu Thr
                85                  90                  95

Phe Gly Gln Gly Thr Lys Val Glu Ile Lys
            100                 105

<210> SEQ ID NO 249
<211> LENGTH: 66
<212> TYPE: DNA
<213> ORGANISM: Artificial Sequence
<220> FEATURE:
<223> OTHER INFORMATION: Chemically synthesized

<400> SEQUENCE: 249
atggacatga gggtccccgc tcagctcctg gggctcctgc tgctctggct cccaggtgcc      60
aaatgt                                                                66

<210> SEQ ID NO 250
<211> LENGTH: 22
<212> TYPE: PRT
<213> ORGANISM: Artificial Sequence
<220> FEATURE:
<223> OTHER INFORMATION: Chemically synthesized

<400> SEQUENCE: 250

Met Asp Met Arg Val Pro Ala Gln Leu Leu Gly Leu Leu Leu Leu Trp
1               5                   10                  15

Leu Pro Gly Ala Lys Cys
            20

<210> SEQ ID NO 251
<211> LENGTH: 324
<212> TYPE: DNA
<213> ORGANISM: Artificial Sequence
<220> FEATURE:
<223> OTHER INFORMATION: Chemically synthesized

<400> SEQUENCE: 251
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg ttaa                                            324

<210> SEQ ID NO 252
<211> LENGTH: 107

<212> TYPE: PRT
<213> ORGANISM: Artificial Sequence
<220> FEATURE:
<223> OTHER INFORMATION: Chemically synthesized

<400> SEQUENCE: 252

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 253
<211> LENGTH: 32
<212> TYPE: PRT
<213> ORGANISM: Artificial Sequence
<220> FEATURE:
<223> OTHER INFORMATION: Chemically synthesized

<400> SEQUENCE: 253

Gly Val Pro Ser Arg Phe Ser Gly Ser Gly Ser Gly Thr Asp Phe Thr
 1               5                  10                  15

Leu Thr Ile Ser Cys Leu Gln Ser Glu Asp Phe Ala Thr Tyr Tyr Cys
            20                  25                  30

<210> SEQ ID NO 254
<211> LENGTH: 32
<212> TYPE: PRT
<213> ORGANISM: Artificial Sequence
<220> FEATURE:
<223> OTHER INFORMATION: Chemically synthesized

<400> SEQUENCE: 254

Gly Val Pro Ser Arg Phe Ser Gly Ser Gly Ser Gly Thr Glu Phe Thr
 1               5                  10                  15

Leu Thr Ile Ser Ser Leu Gln Pro Glu Asp Phe Ala Thr Tyr Tyr Cys
            20                  25                  30

<210> SEQ ID NO 255
<211> LENGTH: 32
<212> TYPE: PRT
<213> ORGANISM: Artificial Sequence
<220> FEATURE:
<223> OTHER INFORMATION: Chemically synthesized

<400> SEQUENCE: 255

Gly Ile Pro Ala Arg Phe Ser Gly Ser Gly Pro Gly Thr Asp Phe Thr
 1               5                  10                  15

Leu Thr Ile Ser Ser Leu Glu Pro Glu Asp Phe Ala Val Tyr Tyr Cys
            20                  25                  30

<210> SEQ ID NO 256
<211> LENGTH: 32
<212> TYPE: PRT

```
<213> ORGANISM: Artificial Sequence
<220> FEATURE:
<223> OTHER INFORMATION: Chemically synthesized

<400> SEQUENCE: 256

Gly Val Pro Ser Arg Phe Ser Gly Ser Gly Ser Gly Thr Asp Phe Thr
1               5                   10                  15

Leu Thr Ile Asn Ser Leu Glu Ala Glu Asp Ala Ala Thr Tyr Tyr Cys
            20                  25                  30

<210> SEQ ID NO 257
<211> LENGTH: 32
<212> TYPE: PRT
<213> ORGANISM: Artificial Sequence
<220> FEATURE:
<223> OTHER INFORMATION: Chemically synthesized

<400> SEQUENCE: 257

Gly Ile Pro Ala Arg Phe Ser Gly Ser Gly Ser Gly Thr Asp Phe Thr
1               5                   10                  15

Leu Thr Ile Ser Ser Leu Gln Pro Glu Asp Phe Ala Val Tyr Tyr Cys
            20                  25                  30

<210> SEQ ID NO 258
<211> LENGTH: 32
<212> TYPE: PRT
<213> ORGANISM: Artificial Sequence
<220> FEATURE:
<223> OTHER INFORMATION: Chemically synthesized

<400> SEQUENCE: 258

Gly Val Pro Ser Arg Phe Ser Gly Ser Gly Ser Gly Thr Asp Phe Thr
1               5                   10                  15

Phe Thr Ile Ser Ser Leu Glu Ala Glu Asp Ala Ala Thr Tyr Tyr Cys
            20                  25                  30

<210> SEQ ID NO 259
<211> LENGTH: 32
<212> TYPE: PRT
<213> ORGANISM: Artificial Sequence
<220> FEATURE:
<223> OTHER INFORMATION: Chemically synthesized

<400> SEQUENCE: 259

Gly Ile Pro Pro Arg Phe Ser Gly Ser Gly Tyr Gly Thr Asp Phe Thr
1               5                   10                  15

Leu Thr Ile Asn Asn Ile Glu Ser Glu Asp Ala Ala Tyr Tyr Phe Cys
            20                  25                  30

<210> SEQ ID NO 260
<211> LENGTH: 32
<212> TYPE: PRT
<213> ORGANISM: Artificial Sequence
<220> FEATURE:
<223> OTHER INFORMATION: Chemically synthesized

<400> SEQUENCE: 260

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 261
<211> LENGTH: 23
<212> TYPE: PRT
```

<213> ORGANISM: Artificial Sequence
<220> FEATURE:
<223> OTHER INFORMATION: Chemically synthesized

<400> SEQUENCE: 261

Asp Ile Val Met Thr Gln Thr Pro Leu Ser Leu Pro Val Thr Pro Gly
1               5                   10                  15

Glu Pro Ala Ser Ile Ser Cys
            20

<210> SEQ ID NO 262
<211> LENGTH: 23
<212> TYPE: PRT
<213> ORGANISM: Artificial Sequence
<220> FEATURE:
<223> OTHER INFORMATION: Chemically synthesized

<400> SEQUENCE: 262

Asp Ile Val Met Thr Gln Thr Pro Leu Ser Leu Ser Val Thr Pro Gly
1               5                   10                  15

Gln Pro Ala Ser Ile Ser Cys
            20

<210> SEQ ID NO 263
<211> LENGTH: 23
<212> TYPE: PRT
<213> ORGANISM: Artificial Sequence
<220> FEATURE:
<223> OTHER INFORMATION: Chemically synthesized

<400> SEQUENCE: 263

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 264
<211> LENGTH: 23
<212> TYPE: PRT
<213> ORGANISM: Artificial Sequence
<220> FEATURE:
<223> OTHER INFORMATION: Chemically synthesized

<400> SEQUENCE: 264

Glu Thr Thr Leu Thr Gln Ser Pro Ala Phe Met Ser Ala Thr Pro Gly
1               5                   10                  15

Asp Lys Val Asn Ile Ser Cys
            20

<210> SEQ ID NO 265
<211> LENGTH: 23
<212> TYPE: PRT
<213> ORGANISM: Artificial Sequence
<220> FEATURE:
<223> OTHER INFORMATION: Chemically synthesized

<400> SEQUENCE: 265

Ala Ile Arg Met Thr Gln Ser Pro Phe Ser Leu Ser Ala Ser Val Gly
1               5                   10                  15

Asp Arg Val Thr Ile Thr Cys
            20

<210> SEQ ID NO 266
<211> LENGTH: 23
<212> TYPE: PRT

<213> ORGANISM: Artificial Sequence
<220> FEATURE:
<223> OTHER INFORMATION: Chemically synthesized

<400> SEQUENCE: 266

Ala Ile Gln Leu Thr Gln Ser Pro Ser Ser Leu Ser Ala Ser Val Gly
 1               5                  10                  15

Asp Arg Val Thr Ile Thr Cys
            20

<210> SEQ ID NO 267
<211> LENGTH: 23
<212> TYPE: PRT
<213> ORGANISM: Artificial Sequence
<220> FEATURE:
<223> OTHER INFORMATION: Chemically synthesized

<400> SEQUENCE: 267

Asn Ile Gln Met Thr Gln Ser Pro Ser Ala Met Ser Ala Ser Val Gly
 1               5                  10                  15

Asp Arg Val Thr Ile Thr Cys
            20

<210> SEQ ID NO 268
<211> LENGTH: 23
<212> TYPE: PRT
<213> ORGANISM: Artificial Sequence
<220> FEATURE:
<223> OTHER INFORMATION: Chemically synthesized

<400> SEQUENCE: 268

Asp Val Val Met Thr Gln Ser Pro Leu Ser Leu Pro Val Thr Leu Gly
 1               5                  10                  15

Gln Pro Ala Ser Ile Ser Cys
            20

<210> SEQ ID NO 269
<211> LENGTH: 23
<212> TYPE: PRT
<213> ORGANISM: Artificial Sequence
<220> FEATURE:
<223> OTHER INFORMATION: Chemically synthesized

<400> SEQUENCE: 269

Asp Ile Val Met Thr Gln Thr Pro Leu Ser Ser Pro Val Thr Leu Gly
 1               5                  10                  15

Gln Pro Ala Ser Ile Ser Cys
            20

<210> SEQ ID NO 270
<211> LENGTH: 23
<212> TYPE: PRT
<213> ORGANISM: Artificial Sequence
<220> FEATURE:
<223> OTHER INFORMATION: Chemically synthesized

<400> SEQUENCE: 270

Asp Val Val Met Thr Gln Ser Pro Ala Phe Leu Ser Val Thr Pro Gly
 1               5                  10                  15

Glu Lys Val Thr Ile Thr Cys
            20

<210> SEQ ID NO 271
<211> LENGTH: 23
<212> TYPE: PRT

```
<213> ORGANISM: Artificial Sequence
<220> FEATURE:
<223> OTHER INFORMATION: Chemically synthesized

<400> SEQUENCE: 271

Val Ile Trp Met Thr Gln Ser Pro Ser Leu Leu Ser Ala Ser Thr Gly
 1               5                  10                  15

Asp Arg Val Thr Ile Ser Cys
            20

<210> SEQ ID NO 272
<211> LENGTH: 23
<212> TYPE: PRT
<213> ORGANISM: Artificial Sequence
<220> FEATURE:
<223> OTHER INFORMATION: Chemically synthesized

<400> SEQUENCE: 272

Ala Ile Arg Met Thr Gln Ser Pro Ser Ser Phe Ser Ala Ser Thr Gly
 1               5                  10                  15

Asp Arg Val Thr Ile Thr Cys
            20

<210> SEQ ID NO 273
<211> LENGTH: 15
<212> TYPE: PRT
<213> ORGANISM: Artificial Sequence
<220> FEATURE:
<223> OTHER INFORMATION: Chemically synthesized

<400> SEQUENCE: 273

Trp Phe Gln Gln Lys Pro Gly Lys Ala Pro Lys Ser Leu Ile Tyr
 1               5                  10                  15

<210> SEQ ID NO 274
<211> LENGTH: 15
<212> TYPE: PRT
<213> ORGANISM: Artificial Sequence
<220> FEATURE:
<223> OTHER INFORMATION: Chemically synthesized

<400> SEQUENCE: 274

Trp Tyr Gln Gln Lys Pro Ala Lys Ala Pro Lys Leu Phe Ile Tyr
 1               5                  10                  15

<210> SEQ ID NO 275
<211> LENGTH: 15
<212> TYPE: PRT
<213> ORGANISM: Artificial Sequence
<220> FEATURE:
<223> OTHER INFORMATION: Chemically synthesized

<400> SEQUENCE: 275

Trp Tyr Leu Gln Lys Pro Gly Gln Pro Pro Gln Leu Leu Ile Tyr
 1               5                  10                  15

<210> SEQ ID NO 276
<211> LENGTH: 15
<212> TYPE: PRT
<213> ORGANISM: Artificial Sequence
<220> FEATURE:
<223> OTHER INFORMATION: Chemically synthesized

<400> SEQUENCE: 276

Trp Tyr Gln Gln Lys Pro Gly Lys Ala Pro Glu Leu Leu Ile Tyr
 1               5                  10                  15
```

<210> SEQ ID NO 277
<211> LENGTH: 15
<212> TYPE: PRT
<213> ORGANISM: Artificial Sequence
<220> FEATURE:
<223> OTHER INFORMATION: Chemically synthesized

<400> SEQUENCE: 277

Trp Tyr Gln Gln Lys Pro Gly Lys Val Pro Lys Leu Leu Ile Tyr
 1               5                  10                  15

<210> SEQ ID NO 278
<211> LENGTH: 15
<212> TYPE: PRT
<213> ORGANISM: Artificial Sequence
<220> FEATURE:
<223> OTHER INFORMATION: Chemically synthesized

<400> SEQUENCE: 278

Trp Tyr Gln Gln Lys Pro Glu Lys Ala Pro Lys Ser Leu Ile Tyr
 1               5                  10                  15

<210> SEQ ID NO 279
<211> LENGTH: 15
<212> TYPE: PRT
<213> ORGANISM: Artificial Sequence
<220> FEATURE:
<223> OTHER INFORMATION: Chemically synthesized

<400> SEQUENCE: 279

Trp Phe Gln Gln Arg Pro Gly Gln Ser Pro Arg Arg Leu Ile Tyr
 1               5                  10                  15

<210> SEQ ID NO 280
<211> LENGTH: 15
<212> TYPE: PRT
<213> ORGANISM: Artificial Sequence
<220> FEATURE:
<223> OTHER INFORMATION: Chemically synthesized

<400> SEQUENCE: 280

Trp Tyr Gln Gln Lys Pro Asp Gln Ser Pro Lys Leu Leu Ile Lys
 1               5                  10                  15

<210> SEQ ID NO 281
<211> LENGTH: 15
<212> TYPE: PRT
<213> ORGANISM: Artificial Sequence
<220> FEATURE:
<223> OTHER INFORMATION: Chemically synthesized

<400> SEQUENCE: 281

Trp Phe Gln Gln Lys Pro Gly Lys Val Pro Lys His Leu Ile Tyr
 1               5                  10                  15

<210> SEQ ID NO 282
<211> LENGTH: 15
<212> TYPE: PRT
<213> ORGANISM: Artificial Sequence
<220> FEATURE:
<223> OTHER INFORMATION: Chemically synthesized

<400> SEQUENCE: 282

Trp Tyr Gln Gln Lys Pro Gly Lys Ala Pro Lys Arg Leu Ile Tyr
 1               5                  10                  15

<210> SEQ ID NO 283

```
<211> LENGTH: 15
<212> TYPE: PRT
<213> ORGANISM: Artificial Sequence
<220> FEATURE:
<223> OTHER INFORMATION: Chemically synthesized

<400> SEQUENCE: 283

Trp Leu Gln Gln Arg Pro Gly Gln Pro Pro Arg Leu Leu Ile Tyr
1               5                   10                  15

<210> SEQ ID NO 284
<211> LENGTH: 15
<212> TYPE: PRT
<213> ORGANISM: Artificial Sequence
<220> FEATURE:
<223> OTHER INFORMATION: Chemically synthesized

<400> SEQUENCE: 284

Trp Tyr Gln Gln Lys Pro Gly Glu Ala Ala Ile Phe Ile Ile Gln
1               5                   10                  15

<210> SEQ ID NO 285
<211> LENGTH: 95
<212> TYPE: PRT
<213> ORGANISM: Artificial Sequence
<220> FEATURE:
<223> OTHER INFORMATION: Chemically synthesized

<400> SEQUENCE: 285

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 286
<211> LENGTH: 95
<212> TYPE: PRT
<213> ORGANISM: Artificial Sequence
<220> FEATURE:
<223> OTHER INFORMATION: Chemically synthesized

<400> SEQUENCE: 286

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95
```

```
<210> SEQ ID NO 287
<211> LENGTH: 95
<212> TYPE: PRT
<213> ORGANISM: Artificial Sequence
<220> FEATURE:
<223> OTHER INFORMATION: Chemically synthesized

<400> SEQUENCE: 287
```

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95

```
<210> SEQ ID NO 288
<211> LENGTH: 95
<212> TYPE: PRT
<213> ORGANISM: Artificial Sequence
<220> FEATURE:
<223> OTHER INFORMATION: Chemically synthesized

<400> SEQUENCE: 288
```

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95

```
<210> SEQ ID NO 289
<211> LENGTH: 95
<212> TYPE: PRT
<213> ORGANISM: Artificial Sequence
<220> FEATURE:
<223> OTHER INFORMATION: Chemically synthesized

<400> SEQUENCE: 289
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

```
Glu Asp Val Ala Thr Tyr Tyr Cys Gln Lys Tyr Asn Ser Ala Pro
                85                  90                  95

<210> SEQ ID NO 290
<211> LENGTH: 95
<212> TYPE: PRT
<213> ORGANISM: Artificial Sequence
<220> FEATURE:
<223> OTHER INFORMATION: Chemically synthesized

<400> SEQUENCE: 290

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95

<210> SEQ ID NO 291
<211> LENGTH: 95
<212> TYPE: PRT
<213> ORGANISM: Artificial Sequence
<220> FEATURE:
<223> OTHER INFORMATION: Chemically synthesized

<400> SEQUENCE: 291

Asn Ile Gln Met Thr Gln Ser Pro Ser Ala Met Ser Ala Ser Val Gly
 1               5                  10                  15

Asp Arg Val Thr Ile Thr Cys Arg Ala Arg Gln Gly Ile Ser Asn Tyr
                20                  25                  30

Leu Ala Trp Phe Gln Gln Lys Pro Gly Lys Val Pro Lys His Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95

<210> SEQ ID NO 292
<211> LENGTH: 95
<212> TYPE: PRT
<213> ORGANISM: Artificial Sequence
<220> FEATURE:
<223> OTHER INFORMATION: Chemically synthesized

<400> SEQUENCE: 292

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
                20                  25                  30

Leu Ala Trp Phe Gln Gln Lys Pro Gly Lys Ala Pro Lys Ser Leu Ile
            35                  40                  45
```

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro
                 85                  90                  95

<210> SEQ ID NO 293
<211> LENGTH: 95
<212> TYPE: PRT
<213> ORGANISM: Artificial Sequence
<220> FEATURE:
<223> OTHER INFORMATION: Chemically synthesized

<400> SEQUENCE: 293

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro
                 85                  90                  95

<210> SEQ ID NO 294
<211> LENGTH: 95
<212> TYPE: PRT
<213> ORGANISM: Artificial Sequence
<220> FEATURE:
<223> OTHER INFORMATION: Chemically synthesized

<400> SEQUENCE: 294

Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
                 20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro
                 85                  90                  95

<210> SEQ ID NO 295
<211> LENGTH: 95
<212> TYPE: PRT
<213> ORGANISM: Artificial Sequence
<220> FEATURE:
<223> OTHER INFORMATION: Chemically synthesized

<400> SEQUENCE: 295

Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
                 20                  25                  30

```
Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro
                 85                  90                  95

<210> SEQ ID NO 296
<211> LENGTH: 95
<212> TYPE: PRT
<213> ORGANISM: Artificial Sequence
<220> FEATURE:
<223> OTHER INFORMATION: Chemically synthesized

<400> SEQUENCE: 296

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro
                 85                  90                  95

<210> SEQ ID NO 297
<211> LENGTH: 95
<212> TYPE: PRT
<213> ORGANISM: Artificial Sequence
<220> FEATURE:
<223> OTHER INFORMATION: Chemically synthesized

<400> SEQUENCE: 297

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro
                 85                  90                  95

<210> SEQ ID NO 298
<211> LENGTH: 95
<212> TYPE: PRT
<213> ORGANISM: Artificial Sequence
<220> FEATURE:
<223> OTHER INFORMATION: Chemically synthesized

<400> SEQUENCE: 298
```

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro
                85                  90                  95
```

<210> SEQ ID NO 299
<211> LENGTH: 95
<212> TYPE: PRT
<213> ORGANISM: Artificial Sequence
<220> FEATURE:
<223> OTHER INFORMATION: Chemically synthesized

<400> SEQUENCE: 299

```
Ala Ile Arg Met Thr Gln Ser Pro Phe Ser Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Ala Lys Ala Pro Lys Leu Phe Ile
        35                  40                  45

Tyr Tyr Ala Ser Ser Leu Gln Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Pro
                85                  90                  95
```

<210> SEQ ID NO 300
<211> LENGTH: 95
<212> TYPE: PRT
<213> ORGANISM: Artificial Sequence
<220> FEATURE:
<223> OTHER INFORMATION: Chemically synthesized

<400> SEQUENCE: 300

```
Ala Ile Arg Met Thr Gln Ser Pro Ser Ser Phe Ser Ala Ser Thr Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Tyr Ser Tyr Pro
                85                  90                  95
```

<210> SEQ ID NO 301
<211> LENGTH: 95
<212> TYPE: PRT
<213> ORGANISM: Artificial Sequence
<220> FEATURE:

<223> OTHER INFORMATION: Chemically synthesized

<400> SEQUENCE: 301

Val Ile Trp Met Thr Gln Ser Pro Ser Leu Ser Ala Ser Thr Gly
1               5                   10                  15

Asp Arg Val Thr Ile Ser Cys Arg Met Ser Gln Gly Ile Ser Ser Tyr
            20                  25                  30

Leu Ala Trp Tyr Gln Gln Lys Pro Gly Lys Ala Pro Glu Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Tyr Ser Phe Pro
                85                  90                  95

<210> SEQ ID NO 302
<211> LENGTH: 95
<212> TYPE: PRT
<213> ORGANISM: Artificial Sequence
<220> FEATURE:
<223> OTHER INFORMATION: Chemically synthesized

<400> SEQUENCE: 302

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro
                85                  90                  95

<210> SEQ ID NO 303
<211> LENGTH: 95
<212> TYPE: PRT
<213> ORGANISM: Artificial Sequence
<220> FEATURE:
<223> OTHER INFORMATION: Chemically synthesized

<400> SEQUENCE: 303

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95

<210> SEQ ID NO 304

```
<211> LENGTH: 101
<212> TYPE: PRT
<213> ORGANISM: Artificial Sequence
<220> FEATURE:
<223> OTHER INFORMATION: Chemically synthesized

<400> SEQUENCE: 304

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro
            100

<210> SEQ ID NO 305
<211> LENGTH: 101
<212> TYPE: PRT
<213> ORGANISM: Artificial Sequence
<220> FEATURE:
<223> OTHER INFORMATION: Chemically synthesized

<400> SEQUENCE: 305

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro
            100

<210> SEQ ID NO 306
<211> LENGTH: 100
<212> TYPE: PRT
<213> ORGANISM: Artificial Sequence
<220> FEATURE:
<223> OTHER INFORMATION: Chemically synthesized

<400> SEQUENCE: 306

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45
```

```
Pro Arg Arg Leu Ile Tyr Lys Val Ser Asn Arg Asp Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro
        100

<210> SEQ ID NO 307
<211> LENGTH: 100
<212> TYPE: PRT
<213> ORGANISM: Artificial Sequence
<220> FEATURE:
<223> OTHER INFORMATION: Chemically synthesized

<400> SEQUENCE: 307

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
                 20                  25                  30

Asp Gly Asn Thr Tyr Leu Asn Trp Phe Gln Gln Arg Pro Gly Gln Ser
             35                  40                  45

Pro Arg Arg Leu Ile Tyr Lys Val Ser Asn Trp Asp Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro
        100

<210> SEQ ID NO 308
<211> LENGTH: 100
<212> TYPE: PRT
<213> ORGANISM: Artificial Sequence
<220> FEATURE:
<223> OTHER INFORMATION: Chemically synthesized

<400> SEQUENCE: 308

Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu His Ser
                 20                  25                  30

Asp Gly Lys Thr Tyr Leu Tyr Trp Tyr Leu Gln Lys Pro Gly Gln Ser
             35                  40                  45

Pro Gln Leu Leu Ile Tyr Glu Val Ser Ser Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Ile His Leu Pro
        100

<210> SEQ ID NO 309
<211> LENGTH: 100
<212> TYPE: PRT
<213> ORGANISM: Artificial Sequence
<220> FEATURE:
```

<223> OTHER INFORMATION: Chemically synthesized

<400> SEQUENCE: 309

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro
            100

<210> SEQ ID NO 310
<211> LENGTH: 100
<212> TYPE: PRT
<213> ORGANISM: Artificial Sequence
<220> FEATURE:
<223> OTHER INFORMATION: Chemically synthesized

<400> SEQUENCE: 310

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100

<210> SEQ ID NO 311
<211> LENGTH: 100
<212> TYPE: PRT
<213> ORGANISM: Artificial Sequence
<220> FEATURE:
<223> OTHER INFORMATION: Chemically synthesized

<400> SEQUENCE: 311

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
            85                  90                  95

Leu Gln Thr Pro
            100

<210> SEQ ID NO 312
<211> LENGTH: 100
<212> TYPE: PRT
<213> ORGANISM: Artificial Sequence
<220> FEATURE:
<223> OTHER INFORMATION: Chemically synthesized

<400> SEQUENCE: 312

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
            85                  90                  95

Thr Gln Phe Pro
            100

<210> SEQ ID NO 313
<211> LENGTH: 96
<212> TYPE: PRT
<213> ORGANISM: Artificial Sequence
<220> FEATURE:
<223> OTHER INFORMATION: Chemically synthesized

<400> SEQUENCE: 313

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
            85                  90                  95

<210> SEQ ID NO 314
<211> LENGTH: 96
<212> TYPE: PRT
<213> ORGANISM: Artificial Sequence
<220> FEATURE:
<223> OTHER INFORMATION: Chemically synthesized

<400> SEQUENCE: 314

Glu Ile Val Leu Thr Gln Ser Pro Ala Thr Leu Ser Leu Ser Pro Gly
1               5                   10                  15

-continued

Glu Arg Ala Thr Leu Ser Cys Gly Ala Ser Gln Ser Val Ser Ser
            20                  25                  30

Tyr Leu Ala Trp Tyr Gln Gln Lys Pro Gly Leu Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 315
<211> LENGTH: 95
<212> TYPE: PRT
<213> ORGANISM: Artificial Sequence
<220> FEATURE:
<223> OTHER INFORMATION: Chemically synthesized

<400> SEQUENCE: 315

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95

<210> SEQ ID NO 316
<211> LENGTH: 95
<212> TYPE: PRT
<213> ORGANISM: Artificial Sequence
<220> FEATURE:
<223> OTHER INFORMATION: Chemically synthesized

<400> SEQUENCE: 316

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95

<210> SEQ ID NO 317
<211> LENGTH: 95
<212> TYPE: PRT
<213> ORGANISM: Artificial Sequence
<220> FEATURE:
<223> OTHER INFORMATION: Chemically synthesized

<400> SEQUENCE: 317

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 318
<211> LENGTH: 95
<212> TYPE: PRT
<213> ORGANISM: Artificial Sequence
<220> FEATURE:
<223> OTHER INFORMATION: Chemically synthesized

<400> SEQUENCE: 318

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His
                85                  90                  95

<210> SEQ ID NO 319
<211> LENGTH: 96
<212> TYPE: PRT
<213> ORGANISM: Artificial Sequence
<220> FEATURE:
<223> OTHER INFORMATION: Chemically synthesized

<400> SEQUENCE: 319

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ser Trp Tyr Gln Gln Lys Pro Gly Gln Ala Pro Arg Leu Leu
            35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

<210> SEQ ID NO 320
<211> LENGTH: 101
<212> TYPE: PRT
<213> ORGANISM: Artificial Sequence

```
<220> FEATURE:
<223> OTHER INFORMATION: Chemically synthesized

<400> SEQUENCE: 320

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Tyr Ser Thr Pro
            100

<210> SEQ ID NO 321
<211> LENGTH: 95
<212> TYPE: PRT
<213> ORGANISM: Artificial Sequence
<220> FEATURE:
<223> OTHER INFORMATION: Chemically synthesized

<400> SEQUENCE: 321

Glu Thr Thr Leu Thr Gln Ser Pro Ala Phe Met Ser Ala Thr Pro Gly
 1               5                  10                  15

Asp Lys Val Asn Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Pro Pro Arg Phe Ser Gly
 50                  55                  60

Ser Gly Tyr Gly Thr Asp Phe Thr Leu Thr Ile Asn Asn Ile Glu Ser
 65                  70                  75                  80

Glu Asp Ala Ala Tyr Tyr Phe Cys Leu Gln His Asp Asn Phe Pro
                85                  90                  95

<210> SEQ ID NO 322
<211> LENGTH: 95
<212> TYPE: PRT
<213> ORGANISM: Artificial Sequence
<220> FEATURE:
<223> OTHER INFORMATION: Chemically synthesized

<400> SEQUENCE: 322

Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
 50                  55                  60

Ser Gly Ser Gly Thr Asp Phe Thr Leu Thr Ile Asn Ser Leu Glu Ala
 65                  70                  75                  80
```

```
Glu Asp Ala Ala Thr Tyr Tyr Cys His Gln Ser Ser Ser Leu Pro
                85                  90                  95
```

<210> SEQ ID NO 323
<211> LENGTH: 95
<212> TYPE: PRT
<213> ORGANISM: Artificial Sequence
<220> FEATURE:
<223> OTHER INFORMATION: Chemically synthesized

<400> SEQUENCE: 323

```
Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Ser Ile Gly Ser Ser
                20                  25                  30

Leu His Trp Tyr Gln Gln Lys Pro Asp Gln Ser Pro Lys Leu Leu Ile
            35                  40                  45

Lys Tyr Ala Ser Gln Ser Phe Ser Gly Val Pro Ser Arg Phe Ser Gly
50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro
                85                  90                  95
```

<210> SEQ ID NO 324
<211> LENGTH: 95
<212> TYPE: PRT
<213> ORGANISM: Artificial Sequence
<220> FEATURE:
<223> OTHER INFORMATION: Chemically synthesized

<400> SEQUENCE: 324

```
Asp Val Val Met Thr Gln Ser Pro Ala Phe Leu Ser Val Thr Pro Gly
 1               5                  10                  15

Glu Lys Val Thr Ile Thr Cys Gln Ala Ser Glu Gly Ile Gly Asn Tyr
                20                  25                  30

Leu Tyr Trp Tyr Gln Gln Lys Pro Asp Gln Ala Pro Lys Leu Leu Ile
            35                  40                  45

Lys Tyr Ala Ser Gln Ser Ile Ser Gly Val Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Asn Lys His Pro
                85                  90                  95
```

<210> SEQ ID NO 325
<211> LENGTH: 98
<212> TYPE: PRT
<213> ORGANISM: Artificial Sequence
<220> FEATURE:
<223> OTHER INFORMATION: Chemically synthesized

<400> SEQUENCE: 325

```
Gln Ser Val Leu Thr Gln Pro Pro Ser Val Ser Glu Ala Pro Arg Gln
 1               5                  10                  15

Arg Val Thr Ile Ser Cys Ser Gly Ser Ser Ser Asn Ile Gly Asn Asn
                20                  25                  30

Ala Val Asn Trp Tyr Gln Gln Leu Pro Gly Lys Ala Pro Lys Leu Leu
            35                  40                  45

Ile Tyr Tyr Asp Asp Leu Leu Pro Ser Gly Val Ser Asp Arg Phe Ser
50                  55                  60
```

```
Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly

<210> SEQ ID NO 326
<211> LENGTH: 99
<212> TYPE: PRT
<213> ORGANISM: Artificial Sequence
<220> FEATURE:
<223> OTHER INFORMATION: Chemically synthesized

<400> SEQUENCE: 326

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
             20                  25                  30

Tyr Asp Val His Trp Tyr Gln Gln Leu Pro Gly Thr Ala Pro Lys Leu
         35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly

<210> SEQ ID NO 327
<211> LENGTH: 98
<212> TYPE: PRT
<213> ORGANISM: Artificial Sequence
<220> FEATURE:
<223> OTHER INFORMATION: Chemically synthesized

<400> SEQUENCE: 327

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
             20                  25                  30

Thr Val Asn Trp Tyr Gln Gln Leu Pro Gly Thr Ala Pro Lys Leu Leu
         35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly

<210> SEQ ID NO 328
<211> LENGTH: 98
<212> TYPE: PRT
<213> ORGANISM: Artificial Sequence
<220> FEATURE:
<223> OTHER INFORMATION: Chemically synthesized

<400> SEQUENCE: 328
```

```
Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
                20                  25                  30

Tyr Val Tyr Trp Tyr Gln Gln Leu Pro Gly Thr Ala Pro Lys Leu Leu
                35                  40                  45

Ile Tyr Arg Asn Asn Gln Arg Pro Ser Gly Val Pro Asp Arg Phe Ser
             50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly
```

<210> SEQ ID NO 329
<211> LENGTH: 98
<212> TYPE: PRT
<213> ORGANISM: Artificial Sequence
<220> FEATURE:
<223> OTHER INFORMATION: Chemically synthesized

<400> SEQUENCE: 329

```
Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
                35                  40                  45

Ile Tyr Asp Asn Asn Lys Arg Pro Ser Gly Ile Pro Asp Arg Phe Ser
             50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala
```

<210> SEQ ID NO 330
<211> LENGTH: 99
<212> TYPE: PRT
<213> ORGANISM: Artificial Sequence
<220> FEATURE:
<223> OTHER INFORMATION: Chemically synthesized

<400> SEQUENCE: 330

```
Gln Ser Ala Leu Thr Gln Pro Pro Ser Ala Ser Gly Ser Pro Gly Gln
 1               5                  10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
                35                  40                  45

Met Ile Tyr Glu Val Ser Lys Arg Pro Ser Gly Val Pro Asp Arg Phe
             50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Tyr Ala Gly Ser
                 85                  90                  95

Asn Asn Phe
```

-continued

<210> SEQ ID NO 331
<211> LENGTH: 99
<212> TYPE: PRT
<213> ORGANISM: Artificial Sequence
<220> FEATURE:
<223> OTHER INFORMATION: Chemically synthesized

<400> SEQUENCE: 331

Gln Ser Ala Leu Thr Gln Pro Arg Ser Val Ser Gly Ser Pro Gly Gln
 1               5                  10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Phe

<210> SEQ ID NO 332
<211> LENGTH: 99
<212> TYPE: PRT
<213> ORGANISM: Artificial Sequence
<220> FEATURE:
<223> OTHER INFORMATION: Chemically synthesized

<400> SEQUENCE: 332

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu

<210> SEQ ID NO 333
<211> LENGTH: 99
<212> TYPE: PRT
<213> ORGANISM: Artificial Sequence
<220> FEATURE:
<223> OTHER INFORMATION: Chemically synthesized

<400> SEQUENCE: 333

Gln Ser Ala Leu Thr Gln Pro Pro Ser Val Ser Gly Ser Pro Gly Gln
 1               5                  10                  15

Ser Val Thr Ile Ser Cys Thr Gly Thr Ser Ser Asp Val Gly Ser Tyr
                20                  25                  30

Asn Arg Val Ser Trp Tyr Gln Gln Pro Gly Thr Ala Pro Lys Leu
            35                  40                  45

Met Ile Tyr Glu Val Ser Asn Arg Pro Ser Gly Val Pro Asp Arg Phe
                50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Leu Tyr Thr Ser Ser
                 85                  90                  95

Ser Thr Phe

<210> SEQ ID NO 334
<211> LENGTH: 99
<212> TYPE: PRT
<213> ORGANISM: Artificial Sequence
<220> FEATURE:
<223> OTHER INFORMATION: Chemically synthesized

<400> SEQUENCE: 334

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Ser Tyr
                 20                  25                  30

Asn Leu Val Ser Trp Tyr Gln Gln His Pro Gly Lys Ala Pro Lys Leu
             35                  40                  45

Met Ile Tyr Glu Val Ser Lys Arg Pro Ser Gly Val Ser Asn Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                 85                  90                  95

Ser Thr Phe

<210> SEQ ID NO 335
<211> LENGTH: 95
<212> TYPE: PRT
<213> ORGANISM: Artificial Sequence
<220> FEATURE:
<223> OTHER INFORMATION: Chemically synthesized

<400> SEQUENCE: 335

Ser Tyr Glu Leu Thr Gln Pro Pro Ser Val Ser Val Ser Pro Gly Gln
 1               5                  10                  15

Thr Ala Ser Ile Thr Cys Ser Gly Asp Lys Leu Gly Asp Lys Tyr Ala
                 20                  25                  30

Cys Trp Tyr Gln Gln Lys Pro Gly Gln Ser Pro Val Leu Val Ile Tyr
             35                  40                  45

Gln Asp Ser Lys Arg Pro Ser Gly Ile Pro Glu Arg Phe Ser Gly Ser
         50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Thr Ala
                 85                  90                  95

<210> SEQ ID NO 336
<211> LENGTH: 95
<212> TYPE: PRT
<213> ORGANISM: Artificial Sequence
<220> FEATURE:
<223> OTHER INFORMATION: Chemically synthesized

<400> SEQUENCE: 336

```
Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ser Ser Thr Ala
                85                  90                  95
```

<210> SEQ ID NO 337
<211> LENGTH: 96
<212> TYPE: PRT
<213> ORGANISM: Artificial Sequence
<220> FEATURE:
<223> OTHER INFORMATION: Chemically synthesized

<400> SEQUENCE: 337

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Ser Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ser Ser Gly Asn His
                85                  90                  95
```

<210> SEQ ID NO 338
<211> LENGTH: 96
<212> TYPE: PRT
<213> ORGANISM: Artificial Sequence
<220> FEATURE:
<223> OTHER INFORMATION: Chemically synthesized

<400> SEQUENCE: 338

```
Ser Tyr Glu Leu Thr Gln Pro Pro Ser Val Ser Val Ser Leu Gly Gln
1               5                   10                  15

Met Ala Arg Ile Thr Cys Ser Gly Glu Ala Leu Pro Lys Lys Tyr Ala
            20                  25                  30

Tyr Trp Tyr Gln Gln Lys Pro Gly Gln Phe Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Ile Val Thr Leu Thr Ile Ser Gly Val Gln Ala Glu
65                  70                  75                  80

Asp Glu Ala Asp Tyr Tyr Cys Leu Ser Ala Asp Ser Ser Gly Thr Tyr
                85                  90                  95
```

<210> SEQ ID NO 339
<211> LENGTH: 96
<212> TYPE: PRT
<213> ORGANISM: Artificial Sequence
<220> FEATURE:

<223> OTHER INFORMATION: Chemically synthesized

<400> SEQUENCE: 339

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

<210> SEQ ID NO 340
<211> LENGTH: 96
<212> TYPE: PRT
<213> ORGANISM: Artificial Sequence
<220> FEATURE:
<223> OTHER INFORMATION: Chemically synthesized

<400> SEQUENCE: 340

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

<210> SEQ ID NO 341
<211> LENGTH: 94
<212> TYPE: PRT
<213> ORGANISM: Artificial Sequence
<220> FEATURE:
<223> OTHER INFORMATION: Chemically synthesized

<400> SEQUENCE: 341

Ser Tyr Glu Leu Thr Gln Leu Pro Ser Val Ser Val Ser Pro Gly Gln
1               5                   10                  15

Thr Ala Arg Ile Thr Cys Ser Gly Asp Val Leu Gly Glu Asn Tyr Ala
            20                  25                  30

Asp Trp Tyr Gln Gln Lys Pro Gly Gln Ala Pro Glu Leu Val Ile Tyr
        35                  40                  45

Glu Asp Ser Glu Arg Tyr Pro Gly Ile Pro Arg Phe Ser Gly Ser
    50                  55                  60

Thr Ser Gly Asn Thr Thr Thr Leu Thr Ile Ser Arg Val Leu Thr Glu
65                  70                  75                  80

Asp Glu Ala Asp Tyr Tyr Cys Leu Ser Gly Asp Glu Asp Asn
                85                  90

<210> SEQ ID NO 342

```
<211> LENGTH: 96
<212> TYPE: PRT
<213> ORGANISM: Artificial Sequence
<220> FEATURE:
<223> OTHER INFORMATION: Chemically synthesized

<400> SEQUENCE: 342

Ser Tyr Glu Leu Met Gln Pro Pro Ser Val Ser Val Ser Pro Gly Gln
 1               5                  10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
         35                  40                  45

Lys Asp Ser Glu Arg Pro Ser Gly Ile Pro Glu Arg Phe Ser Gly Ser
     50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gln Ser Ala Asp Ser Ser Gly Thr Tyr
                 85                  90                  95

<210> SEQ ID NO 343
<211> LENGTH: 94
<212> TYPE: PRT
<213> ORGANISM: Artificial Sequence
<220> FEATURE:
<223> OTHER INFORMATION: Chemically synthesized

<400> SEQUENCE: 343

Ser Tyr Glu Leu Thr Gln Pro Ser Ser Val Ser Val Ser Pro Gly Gln
 1               5                  10                  15

Thr Ala Arg Ile Thr Cys Ser Gly Asp Val Leu Ala Lys Lys Tyr Ala
            20                  25                  30

Arg Trp Phe Gln Gln Lys Pro Gly Gln Ala Pro Val Leu Val Ile Tyr
         35                  40                  45

Lys Asp Ser Glu Arg Pro Ser Gly Ile Pro Glu Arg Phe Ser Gly Ser
     50                  55                  60

Ser Ser Gly Thr Thr Val Thr Leu Thr Ile Ser Gly Ala Gln Val Glu
 65                  70                  75                  80

Asp Glu Ala Asp Tyr Tyr Cys Tyr Ser Ala Ala Asp Asn Asn
                 85                  90

<210> SEQ ID NO 344
<211> LENGTH: 103
<212> TYPE: PRT
<213> ORGANISM: Artificial Sequence
<220> FEATURE:
<223> OTHER INFORMATION: Chemically synthesized

<400> SEQUENCE: 344

Leu Pro Val Leu Thr Gln Pro Pro Ser Ala Ser Ala Leu Leu Gly Ala
 1               5                  10                  15

Ser Ile Lys Leu Thr Cys Thr Leu Ser Ser Glu His Ser Thr Tyr Thr
            20                  25                  30

Ile Glu Trp Tyr Gln Gln Arg Pro Gly Arg Ser Pro Gln Tyr Ile Met
         35                  40                  45

Lys Val Lys Ser Asp Gly Ser His Ser Lys Gly Asp Gly Ile Pro Asp
     50                  55                  60

Arg Phe Met Gly Ser Ser Ser Gly Ala Asp Arg Tyr Leu Thr Phe Ser
 65                  70                  75                  80
```

```
Asn Leu Gln Ser Asp Asp Glu Ala Glu Tyr His Cys Gly Glu Ser His
            85                  90                  95

Thr Ile Asp Gly Gln Val Gly
            100

<210> SEQ ID NO 345
<211> LENGTH: 99
<212> TYPE: PRT
<213> ORGANISM: Artificial Sequence
<220> FEATURE:
<223> OTHER INFORMATION: Chemically synthesized

<400> SEQUENCE: 345

Gln Pro Val Leu Thr Gln Ser Ser Ala Ser Ala Ser Leu Gly Ser
 1               5                  10                  15

Ser Val Lys Leu Thr Cys Thr Leu Ser Ser Gly His Ser Ser Tyr Ile
                20                  25                  30

Ile Ala Trp His Gln Gln Pro Gly Lys Ala Pro Arg Tyr Leu Met
            35                  40                  45

Lys Leu Glu Gly Ser Gly Ser Tyr Asn Lys Gly Ser Gly Val Pro Asp
        50                  55                  60

Arg Phe Ser Gly Ser Ser Ser Gly Ala Asp Arg Tyr Leu Thr Ile Ser
 65                  70                  75                  80

Asn Leu Gln Leu Glu Asp Glu Ala Asp Tyr Tyr Cys Glu Thr Trp Asp
                85                  90                  95

Ser Asn Thr

<210> SEQ ID NO 346
<211> LENGTH: 99
<212> TYPE: PRT
<213> ORGANISM: Artificial Sequence
<220> FEATURE:
<223> OTHER INFORMATION: Chemically synthesized

<400> SEQUENCE: 346

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gly His Ser Ser Tyr Ala
                20                  25                  30

Ile Ala Trp His Gln Gln Pro Glu Lys Gly Pro Arg Tyr Leu Met
            35                  40                  45

Lys Leu Asn Ser Asp Gly Ser His Ser Lys Gly Asp Gly Ile Pro Asp
        50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gln Thr Trp Gly
                85                  90                  95

Thr Gly Ile

<210> SEQ ID NO 347
<211> LENGTH: 104
<212> TYPE: PRT
<213> ORGANISM: Artificial Sequence
<220> FEATURE:
<223> OTHER INFORMATION: Chemically synthesized

<400> SEQUENCE: 347

Gln Pro Val Leu Thr Gln Pro Pro Ser Ser Ser Ala Ser Pro Gly Glu
 1               5                  10                  15
```

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser Asp Lys Gln Gly Ser Gly Val
    50                  55                  60

Pro Ser Arg Phe Ser Gly Ser Lys Asp Ala Ser Ala Asn Thr Gly Ile
65                  70                  75                  80

Leu Leu Ile Ser Gly Leu Gln Ser Glu Asp Glu Ala Asp Tyr Tyr Cys
                85                  90                  95

Met Ile Trp Pro Ser Asn Ala Ser
            100

<210> SEQ ID NO 348
<211> LENGTH: 104
<212> TYPE: PRT
<213> ORGANISM: Artificial Sequence
<220> FEATURE:
<223> OTHER INFORMATION: Chemically synthesized

<400> SEQUENCE: 348

Gln Ala Val Leu Thr Gln Pro Ala Ser Leu Ser Ala Ser Pro Gly Ala
1               5                   10                  15

Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr
            35                  40                  45

Leu Leu Arg Tyr Lys Ser Asp Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Ser Ala Ser
            100

<210> SEQ ID NO 349
<211> LENGTH: 105
<212> TYPE: PRT
<213> ORGANISM: Artificial Sequence
<220> FEATURE:
<223> OTHER INFORMATION: Chemically synthesized

<400> SEQUENCE: 349

Gln Pro Val Leu Thr Gln Pro Ser Ser His Ser Ala Ser Ser Gly Ala
1               5                   10                  15

Ser Val Arg Leu Thr Cys Met Leu Ser Ser Gly Phe Ser Val Gly Asp
            20                  25                  30

Phe Trp Ile Arg Trp Tyr Gln Gln Lys Pro Gly Asn Pro Pro Arg Tyr
            35                  40                  45

Leu Leu Tyr Tyr His Ser Asp Ser Asn Lys Gln Gln Gly Ser Gly Val
    50                  55                  60

Pro Ser Arg Phe Ser Gly Ser Asn Asp Ala Ser Ala Asn Ala Gly Ile
65                  70                  75                  80

Leu Arg Ile Ser Gly Leu Gln Pro Glu Asp Glu Ala Asp Tyr Tyr Cys
                85                  90                  95

Gly Thr Trp His Ser Asn Ser Lys Thr
            100                 105

```
<210> SEQ ID NO 350
<211> LENGTH: 98
<212> TYPE: PRT
<213> ORGANISM: Artificial Sequence
<220> FEATURE:
<223> OTHER INFORMATION: Chemically synthesized

<400> SEQUENCE: 350

Asn Phe Met Leu Thr Gln Pro His Ser Val Ser Glu Ser Pro Gly Lys
 1               5                  10                  15

Thr Val Thr Ile Ser Cys Thr Arg Ser Ser Gly Ser Ile Ala Ser Asn
             20                  25                  30

Tyr Val Gln Trp Tyr Gln Gln Arg Pro Gly Ser Ser Pro Thr Thr Val
         35                  40                  45

Ile Tyr Glu Asp Asn Gln Arg Pro Ser Gly Val Pro Asp Arg Phe Ser
     50                  55                  60

Gly Ser Ile Asp Ser Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Ser Asn

<210> SEQ ID NO 351
<211> LENGTH: 98
<212> TYPE: PRT
<213> ORGANISM: Artificial Sequence
<220> FEATURE:
<223> OTHER INFORMATION: Chemically synthesized

<400> SEQUENCE: 351

Gln Thr Val Val Thr Gln Glu Pro Ser Leu Thr Val Ser Pro Gly Gly
 1               5                  10                  15

Thr Val Thr Leu Thr Cys Ala Ser Ser Thr Gly Ala Val Thr Ser Gly
             20                  25                  30

Tyr Tyr Pro Asn Trp Phe Gln Gln Lys Pro Gly Gln Ala Pro Arg Ala
         35                  40                  45

Leu Ile Tyr Ser Thr Ser Asn Lys His Ser Trp Thr Pro Ala Arg Phe
     50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Leu Leu Tyr Tyr Gly Gly
                 85                  90                  95

Ala Gln

<210> SEQ ID NO 352
<211> LENGTH: 98
<212> TYPE: PRT
<213> ORGANISM: Artificial Sequence
<220> FEATURE:
<223> OTHER INFORMATION: Chemically synthesized

<400> SEQUENCE: 352

Gln Ala Val Val Thr Gln Glu Pro Ser Leu Thr Val Ser Pro Gly Gly
 1               5                  10                  15

Thr Val Thr Leu Thr Cys Gly Ser Ser Thr Gly Ala Val Thr Ser Gly
             20                  25                  30

His Tyr Pro Tyr Trp Phe Gln Gln Lys Pro Gly Gln Ala Pro Arg Thr
         35                  40                  45
```

```
Leu Ile Tyr Asp Thr Ser Asn Lys His Ser Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Leu Leu Ser Tyr Ser Gly
                85                  90                  95

Ala Arg

<210> SEQ ID NO 353
<211> LENGTH: 98
<212> TYPE: PRT
<213> ORGANISM: Artificial Sequence
<220> FEATURE:
<223> OTHER INFORMATION: Chemically synthesized

<400> SEQUENCE: 353

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
                20                  25                  30

Tyr Tyr Pro Ser Trp Tyr Gln Gln Thr Pro Gly Gln Ala Pro Arg Thr
            35                  40                  45

Leu Ile Tyr Ser Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile

<210> SEQ ID NO 354
<211> LENGTH: 104
<212> TYPE: PRT
<213> ORGANISM: Artificial Sequence
<220> FEATURE:
<223> OTHER INFORMATION: Chemically synthesized

<400> SEQUENCE: 354

Gln Pro Val Leu Thr Gln Pro Pro Ser Ala Ser Ala Ser Leu Gly Ala
1               5                   10                  15

Ser Val Thr Leu Thr Cys Thr Leu Ser Ser Gly Tyr Ser Asn Tyr Lys
                20                  25                  30

Val Asp Trp Tyr Gln Gln Arg Pro Gly Lys Gly Pro Arg Phe Val Met
            35                  40                  45

Arg Val Gly Thr Gly Gly Ile Val Gly Ser Lys Gly Asp Gly Ile Pro
    50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Ser Gly Ser Asn Phe Val
                100

<210> SEQ ID NO 355
<211> LENGTH: 98
<212> TYPE: PRT
<213> ORGANISM: Artificial Sequence
<220> FEATURE:
<223> OTHER INFORMATION: Chemically synthesized
```

<400> SEQUENCE: 355

```
Gln Ala Gly Leu Thr Gln Pro Pro Ser Val Ser Lys Gly Leu Arg Gln
  1               5                  10                  15

Thr Ala Thr Leu Thr Cys Thr Gly Asn Ser Asn Asn Val Gly Asn Gln
             20                  25                  30

Gly Ala Ala Trp Leu Gln Gln His Gln Gly His Pro Pro Lys Leu Leu
         35                  40                  45

Ser Tyr Arg Asn Asn Arg Pro Ser Gly Ile Ser Glu Arg Leu Ser
 50                  55                  60

Ala Ser Arg Ser Gly Asn Thr Ala Ser Leu Thr Ile Thr Gly Leu Gln
 65                  70                  75                  80

Pro Glu Asp Glu Ala Asp Tyr Tyr Cys Ser Ala Trp Asp Ser Ser Leu
                 85                  90                  95

Ser Ala
```

<210> SEQ ID NO 356
<211> LENGTH: 1407
<212> TYPE: DNA
<213> ORGANISM: Artificial Sequence
<220> FEATURE:
<223> OTHER INFORMATION: Chemically synthesized

<400> SEQUENCE: 356

| | |
|---|---:|
| atggagtttg ggctgagctg gcttttctt gtggctattt taaaaggtgt ccagtgtcag | 60 |
| gtccagctgc agcagtctgg ggctgaactg gcaagacctg gggcctcagt gaagatgtcc | 120 |
| tgcaaggctt ctggctacac ctttactagg tacacgatgc actgggtaaa acagaggcct | 180 |
| ggacagggtc tggaatggat tggatacatt aatcctagcc gtggttatac taattacaat | 240 |
| cagaagttca aggacaaggc cacattgact acagacaaat cctccagcac agcctacatg | 300 |
| caactgagca gcctgacatc tgaggactct gcagtctatt actgtgcaag atattatgat | 360 |
| gatcattact gccttgacta ctggggccaa ggcaccactc tcacagtctc ctcagcctcc | 420 |
| accaagggcc catcggtctt ccccctggca ccctcctcca agagcacctc tgggggcaca | 480 |
| gcggccctgg gctgcctggt caaggactac ttccccgaac cggtgacggt gtcgtggaac | 540 |
| tcaggcgccc tgaccagcgg cgtgcacacc ttcccggctg tcctacagtc ctcaggactc | 600 |
| tactccctca gcagcgtggt gaccgtgccc tccagcagct tgggcaccca gacctacatc | 660 |
| tgcaacgtga atcacaagcc cagcaacacc aaggtggaca gagagttga gcccaaatct | 720 |
| tgtgacaaaa ctcacacatg cccaccgtgc ccagcacctg aactcctggg gggaccgtca | 780 |
| gtcttcctct tccccccaaa acccaaggac accctcatga tctcccggac ccctgaggtc | 840 |
| acatgcgtgt ggtggacgt gagccacgaa gaccctgagg tcaagttcaa ctggtacgtg | 900 |
| gacggcgtgg aggtgcataa tgccaagaca aagccgcggg aggagcagta caacagcacg | 960 |
| taccgtgtgg tcagcgtcct caccgtcctg caccaggact ggctgaatgg caaggagtac | 1020 |
| aagtgcaagg tctccaacaa agccctccca gcccccatcg agaaaaccat ctccaaagcc | 1080 |
| aaagggcagc cccgagaacc acaggtgtac accctgcccc catcccggga tgagctgacc | 1140 |
| aagaaccagg tcagcctgac ctgcctggtc aaaggcttct atcccagcga catcgccgtg | 1200 |
| gagtgggaga gcaatgggca gccggagaac aactacaaga ccacgcctcc cgtgctggac | 1260 |
| tccgacggct ccttcttcct ctacagcaag ctcaccgtgg acaagagcag gtggcagcag | 1320 |
| gggaacgtct tctcatgctc cgtgatgcat gaggctctgc acaaccacta cacgcagaag | 1380 |
| agcctctccc tgtctccggg taaatga | 1407 |

<210> SEQ ID NO 357
<211> LENGTH: 717
<212> TYPE: DNA
<213> ORGANISM: Artificial Sequence
<220> FEATURE:
<223> OTHER INFORMATION: Chemically synthesized

<400> SEQUENCE: 357

```
atggacatga gggtccccgc tcagctcctg gggctcctgc tgctctggct cccaggtgcc    60
aaatgtcaaa ttgttctcac ccagtctcca gcaatcatgt ctgcatctcc aggggagaag   120
gtcaccatga cctgcagtgc cagctcaagt gtaagttaca tgaactggta ccagcagaag   180
tcaggcacct cccccaaaag atggatttat gacacatcca actggcttc tggagtccct    240
gctcacttca gggcagtgg gtctgggacc tcttactctc tcacaatcag cggcatggag   300
gctgaagatg ctgccactta ttactgccag cagtggagta gtaacccatt cacgttcggc   360
tcggggacaa agttggaaat aaaccgggct gatcgaactg tggctgcacc atctgtcttc   420
atcttcccgc catctgatga gcagttgaaa tctggaactg cctctgttgt gtgcctgctg   480
aataacttct atcccagaga ggccaaagta cagtggaagg tggataacgc cctccaatcg   540
ggtaactccc aggagagtgt cacagagcag gacagcaagg acagcaccta cagcctcagc   600
agcaccctga cgctgagcaa agcagactac gagaaacaca agtctacgc ctgcgaagtc    660
acccatcagg gcctgagctc gcccgtcaca aagagcttca caggggaga gtgttaa      717
```

<210> SEQ ID NO 358
<211> LENGTH: 468
<212> TYPE: PRT
<213> ORGANISM: Artificial Sequence
<220> FEATURE:
<223> OTHER INFORMATION: Chemically synthesized

<400> SEQUENCE: 358

```
Met Glu Phe Gly Leu Ser Trp Leu Phe Leu Val Ala Ile Leu Lys Gly
  1               5                  10                  15
Val Gln Cys Gln Val Gln Leu Gln Gln Ser Gly Ala Glu Leu Ala Arg
             20                  25                  30
Pro Gly Ala Ser Val Lys Met Ser Cys Lys Ala Ser Gly Tyr Thr Phe
         35                  40                  45
Thr Arg Tyr Thr Met His Trp Val Lys Gln Arg Pro Gly Gln Gly Leu
     50                  55                  60
Glu Trp Ile Gly Tyr Ile Asn Pro Ser Arg Gly Tyr Thr Asn Tyr Asn
 65                  70                  75                  80
Gln Lys Phe Lys Asp Lys Ala Thr Leu Thr Thr Asp Lys Ser Ser Ser
                 85                  90                  95
Thr Ala Tyr Met Gln Leu Ser Ser Leu Thr Ser Glu Asp Ser Ala Val
                100                 105                 110
Tyr Tyr Cys Ala Arg Tyr Tyr Asp Asp His Tyr Cys Leu Asp Tyr Trp
            115                 120                 125
Gly Gln Gly Thr Thr Leu Thr Val Ser Ser Ala Ser Thr Lys Gly Pro
        130                 135                 140
Ser Val Phe Pro Leu Ala Pro Ser Ser Lys Ser Thr Ser Gly Gly Thr
145                 150                 155                 160
Ala Ala Leu Gly Cys Leu Val Lys Asp Tyr Phe Pro Glu Pro Val Thr
                165                 170                 175
Val Ser Trp Asn Ser Gly Ala Leu Thr Ser Gly Val His Thr Phe Pro
                180                 185                 190
```

```
Ala Val Leu Gln Ser Ser Gly Leu Tyr Ser Leu Ser Ser Val Val Thr
            195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Val
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 359
<211> LENGTH: 468
<212> TYPE: PRT
<213> ORGANISM: Artificial Sequence
<220> FEATURE:
<223> OTHER INFORMATION: Chemically synthesized

<400> SEQUENCE: 359

Met Glu Phe Gly Leu Ser Trp Leu Phe Leu Val Ala Ile Leu Lys Gly
1               5                   10                  15

Val Gln Cys Gln Val Gln Leu Gln Gln Ser Gly Ala Glu Leu Ala Arg
            20                  25                  30

Pro Gly Ala Ser Val Lys Met Ser Cys Lys Ala Ser Gly Tyr Thr Phe
        35                  40                  45

Thr Arg Tyr Thr Met His Trp Val Lys Gln Arg Pro Gly Gln Gly Leu
    50                  55                  60

Glu Trp Ile Gly Tyr Ile Asn Pro Ser Arg Gly Tyr Thr Asn Tyr Asn
65                  70                  75                  80
```

```
Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Asp Asp His Tyr Cys Leu Asp Tyr Trp
        115                 120                 125

Gly Gln Gly Thr Thr Leu Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 360
<211> LENGTH: 238
<212> TYPE: PRT
<213> ORGANISM: Artificial Sequence
```

<220> FEATURE:
<223> OTHER INFORMATION: Chemically synthesized

<400> SEQUENCE: 360

Met Asp Met Arg Val Pro Ala Gln Leu Leu Gly Leu Leu Leu Leu Trp
1               5                   10                  15

Leu Pro Gly Ala Lys Cys Gln Ile Val Leu Thr Gln Ser Pro Ala Ile
            20                  25                  30

Met Ser Ala Ser Pro Gly Glu Lys Val Thr Met Thr Cys Ser Ala Ser
        35                  40                  45

Ser Ser Val Ser Tyr Met Asn Trp Tyr Gln Gln Lys Ser Gly Thr Ser
    50                  55                  60

Pro Lys Arg Trp Ile Tyr Asp Thr Ser Lys Leu Ala Ser Gly Val Pro
65                  70                  75                  80

Ala His Phe Arg Gly Ser Gly Ser Gly Thr Ser Tyr Ser Leu Thr Ile
                85                  90                  95

Ser Gly Met Glu Ala Glu Asp Ala Ala Thr Tyr Tyr Cys Gln Gln Trp
            100                 105                 110

Ser Ser Asn Pro Phe Thr Phe Gly Ser Gly Thr Lys Leu Glu Ile Asn
        115                 120                 125

Arg Ala Asp Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 361
<211> LENGTH: 136
<212> TYPE: PRT
<213> ORGANISM: Artificial Sequence
<220> FEATURE:
<223> OTHER INFORMATION: Chemically synthesized

<400> SEQUENCE: 361

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Met
        35                  40                  45

Gly Tyr Ile Asn Pro Ser Arg Gly Tyr Thr Asn Tyr Asn Gln Lys Phe
    50                  55                  60

Lys Asp Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

```
Thr Leu Val Thr Val Ser Ser Ala Ser Thr Lys Gly Pro Ser Val Phe
            115                 120                 125

Pro Leu Ala Pro Ser Ser Lys Ser
        130                 135

<210> SEQ ID NO 362
<211> LENGTH: 136
<212> TYPE: PRT
<213> ORGANISM: Artificial Sequence
<220> FEATURE:
<223> OTHER INFORMATION: Chemically synthesized

<400> SEQUENCE: 362

Gln Val Gln Leu Val Glu Ser Gly Ala Glu Val Lys Lys Pro Gly Ala
  1               5                  10                  15

Ser Val Lys Val Ser Cys Lys Ala Ser Gly Tyr Thr Phe Thr Arg Tyr
             20                  25                  30

Thr Met His Trp Val Arg Gln Ala Pro Gly Lys Gly Leu Glu Trp Met
         35                  40                  45

Gly Tyr Ile Asn Pro Ser Arg Gly Tyr Thr Asn Tyr Asn Gln Lys Phe
     50                  55                  60

Lys Asp Arg Leu Thr Ile Ser Lys Asp Thr Ser Lys Asn Gln Val Val
 65                  70                  75                  80

Leu Thr Met Thr Asn Met Asp Pro Val Asp Thr Ala Thr Tyr Tyr Cys
                 85                  90                  95

Ala Arg Tyr Tyr Asp Asp His Tyr Cys Leu Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser
        130                 135

<210> SEQ ID NO 363
<211> LENGTH: 136
<212> TYPE: PRT
<213> ORGANISM: Artificial Sequence
<220> FEATURE:
<223> OTHER INFORMATION: Chemically synthesized

<400> SEQUENCE: 363

Gln Val Gln Leu Gln Glu Ser Gly Pro Gly Leu Val Lys Pro Ser Glu
  1               5                  10                  15

Thr Leu Ser Leu Thr Cys Ala Val Ser Gly Tyr Thr Phe Thr Arg Tyr
             20                  25                  30

Thr Met His Trp Val Arg Gln Ala Pro Gly Lys Gly Leu Glu Trp Val
         35                  40                  45

Gly Tyr Ile Asn Pro Ser Arg Gly Tyr Thr Asn Tyr Asn Gln Lys Phe
     50                  55                  60

Lys Asp Arg Phe Thr Ile Ser Arg Asp Asp Ser Lys Asn Thr Ala Tyr
 65                  70                  75                  80

Leu Gln Met Asn Ser Leu Lys Thr Glu Asp Thr Ala Val Tyr Tyr Cys
                 85                  90                  95

Thr Arg Tyr Tyr Asp Asp His Tyr Cys Leu Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser
        130                 135
```

```
<210> SEQ ID NO 364
<211> LENGTH: 106
<212> TYPE: PRT
<213> ORGANISM: Artificial Sequence
<220> FEATURE:
<223> OTHER INFORMATION: Chemically synthesized

<400> SEQUENCE: 364

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Lys Pro Gly Gln Pro Pro Lys Leu Leu Ile Tyr
        35                  40                  45

Asp Thr Ser Lys Leu Ala Ser Gly Val Pro Asp Arg Phe Ser Gly Ser
    50                  55                  60

Gly Ser Gly Thr Asp Phe Thr Leu Lys Ile Ser Arg Val Glu Ala Glu
65                  70                  75                  80

Asp Val Gly Val Tyr Tyr Cys Gln Gln Trp Ser Ser Asn Pro Phe Thr
                85                  90                  95

Phe Gly Gln Gly Thr Lys Val Glu Ile Lys
            100                 105

<210> SEQ ID NO 365
<211> LENGTH: 106
<212> TYPE: PRT
<213> ORGANISM: Artificial Sequence
<220> FEATURE:
<223> OTHER INFORMATION: Chemically synthesized

<400> SEQUENCE: 365

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Lys Pro Gly Gln Ala Pro Arg Leu Leu Ile Tyr
        35                  40                  45

Asp Thr Ser Lys Leu Ala Ser Gly Val Pro Asp Arg Phe Ser Gly Ser
    50                  55                  60

Gly Ser Gly Thr Asp Phe Thr Leu Lys Ile Ser Arg Val Glu Ala Glu
65                  70                  75                  80

Asp Val Gly Val Tyr Tyr Cys Gln Gln Trp Ser Ser Asn Pro Phe Thr
                85                  90                  95

Phe Gly Gln Gly Thr Lys Val Glu Ile Lys
            100                 105

<210> SEQ ID NO 366
<211> LENGTH: 106
<212> TYPE: PRT
<213> ORGANISM: Artificial Sequence
<220> FEATURE:
<223> OTHER INFORMATION: Chemically synthesized

<400> SEQUENCE: 366

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30
```

Asn Trp Tyr Gln Gln Lys Pro Gly Lys Ala Pro Lys Leu Leu Ile Tyr
                35                  40                  45

Asp Thr Ser Lys Leu Ala Ser Gly Val Pro Ser Arg Phe Ser Gly Ser
            50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Gln Gln Trp Ser Ser Asn Pro Phe Thr
                85                  90                  95

Phe Gly Gln Gly Thr Lys Val Glu Ile Lys
                100                 105

<210> SEQ ID NO 367
<211> LENGTH: 106
<212> TYPE: PRT
<213> ORGANISM: Artificial Sequence
<220> FEATURE:
<223> OTHER INFORMATION: Chemically synthesized

<400> SEQUENCE: 367

Asp Ile Val Met Thr Gln Ser Pro Leu Ser Leu Pro Val Thr Pro Gly
1               5                   10                  15

Glu Pro Ala Ser Ile Ser Cys Ser Ala Ser Ser Ser Val Ser Tyr Met
                20                  25                  30

Asn Trp Tyr Gln Gln Lys Pro Gly Gln Pro Pro Lys Leu Leu Ile Tyr
                35                  40                  45

Asp Thr Ser Lys Leu Ala Ser Gly Val Pro Ser Arg Phe Ser Gly Ser
            50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Gln Gln Trp Ser Ser Asn Pro Phe Thr
                85                  90                  95

Phe Gly Gln Gly Thr Lys Val Glu Ile Lys
                100                 105

<210> SEQ ID NO 368
<211> LENGTH: 106
<212> TYPE: PRT
<213> ORGANISM: Artificial Sequence
<220> FEATURE:
<223> OTHER INFORMATION: Chemically synthesized

<400> SEQUENCE: 368

Glu Ile Val Met Thr Gln Ser Pro Ala Thr Leu Ser Val Ser Pro Gly
1               5                   10                  15

Glu Arg Ala Thr Leu Ser Cys Ser Ala Ser Ser Ser Val Ser Tyr Met
                20                  25                  30

Asn Trp Tyr Gln Gln Lys Pro Gly Gln Pro Pro Lys Leu Leu Ile Tyr
                35                  40                  45

Asp Thr Ser Lys Leu Ala Ser Gly Val Pro Ser Arg Phe Ser Gly Ser
            50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Gln Gln Trp Ser Ser Asn Pro Phe Thr
                85                  90                  95

Phe Gly Gln Gly Thr Lys Val Glu Ile Lys
                100                 105

<210> SEQ ID NO 369
<211> LENGTH: 106

```
<212> TYPE: PRT
<213> ORGANISM: Artificial Sequence
<220> FEATURE:
<223> OTHER INFORMATION: Chemically synthesized

<400> SEQUENCE: 369

Glu Ile Val Met Thr Gln Ser Pro Ala Thr Leu Ser Val Ser Pro Gly
 1               5                  10                  15

Glu Arg Ala Thr Leu Ser Cys Ser Ala Ser Ser Ser Val Ser Tyr Met
            20                  25                  30

Asn Trp Tyr Gln Gln Lys Pro Gly Gln Ala Pro Arg Leu Leu Ile Tyr
        35                  40                  45

Asp Thr Ser Lys Leu Ala Ser Gly Val Pro Asp Arg Phe Ser Gly Ser
    50                  55                  60

Gly Ser Gly Thr Asp Phe Thr Leu Thr Ile Ser Ser Leu Gln Ala Glu
65                  70                  75                  80

Asp Val Ala Val Tyr Tyr Cys Gln Gln Trp Ser Ser Asn Pro Phe Thr
                85                  90                  95

Phe Gly Gln Gly Thr Lys Val Glu Ile Lys
            100                 105

<210> SEQ ID NO 370
<211> LENGTH: 106
<212> TYPE: PRT
<213> ORGANISM: Artificial Sequence
<220> FEATURE:
<223> OTHER INFORMATION: Chemically synthesized

<400> SEQUENCE: 370

Asp Ile Gln Met Thr Gln Ser Pro Ser Thr Leu Ser Ala Ser Val Gly
 1               5                  10                  15

Asp Arg Val Thr Ile Thr Cys Ser Ala Ser Ser Ser Val Ser Tyr Met
            20                  25                  30

Asn Trp Tyr Gln Gln Lys Pro Gly Lys Ala Pro Lys Leu Leu Ile Tyr
        35                  40                  45

Asp Thr Ser Lys Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Ser Ser Asn Pro Phe Thr
                85                  90                  95

Phe Gly Gln Gly Thr Lys Val Glu Ile Lys
            100                 105

<210> SEQ ID NO 371
<211> LENGTH: 106
<212> TYPE: PRT
<213> ORGANISM: Artificial Sequence
<220> FEATURE:
<223> OTHER INFORMATION: Chemically synthesized

<400> SEQUENCE: 371

Asp Ile Gln Met Thr Gln Ser Pro Ser Thr Leu Ser Ala Ser Val Gly
 1               5                  10                  15

Asp Arg Val Thr Ile Thr Cys Ser Ala Ser Ser Ser Val Ser Tyr Met
            20                  25                  30

Asn Trp Tyr Gln Gln Lys Pro Gly Gln Pro Pro Lys Leu Leu Ile Tyr
        35                  40                  45

Asp Thr Ser Lys Leu Ala Ser Gly Val Pro Ser Arg Phe Ser Gly Ser
    50                  55                  60
```

```
Gly Ser Gly Thr Asp Phe Thr Phe Thr Ile Ser Ser Leu Gln Pro Glu
 65                  70                  75                  80

Asp Ile Ala Thr Tyr Tyr Cys Gln Gln Trp Ser Ser Asn Pro Phe Thr
                 85                  90                  95

Phe Gly Gln Gly Thr Lys Val Glu Ile Lys
            100                 105

<210> SEQ ID NO 372
<211> LENGTH: 106
<212> TYPE: PRT
<213> ORGANISM: Artificial Sequence
<220> FEATURE:
<223> OTHER INFORMATION: Chemically synthesized

<400> SEQUENCE: 372

Asp Ile Gln Met Thr Gln Ser Pro Ser Thr Leu Ser Ala Ser Val Gly
  1               5                  10                  15

Asp Arg Val Thr Ile Thr Cys Ser Ala Ser Ser Ser Val Ser Tyr Met
                 20                  25                  30

Asn Trp Tyr Gln Gln Lys Pro Gly Lys Ala Pro Lys Leu Leu Ile Tyr
             35                  40                  45

Asp Thr Ser Lys Leu Ala Ser Gly Val Pro Asp Arg Phe Ser Gly Ser
     50                  55                  60

Gly Ser Gly Thr Asp Phe Thr Leu Lys Ile Ser Arg Val Glu Ala Glu
 65                  70                  75                  80

Asp Val Gly Val Tyr Tyr Cys Gln Gln Trp Ser Ser Asn Pro Phe Thr
                 85                  90                  95

Phe Gly Gln Gly Thr Lys Val Glu Ile Lys
            100                 105
```

ANTIBODIES AND METHODS FOR MAKING AND USING THEM

RELATED APPLICATIONS

The present application claims the benefit of priority under 35 U.S.C. §119(e) of U.S. provisional application Ser. No. 60/871,069, filed Dec. 20, 2006. The aforementioned application is expressly incorporated herein by reference in its entirety and for all purposes.

REFERENCE TO SEQUENCE LISTING SUBMITTED VIA EFS-WEB

This application was filed electronically via the USPTO EFS-WEB server, as authorized and set forth in MPEP §1730 II.B.2.(a)(A), and this electronic filing includes an electronically submitted sequence (SEQ ID) listing; the entire content of this sequence listing is herein incorporated by reference for all purposes. The sequence listing is identified on the electronically filed .txt file as follows:

| File Name | Date of Creation | Size |
| --- | --- | --- |
| 564462015700.txt | Sep. 7, 2007 | 212,631 bytes |

FIELD OF THE INVENTION

This invention relates generally to genetic engineering, molecular immunology and medicine. In one aspect, the invention provides antibodies, such as chimeric human antibodies (chimeric antibodies with human components), the nucleic acids encoding them, and methods for making and using these immunoglobulins. The invention provides recombinant and synthetic polypeptide and nucleic acid embodiments of these polypeptides. The invention also provides polypeptides comprising, or consisting of, consensus human framework regions, or "Independently Consensused Framework regions (ICFs)", nucleic acids encoding them, and libraries and kits comprising these ICFs and/or antibodies of the invention, individually and in combinatorial libraries and combinations.

BACKGROUND

Antibodies (or Immunoglobulins, Igs) are proteins produced by the immune system in response to the presence of a foreign substance in the body. Immunoglobulins also serve and mediate other functions of the immune system. The nucleic acid sequences that encode immunoglobulins are initially derived from several genes in the genome (germline), which are subsequently rearranged and mutated during maturation to further increase the diversity of the immunoglobulins in their final, mature form. IgG, a typical immunoglobulin, has a Y-shaped structure formed by four chains: two heavy and two light chains, each with a variable and constant region. The variable regions can be further divided into various subregions, such as the framework (FR) and complementarity-determining regions (CDRs).

Immunoglobulins have been used to treat various diseases and conditions, for example allergies, transplant rejection, cancer, and host-versus-graft disease. However, when administering therapeutic antibody preparations to human patients, the antibodies sometimes provoke an undesired and potentially dangerous immune response by the patient to the antibodies themselves ("immunogenicity"), especially after repeated administrations. Immunogenicity can pose a particular problem when the antibody is from a nonhuman source, such as from an animal. When the antibody is derived from mouse, as is frequently used in therapeutic models, the patient may develop a human anti-murine antibody (HAMA) response. To reduce undesired immunogenicity such as HAMA, certain regions of an animal antibody can be replaced with corresponding regions of human antibodies, in essence "humanizing" the antibody. Modified antibodies, such as "chimeric" antibodies and CDR-grafted antibodies, have been developed to reduce immunogenic responses. However, such replacement strategies may not sufficiently minimize immunogenicity and can reduce the therapeutic efficacy of the immunoglobulin. Thus, there is a need for modified immunoglobulins that reduce or eliminate immunogenicity while maintaining or even improving therapeutic efficacy.

SUMMARY OF THE INVENTION

The present invention provides antibodies having a framework derived from one species and sequences responsible for binding to antigen derived from another species. In alternative aspects these antibodies are in isolated, recombinant or synthetic form. In alternative embodiments, at least one, some, or all of the framework segments (or "framework regions", or FRs) of the antibodies of the invention are encoded by nucleic acid sequences derived from germline sequences; and in one aspect, at least one, some, or all of the framework segments are "consensus sequences", as described herein. In one aspect, the antibody framework segments are derived from the animal, e.g., a human, into which the antibody of the invention is to be administered, e.g., as an in vivo immunotherapeutic or immunodiagnostic reagent. The antibody sequences fragments responsible for binding to antigen, also called "complementarity determining regions" (or CDRs), are derived from a non-human animal used to generate a desired antigen specific antibody; in alternative aspects, the antigen can be artificially administered to this animal, or the antigen can be the result of natural or accidental environmental exposure, such as infection or toxin or poison exposure, or by purposeful administration of antigen. In alternative embodiments, the FRs are encoded by "consensus sequences" derived from human genomic polynucleotides, and the CDRs are from a murine source, such as a mouse.

The present invention provides methods ("Human Framework Reassembly" or HuFR) for designing and providing the antibodies of the invention, including the recombinant antibodies, e.g., the recombinant humanized antibodies of the invention, that are more similar in character to antibodies native to the subject to be treated. The method can entail deducing consensus sequences for framework subregions (such as FR1, FR2, FR3, and FR4) of heavy chain (HC) and light chain (LC) variable regions, where the consensus sequence for each subregion is obtained and selected independently of the other framework subregions. Thus, a diverse collection of nucleic acids or polypeptides can be generated from a combinatorial library of independently selected consensus sequences for each framework subregion, which can subsequently be used to make recombinant antibodies, including the recombinant humanized antibodies of the invention. These consensus sequences can be derived from sequences of mature immunoglobulins or germline sequences of particular organisms, such as human, non-human primate, dog, cat, and horse, thus generating antibodies that have reduced immunogenicity in that particular organism, animal and/or human.

The invention provides recombinant heavy or light chain variable region polypeptides, and nucleic acids encoding them, where the variable region can comprise at least three "Independently Consensus'ed Framework" domains (ICF): ICF1, ICF2, and ICF3. The recombinant variable region polypeptide can further comprise an Independently Consensused Framework 4 domain (ICF4).

In one embodiment, each of the ICF domains comprises an amino acid consensus sequence determined from a plurality of amino acid sequences, translated from germline nucleic acid sequences, that each encode at least a portion of a corresponding Kabat framework region (KF) domain, such as KF1, KF2, or KF3. In one embodiment, each of the ICF domains comprises amino acid consensus sequences determined from mature KF domain amino acid sequences. In one embodiment, the process for obtaining such consensus sequences ("consensusing") comprises: aligning a set of amino acid or nucleic acid sequences encoding at least a portion of one Kabat framework subregion (such as KF1, KF2, KF3, or KF4) by inspection or using sequence alignment programs in the art; determining the frequency at which a residue (such as a nucleotide or amino acid) appears at each position for that specific subregion; and synthesizing highly frequent residues into a set of consensus sequences for that subregion, thus generating ICF1, ICF2, ICF3, or ICF4 consensus sequences. Exemplary ICFs are provided for heavy chain ICFs (see Tables 1 and 2) and light chain ICFs (see Tables 3 and 4).

The invention also provides Ig polypeptides comprising a heavy and light chain variable region of the invention, such as a full-length antibody, single chain antibody, bivalent antibody, Fab fragment, or single chain Fv. The ICF1, 2, and 3 domains can be derived from a first animal species and the CDR1, 2, and 3 domains can be derived from a second animal species. Exemplary antibodies are provided that bind to antigens such as CD20 or CD3.

The invention further provides methods for producing polypeptides and nucleic acids of the invention and their combinatorial libraries. Combinatorial libraries of the polypeptides of the invention can combine different ICF1s, ICF2s, and ICF3s in different combinations. Further association of pairs of individual members of heavy chain and light chain libraries can yield libraries of greater than 30,000 antibodies. The combinatorial libraries can be screened for desired properties, such as binding to a desired antigen or reduced immunogenicity.

The invention provides antibody or antigen-binding fragment thereof comprising at least one variable region having a combination of:

(1) light chain BD22084 (SEQ ID NO:225) and heavy chain BD20332 (SEQ ID NO:138);
(2) light chain BD22085 (SEQ ID NO:232) and heavy chain BD20335 (SEQ ID NO:143);
(3) light chain BD22086 (SEQ ID NO:227) and heavy chain BD20335 (SEQ ID NO:143);
(4) light chain BD22088 (SEQ ID NO:229) and heavy chain BD20337 (SEQ ID NO:148);
(5) light chain BD22087 (SEQ ID NO:240) and heavy chain BD20335 (SEQ ID NO:143);
(6) light chain BD22089 (SEQ ID NO:243) and heavy chain BD20335 (SEQ ID NO:143);
(7) light chain BD22090 (SEQ ID NO:234) and heavy chain BD20337 (SEQ ID NO:148);
(8) light chain BD22095 (SEQ ID NO:244) and heavy chain BD20337 (SEQ ID NO:148);
(9) light chain BD22091 (SEQ ID NO:242) and heavy chain BD20337 (SEQ ID NO:148);
(10) light chain BD22108 (SEQ ID NO:230) and heavy chain BD20337 (SEQ ID NO:148);
(11) light chain BD22092 (SEQ ID NO:235) and heavy chain BD20338 (SEQ ID NO:149);
(12) light chain BD22094 (SEQ ID NO:231) and heavy chain BD20337 (SEQ ID NO:148);
(13) light chain BD22096 (SEQ ID NO:241) and heavy chain BD20337 (SEQ ID NO:148);
(14) light chain BD22092 (SEQ ID NO:235) and heavy chain BD20337 (SEQ ID NO:148);
(15) light chain BD22102 (SEQ ID NO:248) and heavy chain BD20337 (SEQ ID NO:148);
(16) light chain BD22097 (SEQ ID NO:246) and heavy chain BD20335 (SEQ ID NO:143).
(17) light chain BD22104 (SEQ ID NO:239) and heavy chain BD20337 (SEQ ID NO:148);
(18) light chain BD22085 (SEQ ID NO:232) and heavy chain BD20339 (SEQ ID NO:150);
(19) light chain BD22107 (SEQ ID NO:226) and heavy chain BD20339 (SEQ ID NO:150);
(20) light chain BD22100 (SEQ ID NO:236) and heavy chain BD20335 (SEQ ID NO:143);
(21) light chain BD22103 (SEQ ID NO:228) and heavy chain BD20337 (SEQ ID NO:148);
(22) light chain BD22105 (SEQ ID NO:237) and heavy chain BD20337 (SEQ ID NO:148);
(23) light chain BD22101 (SEQ ID NO:247) and heavy chain BD20335 (SEQ ID NO:143);
(24) light chain BD22106 (SEQ ID NO:245) and heavy chain BD20333 (SEQ ID NO:142);
(25) light chain BD22108 (SEQ ID NO:230) and heavy chain BD20338 (SEQ ID NO:149);
(26) light chain BD22109 (SEQ ID NO:233) and heavy chain BD20341 (SEQ ID NO:154); or
(27) light chain BD22111 (SEQ ID NO:238) and heavy chain BD20336 (SEQ ID NO:144).

The invention provides antibodies or antigen-binding fragments thereof comprising at least a portion of a heavy chain variable region and at least a portion of a light chain variable region, wherein the light chain portion and the heavy chain portion is at least 90%, 91%, 92%, 93%, 94%, 95%, 96%, 97%, 98% or 99% or complete sequence identity to the respective light and heavy chains of at least one of the following combinations:

(1) light chain BD22084 (SEQ ID NO:225) and heavy chain BD20332 (SEQ ID NO:138);
(2) light chain BD22085 (SEQ ID NO:232) and heavy chain BD20335 (SEQ ID NO:143);
(3) light chain BD22086 (SEQ ID NO:227) and heavy chain BD20335 (SEQ ID NO:143);
(4) light chain BD22088 (SEQ ID NO:229) and heavy chain BD20337 (SEQ ID NO:148);
(5) light chain BD22087 (SEQ ID NO:240) and heavy chain BD20335 (SEQ ID NO:143);
(6) light chain BD22089 (SEQ ID NO:243) and heavy chain BD20335 (SEQ ID NO:143);
(7) light chain BD22090 (SEQ ID NO:234) and heavy chain BD20337 (SEQ ID NO:148);
(8) light chain BD22095 (SEQ ID NO:244) and heavy chain BD20337 (SEQ ID NO:148);
(9) light chain BD22091 (SEQ ID NO:242) and heavy chain BD20337 (SEQ ID NO:148);

(10) light chain BD22108 (SEQ ID NO:230) and heavy chain BD20337 (SEQ ID NO:148);
(11) light chain BD22092 (SEQ ID NO:235) and heavy chain BD20338 (SEQ ID NO:149);
(12) light chain BD22094 (SEQ ID NO:231) and heavy chain BD20337 (SEQ ID NO:148);
(13) light chain BD22096 (SEQ ID NO:241) and heavy chain BD20337 (SEQ ID NO:148);
(14) light chain BD22092 (SEQ ID NO:235) and heavy chain BD20337 (SEQ ID NO:148);
(15) light chain BD22102 (SEQ ID NO:248) and heavy chain BD20337 (SEQ ID NO:148);
(16) light chain BD22097 (SEQ ID NO:246) and heavy chain BD20335 (SEQ ID NO:143).
(17) light chain BD22104 (SEQ ID NO:239) and heavy chain BD20337 (SEQ ID NO:148);
(18) light chain BD22085 (SEQ ID NO:232) and heavy chain BD20339 (SEQ ID NO:150);
(19) light chain BD22107 (SEQ ID NO:226) and heavy chain BD20339 (SEQ ID NO:150);
(20) light chain BD22100 (SEQ ID NO:236) and heavy chain BD20335 (SEQ ID NO:143);
(21) light chain BD22103 (SEQ ID NO:228) and heavy chain BD20337 (SEQ ID NO:148);
(22) light chain BD22105 (SEQ ID NO:237) and heavy chain BD20337 (SEQ ID NO:148);
(23) light chain BD22101 (SEQ ID NO:247) and heavy chain BD20335 (SEQ ID NO:143);
(24) light chain BD22106 (SEQ ID NO:245) and heavy chain BD20333 (SEQ ID NO:142);
(25) light chain BD22108 (SEQ ID NO:230) and heavy chain BD20338 (SEQ ID NO:149);
(26) light chain BD22109 (SEQ ID NO:233) and heavy chain BD20341 (SEQ ID NO:154); or
(27) light chain BD22111 (SEQ ID NO:238) and heavy chain BD20336 (SEQ ID NO:144)

and wherein the at least a portion of a light chain, the at least a portion of the heavy chain, or both are derived at least in part from sequences made by the method comprising:

(1) providing an Independently Consensused Framework 1 (ICF1) domain, comprising an amino acid consensus sequence derived from a plurality of amino acid sequences each comprising amino acids derived from at least a portion of a Kabat framework region 1 (KF1) domain, wherein the plurality of amino acid sequences are translated from a germline sequence of an immunoglobulin variable region gene or obtained from a mature immunoglobulin;

(2) providing at least a portion of a complementarity determining region 1 (CDR1) derived from the variable region of a 1F5 antibody;

(3) providing an Independently Consensused Framework 2 (ICF2) domain, comprising an amino acid consensus sequence derived from a plurality of amino acid sequences each comprising amino acids derived from at least a portion of a Kabat framework region 2 (KF2) domain, wherein the plurality of amino acid sequences translated from a germline sequence of an immunoglobulin variable region gene or obtained from a mature immunoglobulin;

(4) providing at least a portion of a complementarity determining region 2 (CDR2) derived from the variable region of a 1F5 antibody;

(5) providing an Independently Consensused Framework 3 (ICF3) domain, comprising an amino acid consensus sequence derived from a plurality of amino acid sequences each comprising amino acids derived from at least a portion of a Kabat framework region 3 (KF3) domain, wherein the plurality of amino acid sequences are translated from a germline sequence of an immunoglobulin variable region gene or obtained from a mature immunoglobulin;

(6) providing at least a portion of a complementarity determining region 3 (CDR3) derived from the variable region of a 1F5 antibody; and (7) optionally providing an Independently Consensused Framework 4 (ICF4) domain, comprising an amino acid consensus sequence derived from a plurality of amino acid sequences each comprising amino acids derived from at least a portion of a Kabat framework region 4 (KF4) domain, wherein the plurality of amino acid sequences are translated from a germline sequence of an immunoglobulin variable region gene or obtained from a mature immunoglobulin;

wherein at least one ICF is derived from a genomic nucleic acid sequence, (8) joining, in a 5'-to-3' orientation, nucleic acids encoding the ICF1-CDR1-ICF2-CDR2-ICF3-CDR3 and optionally ICF4 domains.

The invention provides antigen binding antibody fragments of the invention, wherein the antibody fragment is an Fab fragment, an Fab' fragment, an F(ab')$_2$ fragment, a single-chain antibody, an Fv fragment, an scFv fragment, an antibody mimetic, an Fd fragment, or an Fd' fragment; or alternatively an antigen binding antibody fragment of c the invention is, or comprises, an antibody fragment fused to an Fc.

The invention provides recombinant, synthetic or isolated antibodies having a structure comprising at least one variable region combination of the invention.

The invention provides chimeric antibodies or antigen binding fragments thereof comprising at least one variable region combination of the invention.

The invention provides chimeric antigen binding antibody fragments of the invention, wherein the chimeric antibody fragment is a chimeric Fab, a chimeric Fab', a chimeric F(ab')$_2$, a chimeric single-chain antibody, a chimeric Fv, a chimeric scFv, an antibody mimetic, a chimeric Fd, or a chimeric Fd'.

The invention provides antibodies or antigen binding fragments thereof that specifically bind to a CD20 antigen and comprise a light chain variable region comprising (a) an ICF1 comprising an amino acid sequence of SEQ ID NOS:43-49; (b) a CDR1 comprising an amino acid sequence of SEQ ID NO:163; (c) an ICF2 comprising an amino acid sequence of SEQ ID NOs:58-61; (d) a CDR2 comprising an amino acid sequence of SEQ ID NO:164; (e) an ICF3 comprising an amino acid sequence of SEQ ID NOs:67-71, 73, or 74; (f) a CDR3 comprising an amino acid sequence of SEQ ID NO:165; and/or (g) an ICF4 comprising the amino acid sequence of SEQ ID NO:83.

The invention provides antibodies or antigen binding fragments thereof that specifically binds to a CD20 antigen and comprises a heavy chain variable region comprising (a) an ICF1 comprising an amino acid sequence of SEQ ID NOs:6 or 7; (b) a CDR1 comprising an amino acid sequence of SEQ ID NO:151; (c) an ICF2 comprising an amino acid sequence of SEQ ID NOs:9, 10, or 11; (d) a CDR2 comprising an amino acid sequence of SEQ ID NO:152; (e) an ICF3 comprising an amino acid sequence of SEQ ID NOS:13, 17, 19, or 20; (f) a CDR3 comprising an amino acid sequence of SEQ ID NO:153; and/or (g) an ICF4 comprising an amino acid sequence of SEQ ID NO:21.

The invention provides pharmaceutical compositions or formulations comprising: (a) an antibody or antigen binding fragment thereof of the invention; and in one aspect, the pharmaceutical composition or formulation further comprises a pharmaceutically acceptable carrier or excipient.

The invention provides methods for treating or ameliorating a disease, infection, condition or toxic exposure comprising: (a) providing a composition comprising an antibody or an antigen binding fragment thereof of the invention; and, (b) administering a sufficient amount of said antibody or antigen binding fragment thereof to an individual in need thereof.

The invention provides methods for suppressing or abrogating an immune response comprising: (a) providing an antibody or antigen binding fragment thereof of the invention; and (b) administering a sufficient amount of said antibody or antigen binding fragment thereof to an individual in need thereof.

The invention provides methods for suppressing or abrogating a B-cell mediated immune response comprising: (a) providing an antibody or antigen binding fragment thereof of the invention; and, (b) administering a sufficient amount of said antibody or antigen binding fragment thereof to an individual in need thereof.

The invention provides methods of treating B-cell lymphoma comprising: (a) providing an antibody or antigen binding fragment thereof of the invention; and, (b) administering a sufficient amount of said antibody or fragment thereof to an individual (e.g., a human) in need thereof.

The invention uses of an antibody or antigen binding fragment thereof of the invention for the manufacture of a pharmaceutical composition for treating a subject (e.g., a human) having a B-cell mediated disease or condition by a method comprising administering an effective amount of said antibody or fragment thereof to said subject; and in one aspect, the disease is B-cell lymphoma.

The details of one or more aspects of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

BRIEF DESCRIPTION OF THE FIGURES

FIG. 2 shows exemplary amino acid sequences derived from genes for human germline kappa light chain variable regions.

FIG. 3 shows exemplary amino acid sequences derived from genes for human germline lambda light chain variable regions.

FIG. 10 depicts the light chain (top) and heavy chain (bottom) nucleic acid sequences of DVSA-CD3, as discussed in detail in Example 4, below.

FIG. 11 depicts the heavy chain (top) and light chain (middle) amino acid sequences of DVSA-CD3, as well as the light chain of DVSA-CD3 (bottom), as discussed in detail in Example 4, below.

FIG. 12 provides an alignment of the heavy and light chains in the top 9 anti-CD3 hits.

Like reference symbols in the various drawings indicate like elements.

DETAILED DESCRIPTION OF THE INVENTION

Figure 1:
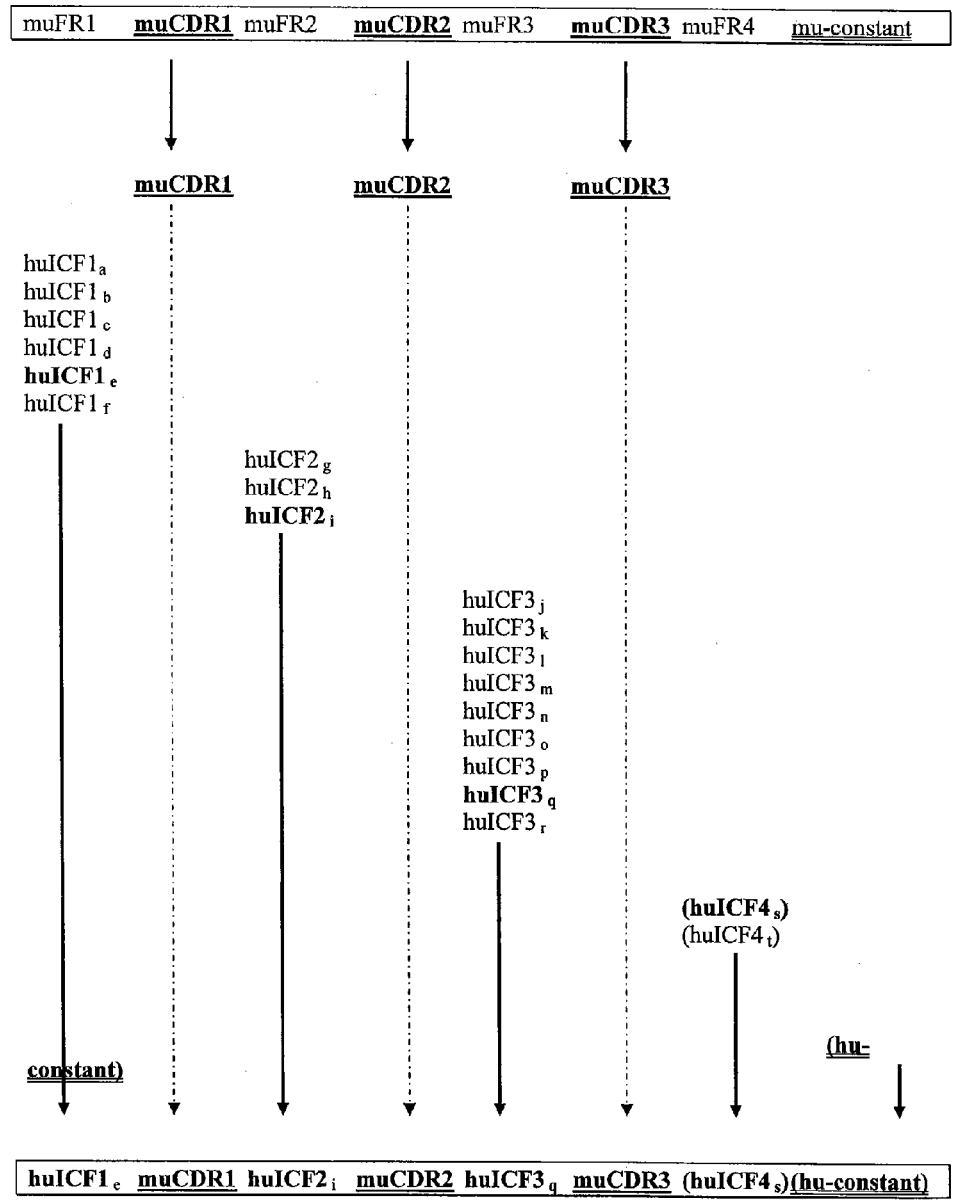
FIG. 1 is a schematic of the components of an exemplary heavy or light chain (amino acid sequences or nucleic acids encoding them), illustrating Human Framework Reassembly. A starting murine chain is shown, from which the sequences for three CDRs (underlined) are obtained. Various Independently Consensused Framework domains (ICFs) are provided for each of the positions corresponding to FR1, FR2, FR3, and optionally FR4. Preferred ICFs are independently selected for each position and assembled with the murine CDRs, optionally with a constant domain (double-underlined), to obtain a recombinant HuFR immunoglobulin chain.
Figure 4:
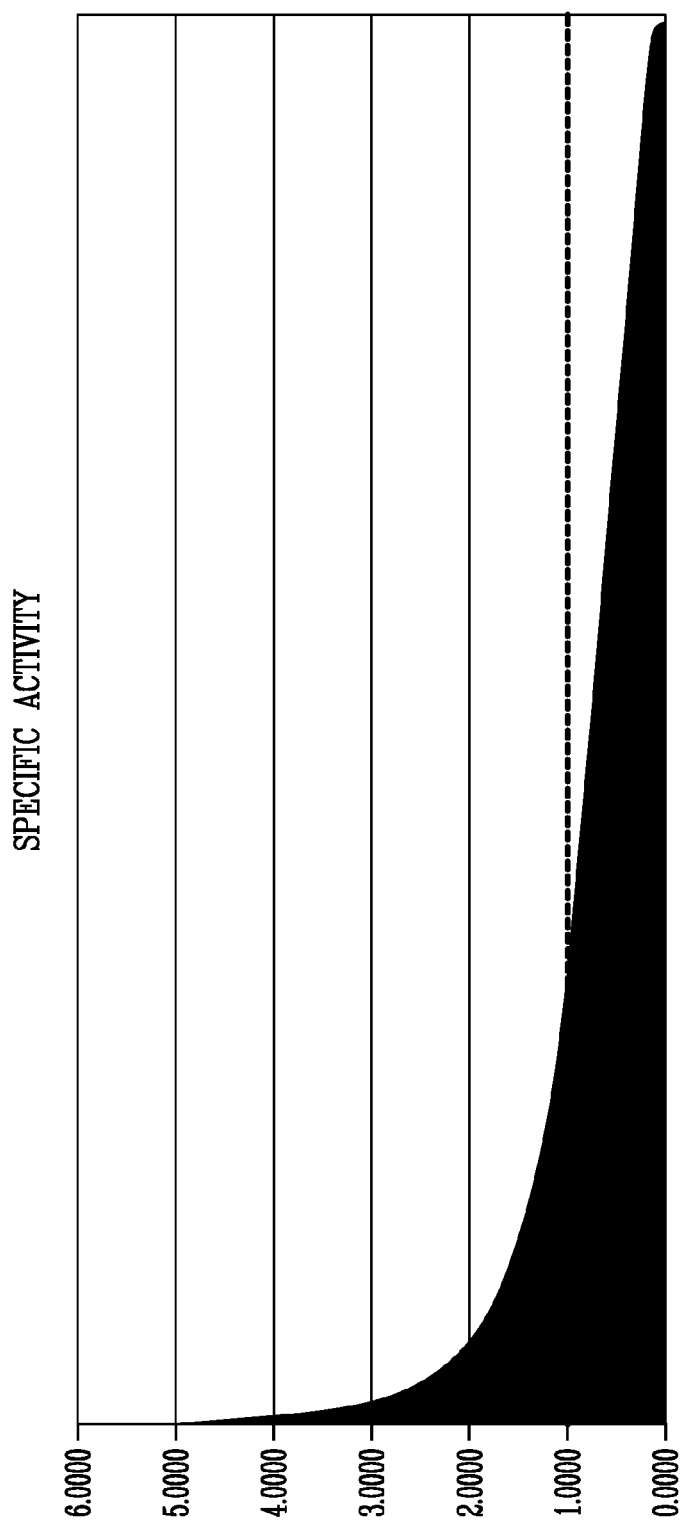
FIG. 4 illustrates a graph of data from an anti-CD20 ELISA assay demonstrating the specific activity of the anti-CD20 HuFR clones in the anti-CD20 cellular ELISA, as discussed in detail in Example 3, below.

The invention provides antibodies, such as chimeric human antibodies (chimeric antibodies with human components), recombinant antibodies, synthetic antibodies, the nucleic acids encoding them, and methods for making and using these immunoglobulins. The invention provides a novel approach to designing antibodies, including chimeric antibodies and/or recombinant or synthetic antibodies. The approach is based, at least in part, upon generating consensus sequences for immunoglobulin variable region framework subregions, where the consensus sequence for each subregion is obtained independently of the other subregions.

In one aspect, the consensus sequences are derived from (are compared to) germline sequences; thus, sequences that are most represented in the germline can be prioritized for antibody design. With a library of independently selected consensus sequences for each framework subregion, a combinatorial library of antibodies can be generated. For example, keeping the CDR regions of a known antibody (that specifically binds to a known antigen), the CDR regions can be reassembled into different framework subregion combinations, thereby creating a large collection of antibodies having the same CDR regions, but different framework sequences. This collection of antibodies can then be tested to determine which framework sequences provide the least immunogenicity while maintaining sufficient binding affinity and avidity toward the target antigen.

The invention provides compositions and libraries comprising heavy chain variable region polypeptides, including chimeric and/or recombinant, heavy chain variable region polypeptides, in addition to nucleic acids encoding them (e.g., that encode the chimeric heavy chain variable region polypeptides of the invention). The invention also provides compositions and libraries of light chain variable region polypeptides, including chimeric and/or recombinant, light chain variable region polypeptides, and nucleic acids encoding them (e.g., that encode the chimeric heavy chain variable region polypeptides). The heavy chain variable region polypeptides of the invention, including the chimeric and/or recombinant heavy chain variable region polypeptides, can be associated with a light chain variable region polypeptide (e.g., a light chain variable region polypeptide of this invention) in order to generate a bivalent immunoglobulin (Ig).

The invention also provides antibody compositions generated from the heavy chain and light chain variable regions comprising ICFs. In alternative embodiments, any CDR from any known antibody (for example, those exemplary antibodies shown in Tables 5-6) can be combined or linked with ICFs, such as those of Tables 1-4. In addition, they can be further combined or linked to a constant domain (CD) (for example, those shown in Tables 7-8) to generate full-length heavy chain variable region polypeptides or full-length light chain variable region polypeptides. Upon combining the polypeptides to generate immunoglobulins, the Igs can serve as functional units for the following non-limiting antibody examples: a single chain antibody, a bivalent antibody (such as a disulfide-linked antibody), a Fab fragment, and a single chain Fv.

Additionally, the present invention provides methods for generating a combinatorial library of nucleic acids that encode heavy chain and light chain variable regions that comprise ICFs. The present invention also provides methods for generating an antibody specific to an antigen and with a decreased immunogenicity.

In alternative embodiments, antibodies of the invention (e.g., the chimeric and/or recombinant antibodies of the invention) include and encompass (refer to), without limitation, monoclonal antibodies, multispecific antibodies, human antibodies, polyclonal antibodies, chimeric antibodies, single-chain Fvs (scFv), single chain antibodies, single domain antibodies, Fab fragments, F(ab) fragments, disulfide-linked Fvs (sdFv), anti-idiotypic (anti-Id) antibodies, and epitope-binding fragments of any of the above. In alternative embodiments, antibodies of the invention (e.g., the chimeric and/or recombinant antibodies of the invention) include immunoglobulin molecules and immunologically active fragments of immunoglobulin molecules, i.e., molecules that contain an antigen binding site. Antibody fragments can also include, but are not limited to, small "antibody mimetics" which are comprised of at least one CDR3 from either a heavy or light chain, at least one CDR1 or CDR2 from the immunoglobulin chain that did not provide the CDR3, and at least one framework region selected from either the heavy or light chain based on its ability to approximate the linkage of the CDRs in the parent molecule (the parent antibody). Immunoglobulin molecules can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass.

In alternative embodiments, antibodies of the invention (e.g., the chimeric and/or recombinant antibodies of the invention) can comprise the equivalent of a native full-length antibody, e.g., comprising two heavy chains paired with two light chains. In alternative embodiments, antibodies of the invention (e.g., the chimeric and/or recombinant antibodies of the invention) can comprise a full-length heavy chain of about 50 kD in size (approximately 446 amino acids in length); which in one aspect can be encoded by a heavy chain variable region gene (about 116 amino acids) and a constant region gene. In alternative embodiments, different constant region genes encoding heavy chain constant region of different isotypes such as alpha, gamma (IgG1, IgG2, IgG3, IgG4), delta, epsilon, and mu sequences are used. In alternative embodiments, a full-length light chain of about 25 kD in size (approximately 214 amino acids in length), as is encoded by a light chain variable region gene and a constant region gene, is used. The variable regions of the light and/or heavy chain participate in binding to an antigen, and the constant regions are generally responsible for the effector functions of the antibody.

In alternative embodiments, antibodies of the invention (e.g., the chimeric and/or recombinant antibodies of the invention) can comprise a "variable region" of a heavy and/or light antibody chain (which is an N-terminal mature domain of an antibody chain). All domains, CDRs, and residue numbers are assigned on the basis of sequence alignments and structural knowledge. In alternative embodiments, antibodies of the invention (e.g., the chimeric and/or recombinant antibodies of the invention) can comprise: $V_H$, which is the variable domain of an antibody heavy chain; or $V_L$, which is the variable domain of an antibody light chain, and alternatively can be of the kappa (κ) or of the lambda (λ) isotype.

In alternative embodiments, antibodies of the invention (e.g., the chimeric and/or recombinant antibodies of the invention) can comprise immunoglobulin light and/or heavy chain variable regions; which in one aspect can comprise or consist of a framework region (FR) that borders and encompasses three or four separate hypervariable regions, also called complementarity determining regions, or CDRs. In alternative embodiments, as in nature, the borderlines between the FR and the CDRs may not always be definite, and can depend on the particular antibody and its degree and location of variability relative to other, similar antibodies. The sequences of the framework regions of different light or heavy chains are relatively conserved within a species. The framework region of an antibody—that is the combined framework regions of the constituent light and heavy chains—serves to position and align the CDRs. The CDRs are primarily responsible for binding to an epitope of an antigen.

In alternative embodiments, the Kabat system (a well known and widely used guide) is used to identify framework regions and CDRs of the invention—see *Sequences of Proteins of Immunological Interest*, E. Kabat et al., U.S. Department of Health and Human Services, (1987) and (1991). Identifying Kabat framework sequence is well known and thus is a routine protocol; see e.g., U.S. Pat. No. 5,840,299; U.S. Pat. App. Pub. No. 20050261480. Kabat et al. list many amino acid sequences for antibodies for each subclass, and list the most commonly occurring amino acid for each residue position in that subclass. Kabat et al. use a method for assigning a residue number to each amino acid in a listed sequence, and this method for assigning residue numbers has become standard in the field. Kabat et al.'s scheme is extendible to other antibodies not included in the compendium by aligning the antibody in question with one of the consensus sequences in Kabat et al. The use of the Kabat et al. numbering system readily identifies amino acids at equivalent positions in different antibodies. For example, an amino acid at the L50 position of a human antibody occupies the equivalence position to an amino acid position L50 of a mouse antibody.

As used in the art, the term "CDR" refers to a complementarity determining region within antibody variable sequences. There are three CDRs in each of the variable regions of the heavy chain and the light chain, which are designated CDR1, CDR2 and CDR3 for each of the variable regions. Because CDRs represent regions of increased variability (relative to the regions of similar sequences), the exact boundaries of these CDRs can defined differently according to different systems. The widely used system described by Kabat (Kabat et al., *Sequences of Proteins of Immunological Interest* (National Institutes of Health, Bethesda, Md. (1987) and (1991)) provides a residue numbering system applicable to any variable region of an antibody, and provides residue boundaries defining the three CDRs. These CDRs may be referred to as "Kabat CDRs". Chothia et al. (*Nature* (1989) 342:877-883; Chothia and Lesk, (1987) *J. Mol. Biol.* 196:901-917) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designate the light chain and the heavy chains regions. These regions may be referred to as Chothia CDRs, which have boundaries that overlap with Kabat CDRs.

The term "framework," "framework region," or "framework sequence" refers to the remaining sequences of a variable region minus the CDRs. Because the exact definition of a CDR sequence can be determined by different systems, the meaning of a framework sequence is subject to correspondingly different interpretations. In one embodiment, the positioning of the six CDRs (CDR1, 2, and 3 of light chain and CDR1, 2, and 3 of heavy chain) within the framework region effectively divides the framework region of each chain into four subregions, designated FR1, FR2, FR3, and FR4. CDR1 is positioned between FR1 and FR2; CDR2 between FR2 and FR3; and CDR3 between FR3 and FR4. Without specifying the particular subregions as FR1, FR2, FR3, or FR4, a framework region, as referred by others, represents the combined subregions FR1, FR2, FR3, and FR4, within the variable region of a single, naturally occurring immunoglobulin chain. In an alternative embodiment, a framework region (FR) of the invention comprises or consists of (represents) any portion of the entire framework sequence, including a sequence consisting of one of the four subregions. In an alternative embodiment, a framework region (FR) of the invention comprises or consists of amino acids derived from a Kabat framework region (KF) domain, wherein the amino acid sequences are derived from germline immunoglobulin sequences.

In one embodiment, the term "germline sequence," with respect to an immunoglobulin sequence, means a genomic sequence (containing immunoglobulin coding sequences) that has not undergone the maturation process that leads to genetic rearrangement and somatic hypermutation for expression of a particular immunoglobulin. (See, e.g., Shapiro et al., (2002) *Crit. Rev. Immunol.* 22(3): 183-200; Marchalonis et al., (2001) *Adv. Exp. Med. Biol.* 484:13-30). A "germline" can include a lineage of cells that give rise to gametes and is continuous through many generations.

In one embodiment, the term "mature", e.g., with respect to mature immunoglobulins, mature (Ab) sequences and/or mature (Ab) forms, and the like, can include any non-germline immunoglobulin sequence; for example, any rearranged or modified germline sequence of any isotype rearranged with any V region, including affinity-matured sequences (e.g., after the process of affinity maturation in vivo or in vitro).

In one embodiment, the term "consensus sequence" comprises, or consists of, (refers to) an amino acid sequence that comprises more frequently occurring amino acid residues at each location in a set of related proteins (for example, immunoglobulins of any particular subclass, e.g., e.g., light chain, such as a kappa or lambda, or isotype) or subunit structure). The consensus sequence may be based on immunoglobulins of a particular species or of many species. In an alternative embodiments, "more frequently" means at least about 5%, 10%, 15%, 20%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% more frequently occurring amino acid residues at each residue location (position) in a set of related proteins, e.g., immunoglobulin sequences of any particular subclass (e.g., light chain, such as a kappa or lambda, or isotype) or subunit structure.

The term "derivative" refers to a molecule that can be formed from another molecule. In the context of a nucleotide (for example, a nucleic acid sequence) or a proteinaceous agent (such as, proteins, polypeptides, peptides and the like; for example, antibodies), a derivative can refer to the agent that comprises an original nucleic acid sequence (such as a germline sequence), or a proteinaceous agent that comprises an amino acid sequence, which has been obtained from an original source or altered by the introduction of amino acid residue substitutions, deletions, and/or additions. A derivative of such an agent possesses a similar or identical sequence as the agent from which it was derived As used herein, a "placeholder" is a nucleic acid sequence encoding an immunoglobulin variable region (for example, a light chain variable region) comprising Kabat framework regions 1, 2, and 3, and the CDRs 1, 2, and 3 of a known immunoglobulin. A placeholder is determined on the basis of a germline variable region nucleic acid sequence identity compared to that of a sequence of a processed, mature antibody (for example, those light chain variable region germline sequences that are most similar to the nucleic acid sequence of the mature antibody). The placeholder, once identified, can then be used as a temporary single chain molecule associated with, for example, a heavy chain variable region molecule of the invention, for the purpose of assessing the functional properties of the heavy chain while associated with a second chain. In one embodiment, the placeholder is a light chain variable region (for example, kappa chain or lambda chain).

As used herein, a "Kabat framework region" (KF) is a variable chain framework region (subregion) that corresponds to the standard Kabat scheme for numbering amino acid residues of immunoglobulins and assigning positions for FRs and CDRs (Kabat, et al. (1991) *Sequences of Proteins of Immunological Interest*, Fifth Edition. NIH Publication No. 91-3242). For example, according to this scheme, the following Kabat numbers can be used to discern the variable heavy chain framework subregions: Kabat framework region 1 (KF1, which can correspond to FR1) comprises from residue 1 to about residue 29; Kabat framework region 2 (KF2, which can correspond to FR2) comprises from about residue 36 to about residue 49; Kabat framework region 3 (KF3, which can correspond to FR3) comprises from about residue 66 to about residue 94; and Kabat framework region 4 (KF4, which can correspond to FR4) comprises from about residue 103 to about residue 113.

In addition, according to this scheme, in alternative embodiments, the following Kabat numbers are used to discern the variable light chain framework regions: Kabat framework region 1 (KF1, which can correspond to FR1) comprises from residue 1 to about residue 23; Kabat framework region 2 (KF2, which can correspond to FR2) comprises from about residue 35 to about residue 49; Kabat framework region 3 comprises from about residue 57 to about residue 88 (KF3, which can correspond to FR3); and Kabat framework region 4 comprises from about residue 96 to about residue 109 (KF4, which can correspond to FR4).

As used herein, "Independently Consensused Framework" (ICF), means a framework region (for example, FR1, FR2, FR3, FR4, and therefore may correspond to KF1, KF2, KF3, or KF4) having an amino acid or nucleic acid coding sequence that is a consensus sequence obtained, for example, from: (1) germline V or J genes, (2) rearranged VDJ genes, (3) rearranged VJ genes, and (4) amino acid sequences (and/or the nucleic acid sequences that encode identical or essentially identical amino acid sequences) of known immunoglobulins. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations." One of skill will recognize that each codon in a nucleic acid sequence (except AUG; which is ordinarily the only codon for methionine) can be modified to yield a functionally identical molecule by standard techniques.

In one embodiment, each ICF comprises a consensus sequence that is selected independently from other ICFs in a variable region. In other words, in one aspect, an ICF consensus sequence is obtained from analyzing a particular framework subregion independent from the other framework subregions (in contrast to a method that analyzes framework consensus sequences by examining entire framework regions and not by independently analyzing the separate framework subregions). Independent selection can entail aligning a pool of ICF germline nucleic acid sequences obtained from a plurality of germline nucleic acid sequences encoding at least some portion of a variable chain framework region and subsequently clustering the sequences according to sequence similarity, wherein sequences from each framework cluster are then used to form a consensus sequence. Upon translation, the consensus sequence demonstrates the most frequent amino acid sequences occurring at each residue position. The domain can be ICF1, ICF2, ICF3, or ICF4. The variable framework region amino acid residues can correspond to the standard Kabat numbering system. An ICF sequence can be identical to the original germline sequence used to determine the ICF domain. A consensus sequence also includes any wobble site changes in the nucleic acid consensus sequence wherein the nucleotide change will still encode the same amino acid sequence. For example, a consensus sequence can be determined for a human based on human germline sequences. Consensus sequences also can be determined for the following non-limiting examples, such as canine, feline, ovine, equine, bovine, porcine, fowl, goat, salmon, and hybridoma cell line, utilizing the appropriate germline sequences.

Immunoglobulin Structures

Immunoglobulins (Igs) are molecules that function as antibodies and are produced by plasma cells in response to an antigen (i.e., by way of an infection or immunization). Immunoglobulins can bind specifically to one or a few closely related antigens. The primary function of immunoglobulins is to bind to antigens, which mediates various effector functions that can ultimately result in protection of the animal. Igs are divided into five different classes, based on the differences in the amino acid sequences in the constant region of the heavy chains for example, gamma (γ) heavy chains (IgG), mu (μ) heavy chains (IgM), alpha (α) heavy chains (IgA), delta heavy chains (IgD), and epsilon (ε) heavy chains (IgE). All Igs within a given class will have similar heavy chain constant regions. The Ig classes can be further divided into subclasses on the basis of small differences in the amino acid sequences in the constant region of the heavy chains. Igs within a subclass can have similar heavy chain constant region amino acid sequences, wherein differences are detected by serological means. For example, the IgG subclasses comprise IgG1, IgG2, IgG3, and IgG4, wherein the heavy chain is classified as being a gamma 1 heavy chain, a gamma 2 heavy chain, and so on due to the amino acid differences. In another example, the IgA subclasses comprise IgA1 and IgA2, wherein the heavy chain is classified as being an alpha 1 heavy chain or an alpha 2 heavy chain due to the amino acid differences.

Immunoglobulins also comprise light chains, such as Kappa light chains or Lambda light chains. The distinctions in the light chain types are based on differences in the amino acid sequence in the constant region of the light chain, which also can be detected by serological means. The light chains can also be divided into subtypes based on differences in the amino acid sequences in the constant region of the light chain. For example, the Lambda subtypes are classified as Lambda 1, Lambda 2, Lambda 3, and Lambda 4.

Immunoglobulins comprise a population of heterogeneous molecules because they are composed of different classes and subclasses of heavy chains. Each heavy chain can subsequently associate with different types and subtypes of light chains. As a result, different immunoglobulin molecules can have different antigen binding properties due to the different $V_H$ and $V_L$ regions. Generally, immunoglobulins comprise a four-chain structure as their basic unit. Full-length Igs comprise two heavy chains (~50-70 kD) covalently linked and two light chains (~23 kD each, such as lambda or kappa chains). Each light chain is also covalently linked to one of the heavy chains. For example, the two heavy chains and the heavy and light chains are held together by inter-chain disulfide bonds and by non-covalent interactions. The number of inter-chain disulfide bonds can vary among different immunoglobulin molecules. Each chain has an N-terminal variable domain ($V_H$ or $V_L$ wherein each are ~110 amino acids in length) and one or more constant domains at the C-terminus. The constant domain of the light chain ($C_L$ which is ~110 amino acids in length) is aligned with and disulfide bonded to the first constant domain of the heavy chain ($C_H$ which is ~330-440 amino acids in length). The light chain variable domain is aligned with the variable domain of the heavy chain. The Ig heavy chain can comprise 2 or more additional $C_H$ domains (such as, $C_{H2}$, $C_{H3}$ and the like). For example, a hinge region can be identified between the $C_{H1}$ and $C_{H2}$ constant domains. This is the region where the arms of the antibody molecule form a Y-shape and allows for some flexibility in the molecule.

As discussed and defined above, the variable domains of the heavy and light chain include framework regions (FRs) and hypervariable regions called complementarity-determining regions (CDRs), and an intrachain disulfide bond. (See e.g. Chothia et al., (1985) *J. Mol. Biol.* 186:651-663; Novotny and Haber, (1985) *Proc. Natl. Acad. Sci. USA* 82:45924596; Padlar et al., (1986) *Mol. Immunol.*, 23(9): 951-960; and S. Miller, J. (1990) *Mol. Biol.*, 216:965-973).

The Ig heavy and light chain variable regions can be divided into groups and subgroups on the basis of their similarities and differences within the framework regions. The variability is the result of the products of the different variable region genes (such as the V, D, and J genes).

VDJ Recombination, Germline Sequences, and Immunoglobulin Diversity

The heavy chain and light chain variable regions of an Ig molecule comprise a V segment (variable gene segment) and a J segment (joining gene segment). A V gene encodes the V-segment and the J-segment refers to a region encoded by a J gene. In addition, the heavy chain variable region comprises a D segment (diversity gene segment), which is encoded by the D gene. The V segments of heavy and light chain variable regions consist of FR1, CDR1, FR2, CDR2, FR3, and a few amino acids of CDR3. The J segment of a light chain variable region includes the remainder of CDR3 and FR4 in its entirety. In the heavy chain variable region, the J segment includes a portion of CDR3 and all of FR4 wherein the D segment comprises the remaining portion of CDR3. For example, to generate a light chain variable region, a J segment is added to the V segment as a consequence of rearrangement of the light chain variable region genes during B-cell differentiation. In the case of the heavy chain, a D segment in addition to a J segment is added to the V segment to generate the heavy chain variable region.

Immunoglobulin diversity is the result of various processes, such as combinatorial assembly (for example, V(D)J recombination), junctional assembly, light chain coupling (for example, different combinations of κ and λ light chains can be used but not all heavy chains pair equally well with a κ and λ), and somatic hypermutation.

Combinatorial assembly of multiple germline genes involves encoding variable regions and a variety of somatic events. V(D)J recombination assembles Ig genes from component V, D, and J gene segments in developing B cells. The somatic events include the random recombination of variable (V) gene segments with diversity (D) and joining (J) gene segments to make a complete $V_H$ region—V(D)J domain of the heavy chain variable region. Briefly, the first recombination event occurs between one D and one J gene segment of the heavy chain locus in the developing B cell, forming the DJ complex. DNA between these two genes is deleted. The D-J recombination event is then followed by the joining of one V gene, from a region upstream of the newly formed DJ complex, resulting in the formation of a rearranged VDJ gene. Other genes between the V and D segments of the new VDJ gene are now deleted. The kappa (κ) and lambda (λ) chains of the immunoglobulin light chain loci recombine similarly to heavy chain variable regions, except the light chains lack a D segment wherein the events can also entail the random recombination of variable (V) and joining (J) gene segments to make a complete $V_L$ region—VJ domain of the light chain variable region.

Junctional diversity also contributes to the Ig diversity achieved during the recombination process. When the D gene segment is joined to the J gene segment, and the V gene segment is subsequently joined to the DJ region, the process in itself is imprecise, and can result in the loss or addition of nucleotides encoding various amino acids at the junctions of the V(D)J domain. These mechanisms involved in generating diversity occur in the developing B cell prior to antigen exposure.

After antigenic stimulation, the expressed Ig genes in B cells undergo somatic mutation or hypermutation (see Maizels (2005) *Ann. Rev. Genet.* 39:23-46), which further contributes to Ig variability. Mature B cells, following activation after encountering an antigen, have the capability to introduce point mutations into the variable regions of immunoglobulin genes (also referred to as affinity maturation); this occurs in specialized lymphoid structures—the germinal centers. Some mutations can cause the Ig to have a higher affinity for the antigen. Antibodies that bind strongly to an antigen are selected for proliferation because they are stimulated more often than an antibody that weakly binds to its antigen.

In addition to the mechanisms described above to generate Ig diversity, a genetically diverse collection of nucleotides derived wholly or partially from sequences that encode expressed immunoglobulins can be used. For example, the sequences may be generated from a cell line by in vitro stimulation, in response to which the rearrangement occurs. Alternatively, part or all of the sequences may be obtained by combining, e.g., unrearranged V segments with D and J segments, using nucleotide synthesis, randomized mutagenesis, and other methods, such as those disclosed in U.S. Pat. No. 5,565,332. Approximately $1.6 \times 10^7$ different antibodies can be produced based on the estimated number of germline gene segments (such as V, D, and J segments of the heavy and light chain variable regions), the random recombination of these segments, and the random pairing of heavy and light chain variable regions ($V_H$—$V_L$) (*Fundamental Immunology* (3rd ed), ed. Paul, Raven Press, New York, N.Y., 1993; *Immunobiology: the immune system in health and disease*, $4^{th}$ ed., Janeway et al., Elsevier Science/Garland Publishing, York, N.Y., 1999). When other processes that contribute to antibody diversity (such as somatic hypermutation) are taken into account, approximately $10^{10}$ different Igs can be generated (*Immunoglobulin Genes*, $2^{nd}$ ed., eds. Jonio et al., Academic Press, San Diego, Calif., 1995; *Immunology*, $3^{rd}$ ed., Kuby, J., W.H. Freeman and Co., New York, N.Y., 1997).

Polypeptides

The present invention provides compositions of recombinant heavy chain variable region polypeptides in addition to nucleic acids that encode the heavy chain variable region polypeptide. The invention also provides compositions of recombinant light chain variable region polypeptides as well as nucleic acids that encode the heavy chain variable region polypeptide. The recombinant heavy chain variable region polypeptide can be coupled to a light chain variable region polypeptide in order to generate an immunoglobulin. The nucleic acid compositions in addition to the nucleic acid sequences that are useful in the methods of this invention, i.e., those that encode at least in part the individual light chain or heavy chain variable region peptides, polypeptides, or proteins, may be naturally occurring, synthetic or a combination thereof. They may be mRNA, DNA or cDNA. In some embodiments of the invention, the nucleic acids encode antibodies. In further embodiments, the nucleic acids encode a single chain antibody, a bivalent antibody, a Fab fragment, or a single chain Fv.

In one embodiment, amino acid sequences that encode Independently Consensused Frameworks (ICFs) are provided to generate a recombinant heavy chain variable region (see Table 1). In another embodiment, nucleic acids that encode amino acid sequences corresponding to ICFs are provided to generate a recombinant heavy chain variable region polypeptide (Table 2). In other embodiments, amino acid sequences that encode Independently Consensused Frameworks are provided to generate a recombinant light chain variable region (see Table 3). In yet further embodiments, nucleic acids that encode amino acid sequences corresponding to ICFs are provided to generate a recombinant light chain variable region polypeptide (Table 4). An ICF (for example, ICF1, ICF2, ICF3, or ICF4) can be a Kabat framework (KF) region (i.e., KF1, KF2, KF3, or KF4) comprising an amino acid or nucleic acid coding sequence that is a consensus sequence obtained, for example, from: (1) germline V or J genes, (2) rearranged VDJ genes, (3) rearranged VJ genes, or (4) amino acid sequences (and/or the nucleic acid sequences that encode identical or essentially identical amino acid sequences) of known Igs.

TABLE 1

Exemplary Amino Acid Sequences for Variable Heavy ($V_H$) Chain ICFs

| Identifier | Amino Acid sequence | SEQ ID NO: |
|---|---|---|
| Heavy Chain IFC1s: | | |
| GL1_8 | EVQLVESGGGLVQPGGSLRLSCAAS | 1 |
| GL2 | QVQLVESGGGVVQPGRSLRLSCAAS | 2 |
| GL3 | QVQLQESGPGLVKPSETLSLTCAVS | 3 |
| GL4 | QVTLKESGPALVKPTQTLTLTCTFS | 4 |

TABLE 1-continued

Exemplary Amino Acid Sequences for Variable Heavy (V$_H$) Chain ICFs

| Identifier | Amino Acid sequence | SEQ ID NO: |
|---|---|---|
| GL5 | QVQLQESGPGLVKPSQTLSLTCTVS | 5 |
| GL6 | EVQLVQSGAEVKKPGESLKISCKGS | 6 |
| GL7 | QVQLVQSGAEVKKPGASVKVSCKAS | 7 |
| GL1a | QVQLVQSGAEVKKPGSSVKVSCKAS | 186 |
| GL2a | QVTLRESGPALVKPTQTLTLTCTFS | 187 |
| GL4a | QVQLQESGPGLVKPSETLSLTCTVS | 188 |
| GL6a | QVQLQQSGPGLVKPSQTLSLTCAIS | 189 |
| GL7a | QVQLVESGAEVKKPGASVKVSCKAS | 181 |
| GL2b | QVQLVQSGGGVVQPGRSLRLSCAAS | 199 |
| Heavy Chain IFC2s: | | |
| GL1_7_8 | WVRQAPGKGLEWVS | 8 |
| GL2_3 | WVRQAPGKGLEWVG | 9 |
| GL4 | WVRQAPGQGLEWMG | 10 |
| GL5 | WVRQAPGKGLEWMG | 11 |
| GL 6 | WIRQPPGKGLEWIG | 12 |
| GL2a | WIRQPPGKALEWLG | 190 |
| GL5a | WVRQMPGKGLEWMG | 191 |
| GL6a | WIRQSPSRGLEWLG | 192 |
| Heavy Chain IFC3s: | | |
| GL1 | RFTISRDNAKNSLYLQMNSLRAEDTAVYYCAR | 13 |
| GL2 | RFTISRDNSKNTLHLQMNSLRAEDTAVYYCKR | 14 |
| GL3 | RFTISRDDSKNTAYLQMNSLKTEDTAVYYCTR | 15 |
| GL4 | RVTISVDTSKNQFSLKLSSVTAADTAVYYCAR | 16 |
| GL5 | RLTISKDTSKNQVVLTMTNMDPVDTATYYCAR | 17 |
| GL6 | RFVFSLDTSVSTAYLQMSSLKAEDTAVYYCAR | 18 |
| GL7 | RVTISADKSISTAYLQWSSLKASDTAMYYCAR | 19 |
| GL8 | RVTITADKSTSTAYMELSSLRSEDTAVYYCAR | 20 |
| GL1a | RFTISRDNAKNSLYLQMNSLRAEDTALYYCAKD | 180 |
| GL1b | RVTITADESTSTAYMELSSLRSEDTAVYYCAR | 193 |
| GL1c | RVTMTRNTSISTAYMELSSLRSEDTAVYYCAR | 194 |
| GL2a | RFTISRDNSKNTLHLQMNSLRAEDTAVYYCKK | 182 |
| GL3a | RFTISRDNSKNSLYLQMNSLRTEDTALYYCAKD | 195 |
| GL3b | RFTISRDNSKNTLYLQMNSLRAEDTAVYYCAR | 196 |
| GL5a | RLTISKDTSKNQVVLTMTNMDPVDTATYYCARI | 183 |
| GL6a | RFVFSLDTSVSTAYLQICSLKAEDTAVYYCAR | 197 |
| GL6b | RITINPDTSKNQFSLQLNSVTPEDTAVYYCAR | 198 |
| GL7a | HVTISADKSISTAYLQWSSLKASDTAMYYCAR | 184 |
| GL8a | RVTMTRDTSTSTAYMELSSLRSEDTAVYYCAR | 185 |
| Heavy Chain IFC4s: | | |
| GL1 | VTVSSASTKGPS | 21 |
|  | VTVSASTKGPS | 206 |
|  | WGQGTVTVSASTKGPS | 207 |

TABLE 2

Exemplary Nucleic Acid Sequences for Variable Heavy (V$_H$) Chain ICFs.

| | | SEQ ID NO: |
|---|---|---|
| Heavy Chain IFC1s: | | |
| GL1 | GAAGTGCAGCTGGTGGAGTCTGGGGGAGGCTTGGTACAGCCTGGCGGGTCCCTG AGACTCTCCTGTGCAGCCTCT | 22 |
| GL2 | CAGGTGCAGCTGGTGGAGTCTGGGGGAGGCGTGGTCCAGCCTGGGAGGTCCCTG AGACTCTCCTGTGCAGCCTCT | 23 |
| GL3 | CAGGTGCAGCTGCAGGAGTCGGGCCCAGGACTGGTGAAGCCTTCGGAGACCCTG TCCCTCACCTGCGCTGTCTCT | 24 |
| GL4 | CAGGTCACCTTGAAGGAGTCTGGTCCTGCGCTGGTGAAACCCACACAGACCCTC ACACTGACCTGCACCTTCTCT | 25 |
| GL5 | CAGGTGCAGCTGCAGGAGTCGGGCCCAGGACTGGTGAAGCCTTCACAGACCCTG TCCCTCACCTGCACTGTCTCT | 26 |
| GL6 | GAGGTGCAGCTGGTGCAGTCTGGAGCAGAGGTGAAAAAGCCCGGGGAGTCTCTG AAGATCTCCTGTAAGGGTTCT | 27 |

TABLE 2-continued

Exemplary Nucleic Acid Sequences for Variable Heavy ($V_H$) Chain ICFs.

| | | SEQ ID NO: |
|---|---|---|
| GL7 | CAGGTGCAGCTGGTGCAGTCTGGGGCTGAGGTGAAGAAGCCTGGGGCTTCGGTGAAGGTCTCCTGCAAGGCTTCT | 28 |

Heavy Chain IFC2s:

| | | |
|---|---|---|
| GL1_7_8 | TGGGTCCGCCAGGCTCCAGGGAAGGGGCTGGAGTGGGTCTCA | 29 |
| GL2_3 | TGGGTCCGCCAGGCTCCAGGCAAGGGGCTAGAGTGGGTGGCA | 30 |
| GL4 | TGGGTCCGCCAGGCTCCAGGGAAGGGGCTGGAGTGGGTTGGC | 31 |
| GL5 | TGGGTGCGACAGGCCCCTGGACAAGGGCTTGAGTGGATGGGA | 32 |
| GL6 | TGGGTGCGACAGGCTCCTGGAAAAGGGCTTGAGTGGATGGGA | 33 |

Heavy Chain IFC3s:

| | | |
|---|---|---|
| GL1 | CGATTCACCATCTCCAGAGACAACGCCAAGAACTCACTGTATCTGCAAATGAACAGCCTGAGAGCCGAGGACACGGCTGTGTATTACTGTGCGAGA | 34 |
| GL2 | CGATTCACCATCTCCAGAGACAACAGCAAAAACTCCCTGTATCTGCAAATGAACAGTCTGAGAACTGAGGACACCGCCTTGTATTACTGTGCAAGA | 35 |
| GL3 | AGGTTCACCATCTCCAGAGATGATTCAAAGAACACGGCGTATCTGCAAATGAACAGCCTGAAAACCGAGGACACGGCCGTGTATTACTGTACTAGA | 36 |
| GL4 | CGAGTTACCATATCAGTAGACACGTCTAAGAACCAGTTCTCCCTGAAGCTGAGCTCTGTGACTGCCGCGGACACGGCCGTGTATTACTGTGCGAGA | 37 |
| GL5 | AGGCTCACCATCTCCAAGGACACCTCCAAAAACCAGGTGGTCCTTACAATGACCAACATGGACCCTGTGGACACAGCCACGTATTACTGTGCACGG | 38 |
| GL6 | CGATTTGTCTTCTCCCTCGACACGTCTGTCAGCACGGCGTATCTTCAGATGTCTAGCCTAAAGGCTGAGGACACGGCCGTCTATTACTGTGCGCGA | 39 |
| GL7 | CGCGTCACCATCTCAGCTGACAAGTCCATCAGCACTGCCTACCTGCAGTGGAGCAGCCTGAAGGCCTCGGACACCGCCATGTATTACTGTGCGAGA | 40 |
| GL8 | AGAGTCACGATTACCGCGGACAAATCCACGAGCACAGCCTACATGGAGCTGAGCAGCCTGAGATCTGAGGACACGGCCGTGTATTACTGTGCGAGA | 41 |

Heavy Chain IFC4s:

| | | |
|---|---|---|
| GL1 | GTCACCGTCTCCTCCGCCTCCACCAAGGGCCCATCG | 42 |

TABLE 3

Exemplary Amino Acid Sequences of Variable Light Chain ($V_\kappa$ or $V_\lambda$) ICFs

| | Amino Acid sequence | SEQ ID NO: |
|---|---|---|
| ICF1 kappa | | |
| VK1_2 | DIQMTQSPSSLSASVGDRVTITC | 43 |
| VK3 | DIQMTQSPSTLSASVGDRVTITC | 44 |
| VK4 | EIVMTQSPATLSVSPGERATLSC | 45 |
| VK5 | EIVLTQSPATLSLSPGERATLSC | 46 |
| VK6 | EIVLTQSPGTLSLSPGERATLSC | 47 |
| VK7 | DIVMTQSPDSLAVSLGERATINC | 48 |
| VK8 | DIVMTQSPLSLPVTPGEPASISC | 49 |
| VK1_2a | DIVMTQSPSSLSASVGDRVTITC | 200 |

TABLE 3-continued

Exemplary Amino Acid Sequences of Variable Light Chain ($V_\kappa$ or $V_\lambda$) ICFs

| | Amino Acid sequence | SEQ ID NO: |
|---|---|---|
| VK4a or VK5a | EIVMTQSPATLSLSPGERATLSC | 201 |
| VK7a | DIQMTQSPDFLAVSLGERATINC | 202 |
| VKa | EIVLTQSPSSLSASVGDRVTITC | 203 |
| | DIVMTQTPLSLPVTPGEPASISC | 261 |
| | DIVMTQTPLSLSVTPGQPASISC | 262 |
| | EIVLTQSPDFQSVTPKEKVTITC | 263 |
| | ETTLTQSPAFMSATPGDKVNISC | 264 |
| | AIRMTQSPFSLSASVGDRVTITC | 265 |
| | AIQLTQSPSSLSASVGDRVTITC | 266 |

TABLE 3-continued

Exemplary Amino Acid Sequences of Variable Light Chain (V$_\kappa$ or V$_\lambda$) ICFs

| | Amino Acid sequence | SEQ ID NO: |
|---|---|---|
| | NIQMTQSPSAMSASVGDRVTITC | 267 |
| | DVVMTQSPLSLPVTLGQPASISC | 268 |
| | DIVMTQTPLSSPVTLGQPASISC | 269 |
| | DVVMTQSPAFLSVTPGEKVTITC | 270 |
| | VIWMTQSPSLLSASTGDRVTISC | 271 |
| | AIRMTQSPSSFSASTGDRVTITC | 272 |
| ICF1 lambda | | |
| VL1 | QSVLTQPPSVSAAPGQKVTISC | 50 |
| VL2 | QSVLTQPPSASGTPGQRVTISC | 51 |
| VL3 | QSALTQPASVSGSPGQSITISC | 52 |
| VL4 | QSALTQPRSVSGSPGQSVTISC | 53 |
| VL5 | SYVLTQPPSVSVAPGKTARITC | 54 |
| VL6 | SSELTQDPAVSVALGQTVRITC | 55 |
| VL7 | SYELTQPPSVSVSPGQTASITC | 56 |
| VL8 | QLVLTQSPSASASLGASVKLTC | 57 |
| ICF2 kappa | | |
| VK1_2_3 | WYQQKPGKAPKLLIY | 58 |
| VK4_5_6 | WYQQKPGQAPRLLIY | 59 |
| VK7 | WYQQKPGQPPKLLIY | 60 |
| VK8 | WYLQKPGQSPQLLIY | 61 |
| VK4_5_6a | WYQQKPCQAPRLLIY | 204 |
| | WFQQKPGKAPKSLIY | 273 |
| | WYQQKPAKAPKLFIY | 274 |
| | WYLQKPGQPPQLLIY | 275 |
| | WYQQKPGKAPELLIY | 276 |
| | WYQQKPGKVPKLLIY | 277 |
| | WYQQKPEKAPKSLIY | 278 |
| | WFQQRPGQSPRRLIY | 279 |

TABLE 3-continued

Exemplary Amino Acid Sequences of Variable Light Chain (V$_\kappa$ or V$_\lambda$) ICFs

| | Amino Acid sequence | SEQ ID NO: |
|---|---|---|
| | WYQQKPDQSPKLLIK | 280 |
| | WFQQKPGKVPKHLIY | 281 |
| | WYQQKPGKAPKRLIY | 282 |
| | WLQQRPGQPPRLLIY | 283 |
| | WYQQKPGEAAIFIIQ | 284 |
| ICF2 lambda | | |
| VL1_2 | WYQQLPGTAPKLLIY | 62 |
| VL3_4 | WYQQHPGKAPKLMIY | 63 |
| VL5_6 | WYQQKPGQAPVLVIY | 64 |
| VL7 | WYQQKPGQSPVLVIY | 65 |
| VL8 | WHQQQPEKGPRYLMY | 66 |
| ICF3 kappa | | |
| VK1 | GVPSRFSGSGSGTDFTLTISSLQPEDFATYYC | 67 |
| VK2 | GVPSRFSGSGSGTDFTFTISSLQPEDIATYYC | 68 |
| VK3 | GVPSRFSGSGSGTEFTLTISSLQPDDFATYYC | 69 |
| VK4 | GIPARFSGSGSGTEFTLTISSLQSEDFAVYYC | 70 |
| VK5 | GIPARFSGSGSGTDFTLTISSLEPEDFAVYYC | 71 |
| VK6 | GIPDRFSGSGSGTDFTLTISRLEPEDFAVYYC | 72 |
| VK7 | GVPDRFSGSGSGTDFTLTISSLQAEDVAVYYC | 73 |
| VK8 | GVPDRFSGSGSGTDFTLKISRVEAEDVGVYYC | 74 |
| | GVPSRFSGSGSGTDFTLTISCLQSEDFATYYC | 253 |
| | GVPSRFSGSGSGTEFTLTISSLQPEDFATYYC | 254 |
| | GIPARFSGSGPGTDFTLTISSLEPEDFAVYYC | 255 |
| | GVPSRFSGSGSGTDFTLTINSLEAEDAATYYC | 256 |
| | GIPARFSGSGSGTDFTLTISSLQPEDFAVYYC | 257 |
| | GVPSRFSGSGSGTDFTFTISSLEAEDAATYYC | 258 |
| | GIPPRFSGSGYGTDFTLTINNIESEDAAYYFC | 259 |
| | GVPSRFSGSGSGTDFTLTISSLQPEDVATYYC | 260 |

TABLE 4

Exemplary Nucleic Acid Sequences for Variable Light Chain ICFs

| | Nucleic Acid Sequence | SEQ ID NO: |
|---|---|---|
| ICF1 kappa | | |
| VK1_2 | GACATCCAGATGACCCAGTCTCCATCCTCCCTGTCTGCATCTGTAGGAG ACAGAGTCACCATCACTTGC | 85 |

TABLE 4-continued

Exemplary Nucleic Acid Sequences for Variable Light Chain ICFs

| | Nucleic Acid Sequence | SEQ ID NO: |
|---|---|---|
| VK3 | GACATCCAGATGACCCAGTCTCCTTCCACCCTGTCTGCATCTGTAGGAG ACAGAGTCACCATCACTTGC | 86 |
| VK4 | GAAATAGTGATGACGCAGTCTCCAGCCACCCTGTCTGTGTCTCCAGGGG AAAGAGCCACCCTCTCCTGC | 87 |
| VK5 | GAAATTGTGTTGACACAGTCTCCAGCCACCCTGTCTTTGTCTCCAGGGG AAAGAGCCACCCTCTCCTGC | 88 |
| VK6 | GAAATTGTGTTGACGCAGTCTCCAGGCACCCTGTCTTTGTCTCCAGGGG AAAGAGCCACCCTCTCCTGC | 89 |
| VK7 | GACATCGTGATGACCCAGTCTCCAGACTCCCTGGCTGTGTCTCTGGGCG AGAGGGCCACCATCAACTGC | 90 |
| VK8 | GATATTGTGATGACCCAGTCTCCACTCTCCCTGCCCGTCACCCCTGGAG AGCCGGCCTCCATCTCCTGC | 91 |
| ICF1 lambda | | |
| VL1 | CAGTCTGTGTTGACGCAGCCGCCCTCAGTGTCTGCGGCCCCAGGACAGA AGGTCACCATCTCCTGC | 92 |
| VL2 | CAGTCTGTGCTGACTCAGCCACCCTCAGCGTCTGGGACCCCCGGGCAGA GGGTCACCATCTCTTGT | 93 |
| VL3 | CAGTCTGCCCTGACTCAGCCTGCCTCCGTGTCTGGGTCTCCTGGACAGT CGATCACCATCTCCTGC | 94 |
| VL4 | CAGTCTGCCCTGACTCAGCCTCGCTCAGTGTCCGGGTCTCCTGGACAGT CAGTCACCATCTCCTGC | 95 |
| VL5 | TCCTATGTGCTGACTCAGCCACCCTCAGTGTCAGTGGCCCCAGGAAAGA CGGCCAGGATTACCTGT | 96 |
| VL6 | TCTTCTGAGCTGACTCAGGACCCTGCTGTGTCTGTGGCCTTGGGACAGA CAGTCAGGATCACATGC | 97 |
| VL7 | TCCTATGAGCTGACTCAGCCACCCTCAGTGTCCGTGTCCCCAGGACAGA CAGCCAGCATCACCTGC | 98 |
| ICF2 kappa | | |
| VK1_2_3 | TGGTATCAGCAGAAACCAGGGAAAGCCCCTAAGCTCCTGATCTAT | 100 |
| VK4_5_6 | TGGTACCAGCAGAAACCTGGCCAGGCTCCCAGGCTCCTCATCTAT | 101 |
| VK7 | TGGTACCAGCAGAAACCAGGACAGCCTCCTAAGCTGCTCATTTAC | 102 |
| VK8 | TGGTATCTGCAGAAGCCAGGGCAGTCTCCACAGCTCCTGATCTAT | 103 |
| ICF2 lambda | | |
| VL1_2 | TGGTACCAGCAGCTCCCAGGAACAGCCCCCAAACTCCTCATCTAT | 104 |
| VL3_4 | TGGTACCAACAGCACCCAGGCAAAGCCCCCAAACTCATGATTTAT | 105 |
| VL5_6 | TGGTACCAGCAGAAGCCAGGCCAGGCCCCTGTGCTGGTCATCTAT | 106 |
| VL7 | TGGTATCAGCAGAAGCCAGGCCAGTCCCCTGTGCTGGTCATCTAT | 107 |
| ICF3 kappa | | |
| VK1 | GGGGTCCCATCAAGGTTCAGTGGCAGTGGATCTGGGACAGATTTCACTC TCACCATCAGCAGTCTGCAACCTGAAGATTTTGCAACTTACTACTGT | 109 |
| VK2 | GGGGTCCCATCAAGGTTCAGTGGAAGTGGATCTGGGACAGATTTTACTT TCACCATCAGCAGCCTGCAGCCTGAAGATATTGCAACATATTACTGT | 110 |
| VK3 | GGGGTCCCATCAAGGTTCAGCGGCAGTGGATCTGGGACAGAATTCACTC TCACCATCAGCAGCCTGCAGCCTGATGATTTTGCAACTTATTACTGC | 111 |
| VK4 | GGCATCCCAGCCAGGTTCAGTGGCAGTGGGTCTGGGACAGAGTTCACTC TCACCATCAGCAGCCTGCAGTCTGAAGATTTTGCAGTTTATTACTGT | 112 |

TABLE 4-continued

Exemplary Nucleic Acid Sequences for Variable Light Chain ICFs

| | Nucleic Acid Sequence | SEQ ID NO: |
|---|---|---|
| VK5 | GGCATCCCAGCCAGGTTCAGTGGCAGTGGGTCTGGGACAGACTTCACTC TCACCATCAGCAGCCTAGAGCCTGAAGATTTTGCAGTTTATTACTGT | 113 |
| VK6 | GGCATCCCAGACAGGTTCAGTGGCAGTGGGTCTGGGACAGACTTCACTC TCACCATCAGCAGACTGGAGCCTGAAGATTTTGCAGTGTATTACTGT | 114 |
| VK7 | GGGGTCCCTGACCGATTCAGTGGCAGCGGGTCTGGGACAGATTTCACTC TCACCATCAGCAGCCTGCAGGCTGAAGATGTGGCAGTTTATTACTGT | 115 |
| VK8 | GGGGTCCCTGACAGGTTCAGTGGCAGTGGATCAGGCACAGATTTTACAC TGAAAATCAGCAGAGTGGAGGCTGAGGATGTTGGGGTTTATTACTGT | 116 |
| ICF3 lambda | | |
| VL1 | GGGATTCCTGACCGATTCTCTGGCTCCAAGTCTGGCACGTCAGCCACCC TGGGCATCACCGGACTCCAGACTGGGGACGAGGCCGATTATTACTGC | 117 |
| VL2 | GGGGTCCCTGACCGATTCTCTGGCTCCAAGTCTGGCACCTCAGCCTCCC TGGCCATCAGTGGGCTCCAGTCTGAGGATGAGGCTGATTATTACTGT | 118 |
| VL3 | GGGGTTTCTAATCGCTTCTCTGGCTCCAAGTCTGGCAACACGGCCTCCC TGACCATCTCTGGGCTCCAGGCTGAGGACGAGGCTGATTATTACTGC | 119 |
| VL4 | GGGGTCCCTGATCGCTTCTCTGGCTCCAAGTCTGGCAACACGGCCTCCC TGACCATCTCTGGGCTCCAGGCTGAGGATGAGGCTGATTATTACTGC | 120 |
| VL5 | GGGATCCCTGAGCGATTCTCTGGCTCCAACTCTGGGAACACGGCCACCC TGACCATCAGCAGGGTCGAAGCCGGGGATGAGGCCGACTATTACTGT | 121 |
| VL6 | GGGATCCCAGACCGATTCTCTGGCTCCAGCTCAGGAAACACAGCTTCCT TGACCATCACTGGGGCTCAGGCGGAAGATGAGGCTGACTATTACTGT | 122 |
| VL7 | GGGATCCCTGAGCGATTCTCTGGCTCCAACTCTGGGAACACAGCCACTC TGACCATCAGCGGGACCCAGGCTATGGATGAGGCTGACTATTACTGT | 123 |
| ICF4 kappa | | |
| VK1 | TTCGGCCAAGGGACCAAGGTGGAAATCAAA | 125 |
| ICF4 lambda | | |
| VL1 | TTCGGCGGAGGGACCAAGCTGACCGTCCTA | 126 |

In addition to the sequences listed in Tables 1 to 4, other ICFs that can be used in the invention are provided (colored or non-underlined subsequences) in FIGS. 24, 32, 33, 34, 38, 39, and in the assembled HuFR sequences disclosed in Examples 3 and 4.

For example, each ICF comprises a consensus sequence that is independently selected, wherein independent selection can involve aligning a pool of ICF germline nucleic acid sequences obtained from a plurality of germline nucleic acid sequences encoding at least some portion of a variable chain Kabat framework region and subsequently clustering the sequences according to sequence similarity. For example, the sequences from each framework cluster are then used to establish a consensus sequence for a heavy chain variable region. In a non-limiting example, the sequences of all germline human $V_H$ exons can be compiled, and each of the exon sequences can be subsequently divided into the framework subregions, FR1, 2, 3, and 4 as prescribed by Kabat et al. (see above).

A set of FR subregion sequences (such as a pool of Kabat FR1 sequences), rather than a sequence of the entire framework that comprises framework subregions 1-4, are then aligned and clustered by sequence similarity. Sequences from each FR subregion cluster (for example, FR1, FR2, FR3, or FR4) can then be used to create a consensus sequence (for example ICF1, ICF2, ICF3, and ICF4), independently derived from the entire framework region, which comprises the most frequent amino acid occurring at each sequence position (see Tables 1 and 2). This consensus process can also be carried out for $V_L$ exons in order to identify the consensus sequences within each framework subregion (Tables 3-4; see also Examples 1-2). For example, the ICF sequences used for assembling the heavy chain variable region resulted in a total of 336 heavy chain variable region combinations (i.e., 7 IFC1 sequences×6 ICF2 sequences×8 ICF3 sequences×1 ICF4 sequence). In another example using the ICF sequences to assemble a light chain variable region (for example a kappa light chain), a total of 224 light chain variable region combinations are possible (i.e., 7 IFC1 sequences×4 ICF2 sequences×8 ICF3 sequences×1 ICF4 sequence). When both the heavy chain and light chain variable region combinations are associated with another, a total of 75,264 heavy chain-light chain complexes (for example, more human-like immunoglobulin molecules) can be generated.

In one embodiment, the heavy chain variable region ICF1 nucleic acid sequence comprises any of SEQ ID NO: 22, 23, 24, 25, 26, 27, or 28. In another embodiment, the heavy chain variable region ICF2 nucleic acid sequence comprises SEQ ID NO: 29, 30, 31, 32, or 33. In a further embodiment, the heavy chain variable region ICF3 nucleic acid sequence comprises SEQ ID NO: 34, 35, 36, 37, 38, 39, 40, or 41. In yet another embodiment of the invention, the heavy chain variable region ICF4 nucleic acid sequence is SEQ ID NO: 42.

In another example, the sequences from each framework cluster can also be used to establish a consensus sequence for a light chain variable region. In one embodiment, the light chain variable region ICF1 nucleic acid sequence comprises SEQ ID NO: 85, 86, 87, 88, 89, 90, 91, 92, 93, 94, 95, 96, 97, or 98. In another embodiment, the light chain variable region ICF2 nucleic acid sequence comprises SEQ ID NO: 100, 101, 102, 103, 104, 105, 106, or 107. In a further embodiment, the light chain variable region ICF3 nucleic acid sequence comprises SEQ ID NO: 109, 110, 111, 112, 113, 114, 115, 116, 117, 118, 119, 120, 121, 122, or 123. In yet another embodiment of the invention, the light chain variable region ICF4 nucleic acid sequence is SEQ ID NO: 125 or 126.

Amino acid sequences from each framework cluster can also be used to establish a consensus sequence for a heavy chain variable region. In one embodiment, the heavy chain variable region ICF1 amino acid sequence comprises any of SEQ ID NO: 1-7, 186, 187, 188, 189, 181, 199. In another embodiment, the heavy chain variable region ICF2 amino acid sequence comprises any of SEQ ID NO: 8-12 or 190-192. In a further embodiment, the heavy chain variable region ICF3 amino acid sequence comprises SEQ ID NO: 13-20, 180, 182-185, or 193-198. In yet another embodiment of the invention, the heavy chain variable region ICF4 amino acid sequence is SEQ ID NO: 21, 206, or 207.

Additionally, amino acid sequences from each framework cluster can also be used to establish a consensus sequence for a light chain variable region. In one embodiment, the light chain variable region ICF1 amino acid sequence comprises any of SEQ ID NO: 43-57 or 200-204. In another embodiment, the light chain variable region ICF2 amino acid sequence comprises SEQ ID NO: 58, 59, 60, 61, 62, 63, 64, 65, 66, or 204. In a further embodiment, the light chain variable region ICF3 amino acid sequence comprises SEQ ID NO: 67, 68, 69, 70, 71, 72, 73, 74, 75, 76, 77, 78, 79, 80, 81, or 82. In yet another embodiment of the invention, the light chain variable region ICF4 amino acid sequence is SEQ ID NO: 83 or 84.

Upon translation, the ICF1, ICF2, ICF3, or ICF4 consensus sequences demonstrate the most frequent amino acid sequences that occur at each residue position. An ICF sequence can be identical to the original germline sequence used to determine the ICF domain. In one embodiment, the ICF sequences comprising a heavy chain variable region are at least 80%, identical to a germline Kabat Framework Region (KFR). In another embodiment, the ICF sequences are at least 85%, 90%, 93%, 95%, 99%, or 100% identical to a germline KFR.

An ICF sequence of a light chain variable region polypeptides of the instant invention also can be identical to the original germline sequence used to determine the ICF domain. In another embodiments the ICF sequences comprising a light chain variable region are at least 70% identical to a germline KFR. In another embodiment, the ICF sequences are at least 50%, 60%, 70%, 80%, 85%, 90%, 93%, 95%, 99%, or 100% identical to a germline KFR.

Upon translation, the ICF1, ICF2, ICF3, or ICF4 consensus sequences demonstrate the most frequent amino acid sequences that occur at each residue position. In one embodiment, the ICF sequences comprising a heavy chain variable region are at least 80%, 85%, 90%, 93%, 95%, 99%, or 100% identical to a mature antibody KFR.

An ICF sequence of a light chain variable region polypeptides of the instant invention also can be identical to the original mature antibody sequence used to determine the ICF domain. In one embodiment, the ICF sequences comprising a light chain variable region are at least 50% identical to a mature antibody KFR. In other embodiments, the ICF sequences comprising a light chain variable region are at least 60%, 70%, 80%, 85%, 90%, 93%, 95%, 99%, or 100% identical to a mature antibody KFR.

The variable framework region amino acid residues can correspond to the standard Kabat numbering system as described above. The Kabat numbering system can correspond to the ICF amino acid sequences of the current invention. For example, ICF1 of the heavy chain variable region can comprise about 25 residues of a Kabat Framework (KF) 1. In one embodiment, ICF1 of the heavy chain variable region comprises at least 20, 25, or at least 29 contiguous residues of a KF1.

In one embodiment, ICF2 of the heavy chain variable region can comprise about 14 residues of a KF2. In one embodiment, ICF2 of the heavy chain variable region comprises at least 10, 12, or 14 contiguous residues of a KF2.

ICF3 of the heavy chain variable region can comprise about 32 residues of a KF3. In one embodiment, ICF3 of the heavy chain variable region comprises at least 25, 30, or 32 contiguous residues of a KF3.

ICF4 of the heavy chain variable region can comprise about 12 residues of a KF4. In one embodiment, ICF4 of the heavy chain variable region comprises at least 8, 10, 12 contiguous residues of a KF4.

The Kabat numbering system can also correspond to the ICF amino acid sequences of a light chain variable region polypeptide of the current invention. For example, ICF1 of a light chain (for example, $V_\kappa$ or $V_\lambda$) variable region can comprise about 22 residues of a Kabat Framework (KF) 1. In one embodiment, ICF1 of a light chain variable region comprises at least 15, 20, or 23 contiguous residues of a KF1.

ICF2 of a light chain variable region can comprise about 15 residues of a KF2. In one embodiment, ICF2 of a light chain variable region comprises at least 10 contiguous residues of a KF2. In another embodiment, ICF2 comprises at least 12 contiguous residues of a KF2. In a further embodiment, ICF2 comprises at least 14 contiguous residues of a KF2.

ICF3 of a light chain variable region can comprise about 32 residues of a KF3. In one embodiment, ICF3 of a light chain variable region comprises at least 25, 30, or 32 contiguous residues of a KF3.

ICF4 of a light chain variable region can comprise about 10 residues of a KF4. In one embodiment, ICF4 of a light chain variable region comprises at least 8, 10, 13 contiguous residues of a KF4.

An ICF nucleic acid consensus sequence can include any wobble site changes in the nucleic acid consensus sequence wherein the nucleotide change will still encode the same amino acid sequence. Because of the degeneracy of the genetic code, a large number of functionally identical nucleic acids encode any given polypeptide. For example, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide.

In certain embodiments, a nucleic acid sequence encoding a heavy chain variable region ICF1 is at least 70%, 75%, 80%, 85%, 90%, 95%, 96%, 97%, 98%, or 99% identical to SEQ ID NO: 22, 23, 24, 25, 26, 27, or 28. In other embodiments, a nucleic acid sequence encoding a heavy chain variable region ICF2 is at least 70%, 75%, 80%, 85%, 90%, 95%, 96%, 97%, 98%, or 99% identical to SEQ ID NO: 29, 30, 31, 32, or 33. In some embodiments, a nucleic acid sequence encoding a heavy chain variable region ICF3 is at least 70%, 75%, 80%, 85%, 90%, 95%, 96%, 97%, 98%, or 99% identical to SEQ ID NO: 34, 35, 36, 37, 38, 39, 40, or 41. In yet further embodiments, a nucleic acid sequence encoding a heavy chain variable region ICF4 at least 70%, 75%, 80%, 85%, 90%, 95%, 96%, 97%, 98%, or 99% identical to SEQ ID NO: 42.

In other embodiments, a nucleic acid sequence encoding a light chain variable region ICF1 is at least 70%, 75%, 80%, 85%, 90%, 95%, 96%, 97%, 98%, or 99% identical to SEQ ID NO: 85, 86, 87, 88, 89, 90, 91, 92, 93, 94, 95, 96, 97, or 98. In certain embodiments, a nucleic acid sequence encoding a light chain variable region ICF2 is at least 70%, 75%, 80%, 85%, 90%, 95%, 96%, 97%, 98%, or 99% identical to SEQ ID NO: 100, 101, 102, 103, 104, 105, 106, or 107. In some embodiments, a nucleic acid sequence encoding a light chain variable region ICF3 is at least 70%, 75%, 80%, 85%, 90%, 95%, 96%, 97%, 98%, or 99% identical to SEQ ID NO: 109, 110, 111, 112, 113, 114, 115, 116, 117, 118, 119, 120, 121, 122, or 123. In yet other embodiments, a nucleic acid sequence encoding a light chain variable region ICF4 is at least 70%, 75%, 80%, 85%, 90%, 95%, 96%, 97%, 98%, or 99% identical to SEQ ID NO: 125 or 126.

Conservative amino acid changes refer to the interchangeability of amino acid residues having similar side chains changes. For example, a group of amino acids having basic side chains is lysine, arginine, and histidine; a group of amino acids having aliphatic-hydroxyl side chains is serine and threonine; a group of amino acids having amide-containing se chains is asparagine and glutamine; a group of amino acids having aliphatic side chains is glycine, alanine, valine, leucine, and isoleucine; a group of amino acids having aromatic side chains tyrosine, phenylalanine, and tryptophan; and a group of amino acids having sulfur-containing side chains is cysteine and methionine.

In certain embodiments, an amino acid sequence encoding a heavy chain variable region ICF1 is at least 70%, 75%, 80%, 85%, 90%, 95%, 96%, 97%, 98%, or 99% identical to SEQ ID NO: 1, 2, 3, 4, 5, 6, or 7. In other embodiments, an amino acid sequence encoding a heavy chain variable region ICF2 is at least 70%, 75%, 80%, 85%, 90%, 95%, 96%, 97%, 98%, or 99% identical to SEQ ID NO: 8, 9, 10, 11, or 12. In some embodiments, an amino acid sequence encoding a heavy chain variable region ICF3 is at least 70%, 75%, 80%, 85%, 90%, 95%, 96%, 97%, 98%, or 99% identical to SEQ ID NO: 13, 14, 15, 16, 17, 18, 19, or 20. In yet further embodiments, an amino acid sequence encoding a heavy chain variable region ICF4 is at least 70%, 75%, 80%, 85%, 90%, 95%, 96%, 97%, 98%, or 99% identical to SEQ ID NO:21.

In other embodiments, a amino acid sequence encoding a light chain variable region ICF1 is at least 70%, 75%, 80%, 85%, 90%, 95%, 96%, 97%, 98%, or 99% identical to SEQ ID NO: 43, 44, 45, 46, 47, 48, 49, 50, 51, 52, 53, 54, 55, 56, or 57. In certain embodiments, a amino acid sequence encoding a light chain variable region ICF2 is at least 70%, 75%, 80%, 85%, 90%, 95%, 96%, 97%, 98%, or 99% identical to SEQ ID NO: 58, 59, 60, 61, 62, 63, 64, 65, or 66. In some embodiments, a amino acid sequence encoding a light chain variable region ICF3 is at least 70%, 75%, 80%, 85%, 90%, 95%, 96%, 97%, 98%, or 99% identical to SEQ ID NO: 67, 68, 69, 70, 71, 72, 73, 74, 75, 76, 77, 78, 79, 80, 81, or 82. In yet other embodiments, an amino acid sequence encoding a light chain variable region ICF4 is at least 70%, 75%, 80%, 85%, 90%, 95%, 96%, 97%, 98%, or 99% identical to SEQ ID NO: 83 or 84.

An ICF nucleic acid or amino acid consensus sequence (for example, one that corresponds to ICF1, ICF2, ICF3, or ICF4) can be determined for a human based on human germline sequences or mature (i.e., rearranged) Antibody sequences. An ICF nucleic acid or amino acid consensus sequence also can be determined for the following non-limiting examples, such as canine, feline, ovine, equine, bovine, porcine, fowl, goat, salmon, and hybridoma cell line, utilizing the appropriate germline sequences.

The present invention provides for antibody compositions generated from the heavy chain and light chain variable regions described above. According to the invention, any CDRs from known antibodies (for example, those shown in Tables 5-6) can be combined with ICFs, such as those of Tables 1-4. In addition, they can be further combined to a constant domain (CD) (for example, those shown in Tables 7-8) to generate full-length heavy chain variable region polypeptides or a full-length light chain variable region polypeptide. These polypeptides can be combined subsequently to generate Igs, wherein the Igs can serve as functional units for the following non-limiting antibody examples: a single chain antibody, a bivalent antibody (such as a disulfide-linked antibody), a Fab fragment, and a single chain Fv.

Immunoglobulin fragments can be generated by proteolytic digestion and have proven to be very useful in elucidating structure/function relationships in immunoglobulins. Ig fragments can include combinations of heavy and light chain variable regions in order to form an antigen-binding site. Antibody fragments include, for example, Fab, Fab', F(ab')$_2$, Fv, scFv, Fd, and Fd' fragments.

For example, Fab fragments can be generated by digestion with papain, wherein the enzyme breaks the immunoglobulin molecule in the hinge region before the H—H inter-chain disulfide bond. This results in the formation of two identical fragments that contain the light chain and the V$_H$ and C$_{H1}$ domains of the heavy chain and additionally comprise the antigen binding sites of the antibody. Each Fab fragment is monovalent whereas the original molecule was divalent. Fc fragments, for example can also be generated by digestion with papain. The enzyme is able to produce a fragment that contains the remainder of the two heavy chains each containing a C$_{H2}$ and C$_{H3}$ domain.

Treatment of immunoglobulins with pepsin results in the cleavage of the heavy chain after the H—H inter-chain disulfide bonds resulting in a fragment that contains both antigen binding sites. This divalent fragment generated by pepsin digest is referred to as F(ab')$_2$. The Fc region of the molecule is digested into small peptides by pepsin. The F(ab')$_2$ fragment can bind its antigen but does not generally mediate the effector functions of antibodies.

Compositions

Each of the compounds of this invention (e.g., compounds described herein) can be used as a composition (e.g., a pharmaceutical composition) when combined with an acceptable carrier or excipient. These compositions (e.g., a pharmaceutical compositions) of the invention can be useful for in vitro or in vivo analysis or for administration to a subject (e.g., a human) in vivo or ex vivo for treating a subject.

Thus, pharmaceutical compositions of this invention can include, in addition to active ingredient(s), a pharmaceutically acceptable excipient, carrier, buffer, stabilizer or other materials well known to those skilled in the art. In one aspect, these materials are non-toxic and do not interfere with the efficacy of the active ingredient. The precise nature of the carrier or other material can depend on the formulation and route of administration.

Pharmaceutical formulations of this invention comprising a protein of the invention, e.g., an antibody or antigen binding fragment thereof of the invention (e.g., as identified by the methods described herein), can be prepared for storage by, e.g., mixing the protein having the desired degree of purity with optional physiologically acceptable carriers, excipients or stabilizers (see, e.g., Remington's Pharmaceutical Sciences latest edition, or the 16th edition, Osol, A. Ed. (1980)), e.g., in the form of lyophilized formulations or aqueous solutions. In alternative embodiments, acceptable carriers, excipients, or stabilizers are those that are non-toxic to recipients (e.g., human patients) at the dosages and concentrations employed, and can include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

In alternative embodiments, acceptable carriers are physiologically acceptable to the administered individual (e.g., a human patient) and retain the therapeutic properties of the compounds with/in which it is administered. Acceptable carriers and their formulations are and generally described in, for example, Remington' pharmaceutical Sciences latest edition (see also the 18th Edition, ed. A. Gennaro, Mack Publishing Co., Easton, Pa. 1990). In one aspect, an exemplary carrier is physiological saline.

"Pharmaceutically acceptable carriers" used to practice this invention can comprise a pharmaceutically acceptable material, composition or vehicle, such as a liquid or solid filler, diluent, excipient, solvent or encapsulating material, involved in carrying or transporting the subject compounds from the administration site of one organ, or portion of the body, to another organ, or portion of the body, or in an ex vivo or in vitro assay system. In alternative embodiments, each carrier is acceptable in the sense of being compatible with the other ingredients of the formulation and not injurious to a subject to whom it is administered. In alternative embodiments, acceptable carrier do not alter the specific activity of the subject compounds.

Pharmaceutical compositions or pharmaceutical formulations of this invention include compositions suitable for pharmaceutical use in a subject. The pharmaceutical compositions and formulations of this invention can include an amount of a compound of this invention and a pharmaceutically or physiologically acceptable carrier.

Compositions (e.g., pharmaceutical compositions or pharmaceutical formulations) of this invention can be formulated to be compatible with a particular route of administration (i.e., systemic or local). Thus, compositions of this invention can include carriers, diluents, or excipients suitable for administration by various routes.

In another embodiment, the compositions can further comprise, if needed, an acceptable additive in order to improve the stability of the compounds in composition and/or to control the release rate of the composition. Acceptable additives do not alter the specific activity of the subject compounds. Exemplary acceptable additives include, but are not limited to, a sugar such as mannitol, sorbitol, glucose, xylitol, trehalose, sorbose, sucrose, galactose, dextran, dextrose, fructose, lactose and mixtures thereof. Acceptable additives can be combined with acceptable carriers and/or excipients such as dextrose. Alternatively, exemplary acceptable additives include, but are not limited to, a surfactant such as polysorbate 20 or polysorbate 80 to increase stability of the peptide and decrease gelling of the solution. The surfactant can be added to the composition in an amount of 0.01% to 5% of the solution. Addition of such acceptable additives increases the stability and half-life of the composition in storage.

The pharmaceutical composition of this invention can be administered, for example, by injection. In alternative embodiments, compositions for injection include aqueous solutions (where water soluble) or dispersions and sterile powders for the extemporaneous preparation of sterile injectable solutions or dispersion. In alternative embodiments, for intravenous administration, suitable carriers include physiological saline, bacteriostatic water, CREMOPHOR EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersion and by the use of surfactants.

Antibacterial and antifungal agents can include, for example, parabens, chlorobutanol, phenol, ascorbic acid and thimerosal. Isotonic agents, for example, sugars, polyalcohols such as manitol, sorbitol, and sodium chloride may be included in the composition. The resulting solutions can be packaged for use as is, or lyophilized; the lyophilized preparation can later be combined with a sterile solution prior to administration.

For intravenous, injection, or injection at the site of affliction, the active ingredient can be in the form of a parenterally acceptable aqueous solution which is pyrogen-free and has suitable pH, isotonicity and stability. Compositions of the invention can comprise (and those of relevant skill in the art are well able to prepare) suitable solutions using, for example, isotonic vehicles such as Sodium Chloride Injection, Ringer's Injection, Lactated Ringer's Injection. Preservatives, stabilizers, buffers, antioxidants and/or other additives may be included, as needed. Sterile injectable solutions can be prepared by incorporating an active ingredient in the required amount in an appropriate solvent with one or a combination of ingredients enumerated above, as required, followed by filtered sterilization. In one aspect, dispersions are prepared by incorporating the active ingredient into a sterile vehicle which contains a basic dispersion medium and the required other ingredients from those enumerated above. In the case of sterile powders for the preparation of sterile injectable solutions, alternative methods of preparation are vacuum drying and freeze drying which yields a powder of the active ingredient plus any additional desired ingredient from a previously sterile-filtered solution thereof.

Compositions can be conventionally administered intravenously, such as by injection of a unit dose, for example. For injection, an active ingredient can be in the form of a parenterally acceptable aqueous solution which is substantially pyrogen-free and has suitable pH, isotonicity and stability. One can prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. Additionally, compositions can be administered via aerosolization. (Lahn et al., Aerosolized Anti-T-cell-Receptor Antibodies Are Effective against Airway Inflammation and Hyperreactivity, Int. Arch. Allegery Immuno., 134: 49-55 (2004)).

One embodiment contemplates the use of the compositions described herein to make a medicament for treating a condition, disease or disorder described herein. Medicaments can be formulated based on the physical characteristics of the patient/subject needing treatment, and can be formulated in single or multiple formulations based on the stage of the condition, disease or disorder. Medicaments can be packaged in a suitable package with appropriate labels for the distribution to hospitals and clinics wherein the label is for the indication of treating a subject having a disease described herein.

Treatment

In one aspect, polypeptides of the invention can specifically bind CD20, a transmembrane surface antigen on B-cell precursors and mature B-cells that is not internalized after binding nor shed from the cell surface. CD20 also expressed a large percentage of B-cells involved in a wide variety of diseases. The antibodies or antigen binding fragments of this invention can be used to treat a subject with a tumorigenic disorder, e.g., a disorder characterized by the presence of tumor cells expressing CD20 including, for example, B cell lymphoma, e.g., NHL.

In alternative aspects, compositions of the invention, and methods of this invention, are used for "inhibition," "amelioration," "treatment" and/or "treating" a disease or condition, and these terms can be used interchangeably and can refer to, for example, stasis of symptoms, prolongation of survival, partial or full amelioration of symptoms, and partial or full eradication of a condition, disease or disorder. The antibodies or antigen binding fragments of this invention can be used to treat a B-cell mediated disease. In one aspect, a "treatment" of the invention can include the suppression or abrogation of an immune response. The antibodies or antigen binding fragments of this invention can be used to suppress or abrogate a B-cell mediated immune response. The antibodies or antigen binding fragments of this invention can be used to in the treatment of cancers, including the stasis, partial or total elimination of a cancerous cells, growth, or tumor. In alternative aspects, treatment or partial elimination includes, for example, a fold reduction in cells, growth or tumor size and/or volume such as about 2-fold, about 3-fold, about 4-fold, about 5-fold, about 10-fold, about 20-fold, about 50-fold, or any fold reduction in between. In alternative aspects, treatment or partial elimination can include a percent reduction in cells, growth or tumor size and/or volume of about 1%, 2%, 3%, 4%, 5%, 10%, 20%, 30%, 40%, 50%, 60%, 70%, 80%, 90%, 95% or any percentage reduction in between.

Examples of tumorigenic diseases which can be treated and/or prevented using compositions or methods of this invention include B cell lymphoma, e.g., NHL, including precursor B cell lymphoblastic leukemia/lymphoma and mature B cell neoplasms, such as B cell chronic lymhocytic leukemia (CLL)/small lymphocytic lymphoma (SLL), B cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B cell lymphoma (MALT type, nodal and splenic type), hairy cell leukemia, diffuse large B cell lymphoma, Burkitt's lymphoma, plasmacytoma, plasma cell myeloma, post-transplant lymphoproliferative disorder, Waldenstrom's macroglobulinemia, and anaplastic large-cell lymphoma (ALCL).

Further examples of B cell non-Hodgkin's lymphomas which can be treated and/or prevented using compositions or methods of this invention are lymphomatoid granulomatosis, primary effusion lymphoma, intravascular large B cell lymphoma, mediastinal large B cell lymphoma, heavy chain diseases (including .gamma., .mu., and .alpha. disease), lymphomas induced by therapy with immunosuppressive agents, such as cyclosporine-induced lymphoma, and methotrexate-induced lymphoma. Examples of immune disorders in which CD20 expressing B cells are involved which can be treated and/or prevented using compositions or methods of this invention include autoimmune disorders, such as psoriasis, psoriatic arthritis, dermatitis, systemic scleroderma and sclerosis, inflammatory bowel disease (IBD), Crohn's disease, ulcerative colitis, respiratory distress syndrome, meningitis, encephalitis, uveitis, glomerulonephritis, eczema, asthma, atherosclerosis, leukocyte adhesion deficiency, multiple sclerosis, Raynaud's syndrome, Sjogren's syndrome, juvenile onset diabetes, Reiter's disease, Behcet's disease, immune complex nephritis, IgA nephropathy, IgM polyneuropathies, immune-mediated thrombocytopenias, such as acute idiopathic thrombocytopenic purpura and chronic idiopathic thrombocytopenic purpura, hemolytic anemia, myasthenia gravis, lupus nephritis, systemic lupus erythematosus, rheumatoid arthritis (RA), atopic dermatitis, pemphigus, Graves' disease, Hashimoto's thyroiditis, Wegener's granulomatosis, Omenn's syndrome, chronic renal failure, acute infectious mononucleosis, HIV, and herpes virus associated diseases. Further examples are severe acute respiratory distress syndrome and choreoretinitis.

In alternative aspects, other diseases and disorders that can be treated and/or prevented using compositions or methods of this invention include those caused by or mediated by infection of B-cells with virus, such as Epstein-Barr virus (EBV).

TABLE 5

Exemplary Nucleic Acid Sequences for CDR Fragments of the Variable Heavy Chain ($V_H$) and Variable Light Chain ($V_\kappa$ or $V_\lambda$) of listed antibodies.

| | Nucleic Acid Sequence | SEQ ID NO: |
|---|---|---|
| VH CDR CD20 IgG | | |
| 1 | GGCTACACATTTACCAGTTACAATATGCAC | 127 |
| 2 | GCTATTTATCCAGGAAATGGTGATACTTCCTACAATCAGAAGTTCAAAGGC | 128 |
| 3 | TCGCACTACGGTAGTAACTACGTAGACTACTTTGACTACTGGGGCCAGGGCACCCTG | 129 |
| CD3 IgG | | |
| 1 | GGCTACACCTTTACTAGGTACACGATGCAC | 133 |
| 2 | TACATTAATCCTAGCCGTGGTTATACTAATTACAATCAGAAGTTCAAGGAC | 134 |

TABLE 5-continued

Exemplary Nucleic Acid Sequences for CDR Fragments of the Variable Heavy Chain ($V_H$) and Variable Light Chain ($V_\kappa$ or $V_\lambda$) of listed antibodies.

| | Nucleic Acid Sequence | SEQ ID NO: |
|---|---|---|
| 3 | TATTATGATGATCATTACTGCCTTGACTAC | 135 |
| LC CDR CD20 IgG | | |
| 1 | AGGGCCAGCTCAAGTTTAAGTTTCATGCAC | 139 |
| 2 | GCCACATCCAACCTGGCTTCT | 140 |
| 3 | CATCAGTGGAGTAGTAACCCGCTCACG | 141 |
| CD3 IgG | | |
| 1 | AGTGCCAGCTCAAGTGTAAGTTACATGAAC | 145 |
| 2 | GACACATCCAAACTGGCTTCT | 146 |
| 3 | CAGCAGTGGAGTAGTAACCCATTCACG | 147 |

TABLE 6

Exemplary Amino Acid Sequences for CDR Fragments of the Variable Heavy Chain ($V_H$) and Variable Light Chain ($V_\kappa$ or $V_\lambda$) of listed antibodies.

| | Amino Acid Sequence | SEQ ID NO: |
|---|---|---|
| VH CDR CD20 IgG | | |
| 1 | GYTFTSYNMH | 151 |
| 2 | AIYPGNGDTSYNQKFKG | 152 |
| 3 | SHYGSNYVDYFDYWGQGTL | 153 |
| CD3 IgG | | |
| 1 | GYTFTRYTMH | 157 |
| 2 | YINPSRGYTNYNQKFKD | 158 |
| 3 | YYDDHYCLDY | 159 |
| LC CDR CD20 IgG | | |
| 1 | RASSSLSFMH | 163 |
| 2 | ATSNLAS | 164 |
| 3 | HQWSSNPLT | 165 |
| CD3 IgG | | |
| 1 | SASSSVSYMN | 169 |
| 2 | DTSKLAS | 170 |
| 3 | QQWSSNPFT | 171 |

TABLE 7

Amino Acid Sequences of Exemplary Constant Domains (CD) of an Ig Heavy Chain and κ Light Chain

| | Amino Acid Sequence | SEQ ID NO: |
|---|---|---|
| HC CD | VFPLAPSSKSTSGGTAALGCLVKDYFPEPVTVSWNSGALTSGVHTFPAVLQSSGLY SLSSVVTVPSSSLGTQTYICNVNHKPSNTKVDKRVEPKSCDKTHTCPPCPAPELLG GPSVFLFPPKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVLDSDGSF FLYSKLTVDKSRWQQGNVFSCSVMHEALHNHYTQKSLSLSPGK | 175 |
| anti-CD20 | VEPKSCDKTHTCPPCPAPELLGGPSVFLFPPKPKDTLMISRTPEVTCVVVDVSHED PEVKFNWYVDGVEVHNAKTKPREEQYNSTYRVVSVLTVLHQDWLNGKEYKCKVSNK ALPAPIEKTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHEALHNHYTQ KSLSLSPGK | 208 |
| κ CD | RTVAAPSVFIFPPSDEQLKSGTASVVCLLNNFYPREAKVQWKVDNALQSGNSQESV TEQDSKDSTY | 176 |
| anti-CD20 | TVAAPSVFIFPPSDEQLKSGTASVVCLLNNFYPREAKVQWKVDNALQSGNSQESVT EQDSKDSTYSLSSTLTLSKADYEKHKVYACEVTHQGLSSPVTKSFNRGEC | 209 |

TABLE 8

Nucleic Acid Sequences encoding Exemplary Constant Domains
(CD) of an Ig Heavy Chain and κ Light Chain

| Nucleic Acid Sequence | SEQ ID NO: |
|---|---|
| HC CD GTCTTCCCCCTGGCACCCTCCTCCAAGAGCACCTCTGGGGGCACAGCGGCCCTGGG CTGCCTGGTCAAGGACTACTTCCCCGAACCGGTGACGGTGTCGTGGAACTCAGGCG CCCTGACCAGCGGCGTGCACACCTTCCCGGCTGTCCTACAGTCCTCAGGACTCTAC TCCCTCAGCAGCGTGGTGACCGTGCCCTCCAGCAGCTTGGGCACCCAGACCTACAT CTGCAACGTGAATCACAAGCCCAGCAACACCAAGGTGGACAAGAGAGTTGAGCCCA AATCTTGTGACAAAACTCACACATGCCCACCGTGCCCAGCACCTGAACTCCTGGGG GGACCGTCAGTCTTCCTCTTCCCCCCAAAACCCAAGGACACCCTCATGATCTCCCG GACCCCTGAGGTCACATGCGTGGTGGTGGACGTGAGCCACGAAGACCCTGAGGTCA AGTTCAACTGGTACGTGGACGGCGTGGAGGTGCATAATGCCAAGACAAAGCCGCGG GAGGAGCAGTACAACAGCACGTACCGTGTGGTCAGCGTCCTCACCGTCCTGCACCA GGACTGGCTGAATGGCAAGGAGTACAAGTGCAAGGTCTCCAACAAAGCCCTCCCAG CCCCCATCGAGAAAACCATCTCCAAAGCCAAAGGGCAGCCCCGAGAACCACAGGTG TACACCCTGCCCCCATCCCGGGATGAGCTGACCAAGAACCAGGTCAGCCTGACCTG CCTGGTCAAAGGCTTCTATCCCAGCGACATCGCCGTGGAGTGGGAGAGCAATGGGC AGCCGGAGAACAACTACAAGACCACGCCTCCCGTGCTGGACTCCGACGGCTCCTTC TTCCTCTACAGCAAGCTCACCGTGGACAAGAGCAGGTGGCAGCAGGGGAACGTCTT CTCATGCTCCGTGATGCATGAGGCTCTGCACAACCACTACACGCAGAAGAGCCTCT CCCTGTCTCCGGGTAAATGA | 178 |
| κ CD CGAACTGTGGCTGCACCATCTGTCTTCATCTTCCCGCCATCTGATGAGCAGTTGAA ATCTGGAACTGCCTCTGTTGTGTGCCTGCTGAATAACTTCTATCCCAGAGAGGCCA AAGTACAGTGGAAGGTGGATAACGCCCTCCAATCGGGTAACTCCCAGGAGAGTGTC ACAGAGCAGGACAGCAAGGACAGCACCTAC | 179 |

In addition to the sequences listed in Tables 5 to 8, other CDRs (underlined) and constant region (double-underlined or yellow-highlighted) are provided in FIGS. 24, 32, 33, 34, 36, 38, 39, 42, and in the original and assembled HuFR sequences disclosed in Examples 3 to 6.

Exemplary Antibodies

In alternative embodiments, compositions of the invention, e.g., chimeric and/or recombinant antibodies of the invention, specifically bind to CD20, which is an unglycosylated phosphoprotein that is expressed on the surface of B cells and serves a B-cell marker. CD20 acts as a regulator of transmembrane calcium conductance and purportedly plays a role in B cell activation and proliferation. In one aspect of the invention, an antibody can be generated containing a more human-like variable region, that is directed at a surface protein of a eukaryotic cell (for example, B cells). In one embodiment, a recombinant heavy chain variable region polypeptide and a recombinant light chain variable region polypeptide of the invention containing the CDRs of an anti-CD20 antibody are used to form an antibody with variable regions more human in characterization. For example, the antibody binds to a CD20 antigen. In one embodiment, the antibody's light chain variable region comprises an ICF1 comprising an amino acid sequence of SEQ ID NOS:43, 44, 45, 46, 47, 38, or 49; a CDR1 comprising an amino acid sequence of SEQ ID NO:163; an ICF2 comprising an amino acid sequence of SEQ ID NOS:58, 59, 60, or 61; a CDR2 comprising an amino acid sequence of SEQ ID NO:164; an ICF3 comprising an amino acid sequence of SEQ ID NOS:67-71, 73, or 74; a CDR3 comprising an amino acid sequence of SEQ ID NO:165; and an ICF4 comprising an amino acid sequence of SEQ ID NO:83. In other embodiments, the antibody's heavy chain variable region comprises an ICF1 comprising an amino acid sequence of SEQ ID NOS: 6 or 7; a CDR1 comprising an amino acid sequence of SEQ ID NO:151; an ICF2 comprising an amino acid sequence of SEQ ID NOS:9, 10, or 11; a CDR2 comprising an amino acid sequence of SEQ ID NO:152; an ICF3 comprising an amino acid sequence of SEQ ID NOS:13, 17, 19, or 20; a CDR3 comprising an amino acid sequence of SEQ ID NO:153; and an ICF4 comprising an amino acid sequence of SEQ ID NO:21.

CD3 is a component of the T-cell receptor complex. It is a surface marker specific to T cells and, thus can be used to specifically identify T cells. According to the invention, an antibody can be generated containing a more human-like variable region, that is directed at a surface protein of a eukaryotic cell (for example, T cells). In one embodiment, a recombinant heavy chain variable region polypeptide and a recombinant light chain variable region polypeptide of the invention containing the CDRs of an anti-CD3 antibody are used to form an antibody with variable regions more human in characterization. For example, the antibody binds to a CD3 antigen. In one embodiment, the antibody's light chain variable region comprises an ICF1 comprising an amino acid sequence of SEQ ID NOS:43-46, or 49; a CDR1 comprising an amino acid sequence of SEQ ID NO:169; an ICF2 comprising an amino acid sequence of SEQ ID NOS:58, 59, or 60; a CDR2 comprising an amino acid sequence of SEQ ID NO:170; an ICF3 comprising an amino acid sequence of SEQ ID NOS:68-69,72, 73, or 74; a CDR3 comprising an amino acid sequence of SEQ ID NO:171; and an ICF4 comprising an amino acid sequence of SEQ ID NO:83. In a further embodiment, the antibody's heavy chain variable region comprises an ICF1 comprising an amino acid sequence of SEQ ID NOS:3, 7, or 181; a CDR1 comprising an amino acid sequence of SEQ ID NO:157; an ICF2 comprising an amino acid sequence of SEQ ID NOS:9 or 11; a CDR2 comprising an amino acid sequence of SEQ ID NO:158; an ICF3 comprising an amino acid sequence of SEQ ID NOS:15, 16, or 17; a CDR3 comprising an amino acid sequence of SEQ ID NO:159; and an ICF4 comprising an amino acid sequence of SEQ ID NO:21.

Nucleic Acids

In one embodiment, nucleic acid sequences of the invention that encode independently consensused heavy chain variable region domains ICF 1, 2, and 3 are provided in addition to sequences encoding complementarity determining regions 1, 2, and 3 of a known immunoglobulin heavy chain variable region (such as that of anti-CD20, anti-CD3). In another embodiment, nucleic acid sequences of the invention that encode independently consensused light chain variable region domains ICF 1, 2, and 3 are provided in addition to sequences encoding complementarity determining regions 1, 2, and 3 of a known immunoglobulin heavy chain variable region (such as that of anti-CD20, anti-CD3). In a further embodiment, nucleic acid sequences that encode independently consensused heavy chain and light chain variable region domain ICF4 are additionally provided. For example, heavy chain variable region ICF 1, 2, 3, and 4 domains and light chain variable region ICF 1, 2, 3, and 4 domains of the current invention have SEQ ID NOs listed in Tables 2 and 4. Nucleic acid sequences corresponding to CDRs 1, 2, and 3 of a known immunoglobulin heavy chain variable region are found in Table 5.

The nucleic acids encoding the heavy chain or light chain variable region ICF domains and CDRs that are provided from above are fused in a 5'-to-3' orientation, forming nucleic acids that generate a heterogeneous population of single nucleic acid molecules. In one embodiment, nucleic acids encoding the heavy chain variable region ICF domains and CDRs are fused in a 5'-to-3' orientation in the following order: a nucleic acid encoding ICF1; a nucleic acid encoding CDR1; a nucleic acid encoding ICF2; a nucleic acid encoding CDR2; a nucleic acid encoding ICF3; and a nucleic acid encoding CDR3. In another embodiment, nucleic acids encoding the light chain variable region ICF domains and CDRs are fused in a 5'-to-3' orientation in the following order: a nucleic acid encoding ICF1; a nucleic acid encoding CDR1; a nucleic acid encoding ICF2; a nucleic acid encoding CDR2; a nucleic acid encoding ICF3; and a nucleic acid encoding CDR3. In a further embodiment, nucleic acid sequences that encode heavy chain and light chain variable region domain ICF4 are fused in a 5'-to-3' orientation the C-terminus of heavy chain or light chain CDR3. For example, heavy chain variable region ICF 1, 2, 3, and 4 domains and light chain variable region ICF 1, 2, 3, and 4 domains of the current invention have SEQ ID NOS listed in Tables 2 and 4. Nucleic acid sequences corresponding to CDRs 1, 2, and 3 of a known immunoglobulin heavy chain variable region are found in Table 5.

An Ig chain obtained by HuFR can be further modified for desired properties using Gene Site Saturation Mutagenesis (GSSM™) or Synthetic Ligation Reassembly (SLR or GeneReassembly™) evolution methods, as described in U.S. Pat. No. 6,171,820, U.S. Pat. No. 6,537,776, U.S. Pat. No. 6,562,594, U.S. Pat. No. 6,605,449, and U.S. Pat. No. 6,764,835.

Vectors

Once the heavy chain or light chain variable region molecule is generated, it can then be cloned into a plasmid and transformed into cells so as to express the heavy chain or light chain variable region polypeptide. In one embodiment, plasmids carrying the heavy chain or light chain variable region polypeptide genes were amplified in *E. coli* and transfected into mammalian cells for production of full-length immunoglobulins.

The cells suitable for culturing can harbor introduced expression vectors (constructs), such as plasmids. The expression vector constructs can be introduced by transfection, lipofection, transformation, injection, electroporation, or infection. The expression vectors can contain coding sequences, or portions thereof, encoding the proteins for expression and production in the culturing process. Such expression vectors can include the required components for the transcription and translation of the inserted coding sequence. Expression vectors containing sequences encoding the produced proteins and polypeptides, as well as the appropriate transcriptional and translational control elements, can be generated using methods well known to and practiced by those skilled in the art. These methods include in vitro recombinant DNA techniques, synthetic techniques, and in vivo genetic recombination which are described in J. Sambrook et al., (1989) *Molecular Cloning, A Laboratory Manual*, Cold Spring Harbor Press, Plainview, N.Y. and in F. M. Ausubel et al., 1989, *Current Protocols in Molecular Biology*, John Wiley & Sons, New York, N.Y. A more detailed description of the types of methods and tools that can be utilized is provided below.

Clones obtained by standard molecular biology protocols can be transfected into suitable host cells, such as mammalian cells, for expression of the desired product. Transfection techniques are carried out using standard techniques established in the art appropriate for the host cell being utilized. For example, mammalian cell transfection can be accomplished using lipofection, protoplast fusion, DEAE-dextran-mediated transfection, $CaPO_4$ co-precipitation, electroporation, direct microinjection, as well as other methods known in the art which can comprise: scraping, direct uptake, osmotic or sucrose shock, lysozyme fusion or erythrocyte fusion, indirect microinjection such as erythrocyte-mediated techniques, and/or by subjecting host cells to electric currents.

Expression

Expression of DNA encoding a protein of interest (for example, heavy chain or light chain variable region polypeptides, glycoproteins such as Igs) in eukaryotic host cells derived from multicellular organisms (for example, mammalian in origin) can be utilized in the context of this invention (*Tissue Cultures*, (1973) Academic Press, Cruz and Patterson, Eds.). Host cells derived from multicellular organisms have the ability to splice out introns and thus can be used directly to express genomic DNA fragments. Useful host cell lines capable of harboring, expressing, and secreting a protein of interest include Chinese hamster ovary cells (CHO), such as CHO-K1 (ATCC CCL-61), DG44 (Chasin et al., 1986, *Som. Cell Molec. Genet*, 12:555-556; Kolkekar et al., 1997, *Biochemistry*, 36:10901-10909; and WO 01/92337 A2), dihydrofolate reductase negative CHO cells (CHOI dhfr-, Urlaub and Chasin, 1980, *Proc. Natl. Acad. Sci. USA*, 77:4216), and dp12.CHO cells (U.S. Pat. No. 5,721,121); monkey kidney CV1 cells transformed by SV40 (COS cells, COS-7, ATCC CRL-1651); human embryonic kidney cells (e.g., 293 cells, or 293 cells subcloned for growth in suspension culture, Graham et al., 1977, *J. Gen. Virol.*, 36:59); baby hamster kidney cells (BHK, ATCC CCL-10); monkey kidney cells (CV1, ATCC CCL-70); African green monkey kidney cells (VERO-76, ATCC CRL-1587; VERO, ATCC CCL-81); mouse Sertoli cells (TM4, Mather, 1980, *Biol. Reprod.*, 23:243-251); human cervical carcinoma cells (HELA, ATCC CCL-2); canine kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TRI cells (Mather, 1982, *Annals NY Acad. Sci.*, 383: 44-68); MCR 5 cells; FS4 cells.

Expression vectors for eukaryotic cells, such as mammalian cells, can include promoters and control sequences compatible with mammalian cells that are well established in the art. Some regulatory elements can be, for example, a CMV promoter or the avian sarcoma virus (ASV) promoter found in various expression vectors. Other commonly used early and late promoters include those from Simian Virus 40 (SV 40)

(Fiers, et al., (1973) *Nature* 273:113), or other viral promoters such as those derived from bovine papilloma, polyoma, and Adenovirus 2 virus. The regulatable promoter, hMTII (Karin, et al., 1982, *Nature* 299:797-802) can also be used, among others known in the art. For recombinant protein expression in cultured insect cells (for example, SF 9 cells), some baculovirus vectors available include the pVL series (Lucklow, V. A., and Summers, M. D., 1989, *Virology* 170:31-39) and the pAc series (Smith et al., 1983, *Mol. Cell. Biol.* 3:2156-2165). A practitioner skilled in the art also understands that enhancer regions (those sequences found upstream or downstream of the promoter region in non-coding DNA regions) are also important in improving expression. Origins of replication can be employed, if needed, from viral sources, for example if utilizing a prokaryotic host for introduction of plasmid DNA.

Host Cells

In alternative embodiments, in addition to mammalian host cells, other eukaryotic organisms also may be used as hosts to express a protein of interest (for example, a polypeptide of the invention, e.g., a heavy chain or light chain variable region polypeptide of the invention, including glycoproteins such as Igs). In alternative embodiments, laboratory strains of the budding yeast *Saccharomyces cerevisiae* can be used as well other yeast strains, such as the fission yeast *Schizosaccharomyces pombe*. Yeast vectors harboring DNA encoding a protein of interest (for example, a polypeptide of the invention) can utilize the 2µ, origin of replication (Broach et al., (1983) *Meth. Enz.* 101:307), or other origins of replications compatible with yeast (for example, Stinchcomb et al., 1979, *Nature* 282:39; Tschempe et al., 1980, *Gene* 10:157; and Clarke et al., 1983, *Meth. Enz.* 101:300). A regulatory element contained within yeast vectors can be a promoter for the synthesis of glycolytic enzymes (Hess et al., 1968, *J. Adv. Enzyme Reg.* 7:149; Holland et al., 1978, *Biochemistry* 17:4900). One skilled in the art can also utilize other promoters wherein growth conditions can regulate the transcription of a regulatable gene. Similar to mammalian expression systems, terminator sequences in yeast expression vectors are also desirable at the 3' end of the coding sequences and are found in the 3' untranslated region following the open reading frame in yeast-derived genes. A recombinant protein of this invention, for example a heavy chain or light chain variable region polypeptide of this invention, glycoproteins such as Igs, can also be expressed in insect cells (for example, using a baculovirus vector).

Various culturing parameters can be used with respect to the host cell being cultured. Appropriate culture conditions for mammalian cells are well known in the art (Cleveland et al., (1983) *J. Immunol. Methods,* 56: 221-234) or can be determined by the skilled artisan (see, for example, *Animal Cell Culture: A Practical Approach* 2$^{nd}$ *Ed.*, (1992) Rickwood, D. and Hames, B. D., eds. (Oxford University Press: New York)), and vary according to the particular host cell selected. Commercially available media can be utilized and include, for example, Minimal Essential Medium (MEM, Sigma, St. Louis, Mo.); Dulbecco's Modified Eagles Medium (DMEM, Sigma); Ham's F10 Medium (Sigma); HyClone cell culture medium (HyClone, Logan, Utah); RPMI-1640 Medium (Sigma); and chemically-defined (CD) media, which are formulated for particular cell types, e.g., CD-CHO Medium (Invitrogen, Carlsbad, Calif.). Any of these media can be supplemented as necessary with the previously defined supplementary components or ingredients, including optional components, in appropriate concentrations or amounts, as necessary or desired.

A protein of interest (for example, a polypeptide of the invention), including a glycoprotein, an immunoglobulin, can be produced by growing cells expressing the desired protein product under a variety of cell culture conditions. A practitioner skilled in the art understands that cell cultures and culturing runs for protein production can include three general types: continuous culture, batch culture, and fed-batch culture. In one aspect, a continuous culture process, a fresh culture medium supplement (for example, feeding medium) is supplied to cells during the culturing period while old culture medium is removed. The product produced during a continuous culture can also be harvested, for example, on a daily basis or continuously. As long as the cells remain alive, and the environmental and culturing conditions are maintained, cells can remain in culture as long as is desired in a continuous culturing process.

The cells of the culture producing a protein of interest (for example, a polypeptide of the invention) can be propagated according to any scheme or routine that is most suitable for the particular mammalian host cell and the particular production plan contemplated. Cell culture conditions can be developed to enhance expansion or growth of a population of mammalian host cells in the growth phase of the cell culture for a period of time that is maximized for such expansion and growth. Also, cell culture conditions can be developed to enhance protein production during the production phase of the cell culture for a period of time. Culture conditions, such as temperature, pH, dissolved oxygen ($DO_2$), that can be used are those used in culturing mammalian host cells that are understood by the individual skilled in the art. An appropriate temperature range for culturing mammalian host cells, such as CHO cells, is between 30 to 40° C., and in one embodiment about 37° C. The pH generally is adjusted to a level between about 6.5 and 7.5 using either an acid or base. A suitable $DO_2$ is between 5-90% of air saturation. These culture conditions can be used to facilitate the culturing of mammalian cells that produce a desired protein of interest.

Methods for Making Antibodies

The present invention also provides methods for generating an antibody specific to an antigen and with a decreased immunogenicity, wherein the antibody comprises heavy chain and light chain variable regions that comprise ICFs. The method for generating this collection comprises providing the combinatorial libraries of heavy chain and light chain nucleic acids (from above) expressed in a cell that produce heavy chain or light chain variable region polypeptides, wherein the variable regions comprising ICFs, and screening an antibody that binds to the antigen and has a reduced immunogenicity. In one embodiment, the combinatorial libraries of light chain and heavy chain variable region nucleic acids can be both transfected into cells according to methods established in the art, and thus have both collections being expressed by a cell. This would enable the light chains and heavy chains to recombine within the cells, generating antibodies that can be screened for binding affinities and/or reduced immunogenicity using methods known in the art.

In another embodiment, combinatorial libraries of heavy chains can be in a first population of cells and the combinatorial libraries of light chains can be in a second population of cells. A method suited to separate expression and screening is described in U.S. Provisional Application 60/849,597, filed Oct. 4, 2006, the entire contents of which are incorporated herein.

Combinatorial Libraries

The present invention provides methods for generating a combinatorial library of nucleic acids that encode heavy chain and light chain variable regions that comprise ICFs. The method for generating this collection comprises providing nucleic acids that encode heavy chain and light chain variable regions comprising ICFs, joining the nucleic acids that encode heavy chain and light chain variable regions in a 5'-to-3' orientation, and expressing the nucleic acids in a cell.

In one embodiment, the method provides a combinatorial library of nucleic acids (or amino acid sequences encoded by them) of heavy chain variable regions. Table G shows an example of sets of ICF1, 2, 3 and 4 that can be used in the combinatorial library.

TABLE G

Exemplary set of ICFs for making combinatorial heavy chain libraries

| ICF 1 | ICF2 | ICF3 | ICF4 |
|---|---|---|---|
| GL1_8 | GL1_7_8 | GL_1 | GL_1 |
| GL_2 | GL2_3 | GL_2 | |
| GL_3 | GL_4 | GL_3 | |
| GL_4 | GL_5 | GL_4 | |
| GL_5 | GL_6 | GL_5 | |
| GL_6 | | GL_6 | |
| GL_7 | | GL_7 | |
| | | GL_8 | |

Using the 4 sets of ICFs in Table G can result in a total of 280 heavy chain combinations (7 ICF1s×5 ICF2s×8 ICF3s×1 ICF4).

For a corresponding light chain library, the sets of ICFs in Table H are examples of ICFs that can be used.

TABLE H

Exemplary sets of ICFs for making combinatorial light chain libraries

| $V_K$ ICF 1 | $V_K$ ICF2 | $V_K$ ICF3 | $V_K$ ICF4 |
|---|---|---|---|
| VK1_2 | VK1_2_3 | VK1 | VK1 |
| VK3 | VK4_5_6 | VK2 | |
| VK4 | VK7 | VK3 | |
| VK5 | VK8 | VK4 | |
| VK6 | | VK5 | |
| VK7 | | VK6 | |
| VK8 | | VK7 | |
| | | VK8 | |

| $V\lambda$ ICF 1 | $V\lambda$ ICF2 | $V\lambda$ ICF3 | $V\lambda$ ICF4 |
|---|---|---|---|
| VL1 | VL1_2 | VL1 | VL1 |
| VL2 | VL3_4 | VL2 | |
| VL3 | VL5_6 | VL3 | |
| VL4 | VL7 | VL4 | |
| VL5 | VL8 | VL5 | |
| VL6 | | VL6 | |
| VL7 | | VL7 | |
| VL8 | | VL8 | |

Thus, combinatorial libraries of 224 kappa chains (7×4×8×1) or 320 (8×5×8×1) lambda chains can be obtained from these sets.

The combinatorial libraries of the invention can be assembled from other sets of ICFs. For example, reduced libraries can be prepared, for example by combining ICF1, ICF2, and ICF3 having the same designation number: VK1_2+VK1_2_3+VK1+VK1 or VK6_VK4_5_6+VK6+VK1, thereby obtaining a reduced, but representative set of 8 kappa chains. Other libraries can be prepared by replacing an ICF with another ICF, as provided in Tables 1 to 4. For example, when selecting a set of ICF1s for a heavy chain library, GL2 can be (a) omitted, (b) replaced by GL2a, GL2b or other ICF1 listed in Table 1 or in the Examples, or (c) replaced by one or more sequences similar to GL2, GL2a, GL2b, or other ICF1, such as corresponding sequences in germline or mature antibodies.

Alternate Exemplary Embodiments

In another embodiment, HuFR can involve a two-step reassembly process involving one or more placeholder nucleic acids. The placeholders can comprise a reduced set of light chain ICFs. A placeholder can also be determined on the basis of a known antibody or a germline variable region nucleic acid sequence identity compared to that of a sequence of a processed, mature antibody (for example, those light chain variable region germline sequences that are most similar to the nucleic acid sequence of the mature antibody). Once identified, the placeholder nucleic acid sequence, after being transfected and expressed in a cell, can then be used as a temporary single light chain molecule that can be coupled to a heavy chain variable region molecule of the invention.

A heavy chain variable region polypeptides that have a desired property, such as binding to an antigen, the best heavy chains. In one embodiment, the nucleic acid sequences encoding the polypeptides selected can be combined with the combinatorial library of light chain variable region nucleic acids expressed in a cell. In another embodiment, antibody clones can be screened, as described above. For example, antibody clones can be screened for enhanced binding affinities, for example the ability to induce apoptosis or to mediate cell death.

Light chain genes are synthesized to serve as placeholder light chains for HC screening purposes. A representative sequence of light chain frameworks from $FR_1$, $FR_2$, $FR_3$, and $FR_4$ was obtained that belongs to the same family (for example, derived from the same original germline sequence) and was utilized as the placeholder light chain gene. 8 families of kappa framework regions and 8 families of lambda framework regions were selected, representing 8 potential kappa or lambda libraries that can be generated for screening purposes.

Once the heavy chain and placeholder light chain for each of the eight families is generated, each of the products can be associated into a library (e.g., the 245 heavy chains generated along with Family 1 of light chains; the 245 heavy chains along with Family 2 of the light chains; etc, until have 8 libraries total). From each of the 8 libraries (each library representing 1 germline family), a total of 1960 antibodies will be screened using binding assays (such as ELISAs). Thus, after all 8 libraries are screened. A total of 15,680 HC candidates will have been examined. From that, the top 10 binding HCs will be further evaluated once the placeholder light chains are removed and replaced with the combinatorial library of light chain variable region nucleic acids that will be determined in the second phase of the HuFR process.

Following library synthesis and cloning, plasmids carrying the antibody genes can be amplified in E. coli and transfected into mammalian cells for the production of a full-length Ig. The resulting antibody supernatants can then be screened in the apoptosis assay. For example, in the case of a CD3 antibody, there were 326 hits selected from the primary screen, 52 confirmed hits, and the top 10 heavy chain hits were selected (see Example 4).

In the second round, the top 10 reassembled heavy chain genes identified by the apoptosis assay can subsequently be combined with a HuFR combinatorial light chain library. This library can be screened for identification of variants with identical or improved properties as compared to the control antibody. For example, in the case of a CD3 antibody, there were 268 hits from the primary screen, 37 confirmed hits, and the top 10 selected. 9 were successfully retransfected and assayed in confirmation assays (see Example 4).

The invention will be further described with reference to the following examples; however, it is to be understood that the invention is not limited to such examples.

EXAMPLES

Example 1

Framework Reassembly Fragments for Light Chain Libraries

The invention provides libraries of light and heavy chain framework region "fragments", or working pieces, that can be used to build-construct chimeric antigen-binding polypeptides. The following example describes exemplary libraries of light chain framework region "fragments", or working pieces, that can be used to build-construct chimeric antigen-binding polypeptides, and an exemplary method for making them.

In one aspect, framework fragments are designed to represent the sequence diversity of human framework regions (FR), for example subregions FR1, FR2, and FR3. In this example, fragment libraries were constructed based on the human germline immunoglobulin light chain variable domains ($V_L$).

Figure 2:
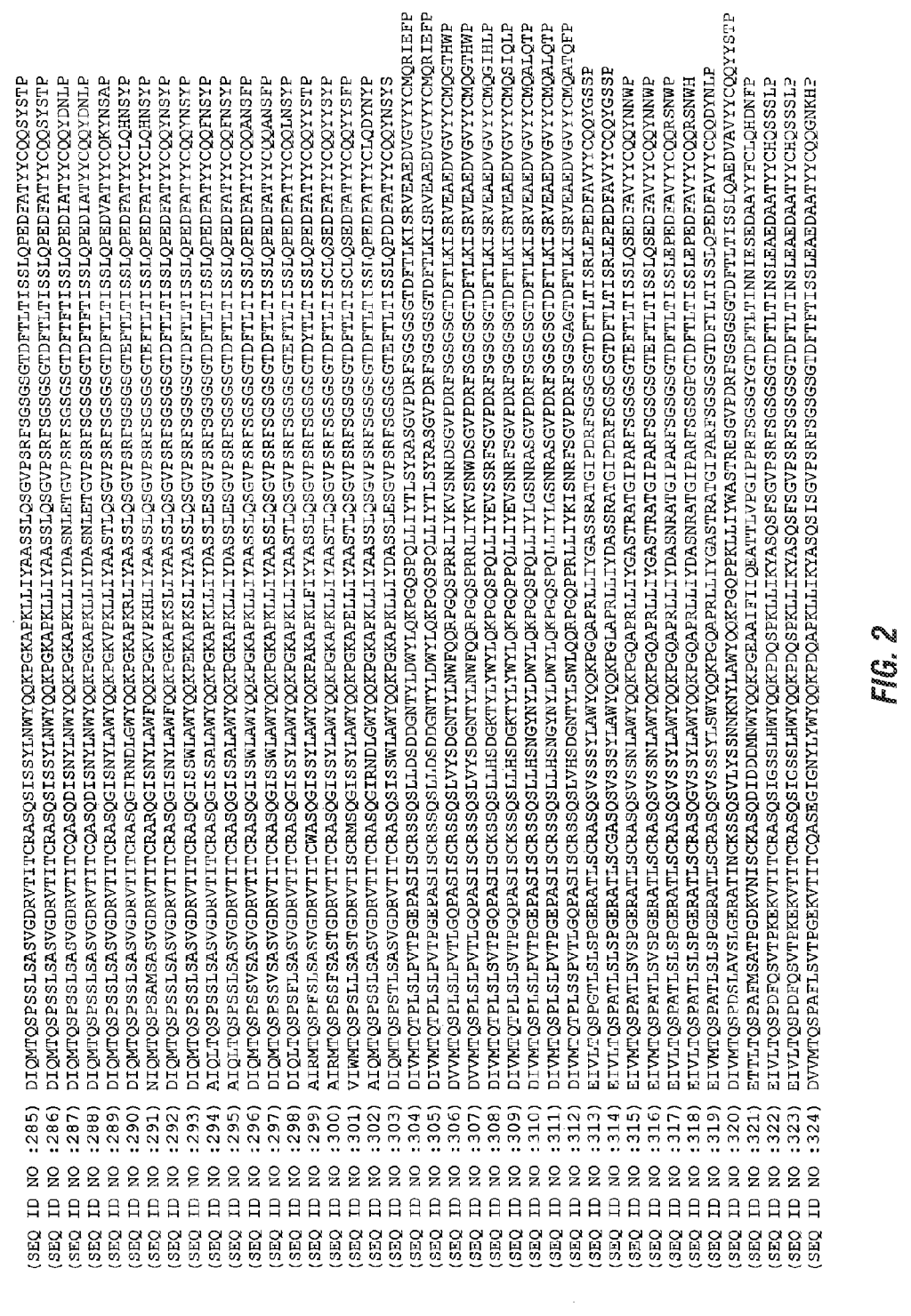
Figure 3:
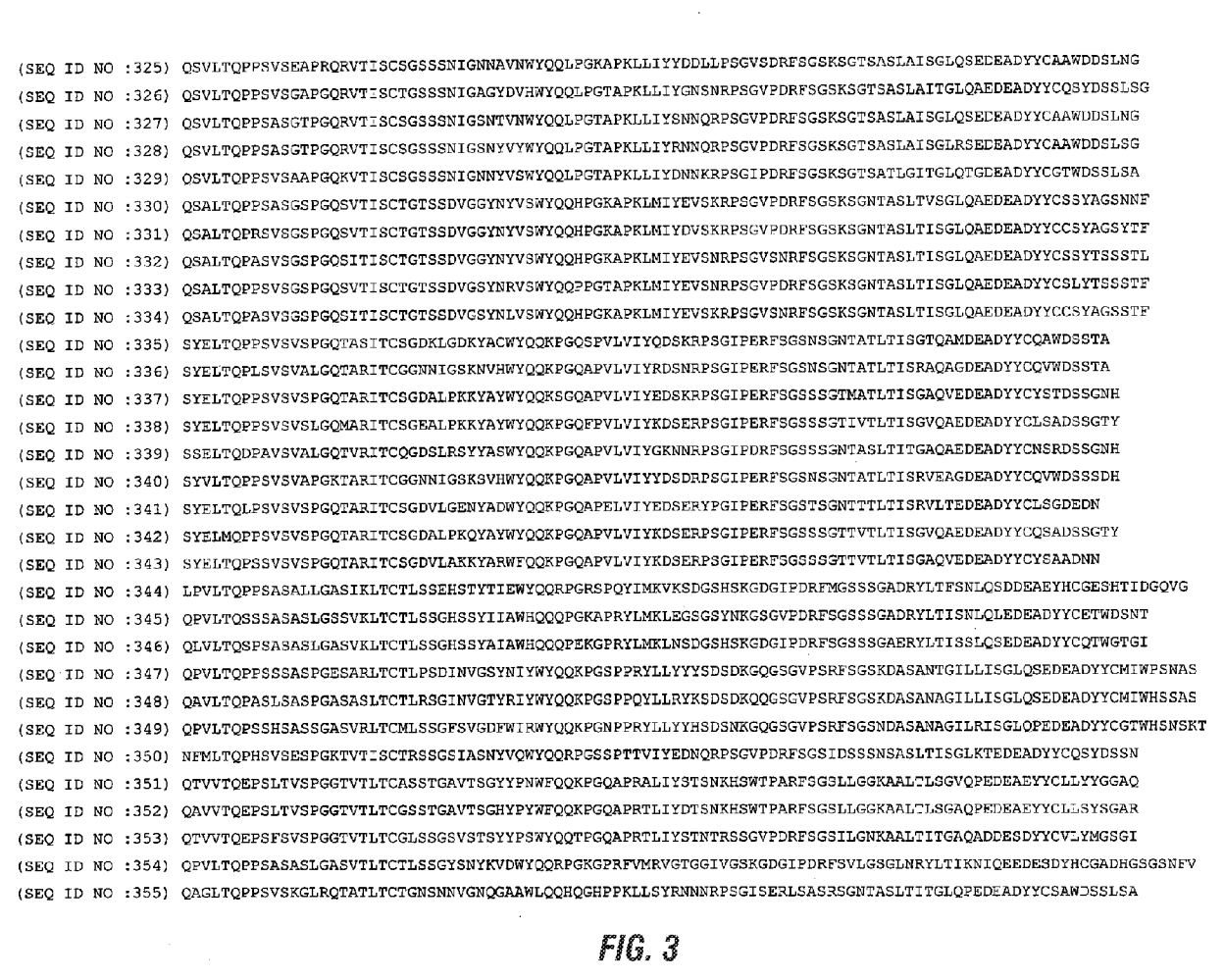

Design of Light Chain Lambda ($V_λ$) Framework Region Fragments for a Reassembly Library To identify sequences for lambda-chain framework regions, the Kabat database of antibody sequences was consulted to determine which human germline genes were used in mature, functional antibodies. Sequence comparison software was used to identify the most similar germline gene for each mature $V_L$. Thus, genes can be compared by the percentage of mature antibodies that may have arisen from them. Based on functional full-length sequences (FIGS. 2-3), top full-length germline sequences were selected to obtain individual FR regions.

To obtain "consensus" sequences that are representative of human FRs, sequences of all human Vκ exons were compiled, and exon sequences were divided into FRs. The following steps were performed for each set of FR sequences. A set of FR sequences was aligned and clustered by sequence similarity. Sequences from each main FR cluster were used to create a consensus sequence, which consisted of the most frequent amino acid occurring at each sequence position. The resulting sequences were 17 consensus $FR_1$s (also referred to as ICF1s), 16 consensus $FR_2$s (also referred to as ICF2s), and 15 consensus $FR_3$s (also referred to as ICF3s). Each of the consensus regions (for example ICF1, ICF2, ICF3) was at least 52% identical to a germline library FR fragment, and at least 65% identical to a mature FR fragment. The FR consensus sequences (for example, ICF1, ICF2, ICF3) were converted to DNA sequences.

A subset of these ICFs can be selected, according to the desired coverage and screening capabilities. The subset fragments were chosen by first including the unique fragments from the ICF Vκ library (in use at the time), and then supplementing this list with consensus fragments based primarily on their relative usage by mature antibodies and secondarily on their coverage of any sequence space missed by the current library.

Example 2

Framework Reassembly Fragments for Heavy Chain Libraries

The invention provides separate libraries for both light and heavy chain ICFs; these libraries made using exemplary methods of this invention. The following example describes exemplary libraries of heavy chain framework region "fragments", or working pieces, that can be used to build-construct chimeric antigen-binding polypeptides, and an exemplary method for making them.

A separate library for heavy chain ICFs was constructed based on the human germline immunoglobulin heavy chain variable domains ($V_H$), and human $V_H$s that have been through the natural, immunological maturation process. Any $V_H$ can be subdivided into complementarity-determining regions (CDRs) and FRs. For each FR, several fragments were designed to represent the diversity seen among natural $V_H$ FRs.

The sequences of all human $V_H$ exons were compiled, and exon sequences were divided into FRs. The following steps were performed for each set of FR sequences. A set of FR sequences was aligned and clustered by sequence similarity. Sequences from each main FR cluster were used to create a consensus sequence (for example, ICF1, ICF2, ICF3), which consisted of the most frequent amino acid occurring at each sequence position. Each FR family amino acid consensus sequence (for example, ICF1, ICF2, ICF3) was reverse-translated to codons in an unbiased manner. These preliminary nucleotide models were aligned with human $V_H$ exons to determine "natural" codon usage. The exon regions that aligned with the primary nucleotide models were used to generate secondary nucleotide models. The secondary nucleotide models were translated for comparison to the original consensus primary structure (for example, ICF1, ICF2, ICF3). Codons in the secondary models, which resulted in a mutation from the consensus sequence (for example, ICF1, ICF2, ICF3), were replaced with human codons that code for the residue seen in the consensus sequence. $FR_3$ had twelve representative fragment sequences; in one experimental library, eight fragments were used. These were selected in order to minimize the difference in sequence diversity between the set of twelve and the set of eight.

Example 3

Anti-Cd20 Antibody

The invention provides a chimeric polypeptide and a chimeric bivalent antibody that specifically binds to the polypeptide CD20, e.g., in one embodiment, human CD20.

A mouse antibody that specifically binds to human CD20 was identified, having biological properties similar to a reference antibody. The mouse hybridoma was cultured, and binding of the mouse antibody to a human CD20+ B cell line (Daudi) was confirmed by Fluorescent-Activated Cell Sorting (FACS) analysis.

Prior to further characterization and assay development, the selected parental mouse antibody was converted to a chimeric anti-CD20 antibody. The chimeric antibody was required for performing comparative biological studies of the selected antibody versus reference antibody (mouse-human chimera). Furthermore, the chimeric antibody was prepared to serve as the appropriate control for the screening assays used in the modification. The parental chimera was prepared so that the sequences encoding the variable regions from the immunoglobulin heavy chain (HC) and light chain (LC) genes were isolated and cloned into a mammalian expression vector containing a human IgG1 constant domain. The resulting chimeric anti-CD20 antibody is referred to as DVSA-CD20.

Assay Development

A cell-based ELISA was established as a simple, rapid, primary screen for the identification of HuFR variants with CD20-binding properties similar to or better than DVSA-CD20. This assay was developed using CD20+ B cell lines in suspension as well as with a stable, adherent HEK-293 cell line expressing the human CD20 protein.

CDC (Complement-Dependent Cytotoxicity) Assay.

A fluorescence-based, 96-well plate assay was developed for evaluating the ability of anti-CD20 variants to bind to CD20+ lymphoma cells. Complement activation was assessed by measurement of cell viability. For this assay, the reference antibody and DVSA-CD20 served as the positive controls. The negative controls included untreated cells, cells treated with complement only, cells treated with an unrelated human IgG and complement, and cells treated with vector control supernatants and complement.

ADCC (Antibody-Dependent, Cell-Mediated Cytotoxicity Assay).

The ability of anti-CD20 antibodies to induce ADCC was assayed. The anti-CD20 antibody variants were tested for similar or improved binding to DVSA-CD20 in the CD20 cellular ELISA and that have similar or improved activity compared to DVSA-CD20 in the CDC assay. To confirm that the anti-CD20 variants retained this effector function, a 96-well ADCC assay was established. Cell death was measured using LDH release. Positive controls for the assay included the reference antibody and the DVSA-CD20 antibody.

Apoptosis Assay.

A FACS-based assay, which measured the loss of plasma membrane integrity, was developed for assessing the ability of anti-CD20 variants to induce apoptosis. For this assay, human CD20 positive B cell lymphoma cells were treated with anti-CD20, stained with Annexin V and propidium iodide, followed by FACS analysis.

Cell Cycle Assay.

The fully murine, parental antibody of DVSA-CD20 has been reported to induce cell proliferation in human PBMCs in vitro in the presence of cross-linking antibodies. The reference antibody did not demonstrate this undesirable activity. To ensure that the anti-CD20 variants did not induce cell proliferation in human B cells, an anti-CD3 cell cycle assay was adapted for this screen. The murine CD20 (muCD20) as reported in the literature induces a modest level of cell proliferation when incubated in the presence of cross-linking antibodies.

Construction of the HuFR Library

Human Framework Reassembly was performed in two rounds. For the first round, a heavy chain library was prepared. The following table shows the ICFs used for CD20 heavy chain assembly (see Tables 1 and 2 for sequences of ICFs) with mouse CDRs, as described schematically in FIG. 1.

| heavy chain ID | ICF1 | ICF2 | ICF3 | ICF4 |
|---|---|---|---|---|
| BD20332 | GL7 | GL2_3 | GL7 | GL1 |
| BD20333 | GL7 | GL2_3 | GL8 | GL1 |
| BD20335 | GL7 | GL5 | GL1 | GL1 |
| BD20336 | GL7 | GL2_3 | GL1 | GL1 |
| BD20337 | GL7 | GL4 | GL7 | GL1 |
| BD20338 | GL6 | GL5 | GL7 | GL1 |
| BD20339 | GL7 | GL5 | GL8 | GL1 |
| BD20341 | GL7 | GL4 | GL8 | GL1 |

The complete nucleotide and amino acid sequences for the heavy chain variable regions are provided as follows:

Nucleotide Sequences of Heavy Chain Variable Regions:

>BD20332
(SEQ ID NO: 99)
CAGGTGCAGCTGGTGCAGTCTGGGGCTGAGGTGAAGAAGCCTGGGGCTTC

GGTGAAGGTCTCCTGCAAGGCTTCTGGCTACACATTTACCAGTTACAATA

TGCACTGGGTCCGCCAGGCTCCAGGCAAGGGGCTAGAGTGGGTGGGTGCT

ATTTATCCAGGAAATGGTGATACTTCCTACAATCAGAAGTTCAAAGGCAG

AGTCACCATCTCAGCTGACAAGTCCATCAGCACTGCCTACCTGCAGTGGA

GCAGCCTGAAGGCCTCGGACACCGCCATGTATTACTGTGCGAGATCGCAC

TACGGTAGTAACTACGTAGACTACTTTGACTACTGGGGCCAGGGCACCCT

GGTCACCGTCTCCTCC

>BD20333
(SEQ ID NO: 108)
CAGGTGCAGCTGGTGCAGTCTGGGGCTGAGGTGAAGAAGCCTGGGGCTTC

GGTGAAGGTCTCCTGCAAGGCTTCTGGCTACACATTTACCAGTTACAATA

TGCACTGGGTCCGCCAGGCTCCAGGGAAGGGGCTGGAGTGGGTTGGTGCT

ATTTATCCAGGAAATGGTGATACTTCCTACAATCAGAAGTTCAAAGGCAG

AGTCACGATTACCGCGGACAAATCCACGAGCACAGCCTACATGGAGCTGA

GCAGCCTGAGATCTGAGGACACGGCCGTGTATTACTGTGCGAGATCGCAC

TACGGTAGTAACTACGTAGACTACTTTGACTACTGGGGCCAGGGCACCCT

GGTCACCGTCTCCTCC

>BD20335
(SEQ ID NO: 124)
CAGGTGCAGCTGGTGCAGTCTGGGGCTGAGGTGAAGAAGCCTGGGGCTTC

GGTGAAGGTCTCCTGCAAGGCTTCTGGCTACACATTTACCAGTTACAATA

TGCACTGGGTGCGACAGGCTCCTGGAAAAGGGCTTGAGTGGATGGGTGCT

ATTTATCCAGGAAATGGTGATACTTCCTACAATCAGAAGTTCAAAGGCAG

ATTCACCATCTCCAGAGACAACGCCAAGAACTCACTGTATCTGCAAATGA

ACAGCCTGAGAGCCGAGGACACGGCTGTGTATTACTGTGCGAGATCGCAC

TACGGTAGTAACTACGTAGACTACTTTGACTACTGGGGCCAGGGCACCCT

GGTCACCGTCTCCTCC

>BD20336
(SEQ ID NO: 130)
CAGGTGCAGCTGGTGCAGTCTGGGGCTGAGGTGAAGAAGCCTGGGGCTTC

GGTGAAGGTCTCCTGCAAGGCTTCTGGCTACACATTTACCAGTTACAATA

TGCACTGGGTCCGCCAGGCTCCAGGGAAGGGGCTGGAGTGGGTTGGTGCT

ATTTATCCAGGAAATGGTGATACTTCCTACAATCAGAAGTTCAAAGGCAG

ATTCACCATCTCCAGAGACAACGCCAAGAACTCACTGTATCTGCAAATGA

ACAGCCTGAGAGCCGAGGACACGGCTGTGTATTACTGTGCGAGATCGCAC

TACGGTAGTAACTACGTAGACTACTTTGACTACTGGGGCCAGGGCACCCT

GGTCACCGTCTCCTCC

-continued

>BD20337
(SEQ ID NO: 131)
CAGGTGCAGCTGGTGCAGTCTGGGGCTGAGGTGAAGAAGCCTGGGCTTC

GGTGAAGGTCTCCTGCAAGGCTTCTGGCTACACATTTACCAGTTACAATA

TGCACTGGGTGCGACAGGCCCCTGGACAAGGGCTTGAGTGGATGGGTGCT

ATTTATCCAGGAAATGGTGATACTTCCTACAATCAGAAGTTCAAAGGCAG

AGTCACCATCTCAGCTGACAAGTCCATCAGCACTGCCTACCTGCAGTGGA

GCAGCCTGAAGGCCTCGGACACCGCCATGTATTACTGTGCGAGATCGCAC

TACGGTAGTAACTACGTAGACTACTTTGACTACTGGGGCCAGGGCACCCT

GGTCACCGTCTCCTCC

>BD20338
(SEQ ID NO: 132)
GAGGTGCAGCTGGTGCAGTCTGGGGCAGAGGTGAAAAAGCCCGGGGAGTC

TCTGAAGATCTCCTGTAAGGGTTCTGGCTACACATTTACCAGTTACAATA

TGCACTGGGTGCGACAGGCTCCTGGAAAAGGGCTTGAGTGGATGGGTGCT

ATTTATCCAGGAAATGGTGATACTTCCTACAATCAGAAGTTCAAAGGCAG

AGTCACCATCTCAGCTGACAAGTCCATCAGCACTGCCTACCTGCAGTGGA

GCAGCCTGAAGGCCTCGGACACCGCCATGTATTACTGTGCGAGATCGCAC

TACGGTAGTAACTACGTAGACTACTTTGACTACTGGGGCCAGGGCACCCT

GGTCACCGTCTCCTCC

>BD20339
(SEQ ID NO: 136)
CAGGTGCAGCTGGTGCAGTCTGGGGCTGAGGTGAAGAAGCCTGGGCTTC

GGTGAAGGTCTCCTGCAAGGCTTCTGGCTACACATTTACCAGTTACAATA

TGCACTGGGTGCGACAGGCTCCTGGAAAAGGGCTTGAGTGGATGGGTGCT

ATTTATCCAGGAAATGGTGATACTTCCTACAATCAGAAGTTCAAAGGCAG

AGTCACGATTACCGCGGACAAATCCACGAGCACAGCCTACATGGAGCTGA

GCAGCCTGAGATCTGAGGACACGGCCGTGTATTACTGTGCGAGATCGCAC

TACGGTAGTAACTACGTAGACTACTTTGACTACTGGGGCCAGGGCACCCT

GGTCACCGTCTCCTCC

>BD20341
(SEQ ID NO: 137)
CAGGTGCAGCTGGTGCAGTCTGGGGCTGAGGTGAAGAAGCCTGGGCTTC

GGTGAAGGTCTCCTGCAAGGCTTCTGGCTACACATTTACCAGTTACAATA

TGCACTGGGTGCGACAGGCCCCTGGACAAGGGCTTGAGTGGATGGGTGCT

ATTTATCCAGGAAATGGTGATACTTCCTACAATCAGAAGTTCAAAGGCAG

AGTCACGATTACCGCGGACAAATCCACGAGCACAGCCTACATGGAGCTGA

GCAGCCTGAGATCTGAGGACACGGCCGTGTATTACTGTGCGAGATCGCAC

TACGGTAGTAACTACGTAGACTACTTTGACTACTGGGGCCAGGGCACCCT

GGTCACCGTCTCCTCC

Amino Acid Sequences of Heavy Chain Variable Regions:

>BD20332
(SEQ ID NO: 138)
QVQLVQSGAEVKKPGASVKVSCKASGYTFTSYNMHWVRQAPGKGLEWVGA

IYPGNGDTSYNQKFKGRVTISADKSISTAYLQWSSLKASDTAMYYCARSH

YGSNYVDYFDYWGQGTLVTVSS

>BD20333
(SEQ ID NO: 142)
QVQLVQSGAEVKKPGASVKVSCKASGYTFTSYNMHWVRQAPGKGLEWVGA

IYPGNGDTSYNQKFKGRVTITADKSTSTAYMELSSLRSEDTAVYYCARSH

YGSNYVDYFDYWGQGTLVTVSS

>BD20335
(SEQ ID NO: 143)
QVQLVQSGAEVKKPGASVKVSCKASGYTFTSYNMHWVRQAPGKGLEWMGA

IYPGNGDTSYNQKFKGRFTISRDNAKNSLYLQMNSLRAEDTAVYYCARSH

YGSNYVDYFDYWGQGTLVTVSS

>BD20336
(SEQ ID NO: 144)
QVQLVQSGAEVKKPGASVKVSCKASGYTFTSYNMHWVRQAPGKGLEWVGA

IYPGNGDTSYNQKFKGRFTISRDNAKNSLYLQMNSLRAEDTAVYYCARSH

YGSNYVDYFDYWGQGTLVTVSS

>BD20337
(SEQ ID NO: 148)
QVQLVQSGAEVKKPGASVKVSCKASGYTFTSYNMHWVRQAPGQGLEWMGA

IYPGNGDTSYNQKFKGRVTISADKSISTAYLQWSSLKASDTAMYYCARSH

YGSNYVDYFDYWGQGTLVTVSS

>BD20338
(SEQ ID NO: 149)
EVQLVQSGAEVKKPGESLKISCKGSGYTFTSYNMHWVRQAPGKGLEWMGA

IYPGNGDTSYNQKFKGRVTISADKSISTAYLQWSSLKASDTAMYYCARSH

YGSNYVDYFDYWGQGTLVTVSS

>BD20339
(SEQ ID NO: 150)
QVQLVQSGAEVKKPGASVKVSCKASGYTFTSYNMHWVRQAPGKGLEWMGA

IYPGNGDTSYNQKFKGRVTITADKSTSTAYMELSSLRSEDTAVYYCARSH

YGSNYVDYFDYWGQGTLVTVSS

>BD20341
(SEQ ID NO: 154)
QVQLVQSGAEVKKPGASVKVSCKASGYTFTSYNMHWVRQAPGQGLEWMGA

IYPGNGDTSYNQKFKGRVTITADKSTSTAYMELSSLRSEDTAVYYCARSH

YGSNYVDYFDYWGQGTLVTVSS

The signal sequence and constant regions associated with the heavy chains are as follows:

>HC signal (SEQ ID NO: 155)
ATGGAGTTTGGGCTGAGCTGGCTTTTTCTTGTGGCTATTTTAAAAGGTGTCCAGTGT >HC signal (SEQ ID NO: 156)
MEFGLSWLFLVAILKGVQC >HC constant (SEQ ID NO: 160)
GCCTCCACCAAGGGCCCATCGGTCTTCCCCCTGGCACCCTCCTCCAAGAGCACCTCTGGGGGCACAGCGGCCCTG
GGCTGCCTGGTCAAGGACTACTTCCCCGAACCGGTGACGGTGTCGTGGAACTCAGGCGCCCTGACCAGCGGCGTG
CACACCTTCCCGGCTGTCCTACAGTCCTCAGGACTCTACTCCCTCAGCAGCGTGGTGACCGTGCCCTCCAGCAGC
TTGGGCACCCAGACCTACATCTGCAACGTGAATCACAAGCCCAGCAACACCAAGGTGGACAAGAGAGTTGAGCCC
AAATCTTGTGACAAAACTCACACATGCCCACCGTGCCCAGCACCTGAACTCCTGGGGGGACCGTCAGTCTTCCTC
TTCCCCCCAAAACCCAAGGACACCCTCATGATCTCCCGGACCCCTGAGGTCACATGCGTGGTGGTGGACGTGAGC
CACGAAGACCCTGAGGTCAAGTTCAACTGGTACGTGGACGGCGTGGAGGTGCATAATGCCAAGACAAAGCCGCGG
GAGGAGCAGTACAACAGCACGTACCGTGTGGTCAGCGTCCTCACCGTCCTGCACCAGGACTGGCTGAATGGCAAG
GAGTACAAGTGCAAGGTCTCCAACAAAGCCCTCCCAGCCCCCATCGAGAAAACCATCTCCAAAGCCAAAGGGCAG
CCCCGAGAACCACAGGTGTACACCCTGCCCCCATCCCGGGATGAGCTGACCAAGAACCAGGTCAGCCTGACCTGC
CTGGTCAAAGGCTTCTATCCCAGCGACATCGCCGTGGAGTGGGAGAGCAATGGGCAGCCGGAGAACAACTACAAG
ACCACGCCTCCCGTGCTGGACTCCGACGGCTCCTTCTTCCTCTACAGCAAGCTCACCGTGGACAAGAGCAGGTGG
CAGCAGGGGAACGTCTTCTCATGCTCCGTGATGCATGAGGCTCTGCACAACCACTACACGCAGAAGAGCCTCTCC
CTGTCTCCGGGTAAATGA >HC constant (SEQ ID NO: 161)
ASTKGPSVFPLAPSSKSTSGGTAALGCLVKDYFPEPVTVSWNSGALTSGVHTFPAVLQSSGLYSLSSVVTVPSSS
LGTQTYICNVNHKPSNTKVDKRVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLDSDGSFFLYSKLTVDKSRW
QQGNVFSCSVMHEALHNHYTQKSLSLSPGK The heavy chain library was then associated with eight placeholder light chains. Each light chain consisted of a fixed set of human frameworks and the mouse CDRs. Plasmids carrying the antibody genes were amplified in *E. coli* and transfected into mammalian cells for production of full-length IgG-containing supernatants for screening in the cellular ELISA. The best reassembled heavy chain genes identified by the cellular ELISA were then combined with a reassembled light chain library as follows:

| light chain ID | ICF1 | ICF2 | ICF3 | ICF4 |
|---|---|---|---|---|
| BD22084 | VK8 | VK7 | VK5 | VK1 |
| BD22107 | VK8 | VK8 | VK5 | VK1 |
| BD22086 | VK8 | VK4_5_6 | VK7 | VK1 |
| BD22103 | VK8 | VK1_2_3 | VK7 | VK1 |
| BD22088 | VK8 | VK7 | VK2 | VK1 |
| BD22108 | VK8 | VK4_5_6 | VK2 | VK1 |
| BD22094 | VK8 | VK4_5_6 | VK3 | VK1 |
| BD22085 | VK7 | VK4_5_6 | VK1 | VK1 |
| BD22109 | VK7 | VK7 | VK5 | VK1 |
| BD22090 | VK8 | VK8 | VK8 | VK1 |
| BD22092 | VK1_2 | VK8 | VK7 | VK1 |
| BD22100 | VK3 | VK4_5_6 | VK2 | VK1 |
| BD22105 | VK6 | VK8 | VK7 | VK1 |
| BD22111 | VK7 | VK1_2_3 | VK3 | VK1 |
| BD22104 | VK4 | VK8 | VK1 | VK1 |
| BD22087 | VK6 | VK1_2_3 | VK3 | VK1 |
| BD22096 | VK5 | VK1_2_3 | VK3 | VK1 |
| BD22091 | VK5 | VK7 | VK4 | VK1 |
| BD22089 | VK5 | VK7 | VK2 | VK1 |
| BD22095 | VK4 | VK7 | VK2 | VK1 |
| BD22106 | VK6 | VK4_5_6 | VK2 | VK1 |
| BD22097 | VK6 | VK7 | VK1 | VK1 |
| BD22101 | VK5 | VK7 | VK1 | VK1 |
| BD22102 | VK4 | VK7 | VK1 | VK1 |

The complete nucleotide and amino acid sequences for the light chain variable regions are provided as follows:
Nucleotide Sequences of Light Chain Variable Regions:

>BD22084
(SEQ ID NO: 162)
GATATTGTGATGACCCAGTCTCCACTCTCCCTGCCCGTCACCCCTGGAGA

GCCGGCCTCCATCTCCTGCAGGGCCAGCTCAAGTTTAAGTTTCATGCACT

GGTATCAGCAGAAACCAGGACAGCCTCCTAAGCTGCTCATTTATGCCACA

TCCAACCTGGCTTCTGGGATCCCAGCCAGGTTCAGTGGCAGTGGGTCTGG

GACAGACTTCACTCTCACCATCAGCAGCCTAGAGCCTGAAGATTTTGCAG

TTTATTACTGTCATCAGTGGAGTAGTAACCCGCTCACGTTCGGCCAAGGT

ACCAAGGTGGAAATCAAA

>BD22107
(SEQ ID NO: 166)
GATATTGTGATGACCCAGTCTCCACTCTCCCTGCCCGTCACCCCTGGAGA

GCCGGCCTCCATCTCCTGCAGGGCCAGCTCAAGTTTAAGTTTCATGCACT

GGTATCTGCAGAAGCCAGGGCAGTCTCCACAGCTCCTGATCTATGCCACA

TCCAACCTGGCTTCTGGGATCCCAGCCAGGTTCAGTGGCAGTGGGTCTGG

GACAGACTTCACTCTCACCATCAGCAGCCTAGAGCCTGAAGATTTTGCAG

TTTATTACTGTCATCAGTGGAGTAGTAACCCGCTCACGTTCGGCCAAGGT

ACCAAGGTGGAAATCAAA

>BD22086
(SEQ ID NO: 167)
GATATTGTGATGACCCAGTCTCCACTCTCCCTGCCCGTCACCCCTGGAGA

GCCGGCCTCCATCTCCTGCAGGGCCAGCTCAAGTTTAAGTTTCATGCACT

GGTATCAGCAGAAACCTGGCCAGGCTCCCAGGCTCCTCATCTATGCCACA

TCCAACCTGGCTTCTGGGTCCCTGACCGATTCAGTGGCAGCGGGTCTGG

GACAGATTTCACTCTCACCATCAGCAGCCTGCAGGCTGAAGATGTGGCAG

TTTATTACTGTCATCAGTGGAGTAGTAACCCGCTCACGTTCGGCCAAGGT

ACCAAGGTGGAAATCAAA

>BD22103
(SEQ ID NO: 168)
GATATTGTGATGACCCAGTCTCCACTCTCCCTGCCCGTCACCCCTGGAGA

GCCGGCCTCCATCTCCTGCAGGGCCAGCTCAAGTTTAAGTTTCATGCACT

GGTATCAGCAGAAACCAGGGAAAGCCCCTAAGCTCCTGATCTATGCCACA

TCCAACCTGGCTTCTGGGTCCCTGACCGATTCAGTGGCAGCGGGTCTGG

GACAGATTTCACTCTCACCATCAGCAGCCTGCAGGCTGAAGATGTGGCAG

TTTATTACTGTCATCAGTGGAGTAGTAACCCGCTCACGTTCGGCCAAGGT

ACCAAGGTGGAAATCAAA

>BD22088
(SEQ ID NO: 172)
GATATTGTGATGACCCAGTCTCCACTCTCCCTGCCCGTCACCCCTGGAGA

GCCGGCCTCCATCTCCTGCAGGGCCAGCTCAAGTTTAAGTTTCATGCACT

GGTATCAGCAGAAACCAGGACAGCCTCCTAAGCTGCTCATTTATGCCACA

TCCAACCTGGCTTCTGGGTCCCATCAAGGTTCAGTGGAAGTGGATCTGG

GACAGATTTTACTTTCACCATCAGCAGCCTGCAGCCTGAAGATATTGCAA

CATATTACTGTCATCAGTGGAGTAGTAACCCGCTCACGTTCGGCCAAGGT

ACCAAGGTGGAAATCAAA

>BD22108
(SEQ ID NO: 173)
GATATTGTGATGACCCAGTCTCCACTCTCCCTGCCCGTCACCCCTGGAGA

GCCGGCCTCCATCTCCTGCAGGGCCAGCTCAAGTTTAAGTTTCATGCACT

GGTATCAGCAGAAACCTGGCCAGGCTCCCAGGCTCCTCATCTATGCCACA

TCCAACCTGGCTTCTGGGGTCCCATCAAGGTTCAGTGGAAGTGGATCTGG

GACAGATTTTACTTTCACCATCAGCAGCCTGCAGCCTGAAGATATTGCAA

CATATTACTGTCATCAGTGGAGTAGTAACCCGCTCACGTTCGGCCAAGGT

ACCAAGGTGGAAATCAAA

>BD22094
(SEQ ID NO: 174)
GATATTGTGATGACCCAGTCTCCACTCTCCCTGCCCGTCACCCCTGGAGA

GCCGGCCTCCATCTCCTGCAGGGCCAGCTCAAGTTTAAGTTTCATGCACT

GGTATCAGCAGAAACCTGGCCAGGCTCCCAGGCTCCTCATCTATGCCACA

TCCAACCTGGCTTCTGGGGTCCCATCAAGGTTCAGCGGCAGTGGATCTGG

GACAGAATTCACTCTCACCATCAGCAGCCTGCAGCCTGATGATTTTGCAA

CTTATTACTGTCATCAGTGGAGTAGTAACCCGCTCACGTTCGGCCAAGGT

ACCAAGGTGGAAATCAAA

>BD22085
(SEQ ID NO: 177)
GACATCGTGATGACCCAGTCTCCAGACTCCCTGGCTGTGTCTCTGGGCGA

GAGGGCCACCATCAACTGCAGGGCCAGCTCAAGTTTAAGTTTCATGCACT

GGTATCAGCAGAAACCTGGCCAGGCTCCCAGGCTCCTCATCTATGCCACA

TCCAACCTGGCTTCTGGGGTCCCATCAAGGTTCAGTGGCAGTGGATCTGG

GACAGATTTCACTCTCACCATCAGCAGTCTGCAACCTGAAGATTTTGCAA

CTTACTACTGTCATCAGTGGAGTAGTAACCCGCTCACGTTCGGCCAAGGT

ACCAAGGTGGAAATCAAA

>BD22109
(SEQ ID NO: 205)
GACATCGTGATGACCCAGTCTCCAGACTCCCTGGCTGTGTCTCTGGGCGA

GAGGGCCACCATCAACTGCAGGGCCAGCTCAAGTTTAAGTTTCATGCACT

GGTATCAGCAGAAACCAGGACAGCCTCCTAAGCTGCTCATTTATGCCACA

TCCAACCTGGCTTCTGGGATCCCAGCCAGGTTCAGTGGCAGTGGGTCTGG

GACAGACTTCACTCTCACCATCAGCAGCCTAGAGCCTGAAGATTTTGCAG

TTTATTACTGTCATCAGTGGAGTAGTAACCCGCTCACGTTCGGCCAAGGT

ACCAAGGTGGAAATCAAA

>BD22090
(SEQ ID NO: 210)
GATATTGTGATGACCCAGTCTCCACTCTCCCTGCCCGTCACCCCTGGAGA

GCCGGCCTCCATCTCCTGCAGGGCCAGCTCAAGTTTAAGTTTCATGCACT

GGTATCTGCAGAAGCCAGGGCAGTCTCCACAGCTCCTGATCTATGCCACA

TCCAACCTGGCTTCTGGGGTCCCTGACAGGTTCAGTGGCAGTGGATCAGG

-continued

```
>BD22092
                                          (SEQ ID NO: 211)
GACATCCAGATGACCCAGTCTCCATCCTCCCTGTCTGCATCTGTAGGAGA

CAGAGTCACCATCACTTGCAGGGCCAGCTCAAGTTTAAGTTTCATGCACT

GGTATCTGCAGAAGCCAGGGCAGTCTCCACAGCTCCTGATCTATGCCACA

TCCAACCTGGCTTCTGGGGTCCCTGACCGATTCAGTGGCAGCGGGTCTGG

GACAGATTTCACTCTCACCATCAGCAGCCTGCAGGCTGAAGATGTGGCAG

TTTATTACTGTCATCAGTGGAGTAGTAACCCGCTCACGTTCGGCCAAGGT

ACCAAGGTGGAAATCAAA

>BD22100
                                          (SEQ ID NO: 212)
GACATCCAGATGACCCAGTCTCCTTCCACCCTGTCTGCATCTGTAGGAGA

CAGAGTCACCATCACTTGCAGGGCCAGCTCAAGTTTAAGTTTCATGCACT

GGTATCAGCAGAAACCTGGCCAGGCTCCCAGGCTCCTCATCTATGCCACA

TCCAACCTGGCTTCTGGGGTCCCATCAAGGTTCAGTGGAAGTGGATCTGG

GACAGATTTTACTTTCACCATCAGCAGCCTGCAGCCTGAAGATATTGCAA

CATATTACTGTCATCAGTGGAGTAGTAACCCGCTCACGTTCGGCCAAGGT

ACCAAGGTGGAAATCAAA

>BD22105
                                          (SEQ ID NO: 213)
GAAATTGTGTTGACCCAGTCTCCAGGCACCCTGTCTTTGTCTCCAGGGGA

AAGAGCCACCCTCTCCTGCAGGGCCAGCTCAAGTTTAAGTTTCATGCACT

GGTATCTGCAGAAGCCAGGGCAGTCTCCACAGCTCCTGATCTATGCCACA

TCCAACCTGGCTTCTGGGGTCCCTGACCGATTCAGTGGCAGCGGGTCTGG

GACAGATTTCACTCTCACCATCAGCAGCCTGCAGGCTGAAGATGTGGCAG

TTTATTACTGTCATCAGTGGAGTAGTAACCCGCTCACGTTCGGCCAAGGT

ACCAAGGTGGAAATCAAA

>BD22111
                                          (SEQ ID NO: 214)
GACATCGTGATGACCCAGTCTCCAGACTCCCTGGCTGTGTCTCTGGGCGA

GAGGGCCACCATCAACTGCAGGGCCAGCTCAAGTTTAAGTTTCATGCACT

GGTATCAGCAGAAACCAGGGAAAGCCCCTAAGCTCCTGATCTATGCCACA

TCCAACCTGGCTTCTGGGGTCCCATCAAGGTTCAGCGGCAGTGGATCTGG

GACAGAATTCACTCTCACCATCAGCAGCCTGCAGCCTGATGATTTTGCAA

CTTATTACTGTCATCAGTGGAGTAGTAACCCGCTCACGTTCGGCCAAGGT

ACCAAGGTGGAAATCAAA

>BD22104
                                          (SEQ ID NO: 215)
GAAATAGTGATGACCCAGTCTCCAGCCACCCTGTCTGTGTCTCCAGGGGA

AAGAGCCACCCTCTCCTGCAGGGCCAGCTCAAGTTTAAGTTTCATGCACT

GGTATCTGCAGAAGCCAGGGCAGTCTCCACAGCTCCTGATCTATGCCACA

TCCAACCTGGCTTCTGGGGTCCCATCAAGGTTCAGTGGCAGTGGATCTGG

GACAGATTTCACTCTCACCATCAGCAGTCTGCAACCTGAAGATTTTGCAA

CTTACTACTGTCATCAGTGGAGTAGTAACCCGCTCACGTTCGGCCAAGGT

ACCAAGGTGGAAATCAAA

>BD22087
                                          (SEQ ID NO: 216)
GAAATTGTGTTGACCCAGTCTCCAGGCACCCTGTCTTTGTCTCCAGGGGA

AAGAGCCACCCTCTCCTGCAGGGCCAGCTCAAGTTTAAGTTTCATGCACT

GGTATCAGCAGAAACCAGGGAAAGCCCCTAAGCTCCTGATCTATGCCACA

TCCAACCTGGCTTCTGGGGTCCCATCAAGGTTCAGCGGCAGTGGATCTGG

GACAGAATTCACTCTCACCATCAGCAGCCTGCAGCCTGATGATTTTGCAA

CTTATTACTGTCATCAGTGGAGTAGTAACCCGCTCACGTTCGGCCAAGGT

ACCAAGGTGGAAATCAAA

>BD22096
                                          (SEQ ID NO: 217)
GAAATTGTGTTGACCCAGTCTCCAGCCACCCTGTCTTTGTCTCCAGGGGA

AAGAGCCACCCTCTCCTGCAGGGCCAGCTCAAGTTTAAGTTTCATGCACT

GGTATCAGCAGAAACCAGGGAAAGCCCCTAAGCTCCTGATCTATGCCACA

TCCAACCTGGCTTCTGGGGTCCCATCAAGGTTCAGCGGCAGTGGATCTGG

GACAGAATTCACTCTCACCATCAGCAGCCTGCAGCCTGATGATTTTGCAA

CTTATTACTGTCATCAGTGGAGTAGTAACCCGCTCACGTTCGGCCAAGGT

ACCAAGGTGGAAATCAAA

>BD22091
                                          (SEQ ID NO: 218)
GAAATTGTGTTGACCCAGTCTCCAGCCACCCTGTCTTTGTCTCCAGGGGA

AAGAGCCACCCTCTCCTGCAGGGCCAGCTCAAGTTTAAGTTTCATGCACT

GGTATCAGCAGAAACCAGGACAGCCTCCTAAGCTGCTCATTTATGCCACA

TCCAACCTGGCTTCTGGGATCCCAGCCAGGTTCAGTGGCAGTGGGTCTGG

GACAGAGTTCACTCTCACCATCAGCAGCCTGCAGTCTGAAGATTTTGCAG

TTTATTACTGTCATCAGTGGAGTAGTAACCCGCTCACGTTCGGCCAAGGT

ACCAAGGTGGAAATCAAA

>BD22089
                                          (SEQ ID NO: 219)
GAAATTGTGTTGACCCAGTCTCCAGCCACCCTGTCTTTGTCTCCAGGGGA

AAGAGCCACCCTCTCCTGCAGGGCCAGCTCAAGTTTAAGTTTCATGCACT

GGTATCAGCAGAAACCAGGACAGCCTCCTAAGCTGCTCATTTATGCCACA

TCCAACCTGGCTTCTGGGGTCCCATCAAGGTTCAGTGGAAGTGGATCTGG

GACAGATTTTACTTTCACCATCAGCAGCCTGCAGCCTGAAGATATTGCAA

CATATTACTGTCATCAGTGGAGTAGTAACCCGCTCACGTTCGGCCAAGGT

ACCAAGGTGGAAATCAAA

>BD22095
                                          (SEQ ID NO: 220)
GAAATAGTGATGACCCAGTCTCCAGCCACCCTGTCTGTGTCTCCAGGGGA

AAGAGCCACCCTCTCCTGCAGGGCCAGCTCAAGTTTAAGTTTCATGCACT

GGTATCAGCAGAAACCAGGACAGCCTCCTAAGCTGCTCATTTATGCCACA

TCCAACCTGGCTTCTGGGGTCCCATCAAGGTTCAGTGGAAGTGGATCTGG

GACAGATTTTACTTTCACCATCAGCAGCCTGCAGCCTGAAGATATTGCAA
```

```
>BD22106
                                      (SEQ ID NO: 221)
GAAATTGTGTTGACCCAGTCTCCAGGCACCCTGTCTTTGTCTCCAGGGGA

AAGAGCCACCCTCTCCTGCAGGGCCAGCTCAAGTTTAAGTTTCATGCACT

GGTATCAGCAGAAACCTGGCCAGGCTCCCAGGCTCCTCATCTATGCCACA

TCCAACCTGGCTTCTGGGGTCCCATCAAGGTTCAGTGGAAGTGGATCTGG

GACAGATTTTACTTTCACCATCAGCAGCCTGCAGCCTGAAGATATTGCAA

CATATTACTGTCATCAGTGGAGTAGTAACCCGCTCACGTTCGGCCAAGGT

ACCAAGGTGGAAATCAAA

>BD22097
                                      (SEQ ID NO: 222)
GAAATTGTGTTGACCCAGTCTCCAGGCACCCTGTCTTTGTCTCCAGGGGA

AAGAGCCACCCTCTCCTGCAGGGCCAGCTCAAGTTTAAGTTTCATGCACT

GGTATCAGCAGAAACCAGGACAGCCTCCTAAGCTGCTCATTTATGCCACA

TCCAACCTGGCTTCTGGGGTCCCATCAAGGTTCAGTGGCAGTGGATCTGG

GACAGATTTCACTCTCACCATCAGCAGTCTGCAACCTGAAGATTTTGCAA

CTTACTACTGTCATCAGTGGAGTAGTAACCCGCTCACGTTCGGCCAAGGT

ACCAAGGTGGAAATCAAA

>BD22101
                                      (SEQ ID NO: 223)
GAAATTGTGTTGACCCAGTCTCCAGCCACCCTGTCTTTGTCTCCAGGGGA

AAGAGCCACCCTCTCCTGCAGGGCCAGCTCAAGTTTAAGTTTCATGCACT

GGTATCAGCAGAAACCAGGACAGCCTCCTAAGCTGCTCATTTATGCCACA

TCCAACCTGGCTTCTGGGGTCCCATCAAGGTTCAGTGGCAGTGGATCTGG

GACAGATTTCACTCTCACCATCAGCAGTCTGCAACCTGAAGATTTTGCAA

CTTACTACTGTCATCAGTGGAGTAGTAACCCGCTCACGTTCGGCCAAGGT

ACCAAGGTGGAAATCAAA

>BD22102
                                      (SEQ ID NO: 224)
GAAATAGTGATGACCCAGTCTCCAGCCACCCTGTCTGTGTCTCCAGGGGA

AAGAGCCACCCTCTCCTGCAGGGCCAGCTCAAGTTTAAGTTTCATGCACT

GGTATCAGCAGAAACCAGGACAGCCTCCTAAGCTGCTCATTTATGCCACA

TCCAACCTGGCTTCTGGGGTCCCATCAAGGTTCAGTGGCAGTGGATCTGG

GACAGATTTCACTCTCACCATCAGCAGTCTGCAACCTGAAGATTTTGCAA

CTTACTACTGTCATCAGTGGAGTAGTAACCCGCTCACGTTCGGCCAAGGT

ACCAAGGTGGAAATCAAA
```

Amino Acid Sequences of Light Chain Variable Regions:

```
>BD22084
                                      (SEQ ID NO: 225)
DIVMTQSPLSLPVTPGEPASISCRASSSLSFMHWYQQKPGQPPKLLIYAT

SNLASGIPARFSGSGSGTDFTLTISSLEPEDFAVYYCHQWSSNPLTFGQG

TKVEIK

>BD22107
                                      (SEQ ID NO: 226)
DIVMTQSPLSLPVTPGEPASISCRASSSLSFMHWYLQKPGQSPQLLIYAT

SNLASGIPARFSGSGSGTDFTLTISSLEPEDFAVYYCHQWSSNPLTFGQG

TKVEIK

>BD22086
                                      (SEQ ID NO: 227)
DIVMTQSPLSLPVTPGEPASISCRASSSLSFMHWYQQKPGQAPRLLIYAT

SNLASGVPDRFSGSGSGTDFTLTISSLQAEDVAVYYCHQWSSNPLTFGQG

TKVEIK

>BD22103
                                      (SEQ ID NO: 228)
DIVMTQSPLSLPVTPGEPASISCRASSSLSFMHWYQQKPGKAPKLLIYAT

SNLASGVPDRFSGSGSGTDFTLTISSLQAEDVAVYYCHQWSSNPLTFGQG

TKVEIK

>BD22088
                                      (SEQ ID NO: 229)
DIVMTQSPLSLPVTPGEPASISCRASSSLSFMHWYQQKPGQPPKLLIYAT

SNLASGVPSRFSGSGSGTDFTFTISSLQPEDIATYYCHQWSSNPLTFGQG

TKVEIK

>BD22108
                                      (SEQ ID NO: 230)
DIVMTQSPLSLPVTPGEPASISCRASSSLSFMHWYQQKPGQAPRLLIYAT

SNLASGVPSRFSGSGSGTDFTFTISSLQPEDIATYYCHQWSSNPLTFGQG

TKVEIK

>BD22094
                                      (SEQ ID NO: 231)
DIVMTQSPLSLPVTPGEPASISCRASSSLSFMHWYQQKPGQAPRLLIYAT

SNLASGVPSRFSGSGSGTEFTLTISSLQPDDFATYYCHQWSSNPLTFGQG

TKVEIK

>BD22085
                                      (SEQ ID NO: 232)
DIVMTQSPDSLAVSLGERATINCRASSSLSFMHWYQQKPGQAPRLLIYAT

SNLASGVPSRFSGSGSGTDFTLTISSLQPEDFATYYCHQWSSNPLTFGQG

TKVEIK

>BD22109
                                      (SEQ ID NO: 233)
DIVMTQSPDSLAVSLGERATINCRASSSLSFMHWYQQKPGQPPKLLIYAT

SNLASGIPARFSGSGSGTDFTLTISSLEPEDFAVYYCHQWSSNPLTFGQG

TKVEIK

>BD22090
                                      (SEQ ID NO: 234)
DIVMTQSPLSLPVTPGEPASISCRASSSLSFMHWYLQKPGQSPQLLIYAT

SNLASGVPDRFSGSGSGTDFTLKISRVEAEDVGVYYCHQWSSNPLTFGQG

TKVEIK

>BD22092
                                      (SEQ ID NO: 235)
DIQMTQSPSSLSASVGDRVTITCRASSSLSFMHWYLQKPGQSPQLLIYAT

SNLASGVPDRFSGSGSGTDFTLTISSLQAEDVAVYYCHQWSSNPLTFGQG

TKVEIK
```

```
>BD22100
                                            (SEQ ID NO: 236)
DIQMTQSPSTLSASVGDRVTITCRASSSLSFMHWYQQKPGQAPRLLIYAT

SNLASGVPSRFSGSGSGTDFTFTISSLQPEDIATYYCHQWSSNPLTFGQG

TKVEIK

>BD22105
                                            (SEQ ID NO: 237)
EIVLTQSPGTLSLSPGERATLSCRASSSLSFMHWYLQKPGQSPQLLIYAT

SNLASGVPDRFSGSGSGTDFTLTISSLQAEDVAVYYCHQWSSNPLTFGQG

TKVEIK

>BD22111
                                            (SEQ ID NO: 238)
DIVMTQSPDSLAVSLGERATINCRASSSLSFMHWYQQKPGKAPKLLIYAT

SNLASGVPSRFSGSGSGTEFTLTISSLQPDDFATYYCHQWSSNPLTFGQG

TKVEIK

>BD22104
                                            (SEQ ID NO: 239)
EIVMTQSPATLSVSPGERATLSCRASSSLSFMHWYLQKPGQSPQLLIYAT

SNLASGVPSRFSGSGSGTDFTLTISSLQPEDFATYYCHQWSSNPLTFGQG

TKVEIK

>BD22087
                                            (SEQ ID NO: 240)
EIVLTQSPGTLSLSPGERATLSCRASSSLSFMHWYQQKPGKAPKLLIYAT

SNLASGVPSRFSGSGSGTEFTLTISSLQPDDFATYYCHQWSSNPLTFGQG

TKVEIK

>BD22096
                                            (SEQ ID NO: 241)
EIVLTQSPATLSLSPGERATLSCRASSSLSFMHWYQQKPGKAPKLLIYAT

SNLASGVPSRFSGSGSGTEFTLTISSLQPDDFATYYCHQWSSNPLTFGQG

TKVEIK

>BD22091
                                            (SEQ ID NO: 242)
EIVLTQSPATLSLSPGERATLSCRASSSLSFMHWYQQKPGQPPKLLIYAT

SNLASGIPARFSGSGSGTEFTLTISSLQSEDFAVYYCHQWSSNPLTFGQG

TKVEIK

>BD22089
                                            (SEQ ID NO: 243)
EIVLTQSPATLSLSPGERATLSCRASSSLSFMHWYQQKPGQPPKLLIYAT

SNLASGVPSRFSGSGSGTDFTFTISSLQPEDIATYYCHQWSSNPLTFGQG

TKVEIK

>BD22095
                                            (SEQ ID NO: 244)
EIVMTQSPATLSVSPGERATLSCRASSSLSFMHWYQQKPGQPPKLLIYAT

SNLASGVPSRFSGSGSGTDFTFTISSLQPEDIATYYCHQWSSNPLTFGQG

TKVEIK

>BD22106
                                            (SEQ ID NO: 245)
EIVLTQSPGTLSLSPGERATLSCRASSSLSFMHWYQQKPGQAPRLLIYAT

SNLASGVPSRFSGSGSGTDFTFTISSLQPEDIATYYCHQWSSNPLTFGQG

TKVEIK

>BD22097
                                            (SEQ ID NO: 246)
EIVLTQSPGTLSLSPGERATLSCRASSSLSFMHWYQQKPGQPPKLLIYAT

SNLASGVPSRFSGSGSGTDFTLTISSLQPEDFATYYCHQWSSNPLTFGQG

TKVEIK

>BD22101
                                            (SEQ ID NO: 247)
EIVLTQSPATLSLSPGERATLSCRASSSLSFMHWYQQKPGQPPKLLIYAT

SNLASGVPSRFSGSGSGTDFTLTISSLQPEDFATYYCHQWSSNPLTFGQG

TKVEIK

>BD22102
                                            (SEQ ID NO: 248)
EIVMTQSPATLSVSPGERATLSCRASSSLSFMHWYQQKPGQPPKLLIYAT

SNLASGVPSRFSGSGSGTDFTLTISSLQPEDFATYYCHQWSSNPLTFGQG

TKVEIK
```

The signal sequence and constant regions associated with the light chains are as follows:

```
>LC signal
                                            (SEQ ID NO: 249)
ATGGACATGAGGGTCCCCGCTCAGCTCCTGGGGCTCCTGCTGCTCTGGCT

CCCAGGTGCCAAATGT

>LC signal
                                            (SEQ ID NO: 250)
MDMRVPAQLLGLLLLWLPGAKC >LC constant
                                            (SEQ ID NO: 251)
CGAACTGTGGCTGCACCATCTGTCTTCATCTTCCCGCCATCTGATGAGCA

GTTGAAATCTGGAACTGCCTCTGTTGTGTGCCTGCTGAATAACTTCTATC

CCAGAGAGGCCAAAGTACAGTGGAAGGTGGATAACGCCCTCCAATCGGGT

AACTCCCAGGAGAGTGTCACAGAGCAGGACAGCAAGGACAGCACCTAC

AGCCTCAGCAGCACCCTGACGCTGAGCAAAGCAGACTACGAGAAACAC

AAAGTCTACGCCTGCGAAGTCACCCATCAGGGCCTGAGCTCGCCCGTCA

CAAAGAGCTTCAACAGGGGAGAGTGTTAA

>LC constant
                                            (SEQ ID NO: 252)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC
```

These were transfected via plasmid Ig chain expression vectors into HEK-293 suspension cells, and the resulting cell culture supernatants were screened.

HuFR Library Screening Results.

Figure 5:
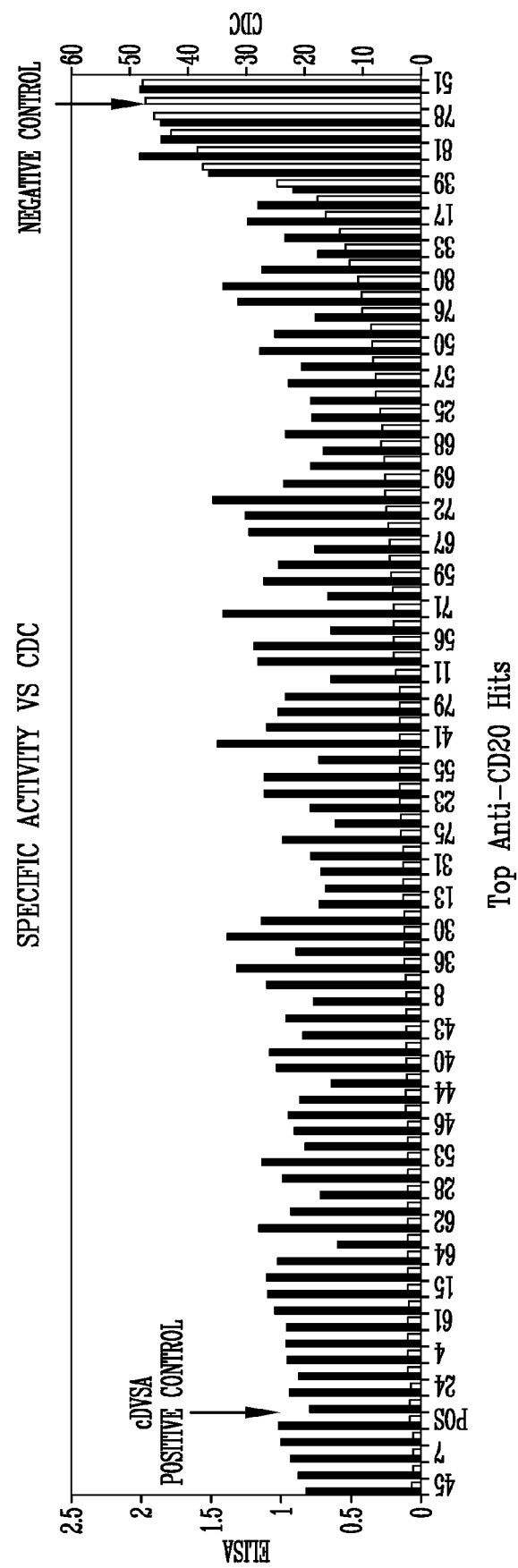
FIG. 5 illustrates a bar graph of data comparing the specific activity of the top anti-CD20 HuFR clones in the anti-CD20 ELISA, as discussed in detail in Example 3, below.

The primary high-throughput screening data for the final HuFR library is shown in FIG. 26, which s illustrates a graph of data from an anti-CD20 ELISA assay demonstrating the specific activity of the anti-CD20 HuFR clones in the anti-CD20 cellular ELISA, using adherent CD20+HEK-293 cells. The specific activity of DVSA-CD20 was set at 1.0. Clones with an activity greater than or equal to 1.0 were tested in the CDC assay. The signal:noise was 4.2 for the quantitative ELISA (CV 8.8%) and 3.6 for the anti-CD20 cellular ELISA (CV 5.7%). The specific activities of the HuFR clones were determined by normalizing the anti-CD20 cellular ELISA binding activity by antibody expression levels (as determined by a quantitative IgG ELISA). The specific activity of DVSA-CD20 was set at 1.0 and arranged by highest specific activity. The best putative hits (>80) were chosen for further analysis. The top putative hits identified from the cellular ELISA were profiled in the CDC assay. A comparison of the top hits in the CD20 cellular ELISA and the CDC assay illustrated that many of the cellular ELISA hits retained cytotoxicity activities similar to DVSA-CD20, as illustrated in FIG. 5. FIG. 5 is a bar graph comparing the specific activity of the top anti-CD20 HuFR clones in the anti-CD20 ELISA (purple, left bars) with the top clone activity in the CDC assay (aqua, right bars). The activities of the DVSA-CD20 positive control (cD-VSA) and negative control (unrelated human IgG) are indicated.

Based on the results of the cellular ELISA and the CDC assay, the top HuFR variants were selected for confirmation and further analysis in the panel of secondary assays. The HuFR heavy and light chains associated in these variants are as follows:

| LC & HC combination | Light Chain | Heavy chain |
|---|---|---|
| 1 | BD22084 | BD20332 |
| 2 | BD22085 | BD20335 |
| 3 | BD22086 | BD20335 |
| 4 | BD22088 | BD20337 |
| 5 | BD22087 | BD20335 |
| 6 | BD22089 | BD20335 |
| 7 | BD22090 | BD20337 |
| 8 | BD22095 | BD20337 |
| 9 | BD22091 | BD20337 |
| 10 | BD22108 | BD20337 |
| 11 | BD22092 | BD20338 |
| 12 | BD22094 | BD20337 |
| 13 | BD22096 | BD20337 |
| 14 | BD22092 | BD20337 |
| 15 | BD22102 | BD20337 |
| 16 | BD22097 | BD20335 |
| 17 | BD22104 | BD20337 |
| 18 | BD22085 | BD20339 |
| 19 | BD22107 | BD20339 |
| 20 | BD22100 | BD20335 |
| 21 | BD22103 | BD20337 |
| 22 | BD22105 | BD20337 |
| 23* | BD22108 | BD20337 |
| 24 | BD22101 | BD20335 |
| 25 | BD22106 | BD20333 |
| 26 | BD22108 | BD20338 |
| 27 | BD22109 | BD20341 |
| 28 | BD22111 | BD20336 |
| 29* | BD22104 | BD20337 |

*Note that LC & HC combination number 23 has the same combination of light chain and heavy chain as number 10 (BD22108 and BD20337). Number 29 has the same heavy/light chain combination as number 17 (BD22104 and BD20337). Nevertheless, combination numbers 23 and 29 have been maintained for consistent presentation of the results below.

Figure 6:
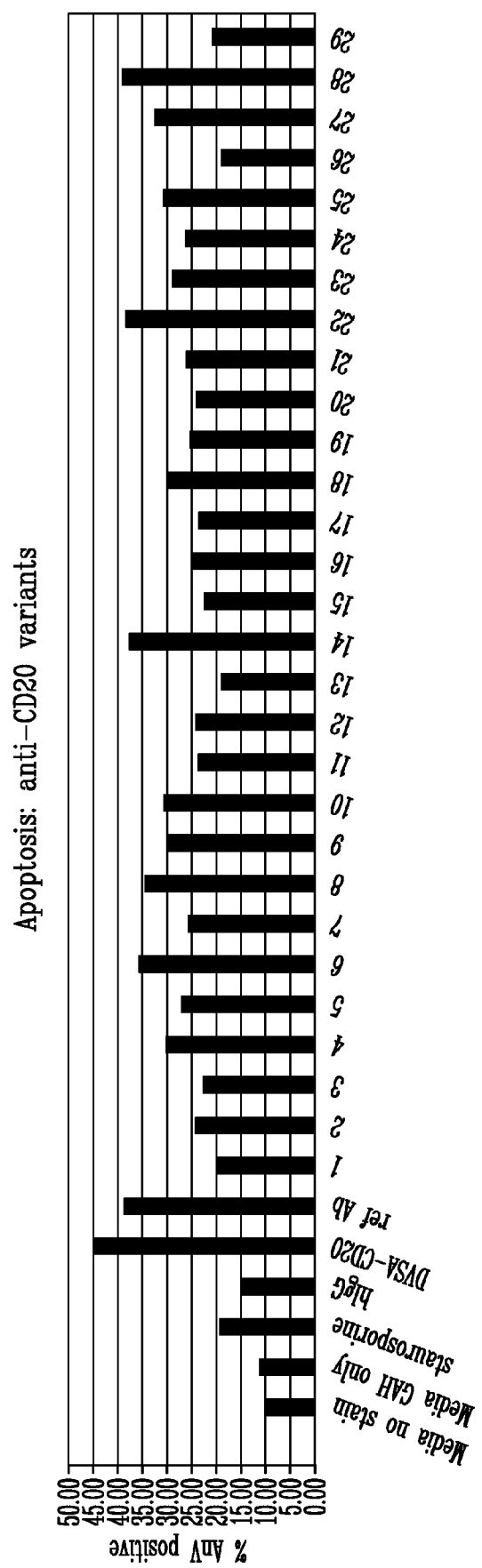
FIG. 6 is a bar graph of an apoptosis assay, which demonstrates that several of the top HuFR hits have activities equal to or better than reference antibody and DVSA-CD20, as discussed in detail in Example 3, below.
Figure 7:
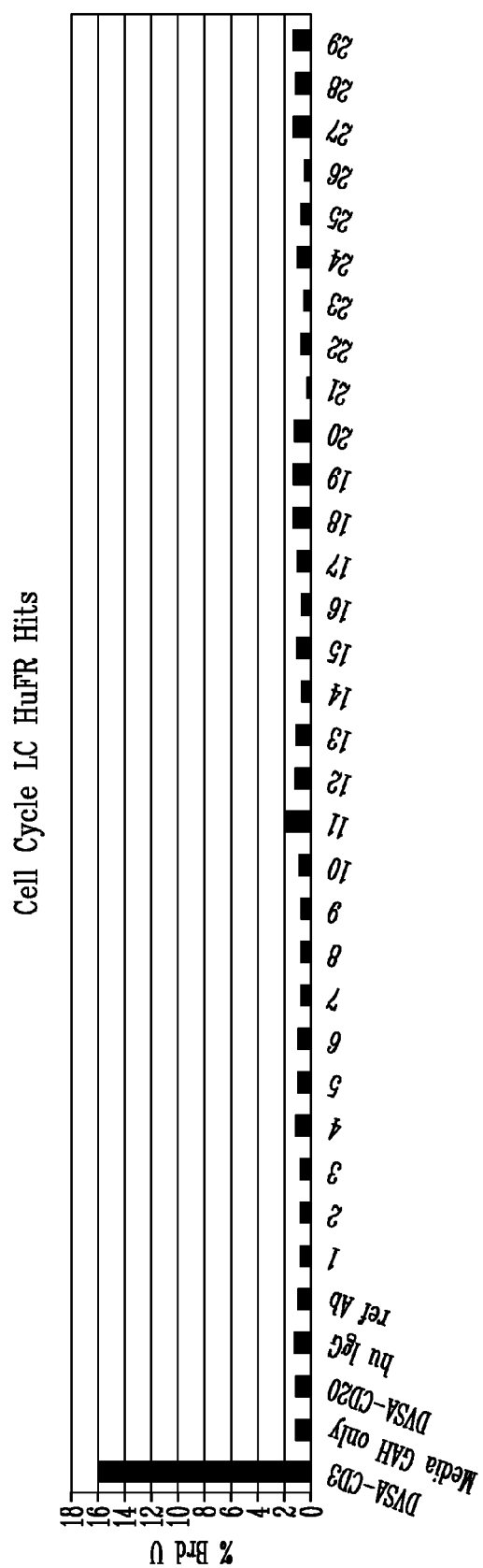
FIG. 7 is for cell cycle assay, which shows that the HuFR anti-CD20 hits do not induce cell proliferation in human PBMC in vitro, as discussed in detail in Example 3, below.

The top variants were transfected into HEK-293 suspension cells and the resulting (unpurified) cell culture supernatants were tested in a panel of secondary assays: apoptosis, see FIG. 6; cell cycle, see FIG. 7; CDC, see FIG. 8; and ADCC, see FIG. 9.

Figure 8:
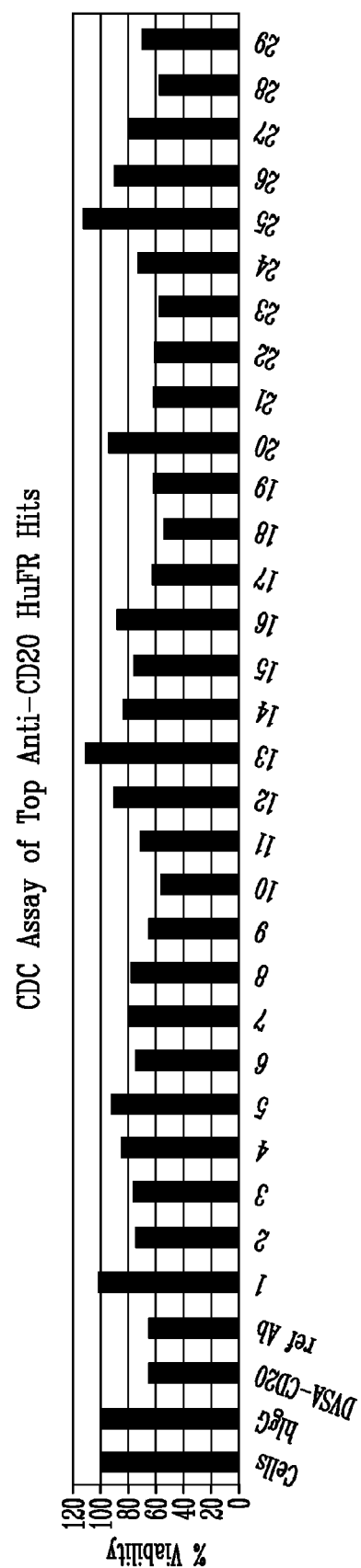
FIG. 8 is a bar graph of a CDC assay, as discussed in detail in Example 3, below.

FIG. 6 is a bar graph of an apoptosis assay, which demonstrates that several of the top HuFR hits have activities equal to or better than reference antibody and DVSA-CD20. Positive controls were staurosporine, the reference antibody, and DVSA-CD20. Negative controls were untreated cells (media no stain), untreated cells cross-linking antibody only (media GAH only), and cells treated with an unrelated human IgG (human). FIG. 7 is for cell cycle assay, which shows that the HuFR anti-CD20 hits do not induce cell proliferation in human PBMC in vitro. DVSA-CD3 was the positive control (lane 1). Negative controls included untreated cells with cross-linking antibody and cells treated with an unrelated human IgG. FIG. 8 is a bar graph of a CDC assay. Several anti-CD20 HuFR hits induce CDC as well as, or better than the reference antibody and DVSA-CD20 (lanes 3 and 4). Negative controls for this assay (100% viability) were untreated cells and cell treated with an unrelated human IgG (lanes 1 and 2).

Figure 9:
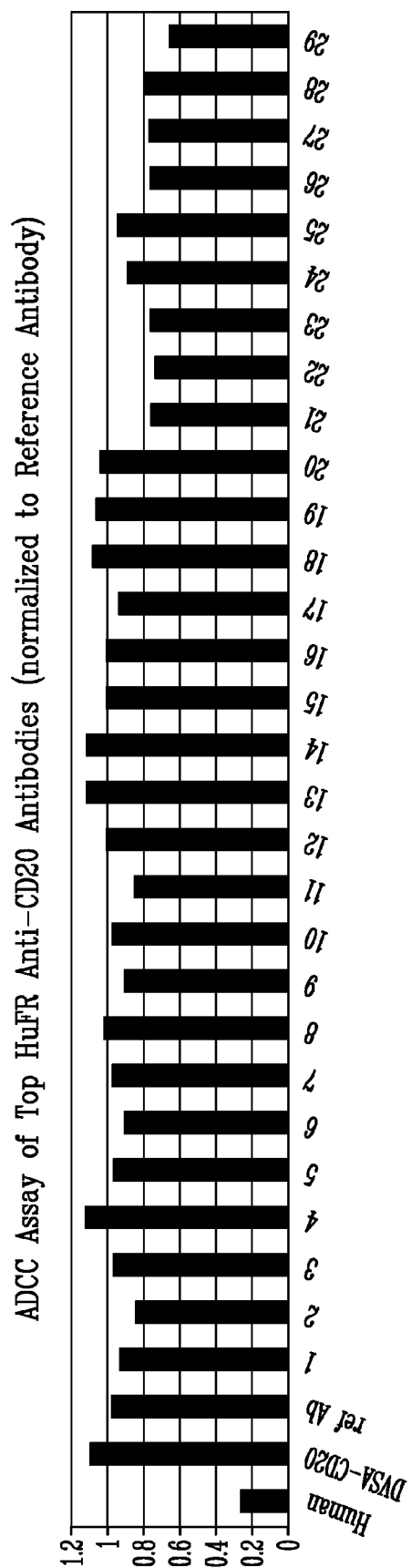
FIG. 9 is a bar graph of an ADCC assay, as discussed in detail in Example 3, below.

FIG. 9 is a bar graph of an ADCC assay, as discussed in detail in Example 4, below. Preliminary ADCC data with a subset of the top anti-CD20 HuFR hits suggest that several of these hits have activity similar to the reference antibody and DVSA-CD20 at a concentration of 1 µg/ml. The negative control for this assay was CD20+ target cells incubated with an irrelevant human IgG (Human) anti-CD3.

A summary of the assay data is shown in Table A. The variants were ranked in order from 1 to 29, starting with best binding activity in the cellular ELISA. A performance of ++ was equivalent to reference antibody. The top 12 variants overall are starred.

TABLE A

| Summary of anti-CD20 variants in panel of secondary cell-based assays | | | | |
|---|---|---|---|---|
| Variant | CDC | Apoptosis | Cell Cycle | ADCC |
| 1 | − | − | ++ | + |
| 2 | + | + | + | ++ |
| 3 | + | + | ++ | ++ |
| 4* | + | + | ++ | +++ |
| 5 | − | ++ | ++ | +++ |
| 6* | + | ++ | ++ | ++ |
| 7 | + | + | ++ | ++ |
| 8* | + | +++ | ++ | ++ |
| 9* | ++ | ++ | ++ | ++ |
| 10* | ++ | + | ++ | ++ |
| 11 | ++ | + | − | + |
| 12 | − | + | ++ | +++ |
| 13 | − | − | ++ | +++ |
| 14* | + | +++ | ++ | ++++ |
| 15* | + | + | ++ | +++ |
| 16 | − | + | ++ | +++ |
| 17* | ++ | + | ++ | ++ |
| 18* | +++ | ++ | + | +++ |
| 19* | ++ | + | + | +++ |
| 20 | − | + | ++ | +++ |
| 21 | ++ | + | +++ | + |
| 22* | ++ | +++ | ++ | + |
| 23 | ++ | + | ++ | + |
| 24 | ++ | + | ++ | + |
| 25 | − | ++ | ++ | +++ |
| 26 | − | + | +++ | + |
| 27 | + | ++ | ++ | + |
| 28* | ++ | +++ | ++ | ++ |
| 29 | ++ | + | + | + |

Example 4

Anti-CD3 Antibody

The invention provides a chimeric polypeptide and a chimeric bivalent antibody that specifically binds to the polypeptide CD3, e.g., in one embodiment, human CD3. In one aspect, a polypeptide of the invention, e.g., a chimeric polypeptide or a chimeric bivalent antibody of the invention, are used to suppress or abrogate an immune response, e.g., to treat (ameliorate) acute allograft rejection in renal transplant patients and steroid-resistant acute allograft rejection in cardiac and hepatic transplant patients, and to treat (ameliorate) autoimmune diseases, serious graft-versus-host disease, to treat (ameliorate) psoriasis and ulcerative colitis, and to ameliorate Type-I diabetes, e.g., by maintaining or improving insulin production in diabetes patients, including recently diagnosed Type-I diabetes patients.

In alternative embodiments, the anti-CD3 antibodies of the invention are useful to treat acute allograft rejection in renal transplant patients and steroid-resistant acute allograft rejection in cardiac and hepatic transplant patients. In alternative embodiments, these antibodies of the invention also are useful to treat autoimmune diseases, including psoriasis and ulcerative colitis, and serious graft-versus-host disease, and to maintain or improve insulin production in recently diagnosed Type-I diabetes patients. Modified anti-CD3s are being evaluated in Phase 2 studies for psoriasis and ulcerative colitis studies.

A reference mouse anti-CD3 antibody was converted to a chimeric, anti-CD3 antibody of this invention. A single amino acid change (T299V) was inserted into the Fc region of the antibody to reduce undesirable cytokine side effects associated with the reference antibody (the Fc region having this T299V mutation is referred to as "Fc null"). Fc null served as an additional control.

The chimeric antibody was also prepared to serve as the appropriate control for establishing the screening assays used in the modification. The parental chimera was prepared so that the reference sequences encoding the variable regions were cloned into a mammalian expression vector containing a human IgG1 constant domain.

FIG. 9 is a bar graph of an ADCC assay, as discussed in detail in Example 4, below. Preliminary ADCC data with a subset of the top anti-CD20 HuFR hits suggest that several of these hits have activity similar to the reference antibody and DVSA-CD20 at a concentration of 1 µg/ml. The negative control for this assay was CD20+ target cells incubated with an irrelevant human IgG (Human) anti-CD3.

The resulting chimeric, anti-CD3 antibody is referred to DVSA-CD3, shown in FIG. 10 and FIG. 11. FIG. 10 depicts the light chain (top) and heavy chain (bottom) nucleic acid sequences of DVSA-CD3. The yellow highlighted text denotes the CDRs. FIG. 11 depicts the heavy chain (top) and light chain (middle) amino acid sequences of DVSA-CD3, as well as the light chain of DVSA-CD3 (bottom). The yellow highlighted text denotes constant regions.

Apoptosis Assay

Jurkat T cells (ATCC Cat. TIB-152), cultured in cell medium (RPMI-1640 (ATCC Cat. 30-2001)/10% FBS (Invitrogen Cat. 10082-147)/0.05 mM 2-mercaptoethanol (Sigma M-7522)), were plated 2 days after the last subculturing at a density of about $2.5 \times 10^4$ cells. Cells were then centrifuged for 5 minutes at 200 g, room temperature. The spent cell culture medium subsequently was aspirated and cells were gently resuspended in fresh medium. The cell number was adjusted to $4.0 \times 10^5$ cells/ml with fresh cell culture medium after cells were counted. Cells were then plated (~50 µl/well) in a 96-well plate. An antibody solution (100 ng/ml, 50 ng/ml, 25 ng/ml or 12.5 ng/ml IgG) made up in cell culture medium was added to the cells and incubated for 24 hours, at 37° C., 5% $CO_2$. The antibodies to be tested (20 ng/ml) were those identified in the screening process. Irrelevant human IgG1 (EMD Biosciences Cat. 400120), DVSA-CD3, DVSA-CD3 (Fc null) served as control antibodies.

The APO-ONE APOPTOSIS ASSAY™ (Promega Cat. G7791) was used. The assay readout was based on the cleavage of fluorescently labeled tetrapeptide substrates in a 96-well format (APO-ONE™ HOMOGENEOUS CASPASE-3/7 Assay, Promega Cat. G7790, G7791). 100 µl/well of the APO-ONE™ reagent/substrate (100:1 dilution) was added to each well and was incubated at room temperature in the dark for 24 hours. The in vitro apoptosis assay established measures the induction of caspase activity in human CD3+ T cells following anti-CD3 antibody treatment. Plates were then read using a fluorescent microplate reader at an excitation wavelength of 485 nm and an emission wavelength of 530 nm.

Construction of the HuFR Anti-Cd3 Libraries

HuFR was performed as in Example 3. In the first round, the antibody supernatants (heavy chain HuFR library associated with kappa placeholder chains) were screened in a high-throughput assay that measured the ability of the antibody variants to induce T-cell signal transduction and subsequent apoptosis. In one experimental run, there were 326 hits selected from the primary screen, 52 hits were confirmed, and the top 10 heavy chain hits were selected. Tables C and D show the top heavy and light chain sequences (see Tables 1 to 4).

In the second round, the top 10 reassembled heavy chain genes identified by the apoptosis assay were then combined with the HuFR light chain library. This library was screened for identification of variants with identical or improved properties as compared to the control DVSA-CD3 (Fc-null). In one experiment, there were 268 hits from the primary screen, 37 confirmed hits, and the top 10 selected. 9 candidate clones were successfully retransfected and assayed in confirmation assays (Table B). The ICFs appearing in the top heavy and light chains are shown in Table C and D.

TABLE B

Heavy and light chains in the top anti-CD3 HuFR antibodies

| HuFR antibody | Heavy chain ID | Light chain ID |
|---|---|---|
| 1 | BD20610 | BD21130 |
| 2 | BD20613 | BD21131 |
| 3 | BD20611 | BD21132 |
| 4 | BD20611 | BD21133 |
| 5 | BD20611 | BD21134 |
| 6 | BD20611 | BD21135 |
| 7 | BD20611 | BD21136 |
| 8 | BD20611 | BD21137 |
| 9 | BD20613 | BD21138 |

TABLE C

ICFs used in the top heavy chains for anti-CD3

| Heavy chain ID | ICF1 | ICF2 | ICF3 | ICF4 |
|---|---|---|---|---|
| BD20610 | GL_7a | GL_5 | GL_4 | GL1 |
| BD20611 | GL_7a | GL_5 | GL_5 | GL1 |
| BD20613 | GL_3 | GL2_3 | GL_3 | GL1 |

TABLE D

ICFs used in the top kappa light chains for anti-CD3

| Light chain ID | ICF1 | ICF2 | ICF3 | ICF4 |
|---|---|---|---|---|
| BD21130 | VK1_2 | VK7 | VK8 | VK1 |
| BD21131 | VK3 | VK4_5_6 | VK8 | VK1 |
| BD21132 | VK5 | VK1_2_3 | VK3 | VK1 |
| BD21133 | VK8 | VK7 | VK3 | VK1 |
| BD21134 | VK4 | VK7 | VK3 | VK1 |
| BD21135 | VK4 | VK4_5_6 | VK7 | VK1 |
| BD21136 | VK3 | VK1_2_3 | VK6 | VK1 |
| BD21137 | VK3 | VK7 | VK2 | VK1 |
| BD21138 | VK3 | VK1_2_3 | VK8 | VK1 |

FIG. 12 provides an alignment of the heavy and light chains in the top 9 anti-CD3 hits.

HuFR Library Screening Results

The top nine (9) CD3 antibody variant heavy chain and light chain candidates were transfected into HEK-293 suspension cells and the resulting cell culture supernatants were tested for apoptosis activity and thermostability. All 9 variants obtained through the human framework reassembly reaction displayed apoptosis activities that were the same or better than the DVSA-CD3 (Fc-null) in vitro (Table E). Negative controls were untreated cells (media) and an irrelevant human IgG (huIgG).

TABLE E

Apo-One Apoptosis Assay of HuFR antibodies

|  | 12.5 ng/ml | 25 ng/ml | 50 ng/ml | 12.5 ng/ml | 25 ng/ml | 50 ng/ml |
|---|---|---|---|---|---|---|
| media | 380 | 380 | 384 | | | |
| huIgG | 250 | 259 | 234 | | | |
| Fc null | 494 | 729 | 1191 | 1.0 | 1.0 | 1.0 |
| variant 1 | 797 | 1217 | 1753 | 1.6 | 1.7 | 1.5 |
| variant 2 | 854 | 1435 | 2156 | 1.7 | 2.0 | 1.8 |
| variant 3 | 649 | 854 | 1132 | 1.3 | 1.2 | 1.0 |
| variant 4 | 1390 | 2348 | 3303 | 2.8 | 3.2 | 2.8 |
| variant 5 | 1163 | 1663 | 2165 | 2.4 | 2.3 | 1.8 |
| variant 6 | 1277 | 2224 | 3498 | 2.6 | 3.1 | 2.9 |
| variant 7 | 2268 | 3477 | 4744 | 4.6 | 4.8 | 4.0 |
| variant 8 | 969 | 1632 | 2559 | 2.0 | 2.2 | 2.1 |
| variant 9 | 885 | 1383 | 2041 | 1.8 | 1.9 | 1.7 |

Thermostability

The 9 HuFR variants were also assayed for thermostability assay to ensure that the structural integrity of the antibody had not been compromised by any of the amino acid changes. The 9 variants obtained through the human framework reassembly reaction have higher melting temperatures than the DVSA-CD3 (Fc-null) antibody.

TABLE F

The thermostability of the 9 variants was not affected by HuFR
The invention provides chimeric polypeptides, described below as variant 1 through variant 9, capable of binding antigen that have thermostable binding activity:

| Antibody | $T_m$ (° C.) |
|---|---|
| DVSA-CD3 (Fc-null) | 59.6 |
| variant 1 | 66.5 |
| variant 2 | 70.5 |
| variant 3 | 64.7 |
| variant 4 | 65.8 |
| variant 5 | 67.7 |
| variant 6 | 65.2 |
| variant 7 | 65.5 |
| variant 8 | 70.7 |
| variant 9 | 63.5 |

The entire disclosures of all patents, patent applications, and publications referred to in this application are hereby incorporated by reference.

What is claimed is:

1. An antibody or antigen-binding fragment thereof comprising at least one variable region having a combination of:
   (1) light chain BD22084 (SEQ ID NO:225) and heavy chain BD20332 (SEQ ID NO:138);
   (2) light chain BD22085 (SEQ ID NO:232) and heavy chain BD20335 (SEQ ID NO:143);
   (3) light chain BD22086 (SEQ ID NO:227) and heavy chain BD20335 SEQ ID NO:143);
   (4) light chain BD22088 (SEQ ID NO:229) and heavy chain BD20337 (SEQ ID NO:148);
   (5) light chain BD22087 (SEQ ID NO:240) and heavy chain BD20335 (SEQ ID NO:143);
   (6) light chain BD22089 (SEQ ID NO:243) and heavy chain BD20335 (SEQ ID NO:143);
   (7) light chain BD22090 (SEQ ID NO:234) and heavy chain BD20337 (SEQ ID NO:148);
   (8) light chain BD22095 (SEQ ID NO:244) and heavy chain BD20337 (SEQ ID NO:148);
   (9) light chain BD22091 (SEQ ID NO:242) and heavy chain BD20337 (SEQ ID NO:148);
   (10) light chain BD22108 (SEQ ID NO:230) and heavy chain BD20337 (SEQ ID NO:148);
   (11) light chain BD22092 (SEQ ID NO:235) and heavy chain BD20338 (SEQ ID NO:149);
   (12) light chain BD22094 (SEQ ID NO:231) and heavy chain BD20337 (SEQ NO: 148);
   (13) light chain BD22096 (SEQ ID NO:241) and heavy chain BD20337 (SEQ ID NO:148);
   (14) light chain BD22092 (SEQ ID NO:235) and heavy chain BD20337 (SEQ ID NO:148);
   (15) light chain BD22102 (SEQ ID NO:248) and heavy chain BD20337 (SEQ ID NO: 148);
   (16) light chain BD22097 (SEQ ID NO:246) and heavy chain BD20335 (SEQ ID NO:143);
   (17) light chain BD22104 (SEQ ID NO:239) and heavy chain BD20337 SEQ ID NO:148);
   (18) light chain BD22085 (SEQ ID NO:232) and heavy chain BD20339 (SEQ ID NO:150);
   (19) light chain BD22107 (SEQ ID NO:226) and heavy chain BD20339 (SEQ ID NO: 150);
   (20) light chain BD22100 (SEQ ID NO:236) and heavy chain BD20335 (SEQ ID NO:143);
   (21) light chain BD22103 (SEQ ID NO:228) and heavy chain BD20337 SEQ ID NO:148);
   (22) light chain BD22105 (SEQ ID NO:237) and heavy chain BD20337 (SEQ ID NO:148);
   (23) light chain BD22101 (SEQ ID NO:247) and heavy chain BD20335 (SEQ ID NO:143);
   (24) light chain BD22106 (SEQ ID NO:245) and heavy chain BD20333 (SEQ ID NO:142);
   (25) light chain BD22108 (SEQ ID NO:230) and heavy chain BD20338 (SEQ ID NO:149);
   (26) light chain BD22109 (SEQ ID NO:233) and heavy chain BD20341 (SEQ ID NO:154); or
   (27) light chain BD22111 (SEQ ID NO:238) and heavy chain BD20336 (SEQ ID NO:144).

2. The antigen binding antibody fragment of claim 1, wherein the antibody fragment is an Fab fragment, an Fab' fragment, an F(ab'), fragment, a single-chain antibody, an Fv fragment, an scFv fragment, an antibody mimetic, an Fd fragment, or an Fd' fragment.

3. The antigen binding antibody fragment of claim 2, wherein the antibody fragment is fused to an Fc.

4. A recombinant, synthetic or isolated antibody having a structure comprising at least one variable region combination of claim 1.

5. A chimeric antibody or antigen binding fragment thereof comprising at least one variable region combination of claim 1.

6. A chimeric antigen binding antibody fragment of claim 5, wherein the chimeric antibody fragment is a chimeric Fab, a chimeric Fab', a chimeric F(ab')$_2$, a chimeric single-chain antibody, a chimeric Fv, a chimeric scFv, an antibody mimetic, a chimeric Fd, or a chimeric Fd'.

7. A pharmaceutical composition or formulation comprising:
   (a) an antibody or antigen binding fragment thereof of claim 1.

8. The pharmaceutical composition or formulation of claim 7, further comprising a pharmaceutically acceptable carrier or excipient.

* * * * *

UNITED STATES PATENT AND TRADEMARK OFFICE
CERTIFICATE OF CORRECTION

PATENT NO. : 8,465,741 B2
APPLICATION NO. : 11/855943
DATED : June 18, 2013
INVENTOR(S) : Frey et al.

It is certified that error appears in the above-identified patent and that said Letters Patent is hereby corrected as shown below:

In the Claims

Col. 266, Claim 2, Line 65:
DELETE "F(ab'),"
ADD --$F(ab')_2$--

Signed and Sealed this
Sixth Day of August, 2013

Teresa Stanek Rea
*Acting Director of the United States Patent and Trademark Office*